US012765995B2

(12) United States Patent
Zamani et al.

(10) Patent No.: US 12,765,995 B2
(45) Date of Patent: Oct. 20, 2026

(54) DEVICES AND SYSTEMS FOR DOCKING A HEART VALVE

(71) Applicant: Edwards Lifesciences Corporation, Irvine, CA (US)

(72) Inventors: Shahram Zamani, Newport Coast, CA (US); Robert James Gerard, Coto de Caza, CA (US); Alison Louise Rodriguez, Irvine, CA (US); Anthony Michael Romero, Corona, CA (US); John J. Desrosiers, San Clemente, CA (US); Izaak Rosen, Irvine, CA (US); Andrew Paul Schaffer, Orange, CA (US); Avina Gupta, Alta Loma, CA (US); Tyler Dale O'Dell, Irvine, CA (US); Yara Baker, Riverside, CA (US); Uyen Duong, Anaheim, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 941 days.

(21) Appl. No.: 17/933,436

(22) Filed: Sep. 19, 2022

(65) Prior Publication Data

US 2023/0011247 A1 Jan. 12, 2023

Related U.S. Application Data

(63) Continuation of application No. PCT/US2021/019770, filed on Feb. 26, 2021.

(Continued)

(51) Int. Cl.

*A61F 2/24* (2006.01)

(52) U.S. Cl.

CPC .... *A61F 2/2409* (2013.01); *A61F 2220/0008* (2013.01); *A61F 2220/005* (2013.01);

(Continued)

(58) Field of Classification Search

CPC ............ A61F 2/2409; A61F 2220/0008; A61F 2220/005; A61F 2220/0075;

(Continued)

(56) References Cited

U.S. PATENT DOCUMENTS

| | | | |
|---|---|---|---|
| 5,203,777 | A | 4/1993 | Lee |
| 6,355,060 | B1 | 3/2002 | Lenker et al. |

(Continued)

FOREIGN PATENT DOCUMENTS

| | | | |
|---|---|---|---|
| JP | 2019503814 | A | 2/2019 |
| WO | 0176510 | A2 | 10/2001 |

(Continued)

*Primary Examiner* — Suzette J Gherbi

(74) *Attorney, Agent, or Firm* — Klarquist Sparkman LLP

(57) ABSTRACT

Expandable docking stations for docking an expandable valve can include a valve seat, one or more sealing portions, and/or one or more retaining portions. The valve seat can include radiopaque markers affixed to a frame or an impermeable member. The radiopaque markers can indicate a deployment location of the valve. The docking stations can be deployed from a catheter including one or more radiopaque markers. Relative positioning of two or more radiopaque markers can provide an indication of the amount of deployment of the docking station.

13 Claims, 134 Drawing Sheets

Related U.S. Application Data

(60) Provisional application No. 63/137,619, filed on Jan. 14, 2021, provisional application No. 62/991,687, filed on Mar. 19, 2020.

(52) U.S. Cl.
CPC ................ *A61F 2220/0075* (2013.01); *A61F 2250/0098* (2013.01)

(58) Field of Classification Search
CPC ............ A61F 2250/0098; A61F 2/2436; A61F 2/2418; A61F 2230/001; A61F 2/2466; A61F 2/2433; A61F 2/2463
See application file for complete search history.

(56) References Cited

U.S. PATENT DOCUMENTS

| | | | | |
|---|---|---|---|---|
| 6,361,557 | B1 | 3/2002 | Gittings et al. | |
| 7,510,575 | B2 | 3/2009 | Spenser et al. | |
| 9,089,422 | B2 | 7/2015 | Ryan et al. | |
| 10,265,166 | B2 | 4/2019 | Schweich, Jr. et al. | |
| 11,166,812 | B2 * | 11/2021 | Spence | A61F 2/2466 |
| 2002/0029079 | A1 * | 3/2002 | Kim | A61F 2/2493 606/198 |
| 2002/0032401 | A1 * | 3/2002 | Fereira | A61K 9/0024 604/892.1 |
| 2002/0156521 | A1 | 10/2002 | Ryan et al. | |
| 2004/0260394 | A1 * | 12/2004 | Douk | A61F 2/2433 606/153 |
| 2006/0020333 | A1 | 1/2006 | Lashinski et al. | |
| 2006/0287717 | A1 | 12/2006 | Rowe et al. | |
| 2007/0010873 | A1 | 1/2007 | Neri | |
| 2007/0043435 | A1 | 2/2007 | Seguin et al. | |
| 2007/0055359 | A1 | 3/2007 | Messer et al. | |
| 2007/0112422 | A1 * | 5/2007 | Dehdashtian | A61F 2/2427 623/2.11 |
| 2007/0244545 | A1 | 10/2007 | Birdsall et al. | |
| 2008/0065205 | A1 | 3/2008 | Nguyen et al. | |
| 2008/0071361 | A1 | 3/2008 | Tuval et al. | |
| 2009/0222082 | A1 * | 9/2009 | Lock | A61F 2/2409 623/2.11 |
| 2014/0188221 | A1 * | 7/2014 | Chung | A61F 2/2445 623/2.18 |
| 2017/0231756 | A1 * | 8/2017 | Armer | A61F 2/2409 623/2.18 |
| 2018/0263764 | A1 * | 9/2018 | Manash | A61F 2/2427 |
| 2019/0000615 | A1 | 1/2019 | Tayeb et al. | |
| 2019/0192292 | A1 | 6/2019 | Schweich, Jr. et al. | |
| 2022/0079749 | A1 * | 3/2022 | Patel | A61F 2/9517 |
| 2025/0143876 | A1 * | 5/2025 | Grosu | A61F 2/2409 |
| 2025/0262052 | A1 * | 8/2025 | Patel | A61F 2/2412 |
| 2025/0312153 | A1 * | 10/2025 | VanEvery | A61N 1/37516 |

FOREIGN PATENT DOCUMENTS

| | | | |
|---|---|---|---|
| WO | WO-2004075789 | A2 | 9/2004 |
| WO | 2005072655 | A1 | 8/2005 |
| WO | 2006009867 | A1 | 1/2006 |
| WO | 2006029062 | A1 | 3/2006 |
| WO | 2005037076 | A3 | 7/2007 |
| WO | 2009094501 | A1 | 7/2009 |
| WO | 2010031060 | A1 | 3/2010 |
| WO | WO-2017136778 | A1 | 8/2017 |
| WO | WO-2019006332 | A1 | 1/2019 |
| WO | WO-2021050637 | A1 | 3/2021 |

* cited by examiner

DEVICES AND SYSTEMS FOR DOCKING A HEART VALVE

REFERENCE TO RELATED APPLICATIONS

This application is a continuation of PCT patent application no. PCT/US2021/019770, filed on Feb. 26, 2021, which application claims the benefit of U.S. Provisional Application No. 62/991,687, filed on Mar. 19, 2020, and U.S. Provisional Application No. 63/137,619, filed on Jan. 14, 2021, the content of each of these applications being incorporated herein by reference in their entirety.

FIELD

The present disclosure relates to heart valves and, in particular, docking stations/stents, delivery systems, and methods for use in implanting a heart valve, e.g., a transcatheter heart valve ("THY").

BACKGROUND

Prosthetic heart valves can be used to treat cardiac valvular disorders. The native heart valves (the aortic, pulmonary, tricuspid and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery.

A transcatheter technique can also be used for introducing and implanting a prosthetic heart valve using a flexible catheter in a manner that is less invasive than open heart surgery. In this technique, a prosthetic valve can be mounted in a crimped state on the end portion of a flexible catheter and advanced through a blood vessel of the subject until the valve reaches the implantation site. The valve at the catheter tip can then be expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Transcatheter heart valves (THVs) can be appropriately sized to be placed inside most native aortic valves. However, with larger native valves, blood vessels, and grafts, aortic transcatheter valves might be too small to secure into the larger implantation or deployment site. In this case, the transcatheter valve may not be large enough to sufficiently expand inside the native valve or other implantation or deployment site to be secured in place.

Replacing the pulmonary valve, which is sometimes referred to as the pulmonic valve, presents significant challenges. The geometry of the pulmonary artery can vary greatly from patient to patient. Typically, the pulmonary artery outflow tract after corrective surgery is too wide for effective placement of a prosthetic heart valve.

SUMMARY

This summary is meant to provide examples and is not intended to be limiting of the scope of the invention in any way. For example, any feature included in an example of this summary is not required by the claims, unless the claims explicitly recite the feature. The description discloses exemplary embodiments of expandable docking stations for an expandable valve, catheters for the expandable docking stations, and handles for the catheters. The docking stations, catheters, and handles can be constructed in a variety of ways.

In one exemplary embodiment, a docking station for a medical device includes a frame, a plurality of radiopaque markers, and an impermeable material. The frame has a plurality of struts extending from a proximal end to a distal end. The struts define a plurality of cells and a valve seat. The radiopaque markers are disposed around the valve seat. The impermeable material is attached to the frame.

In one exemplary embodiment, a system comprises a tube and a docking station frame. The tube has one or more radiopaque markers. The docking station frame is disposed in the tube. The docking station includes one or more radiopaque markers. A position of one or more radiopaque markers of the docking station relative to the radiopaque markers of the tube indicate an amount of deployment of the docking station from the tube.

In one exemplary method of deploying a docking station frame, a radiopaque marker of a docking station frame is positioned at a target location for deployment of a valve seat of a docking station frame. A portion of the docking station frame is deployed from a tube such that a radiopaque marker of the tube becomes substantially aligned with the radiopaque marker of the docking station frame. The radiopaque marker of the tube and the radiopaque marker of the docking station frame are visually confirming to be at the target location. The docking station frame is further deployed and released from the tube.

In one exemplary embodiment, a system includes a delivery catheter assembly and a docking station frame. The delivery catheter assembly includes an outer tube and a connecting tube. The outer tube has a distal end and one or more radiopaque markers disposed at or near the distal end. The connecting tube has one or more radiopaque markers disposed in the outer tube. The docking station frame is disposed in the outer tube and is coupled to the connecting tube. The docking station frame is deployed by retracting the outer tube proximally relative to the connecting tube and the docking station frame. A position of one or more radiopaque markers of the connecting tube relative to the radiopaque markers of the outer tube indicate an amount of deployment of the docking station from the outer tube.

In one exemplary method of deploying a docking station frame, a portion of a docking station frame is deployed from an outer tube with a connecting tube such that a radiopaque marker of the outer tube moves closer to a radiopaque marker of the connecting tube. Alignment of the radiopaque marker of the outer tube with the radiopaque marker of the connecting tube indicates a final point at which the docking station frame is recapturable by the outer tube.

In one exemplary embodiment, a system comprises a delivery catheter assembly and a docking station frame. The delivery catheter assembly includes an elongated nosecone, an outer tube, a docking station connector, and a connecting tube. The outer tube has a distal end and one or more radiopaque markers disposed at or near the distal end. The docking station connector is moveable within the outer tube. The connecting tube is disposed in the outer tube. The connecting tube includes one or more radiopaque markers disposed between the elongated nosecone and the docking station connector. The docking station frame is disposed in the outer tube and is coupled to the docking station connector. The docking station frame includes one or more radiopaque markers. The docking station frame is deployed by retracting the outer tube proximally from the elongated nosecone. The radiopaque markers of the outer tube, the radiopaque markers of the connecting tube, and the radiopaque markers of the docking station frame are configured to visually determine one or more of correct placement of the docking station frame and a final point at which the docking station frame is recapturable by the outer tube.

In one exemplary embodiment, an assembly includes a frame, an elongated nosecone, an outer tube, a docking station connector, and a connecting tube. The frame has a valve seat and a plurality of radiopaque markers disposed around the valve seat. The outer tube has a distal end and one or more radiopaque markers disposed near the distal end. The docking station connector is moveable within the outer tube. The connecting tube is disposed between the elongated nosecone and the docking station connector. The frame is deployed by retracting the outer tube proximally from the elongated nosecone.

Various embodiments and methods described herein can be utilized within a subject in various procedures, including (but not limited to) medical and training procedures. Subjects include (but are not limited to) medical patients, veterinary patients, animal models, cadavers, and simulators of the cardiac and vasculature system (e.g., anthropomorphic phantoms and explant tissue).

Various features as described elsewhere in this disclosure can be included in the examples summarized here and various methods and steps for using the examples and features can be used, including as described elsewhere herein.

Further understanding of the nature and advantages of the disclosed inventions can be obtained from the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 74 is a side view of one embodiment of a frame of a docking station;

FIG. 75 is a side view of another embodiment of a frame of a docking station;

FIG. 76A is a side view of one embodiment of a frame of a docking station;

FIG. 76B is a bottom view of the frame of FIG. 76A;

FIG. 76C is a top view of the frame of FIG. 76A;

FIG. 77A is a side view of another embodiment of a frame of a docking station;

FIG. 77B is a bottom view of the frame of FIG. 77A;

FIG. 77C is a top view of the frame of FIG. 77A;

FIG. 78A is a side view of one embodiment of a docking station having outflow cells;

FIG. 78B is a top view of the docking station of FIG. 78A;

FIG. 79 is a side view of another embodiment of a docking station having outflow cells;

FIG. 80A is a side view of a frame of a docking station of one embodiment;

Figure 80A:
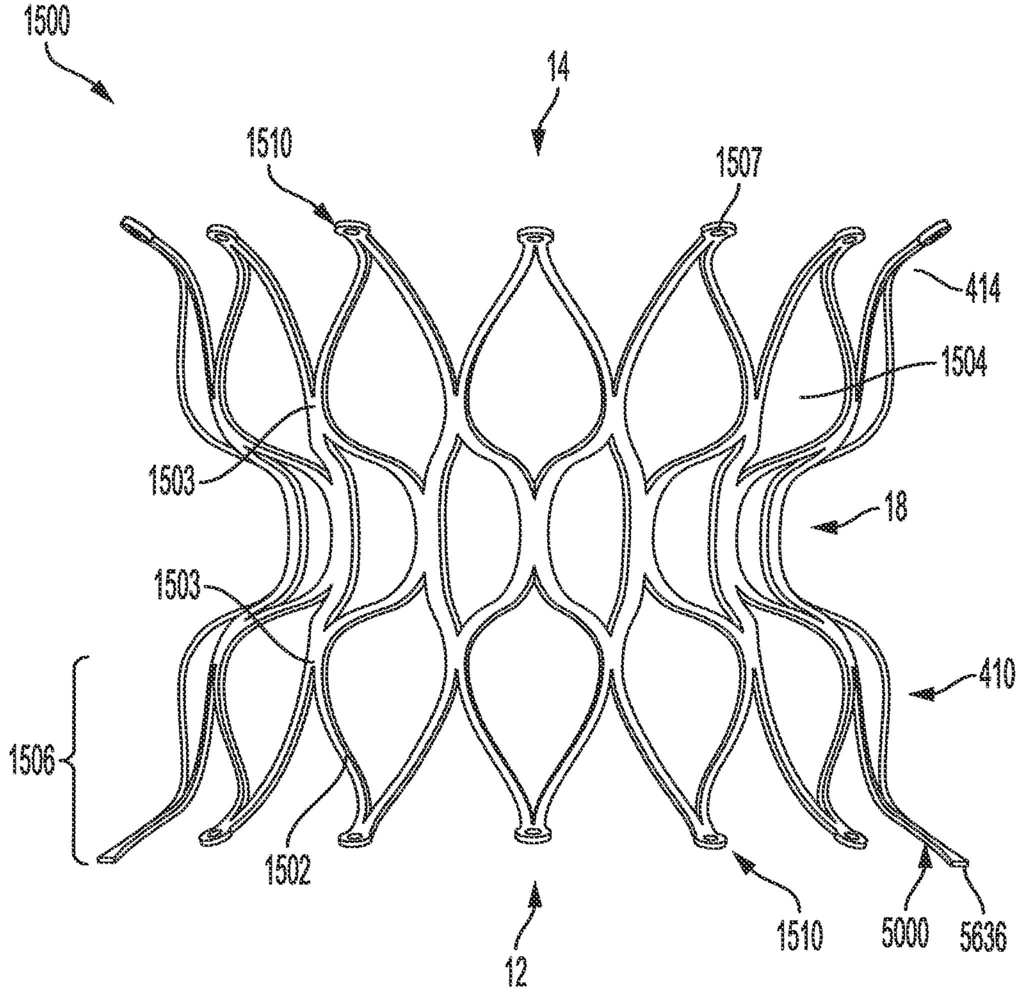
Figure 80B:
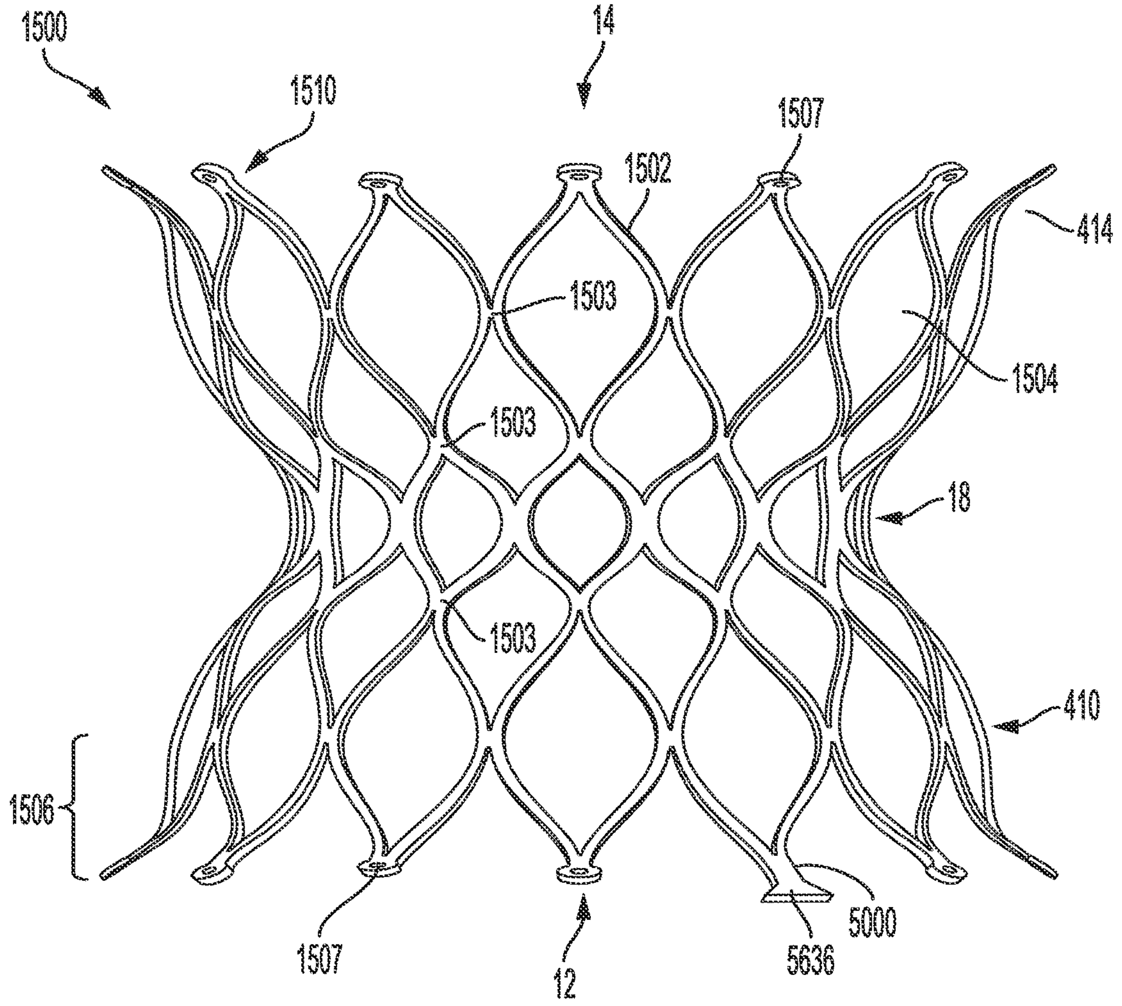
Figure 80C:
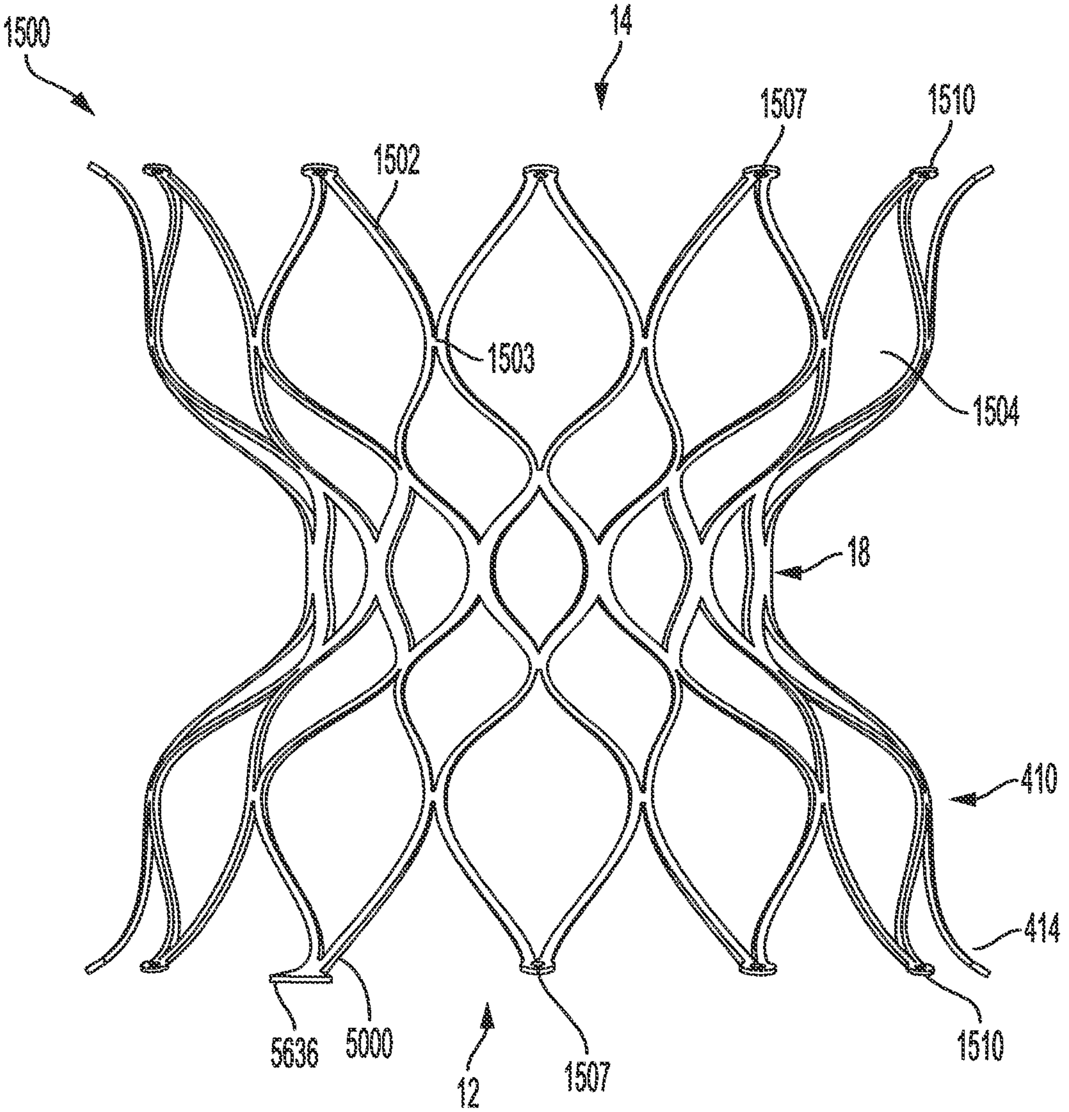
Figure 81A:
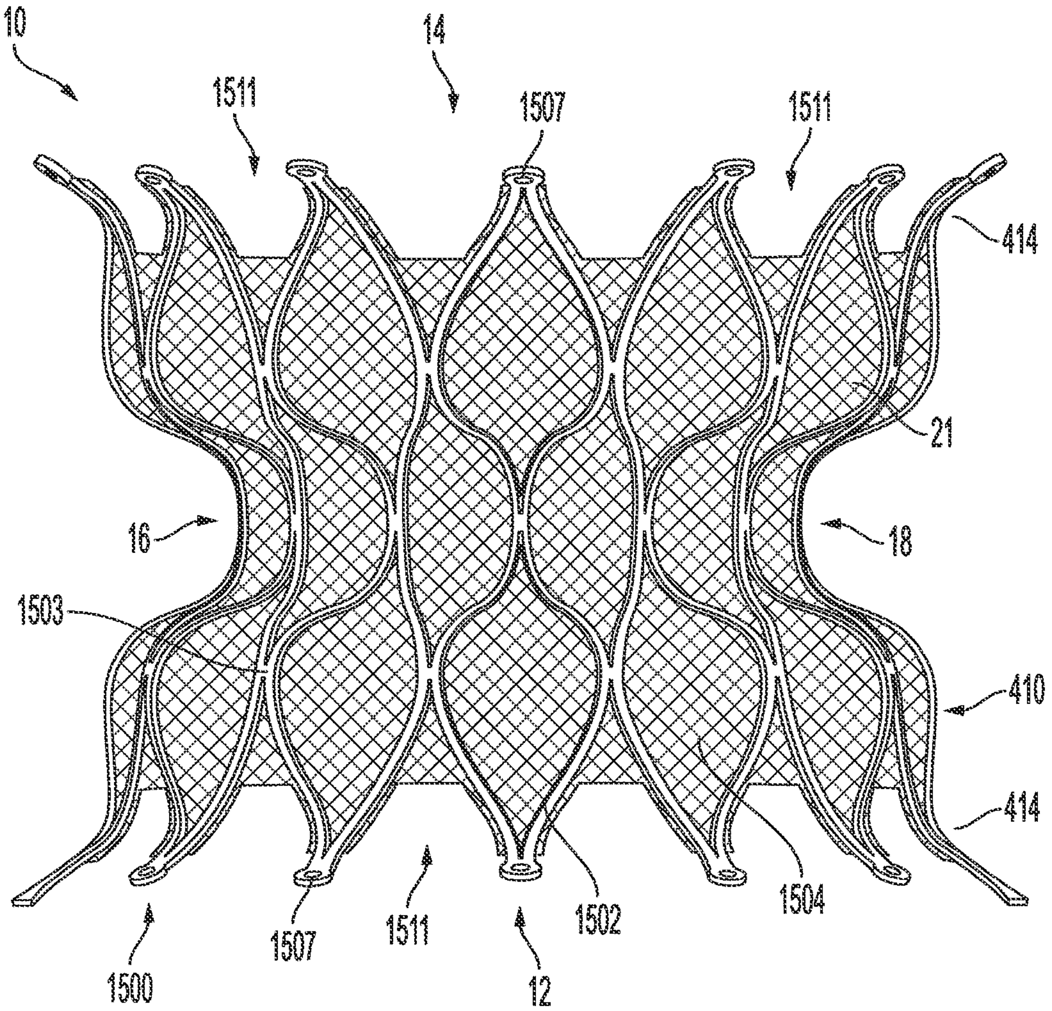
Figure 81B:
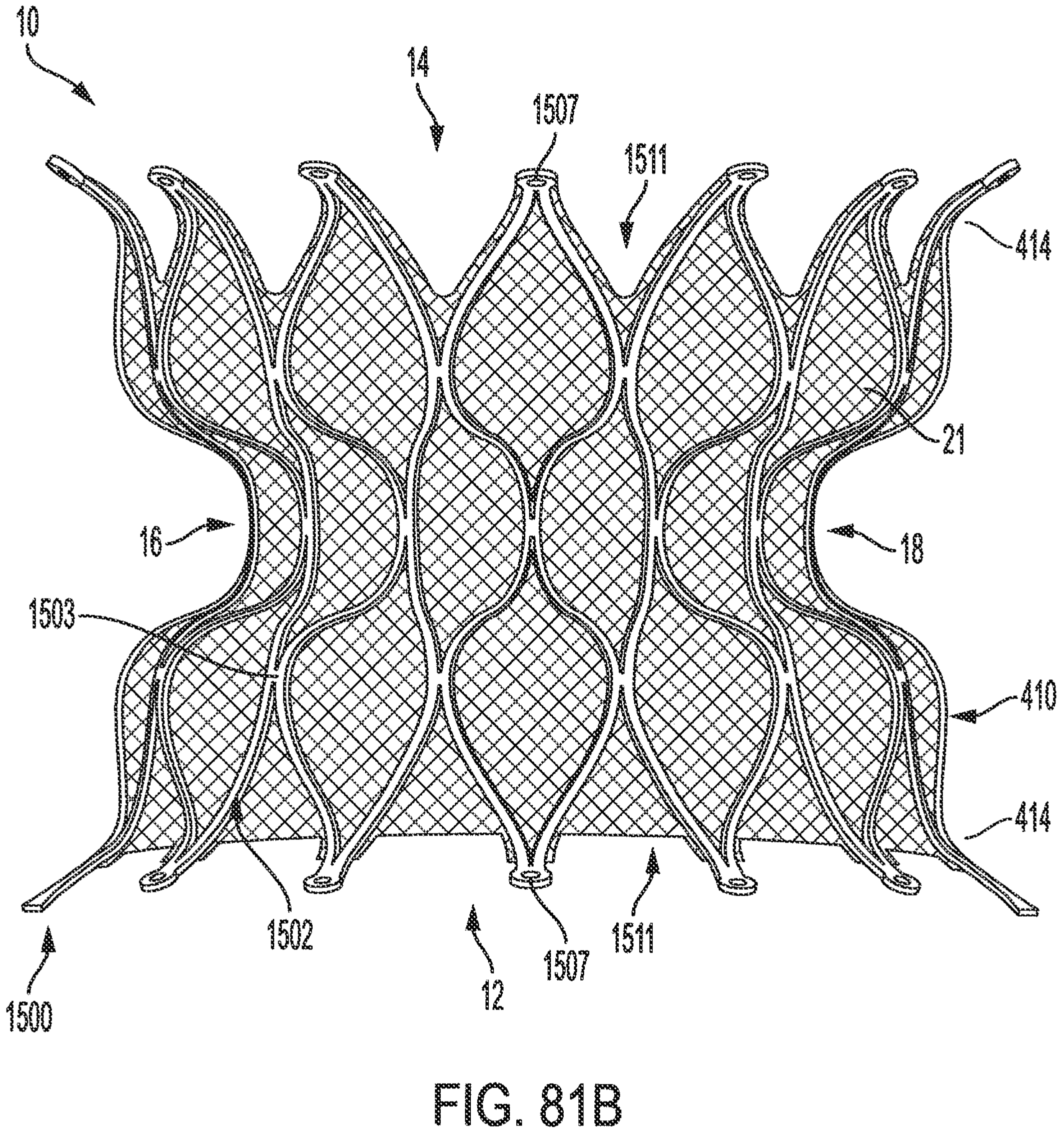
Figure 81C:
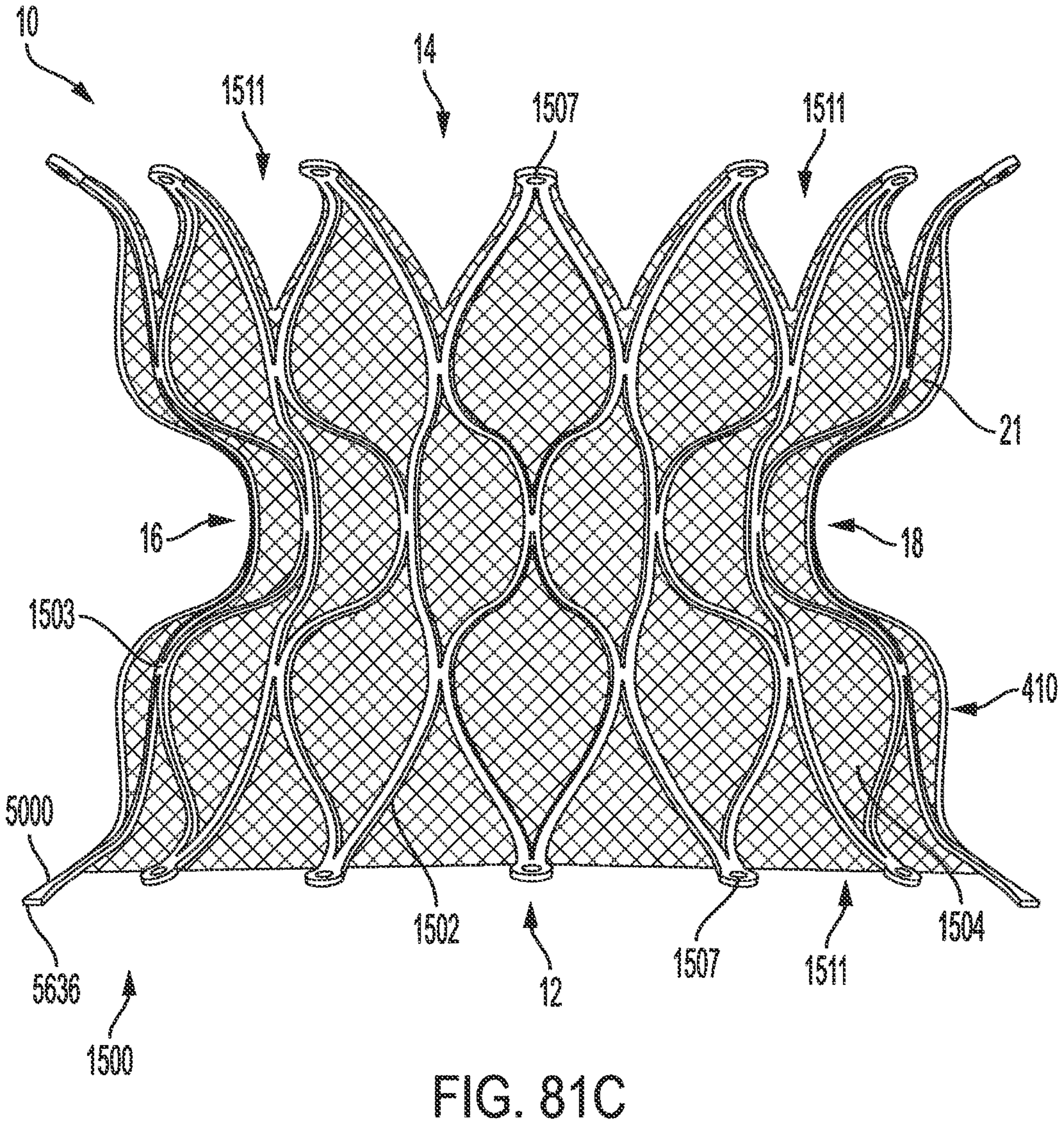
Figure 81D:
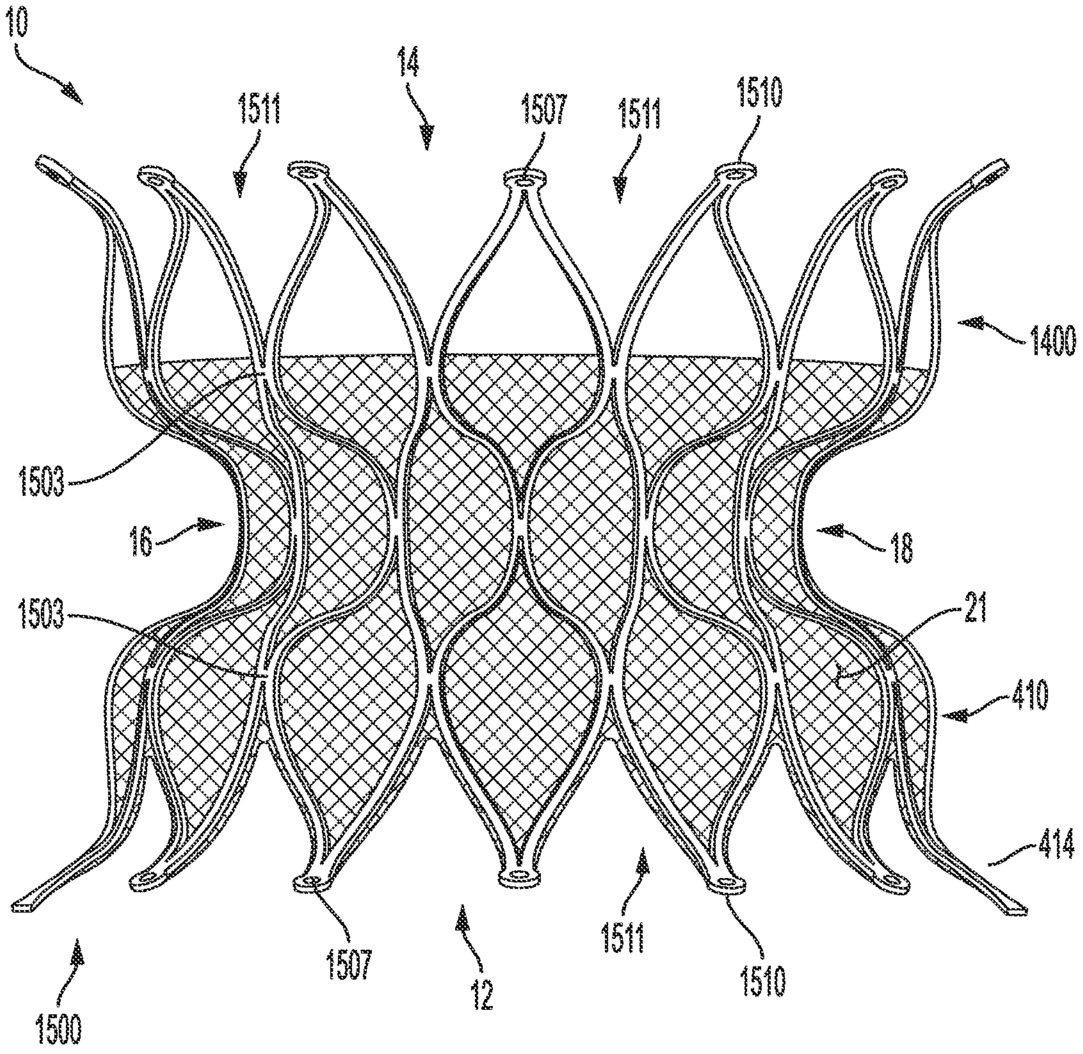
Figure 82A:
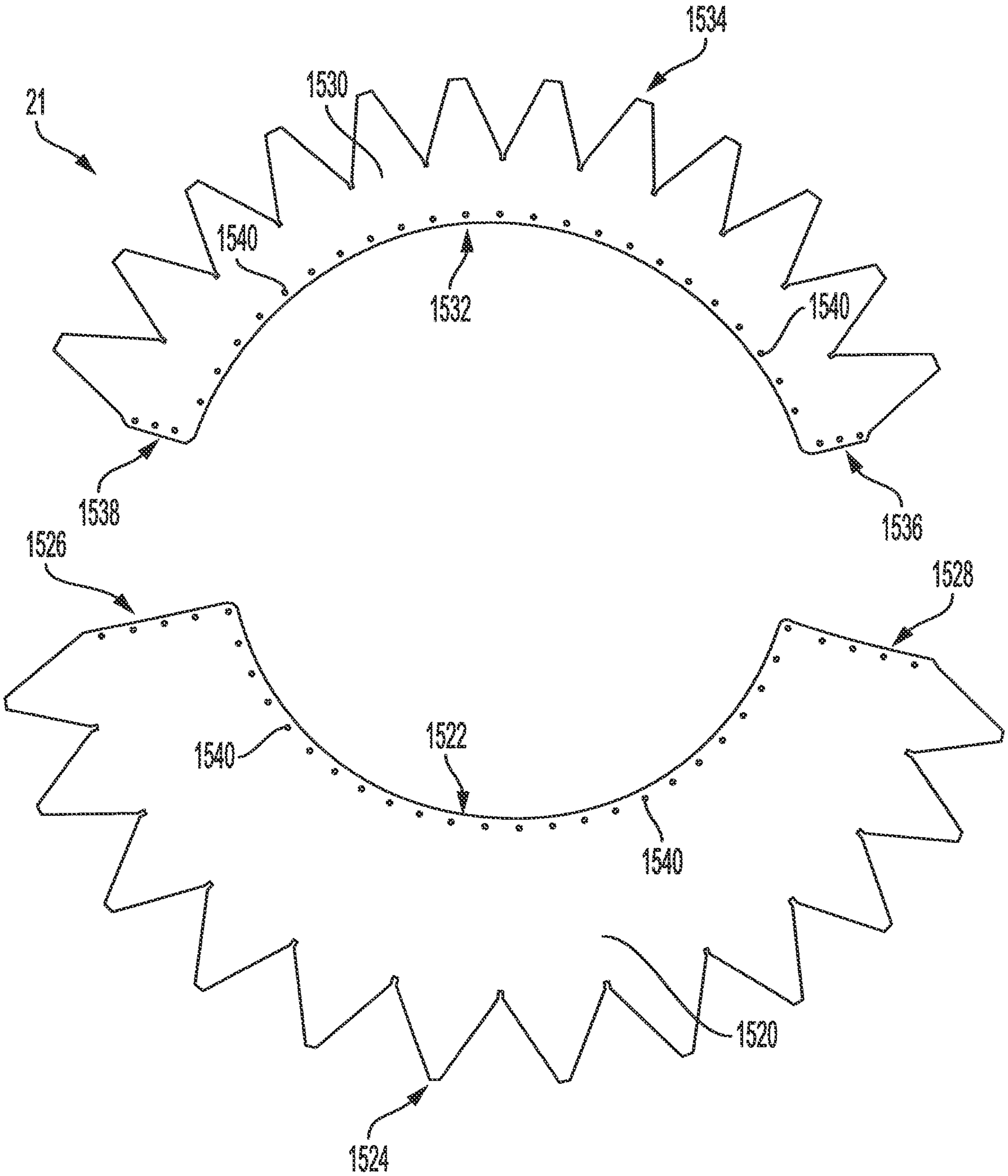
Figure 82B:
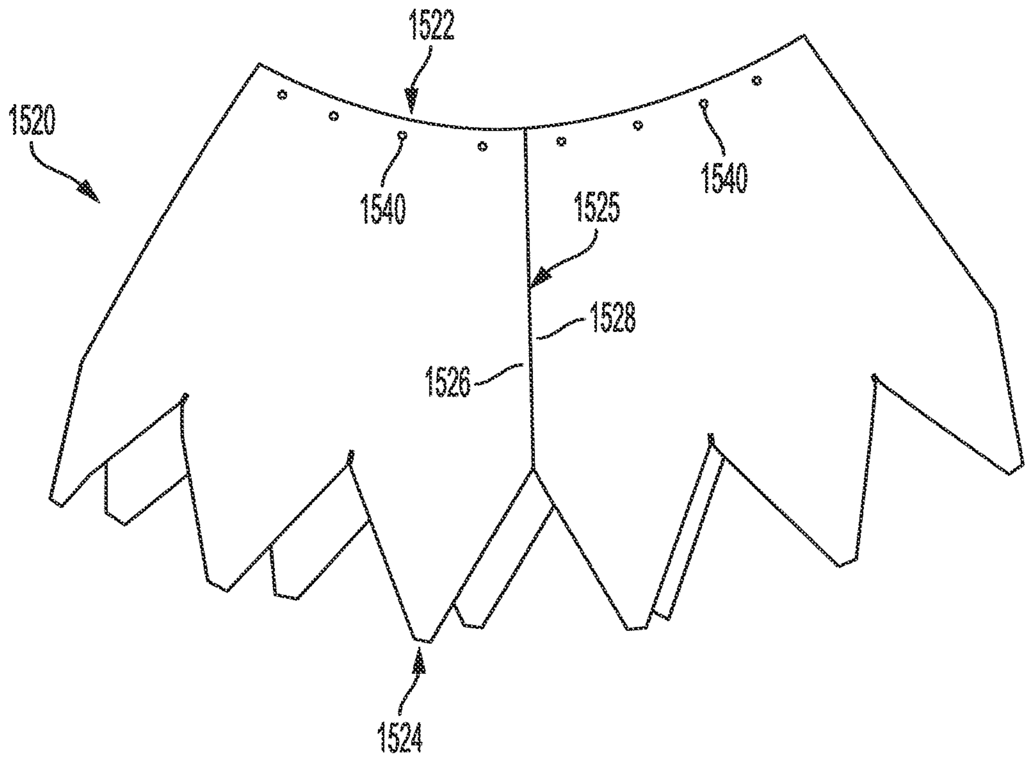
Figure 82C:
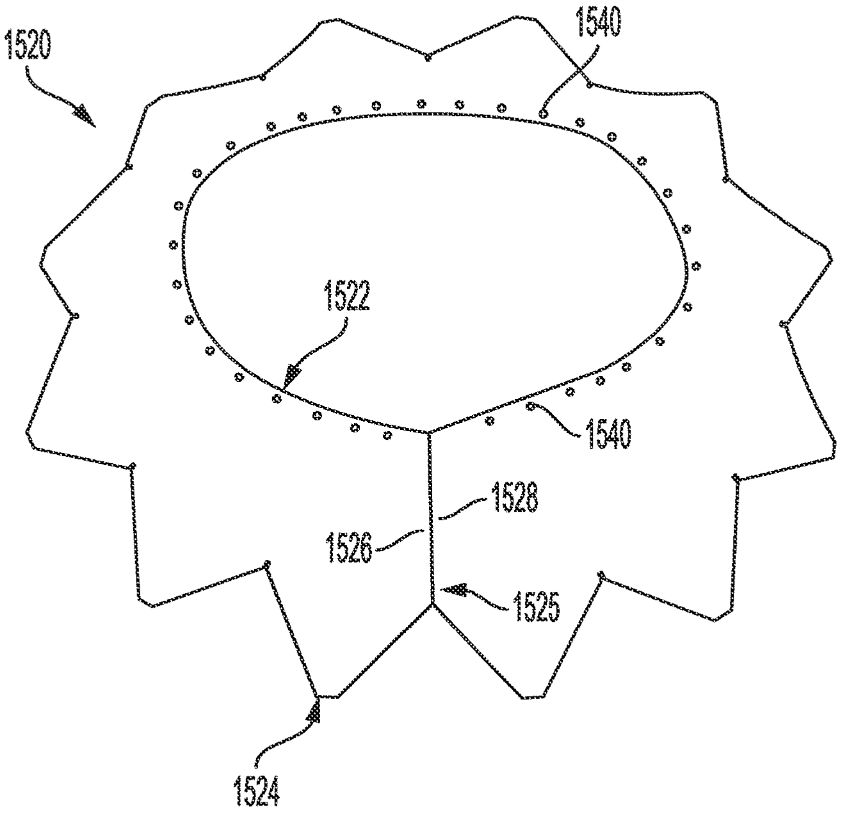
Figure 82D:
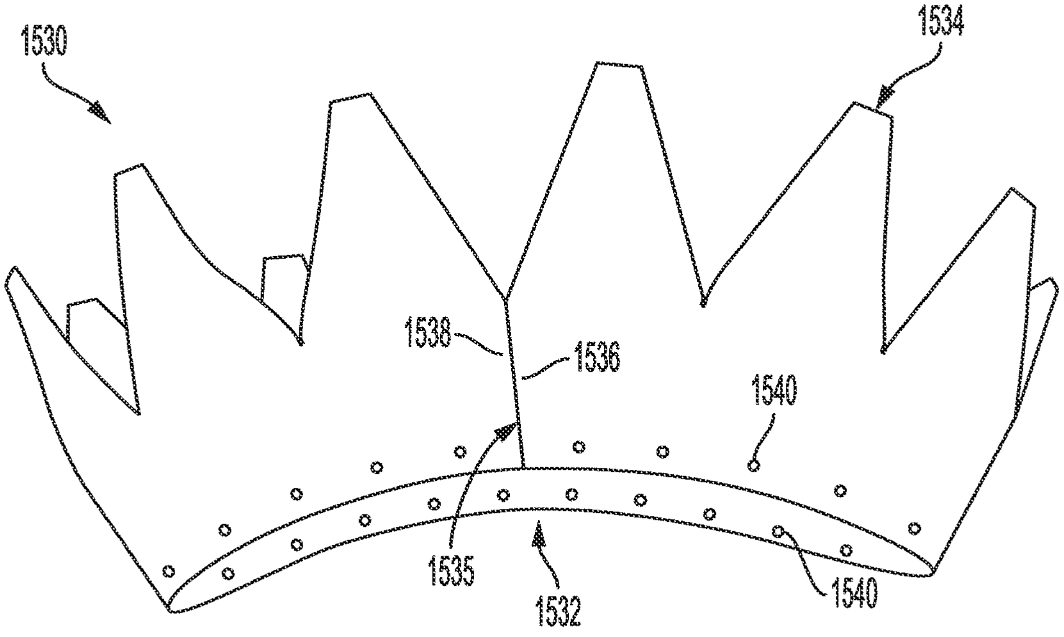
Figure 82E:
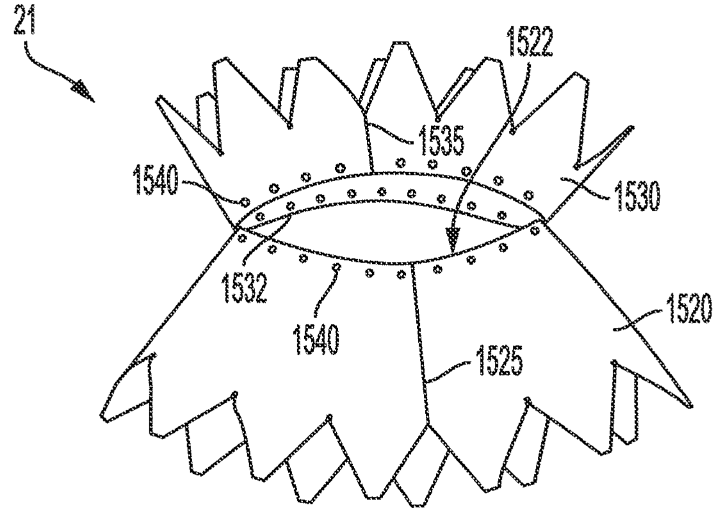
Figure 82F:
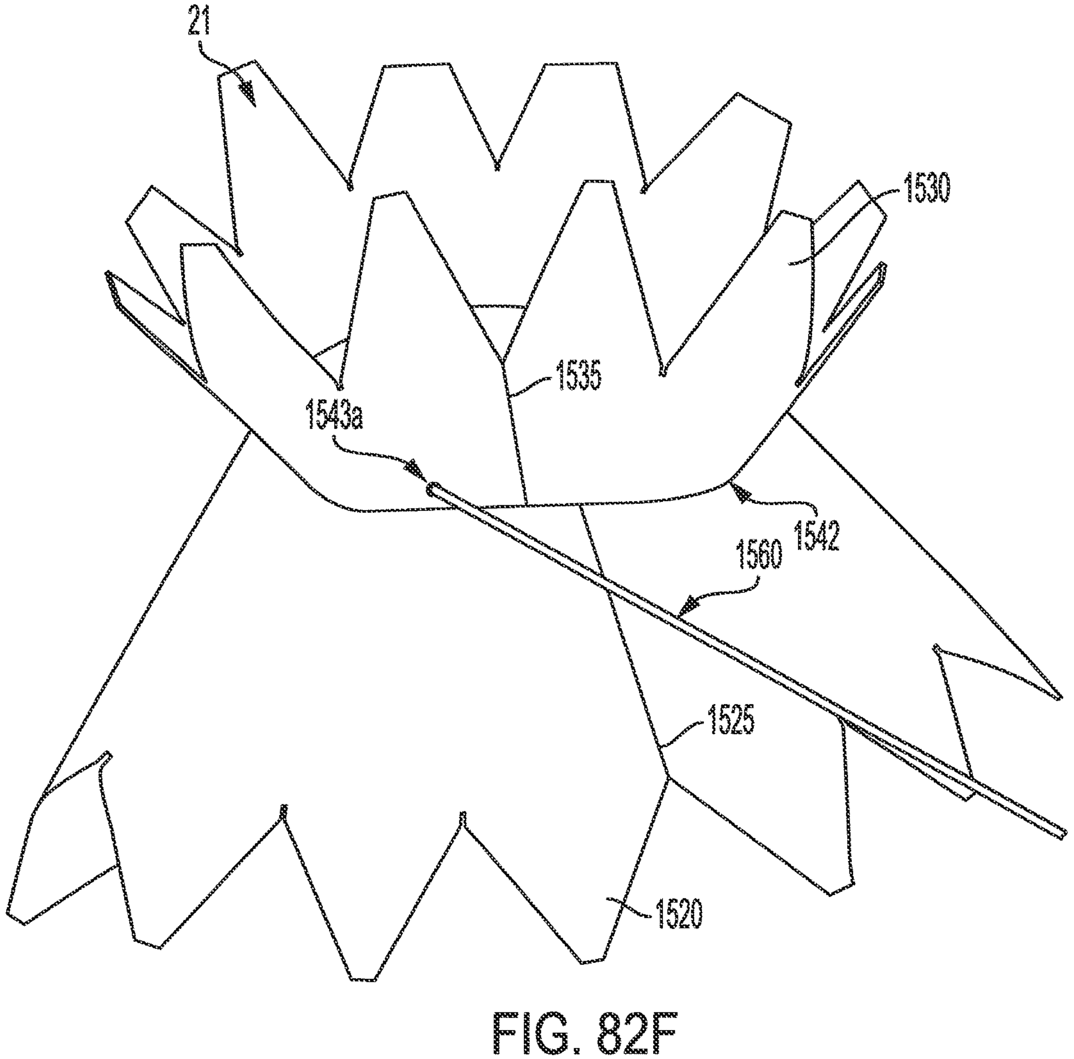
Figure 82G:
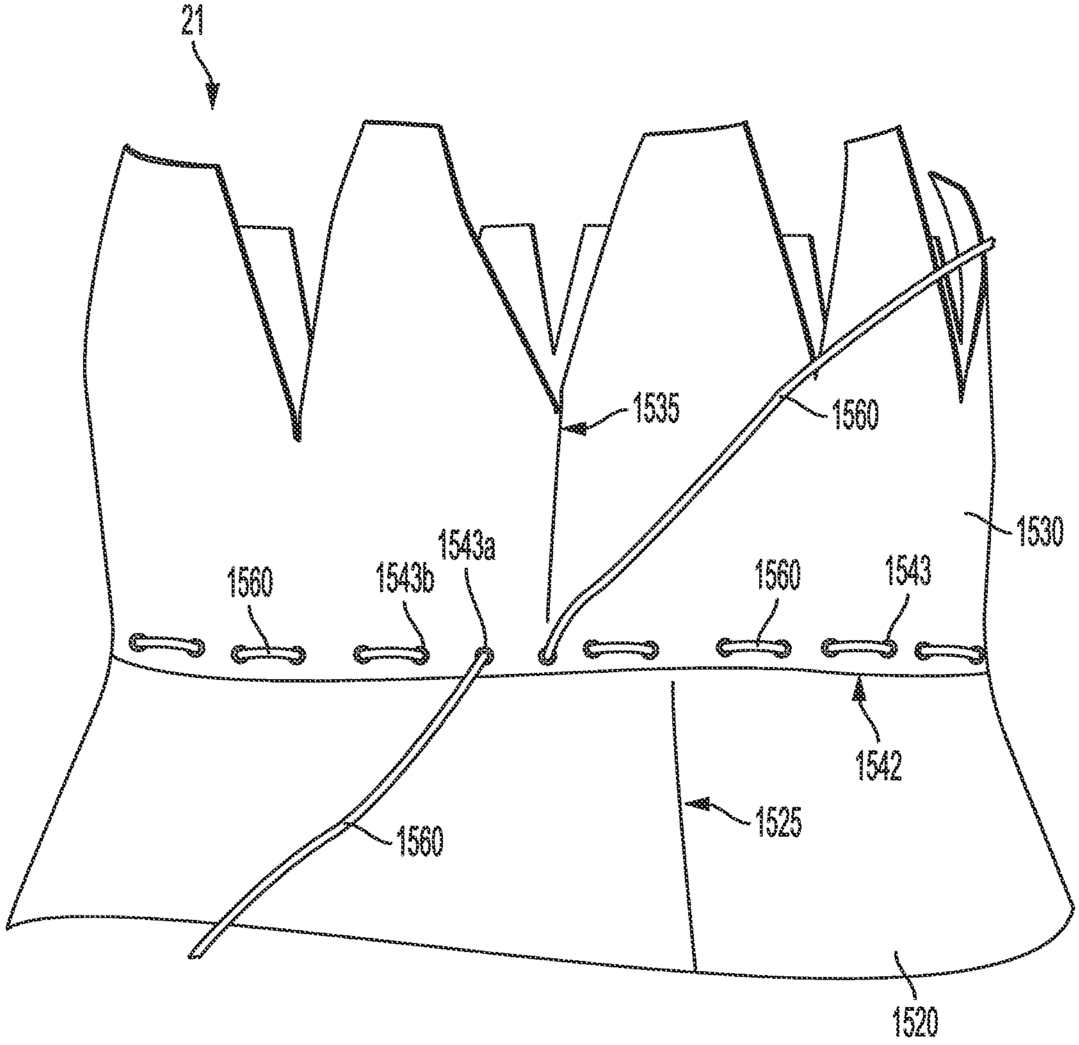
Figure 82H:
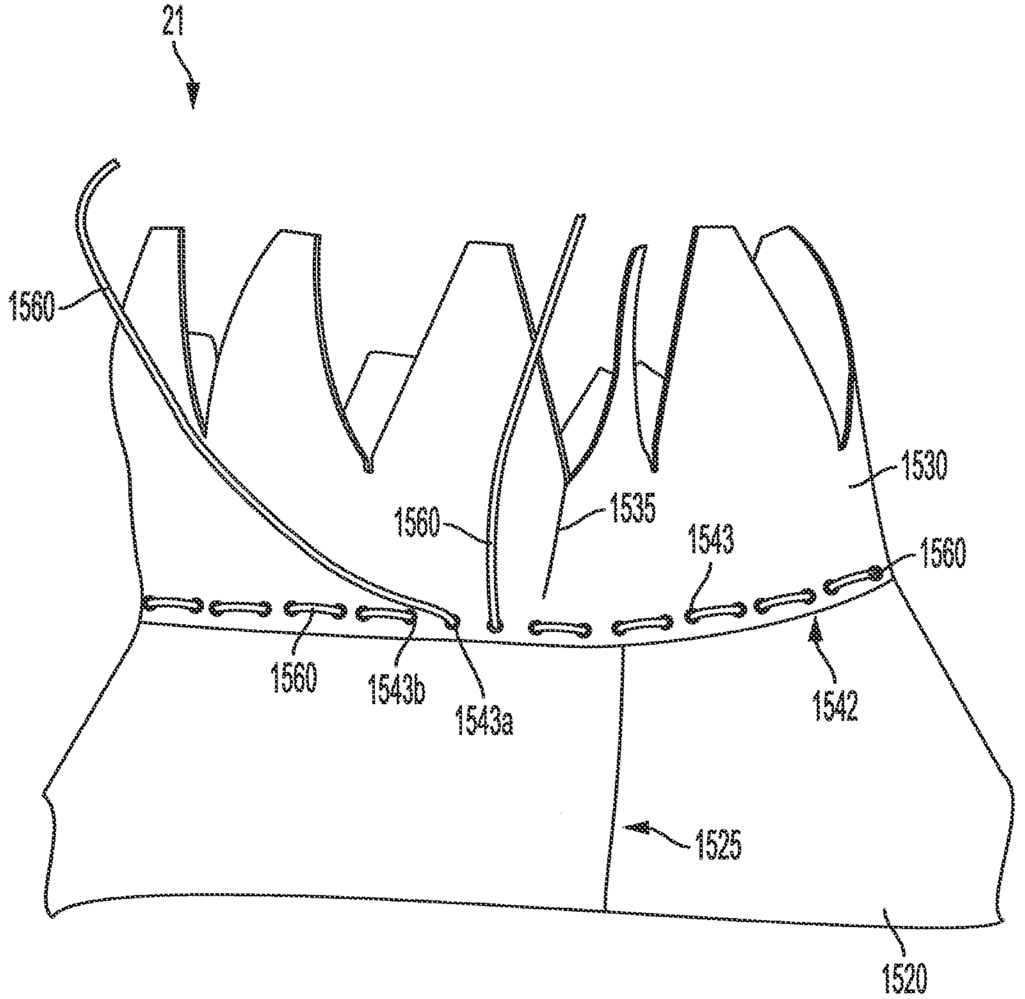
Figure 82I:
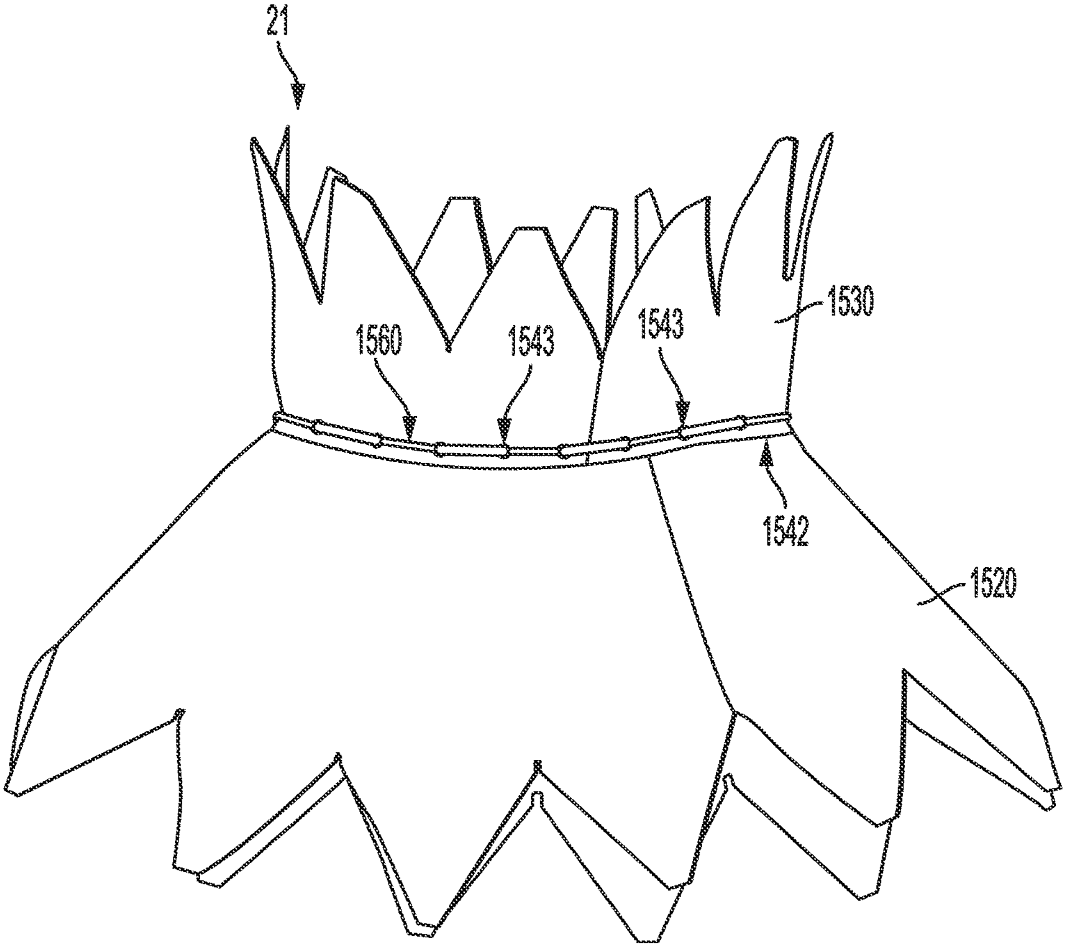
Figure 82J:
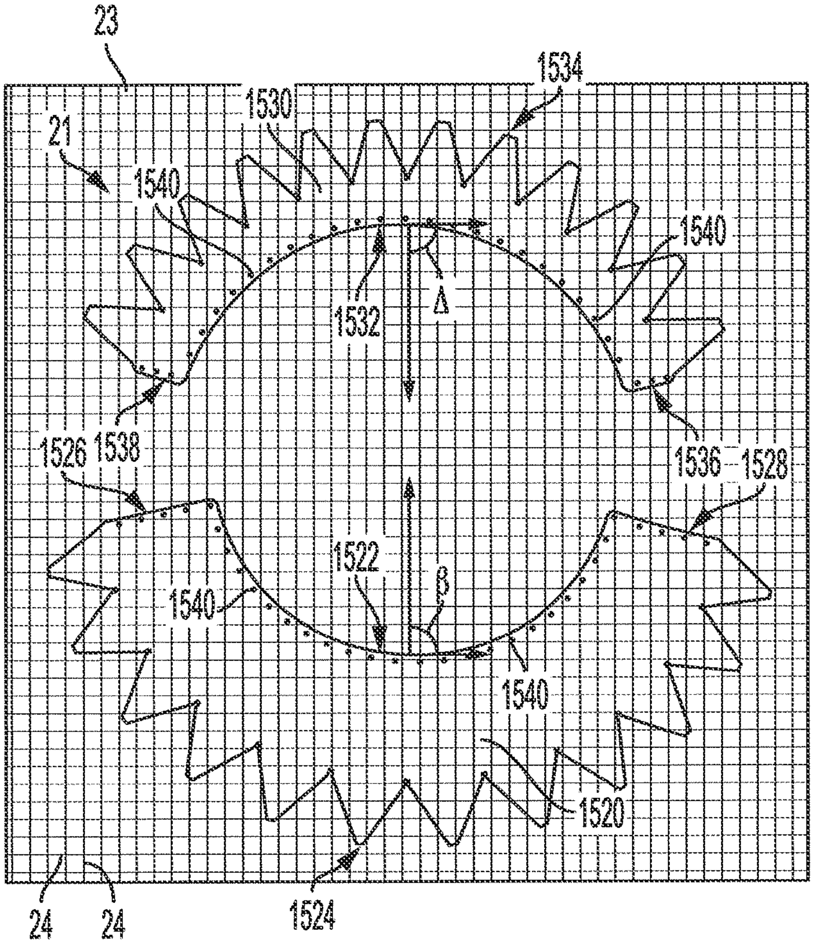
Figure 82K:
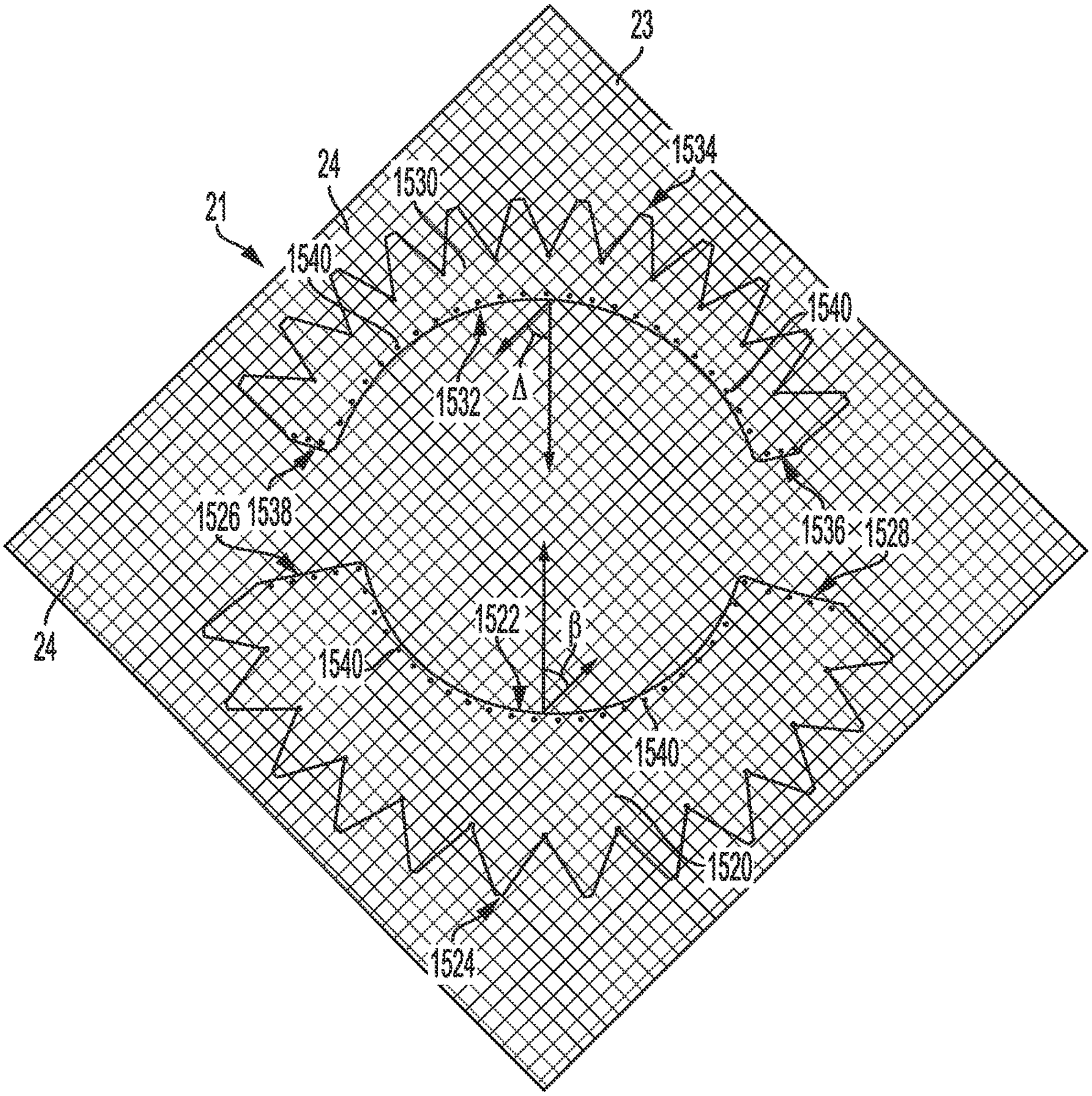
Figure 83:
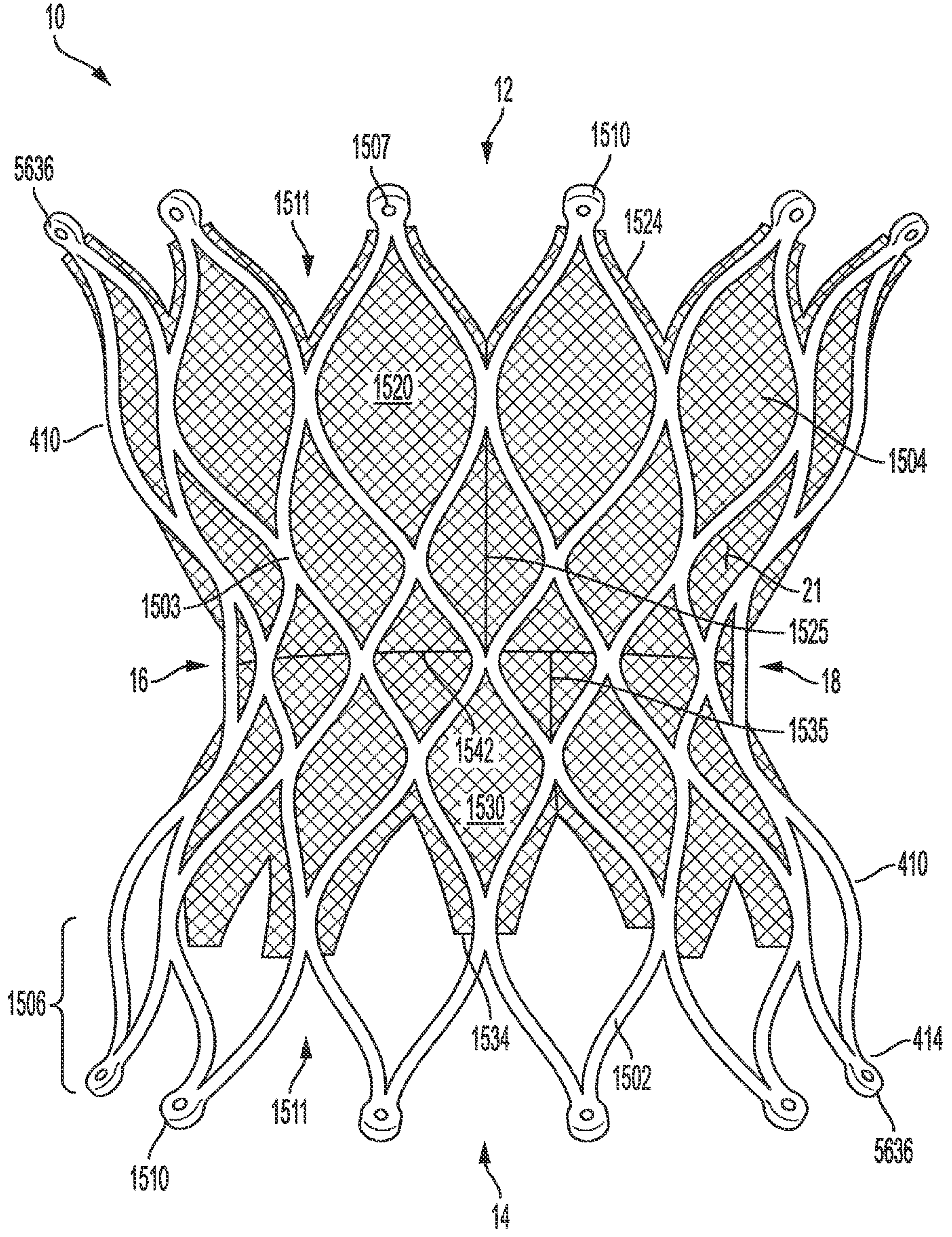
Figure 86A:
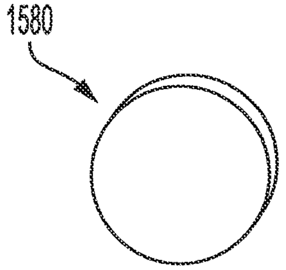
Figure 86B:
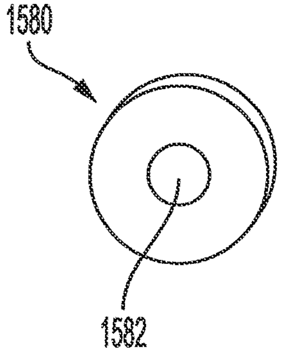
Figure 86C:
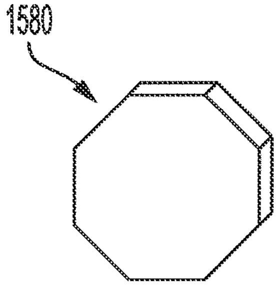
Figure 86D:
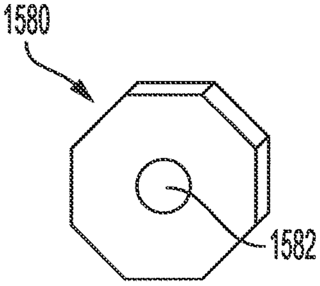
Figure 87A:
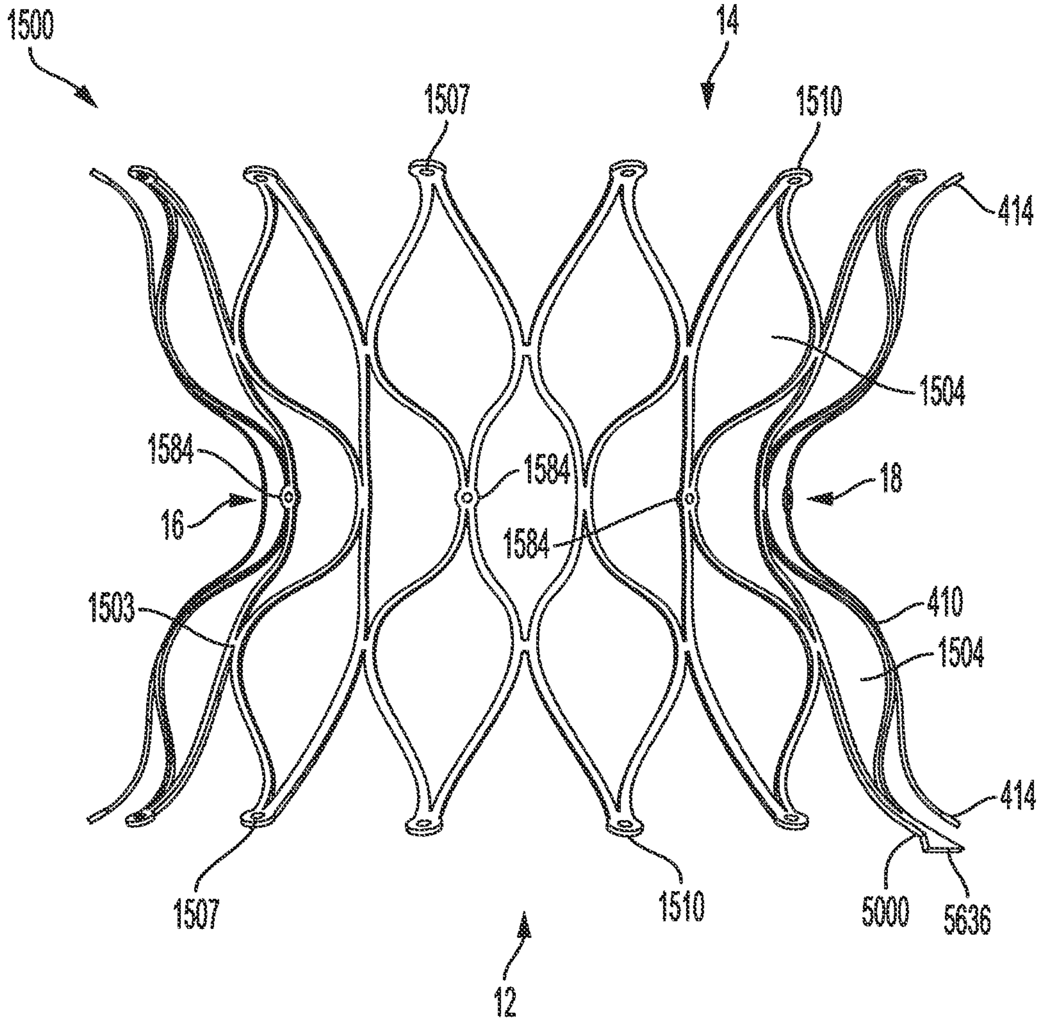
Figure 87B:
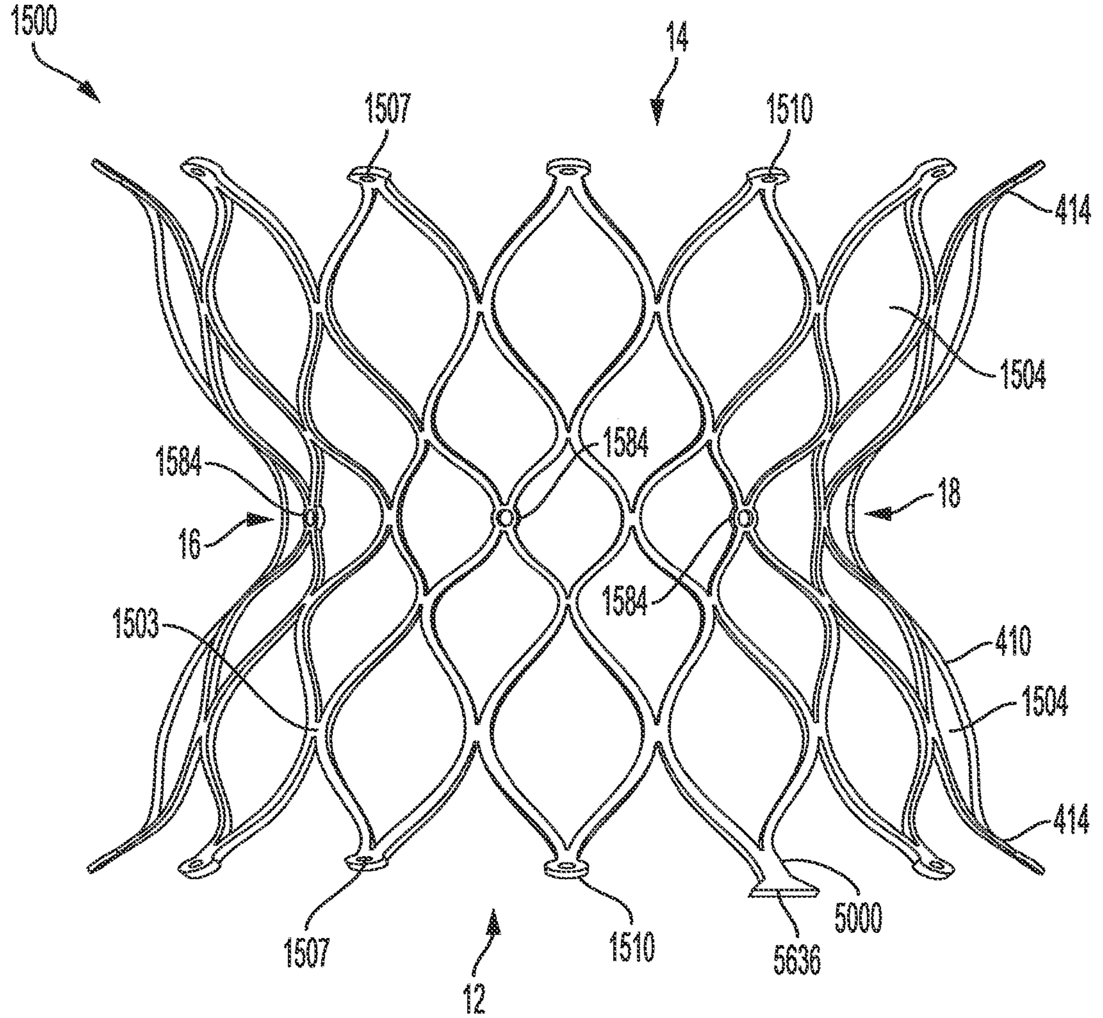
Figure 87C:
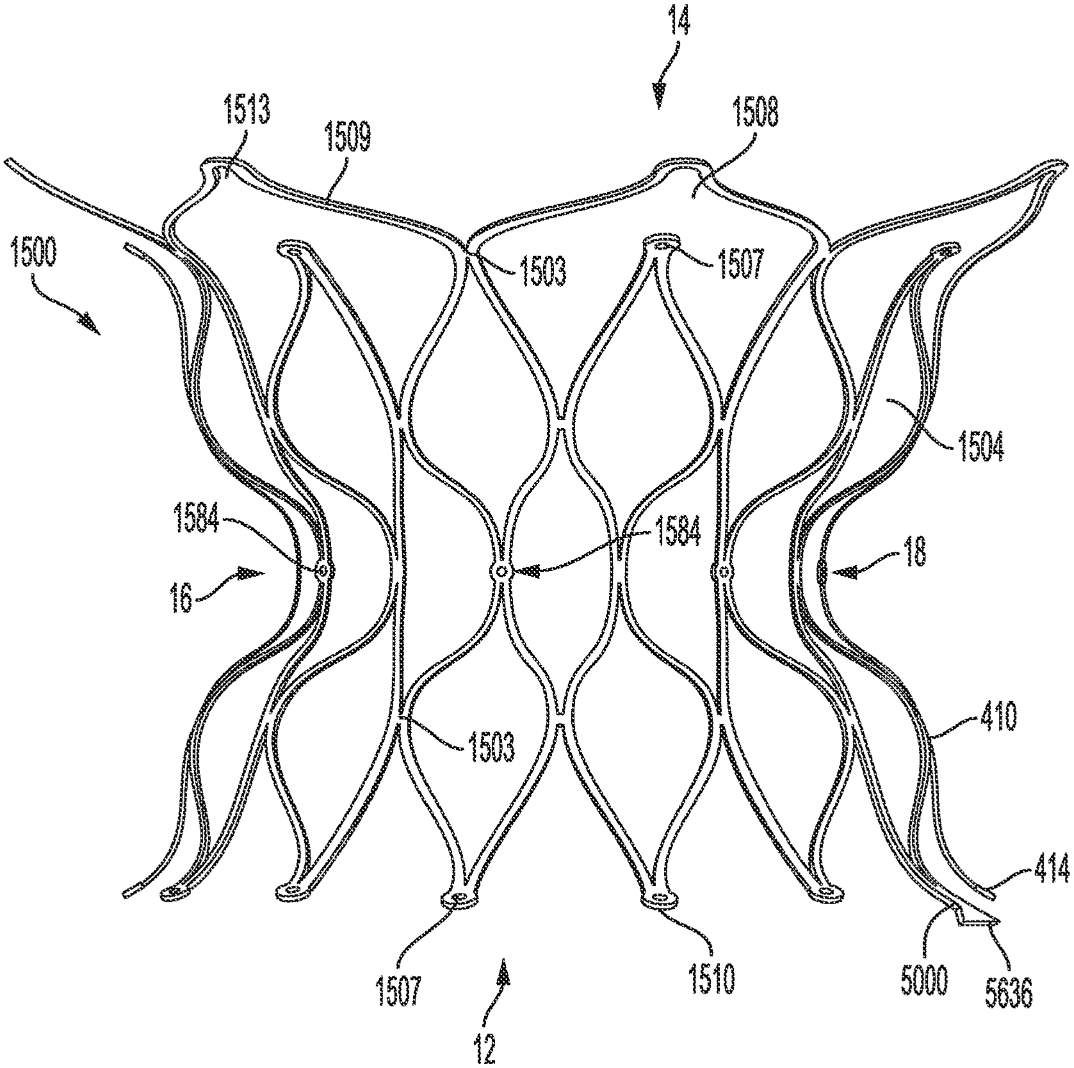
Figure 88:
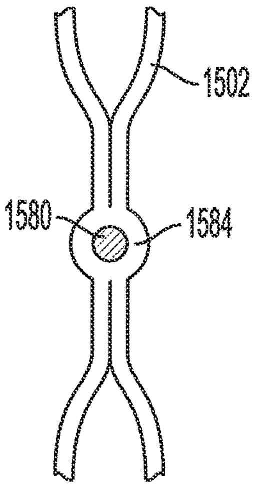
Figure 89A:
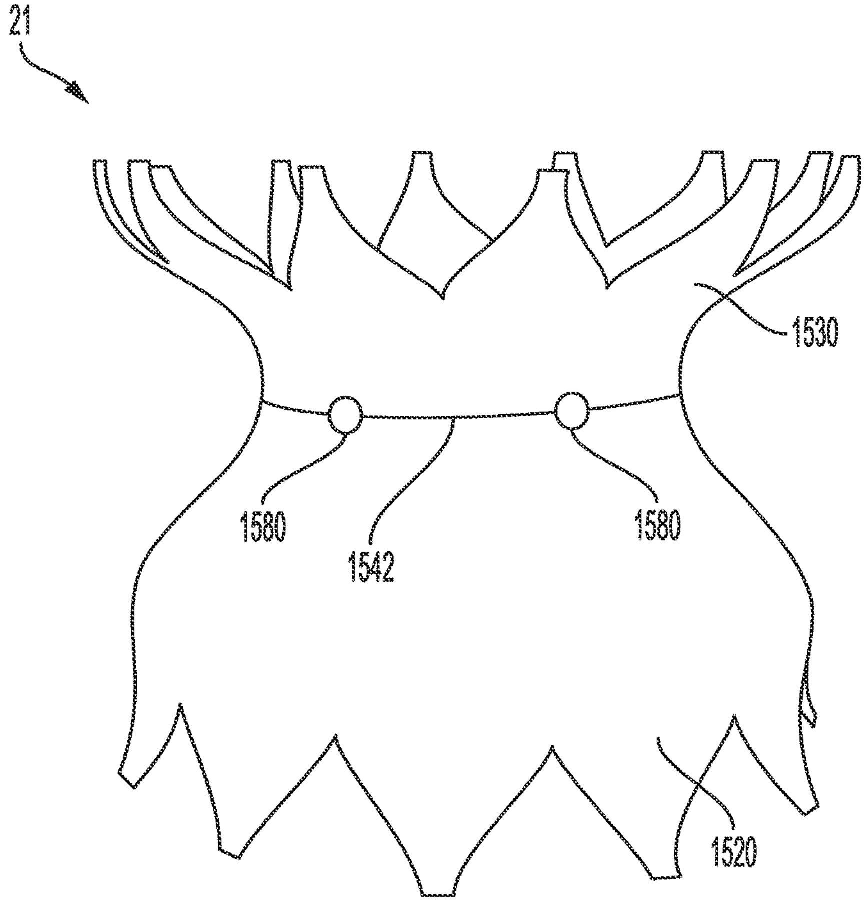
Figure 89B:
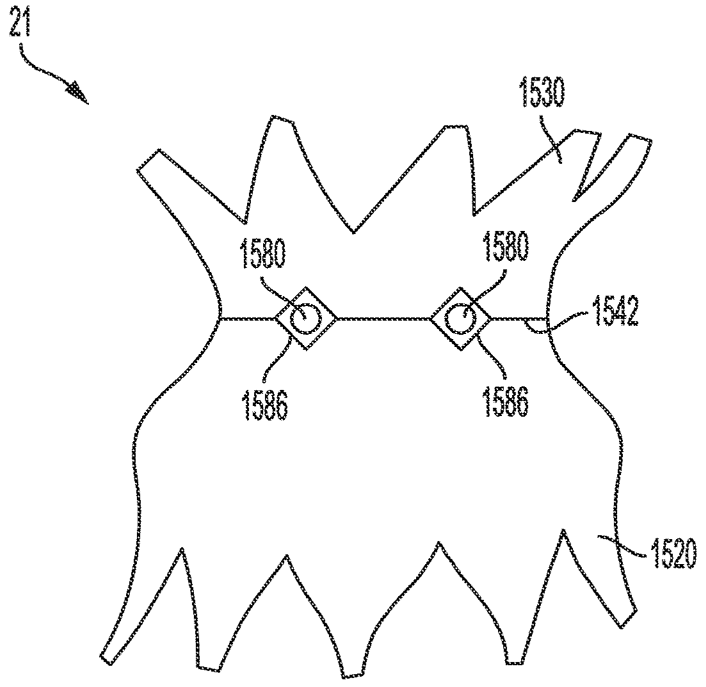
Figure 89C:
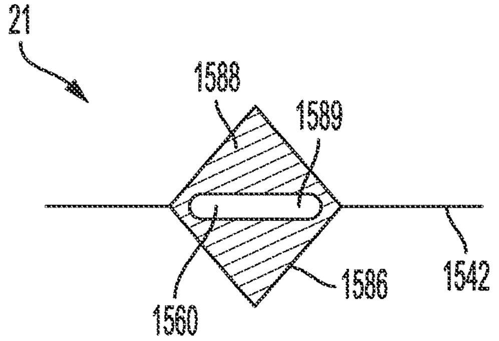
Figure 89D:
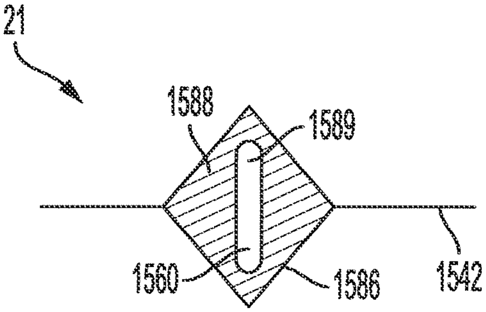
Figure 89E:
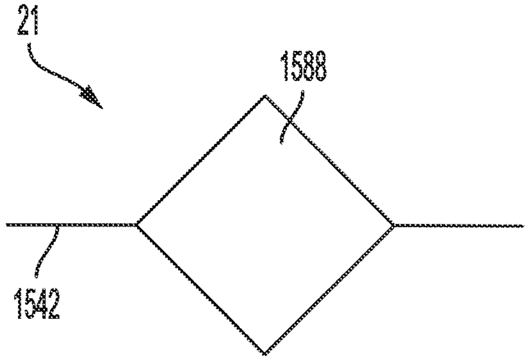
Figure 89F:
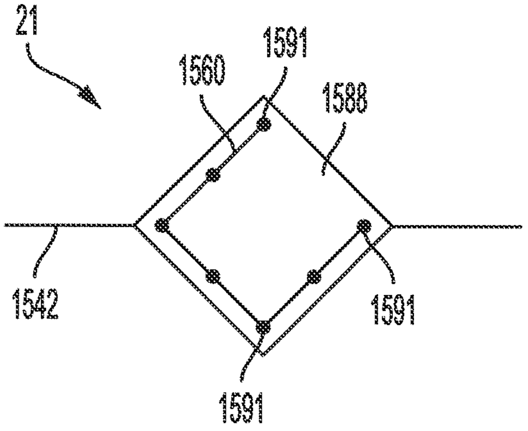
Figure 89G:
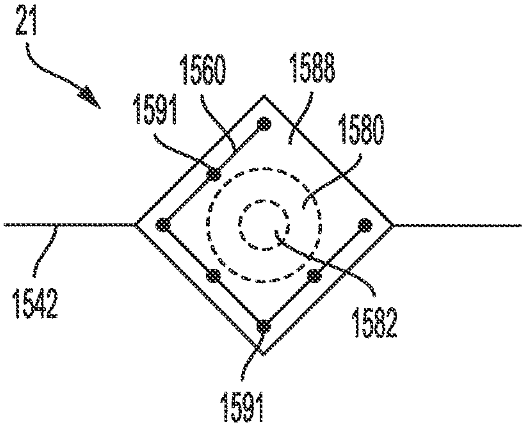
Figure 89H:
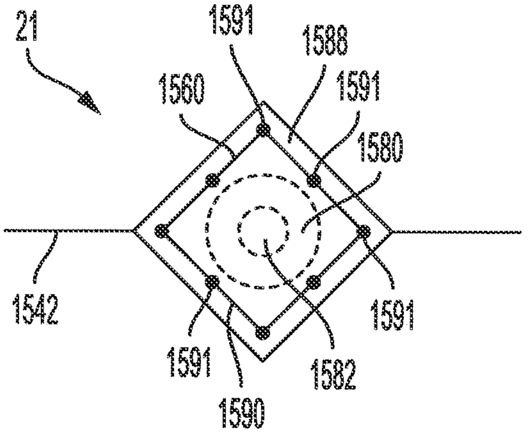
Figure 89I:
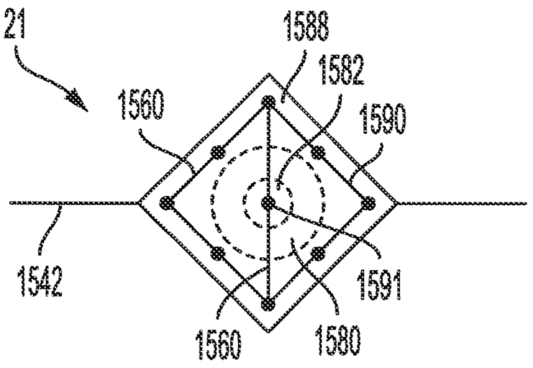
Figure 89J:
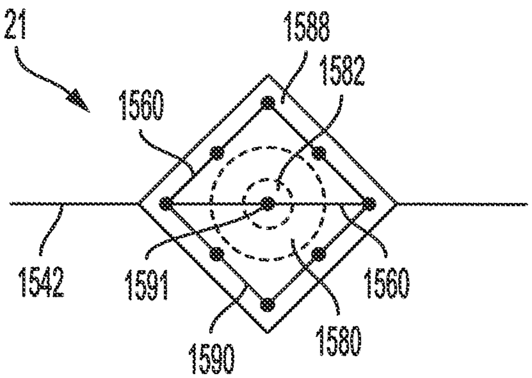
Figure 89K:
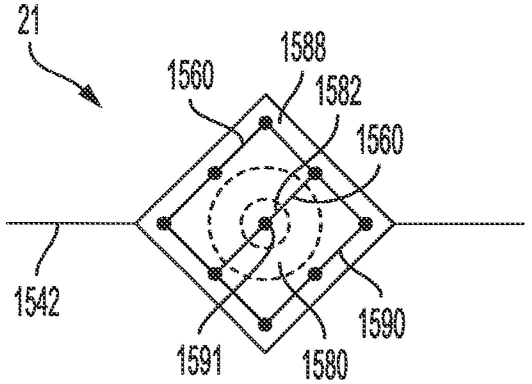
Figure 89L:
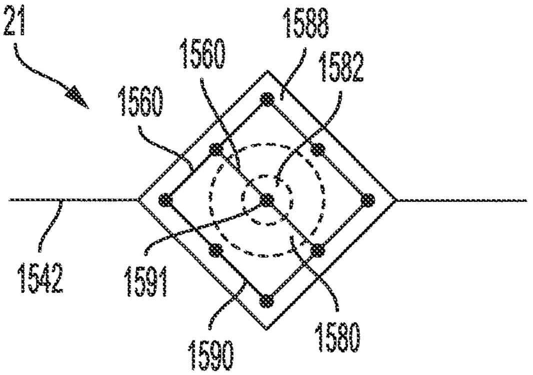
Figure 89M:
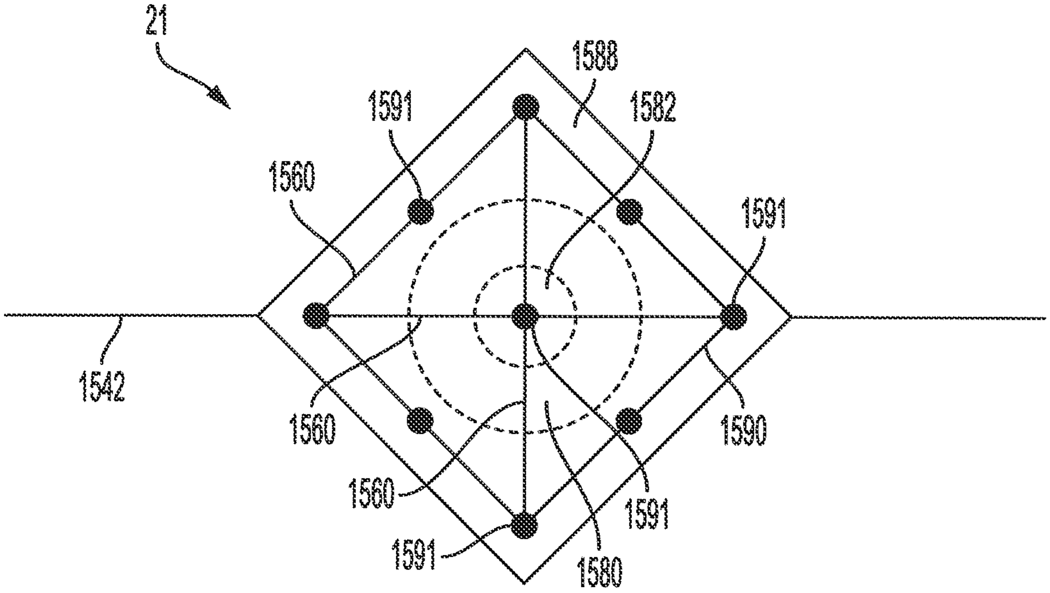
Figure 89N:
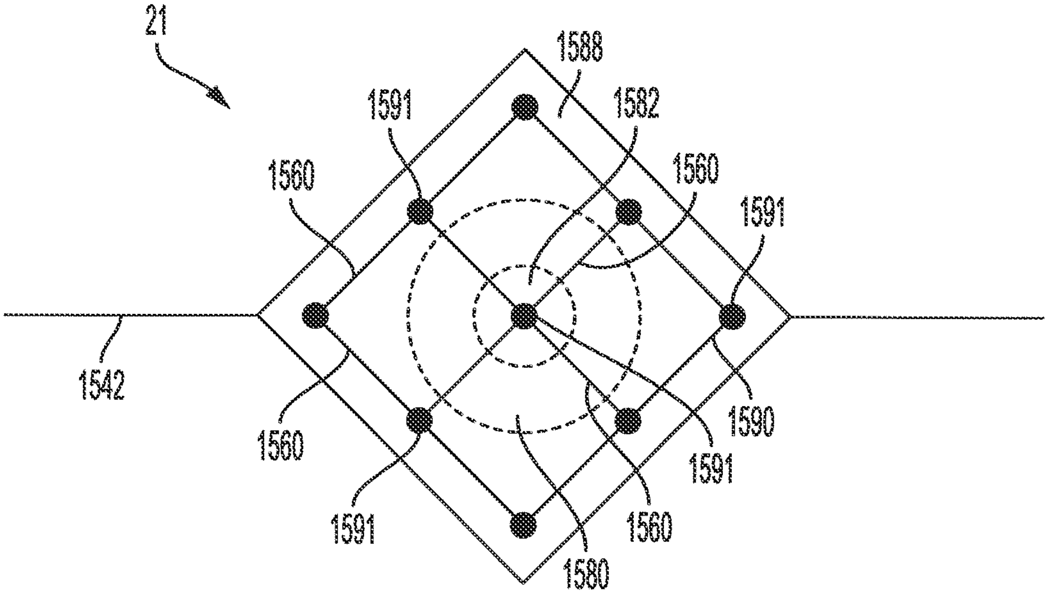
Figure 90A:
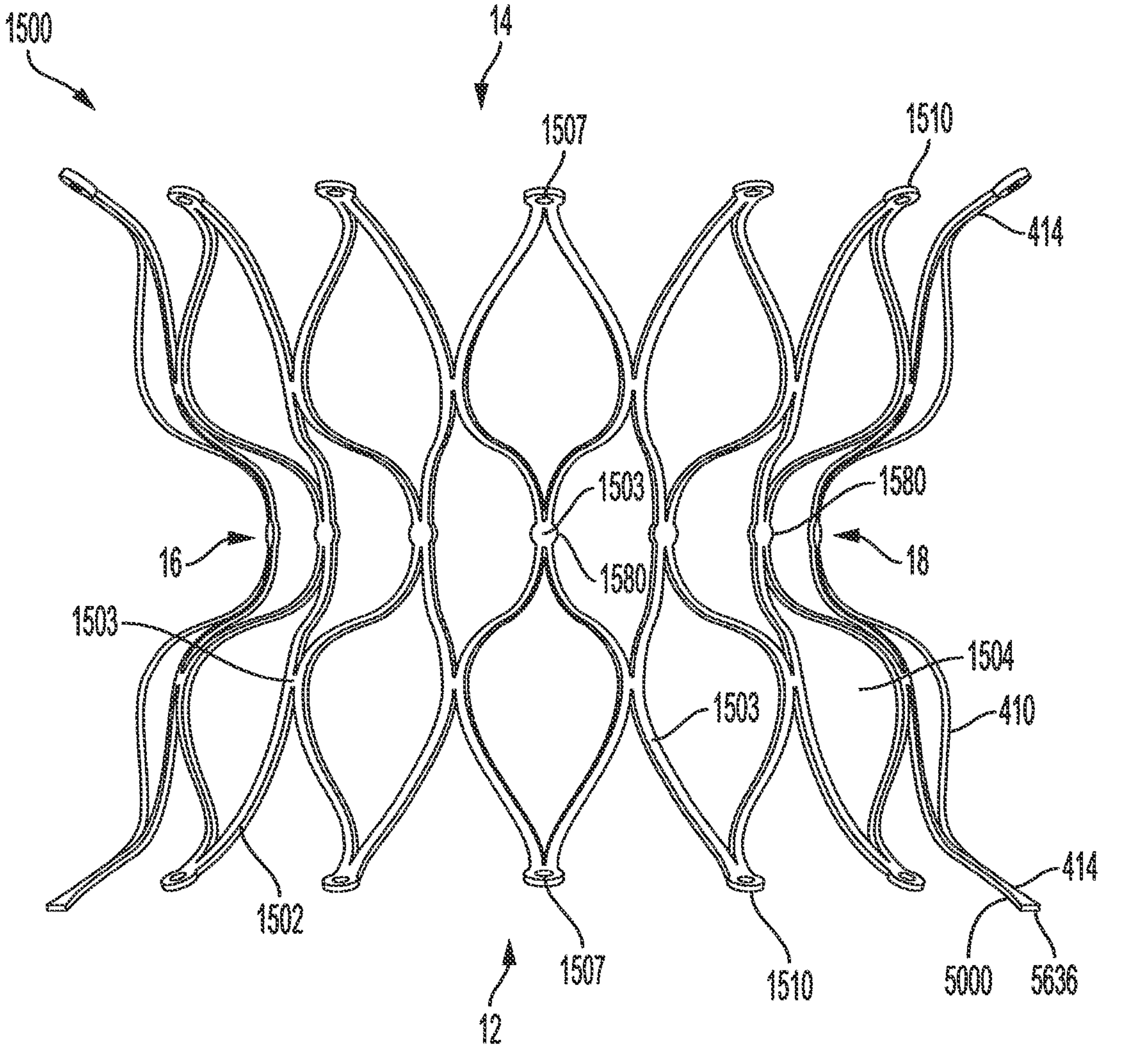
Figure 90B:
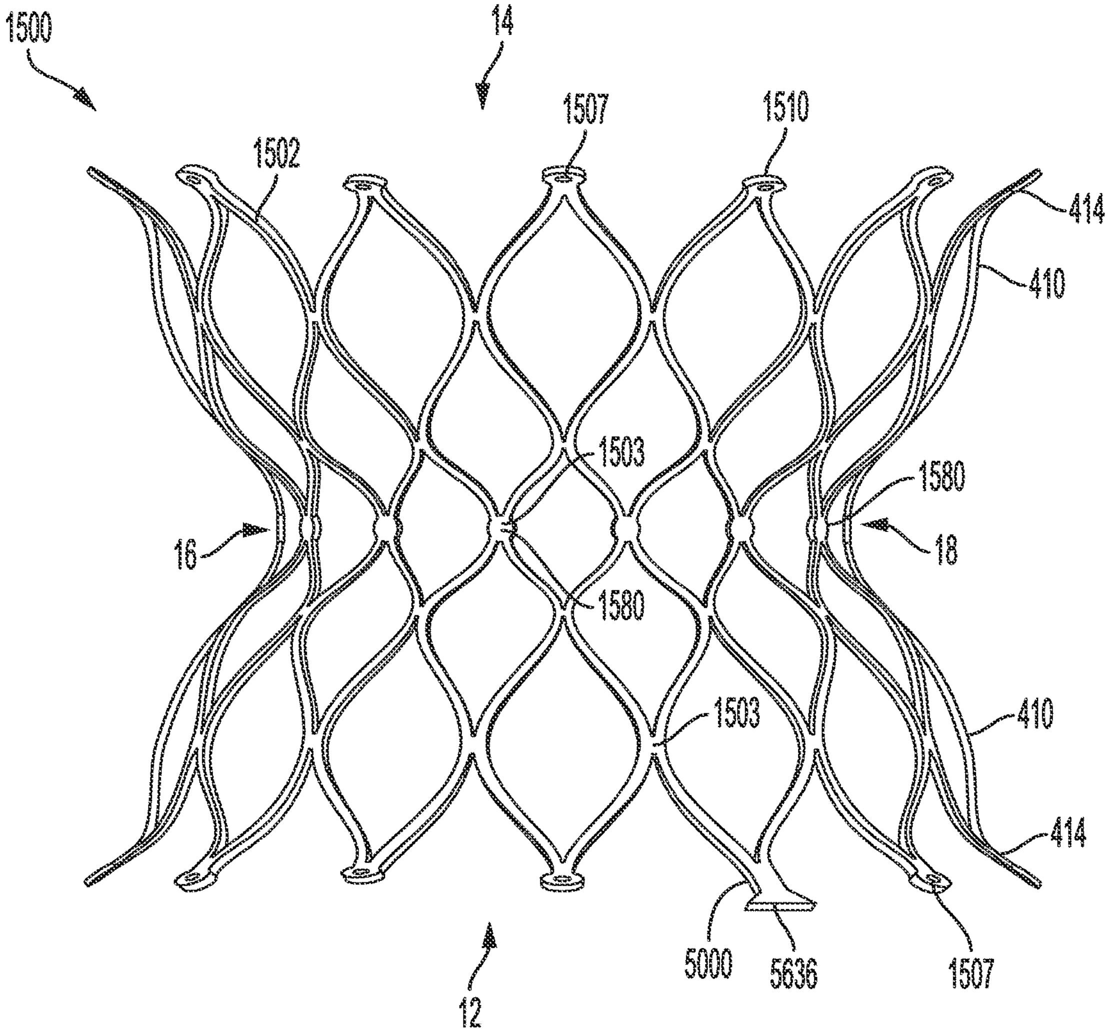
Figure 90C:
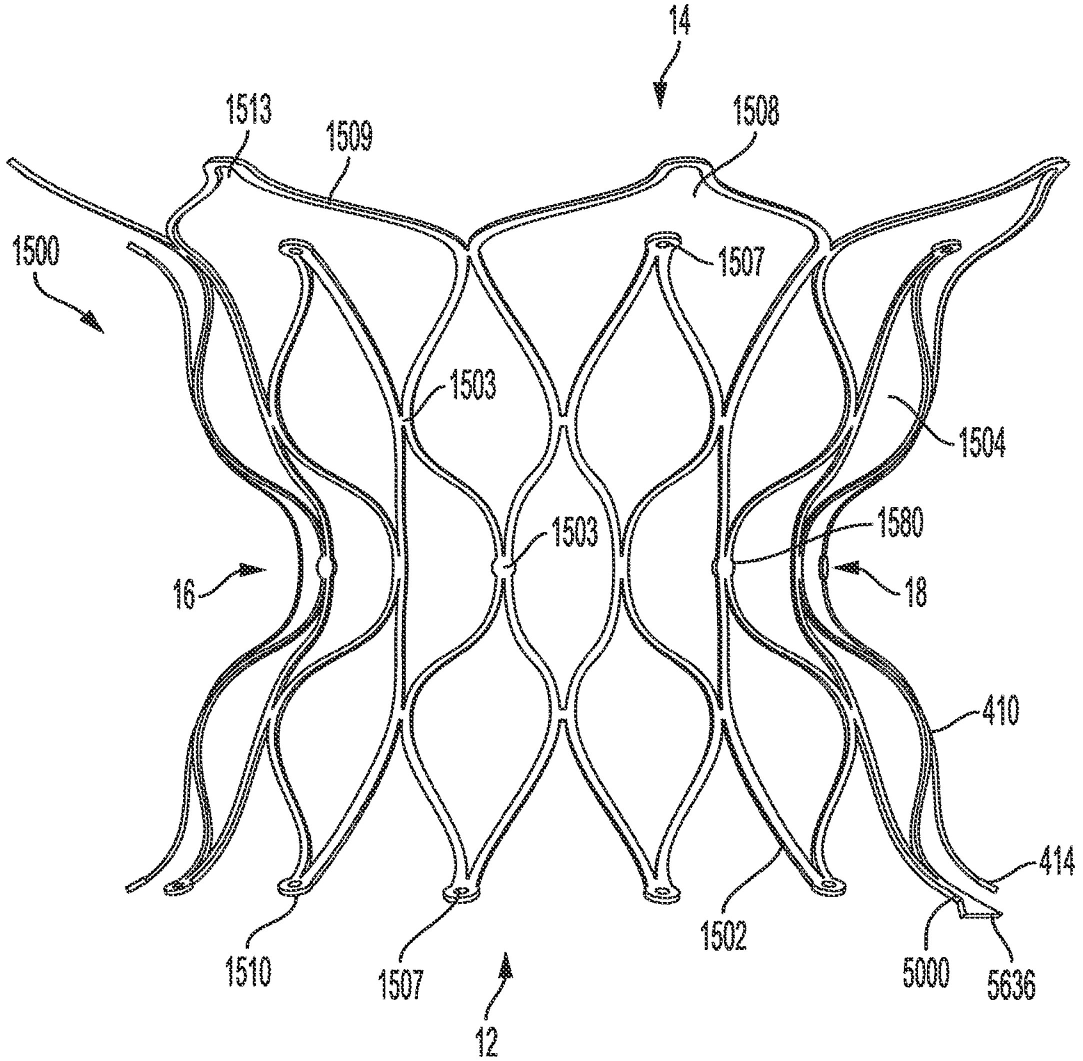
Figure 91:
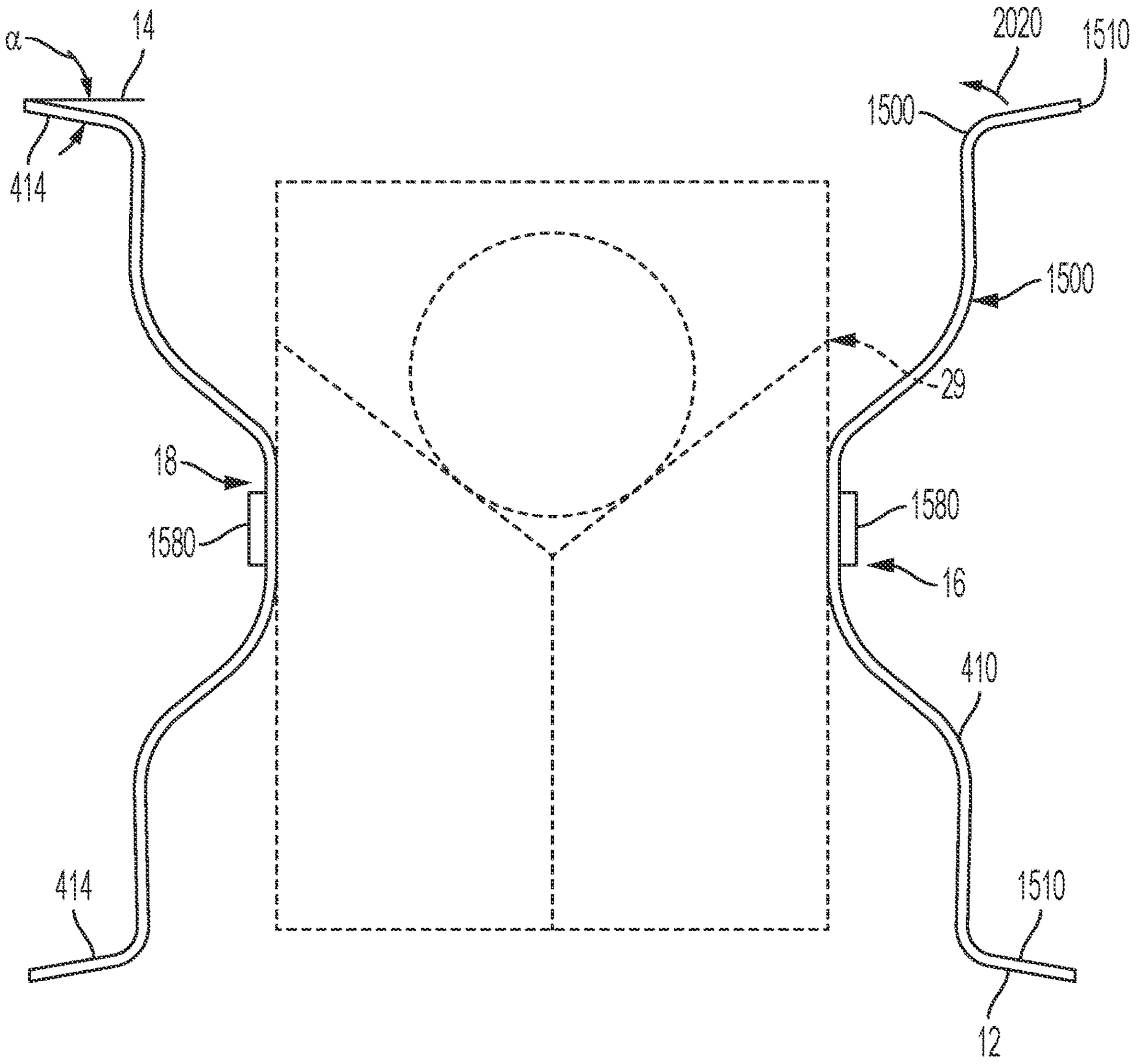
Figure 92A:
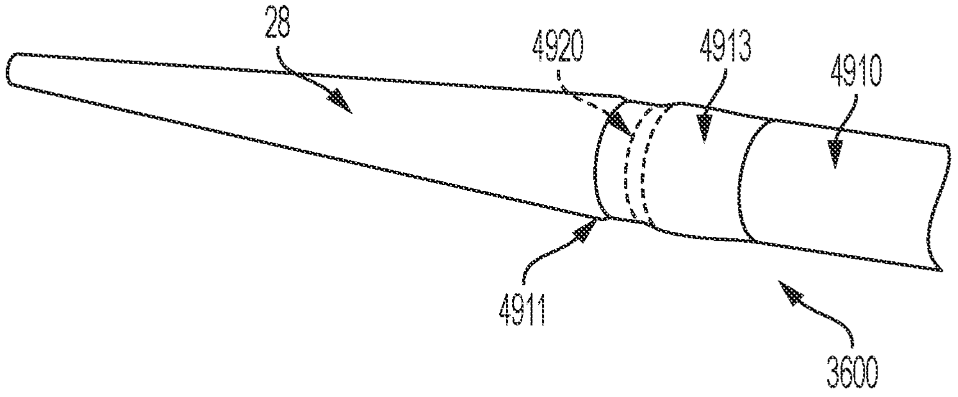
Figure 92B:
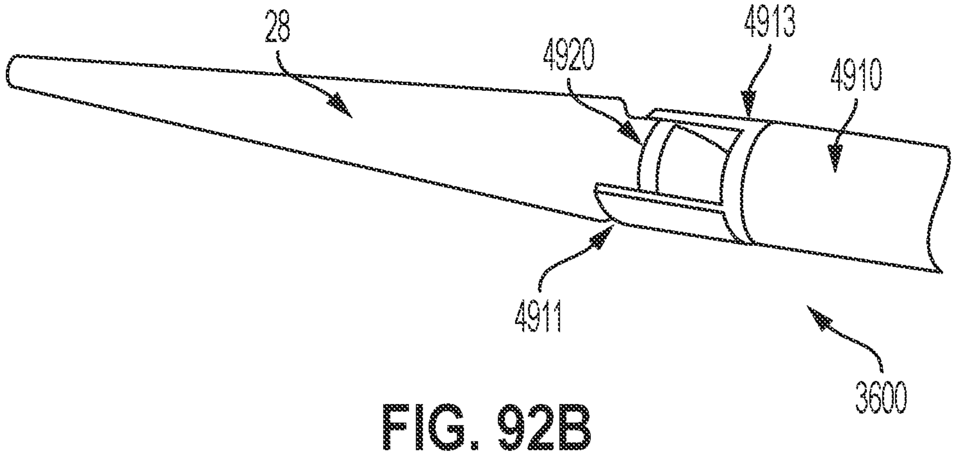
Figure 92C:
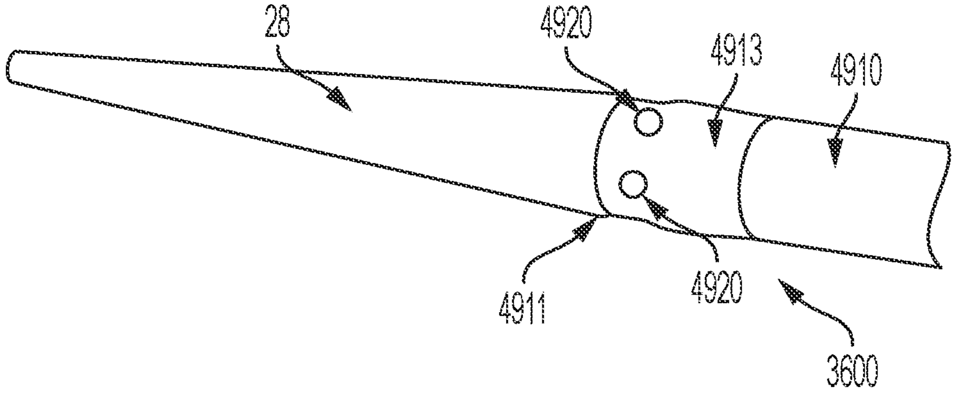
Figure 93A:
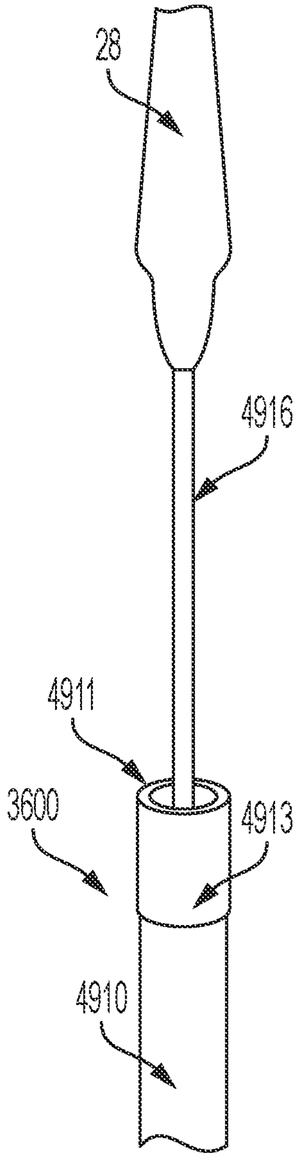
Figure 93B:
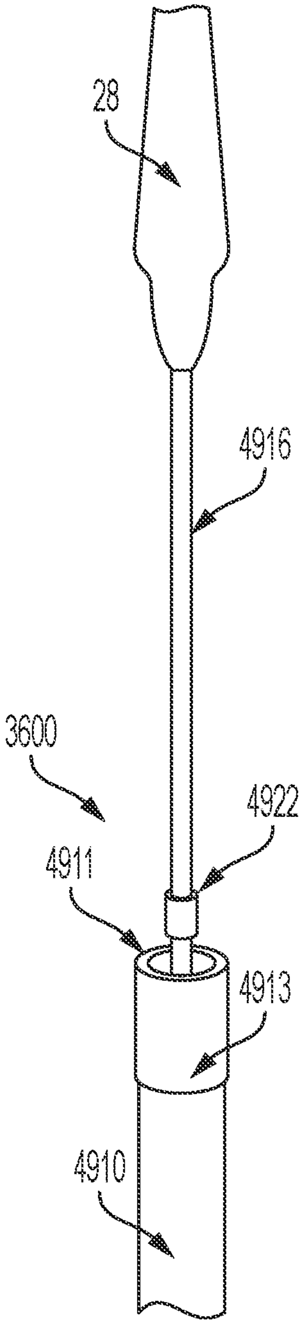
Figure 93C:
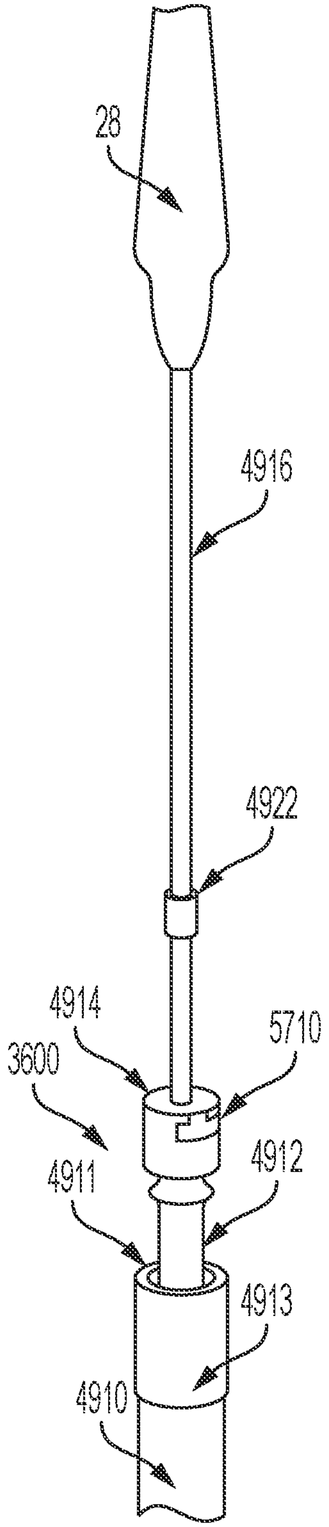
Figure 94:
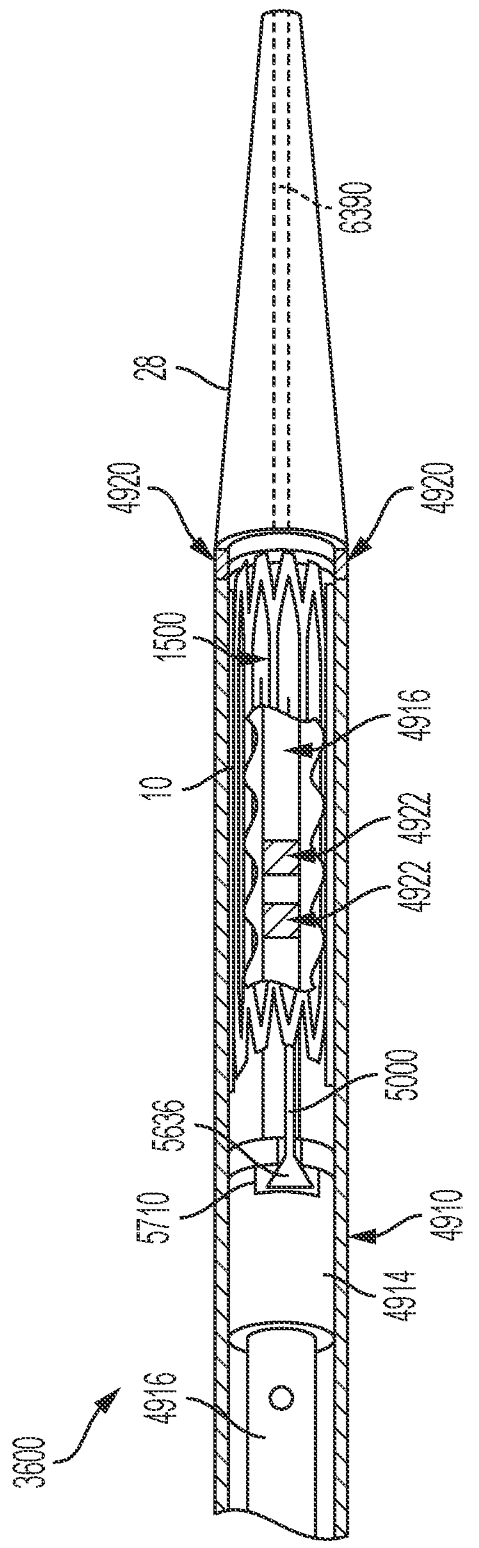
Figure 95A:
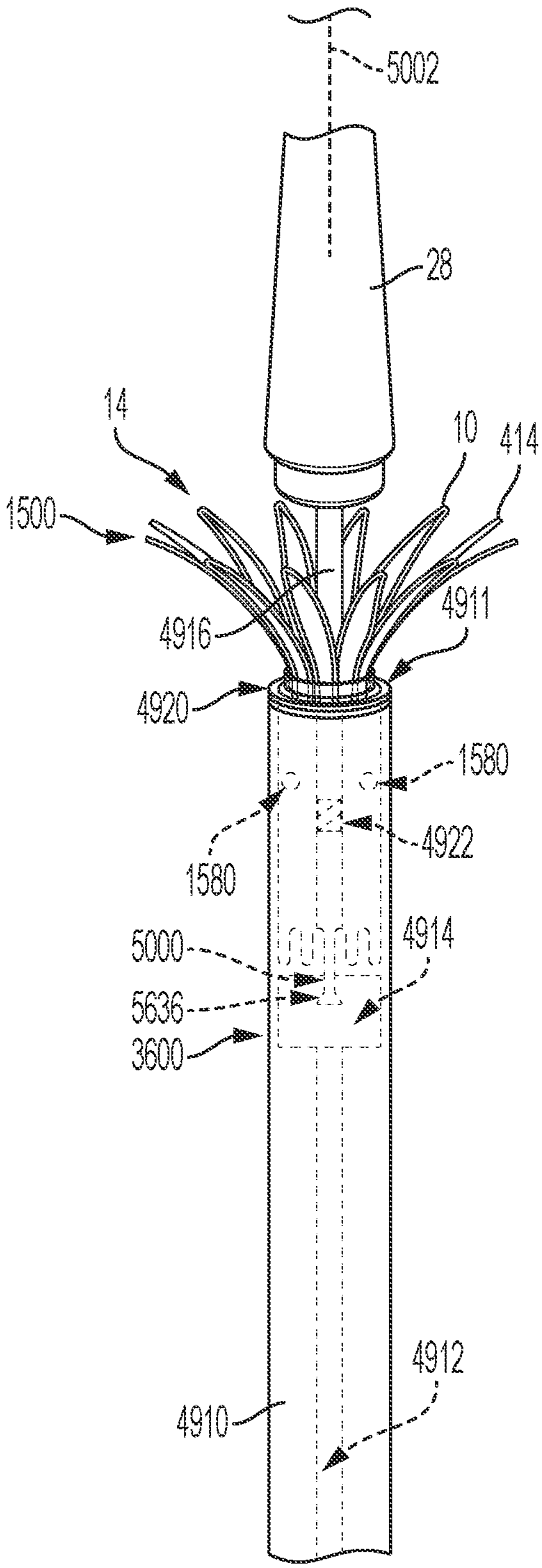
Figure 95B:
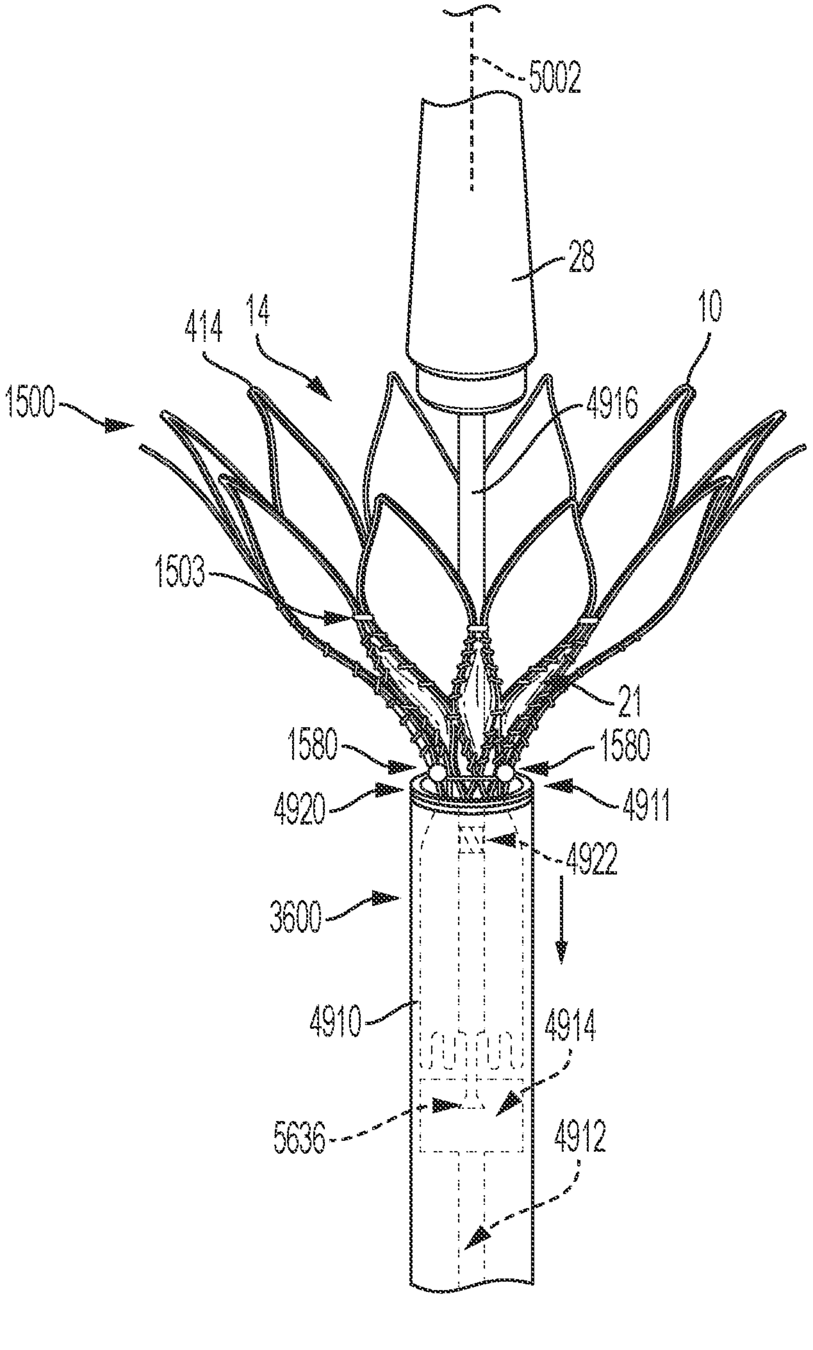
Figure 95C:
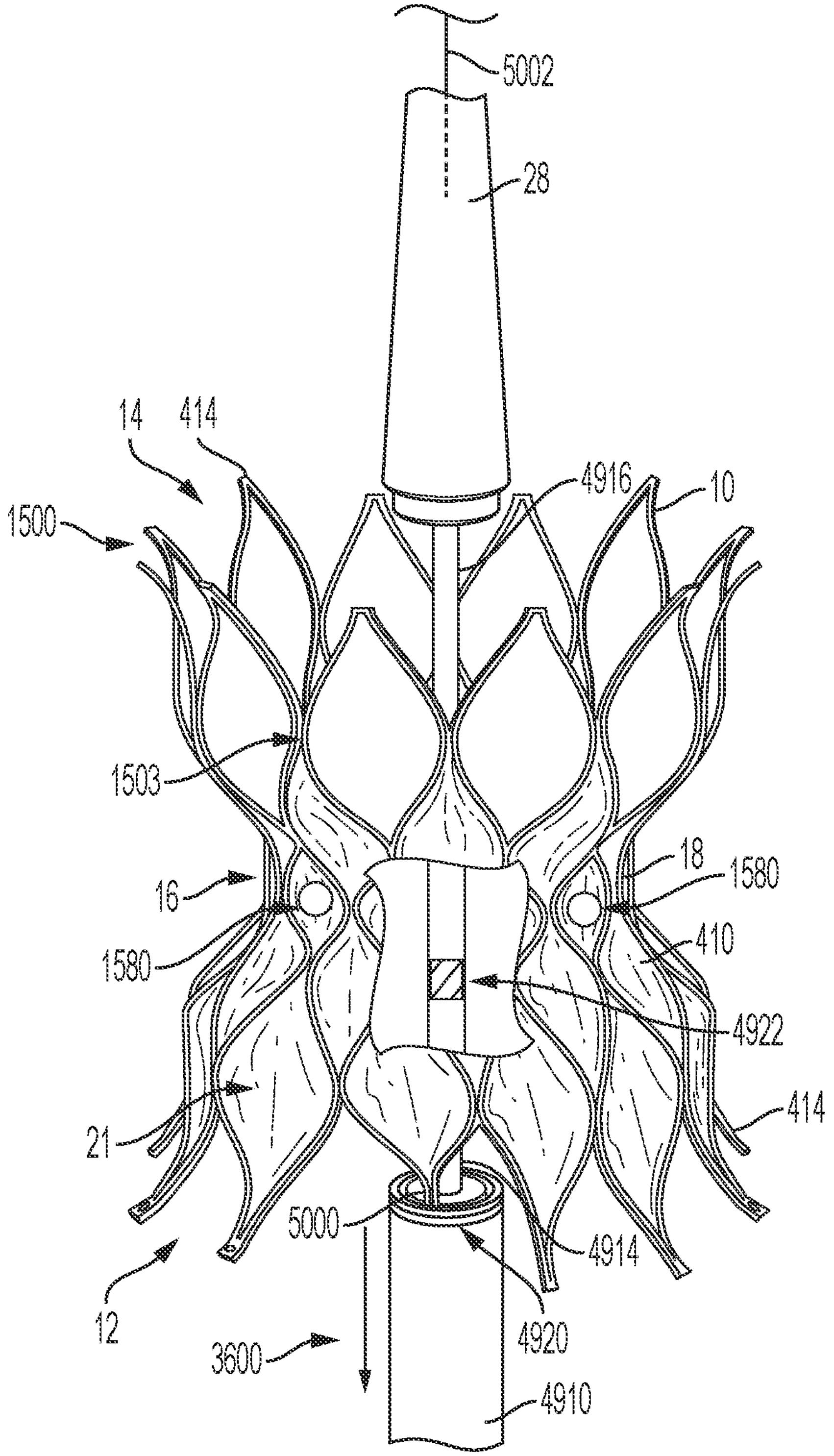
Figure 96A:
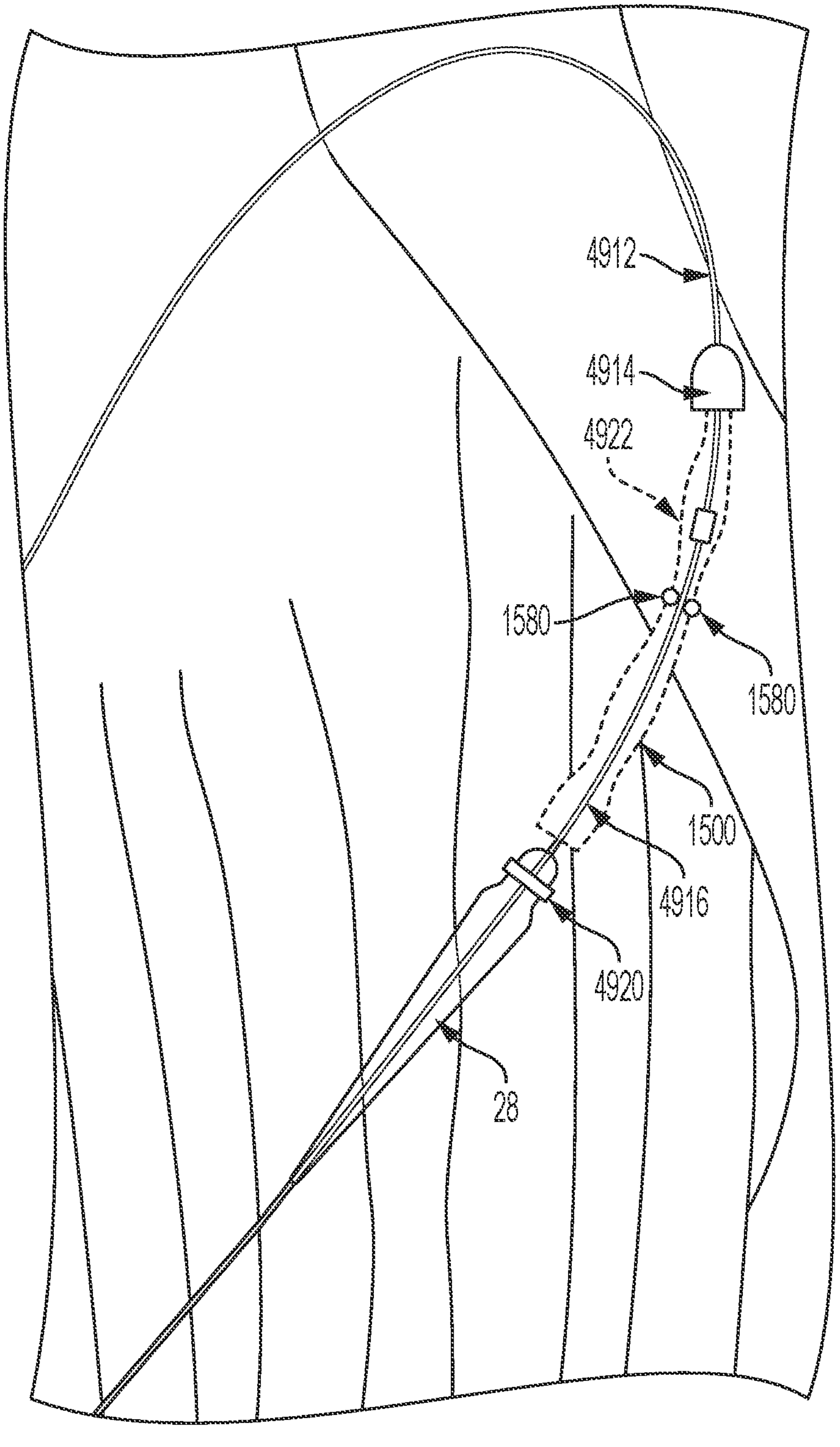
Figure 96B:
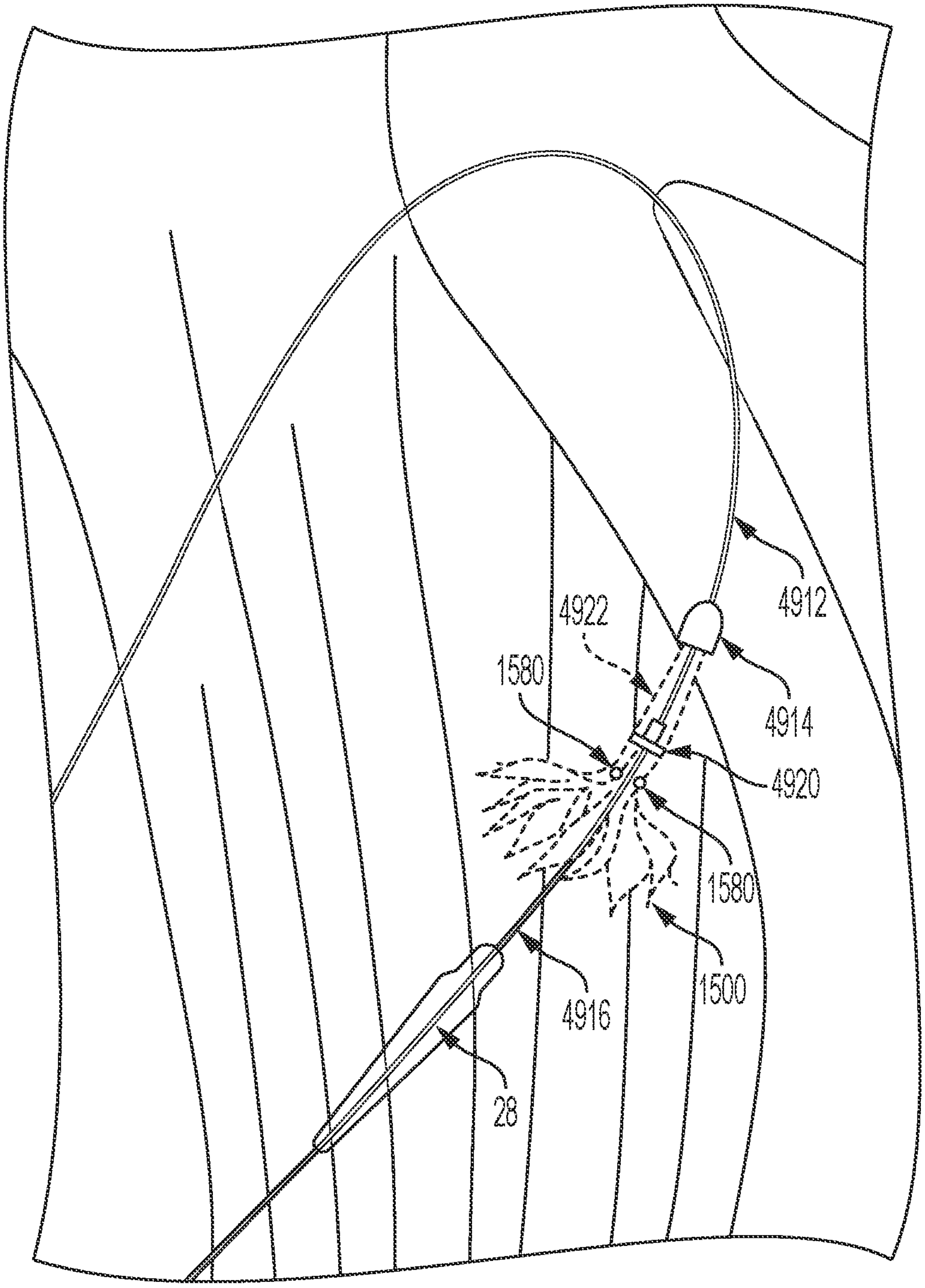

FIG. 80B is a side view of a frame of a docking station of another embodiment;

FIG. 80C is a side view of a frame of a docking station of another embodiment;

FIG. 81A is a side view of a docking station with a frame and an impermeable material according to one embodiment, FIG. 81B is a side view of a docking station with a frame and an impermeable material according to another embodiment, FIG. 81C is a side view of a docking station with a frame and an impermeable material according to another embodiment;

FIG. 81D is a side view of a docking station with a frame and an impermeable material according to another embodiment;

FIG. 82A is a top component of an impermeable material having a proximal portion and a distal portion;

FIG. 82B is a side perspective view of the assembled proximal portion of the impermeable material of FIG. 82A;

FIG. 82C is a top perspective view of the assembled proximal portion of the impermeable material of FIG. 82A;

FIG. 82D is a side perspective view of the assembled distal portion of the impermeable material of FIG. 82A;

FIGS. 82E-82I are side perspective views of the assembly of the impermeable material of FIG. 82A;

FIG. 82J is a top schematic view of the proximal portion and the distal portion of FIG. 82A outlined on a cloth according to one embodiment;

FIG. 82K is a top schematic view of the proximal portion and the distal portion of FIG. 82A outlined on a cloth according to another embodiment;

FIG. 83 is a side view of an impermeable material of one embodiment disposed within a frame of one embodiment;

FIGS. 84A-84I, illustrate one method of affixing the impermeable material and frame of FIG. 83 to one another;

FIGS. 85A-85E, illustrate another method of affixing the impermeable material and frame of FIG. 83 to one another;

FIG. 86A is a side perspective view of a radiopaque marker according to one embodiment;

FIG. 86B is a side perspective view of a radiopaque marker according to another embodiment;

FIG. 86C is a side perspective view of a radiopaque marker according to another embodiment;

FIG. 86D is a side perspective view of a radiopaque marker according to another embodiment;

FIG. 87A is a side perspective view of a frame with marker settings according to one embodiment;

FIG. 87B is a side perspective view of a frame with marker settings according to another embodiment;

FIG. 87C is a side perspective view of a frame with marker settings according to another embodiment;

FIG. 88 is a schematic illustration of a radiopaque marker disposed in a marker setting;

FIG. 89A is a perspective view of an impermeable material with radiopaque markers according to one embodiment;

FIG. 89B is a side view of an impermeable material with radiopaque markers disposed in pockets;

FIG. 89C is a schematic illustration of a pocket covering disposed over a pocket of an impermeable material according to one embodiment;

FIG. 89D is a schematic illustration of a pocket covering disposed over a pocket of an impermeable material according to another embodiment;

FIGS. 89E-89H illustrate a method of affixing a pocket and a radiopaque marker to an impermeable member;

FIG. 89I illustrates an additional step in the method of FIGS. 89E-89H according to one embodiment;

FIG. 89J illustrates an additional step in the method of FIGS. 89E-89H according to another embodiment;

FIG. 89K illustrates an additional step in the method of FIGS. 89E-89H according to another embodiment;

FIG. 89L illustrates an additional step in the method of FIGS. 89E-89H according to another embodiment;

FIG. 89M illustrates an additional step in the method of FIGS. 89E-89H according to another embodiment;

FIG. 89N illustrates an additional step in the method of FIGS. 89E-89H according to another embodiment;

FIG. 90A is a side view of a frame with radiopaque markers according to one embodiment;

FIG. 90B is a side view of a frame with radiopaque markers according to another embodiment;

FIG. 90C is a side view of a frame with radiopaque markers according to another embodiment;

FIG. 91 is a schematic illustration of an expandable transcatheter heart valve positioned in a frame with radiopaque markers;

FIG. 92A is a perspective view of a nosecone and outer tube with a radiopaque marker according to one embodiment;

FIG. 92B is a perspective partial cutaway view of the nosecone and outer tube of FIG. 92A;

FIG. 92C is a perspective nosecone and outer tube with a plurality of radiopaque markers according to another embodiment;

FIGS. 93A-93C illustrate deployment of a delivery catheter assembly without a docking station frame;

FIG. 94 is a sectional partial cutaway view of an exemplary embodiment of a catheter with radiopaque markers and a docking station crimped and loaded in the catheter;

FIGS. 95A-95C illustrate deployment of a docking station with radiopaque markers from a catheter with radiopaque markers; and FIGS. 96A and 96B illustrate deployment of a docking station with radiopaque markers from a catheter with radiopaque markers as viewed under fluoroscopy.

DETAILED DESCRIPTION

The following description refers to the accompanying drawings, which illustrate specific embodiments of the invention. Other embodiments having different structures and operation do not depart from the scope of the present invention. Exemplary embodiments of the present disclosure are directed to devices and methods for providing a docking station or landing zone for a transcatheter heart valve ("THY"), e.g., THV 29. In some exemplary embodiments, docking stations for THVs are illustrated as being used within the pulmonary artery, although the docking stations (e.g., docking station 10) can be used in other areas of the anatomy, heart, or vasculature, such as the superior vena cava or the inferior vena cava. The docking stations described herein can be configured to compensate for the deployed THV being smaller than the space (e.g., anatomy/vasculature/etc.) in which it is to be placed.

Prosthetics, including docking stations, may be utilized in a variety of subjects and procedures. Subjects include (but are not limited to) medical patients, veterinary patients, animal models, cadavers, and simulators of the cardiac and vasculature system (e.g., anthropomorphic phantoms and explant tissue). Procedures include (but are not limited to) medical and training procedures.

It should be noted that various embodiments of docking stations and systems for delivery and implant are disclosed herein, and any combination of these options can be made unless specifically excluded. For example, any of the docking stations devices disclosed, can be used with any type of valve, and/or any delivery system, even if a specific combination is not explicitly described. Likewise, the different constructions of docking stations and valves can be mixed and matched, such as by combining any docking station type/feature, valve type/feature, tissue cover, etc., even if not explicitly disclosed. In short, individual components of the disclosed systems can be combined unless mutually exclusive or otherwise physically impossible.

For the sake of uniformity, in these Figures and others in the application the docking stations are depicted such that the pulmonary bifurcation end is up, while the ventricular end is down. These directions may also be referred to as "distal" as a synonym for up or the pulmonary bifurcation end, and "proximal" as a synonym for down or the ventricular end, which are terms relative to the physician's perspective.

Figure 1A:
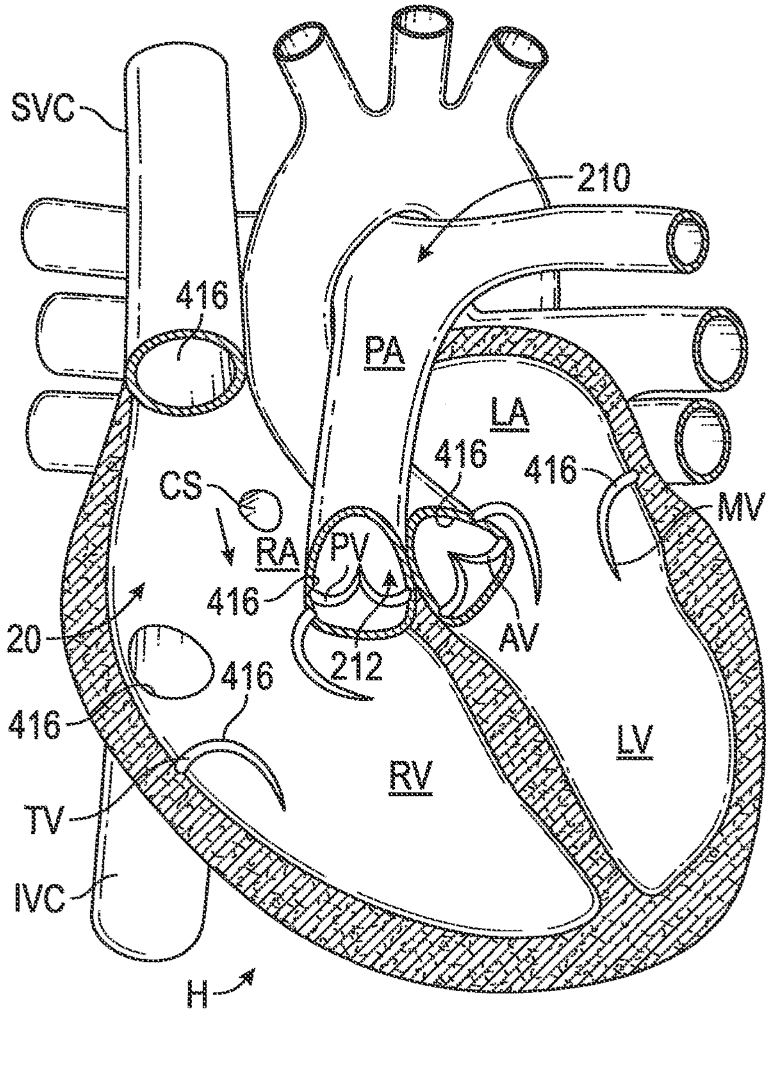
FIG. 1A is a cutaway view of the human heart in a diastolic phase.
Figure 1B:
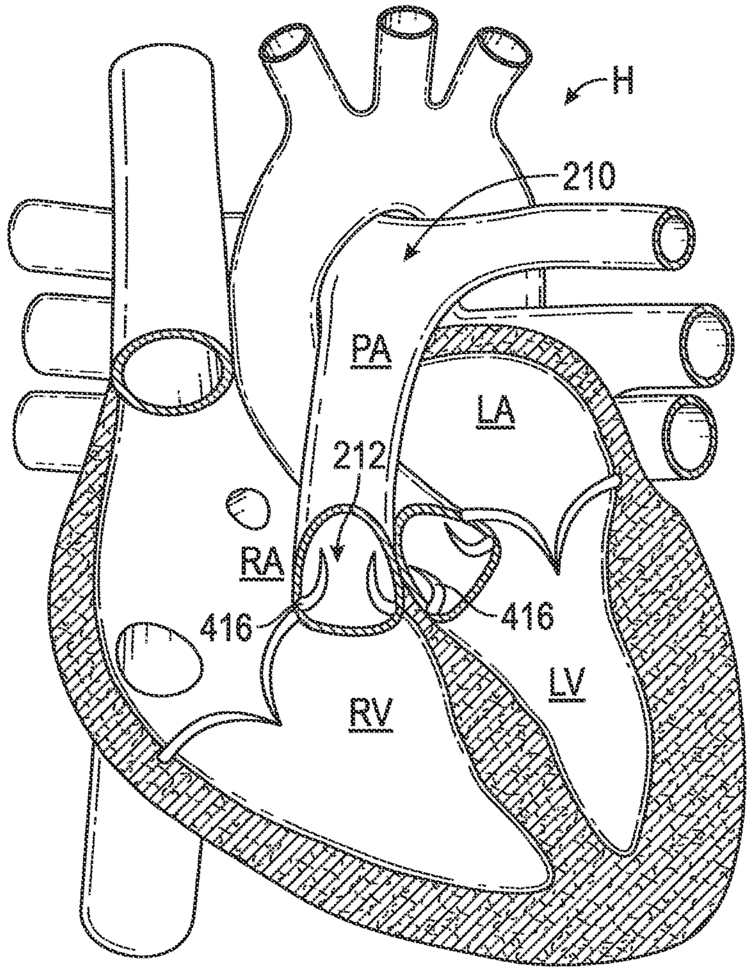
FIG. 1B is a cutaway view of the human heart in a systolic phase.
Figure 2A:
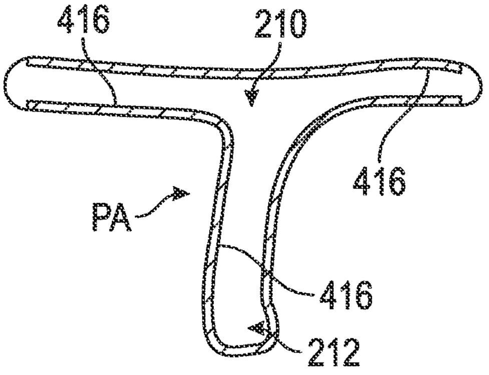
FIGS. 2A-2E are sectional views of pulmonary arteries illustrating that pulmonary arteries can have a variety of different shapes and sizes.
Figure 2B:
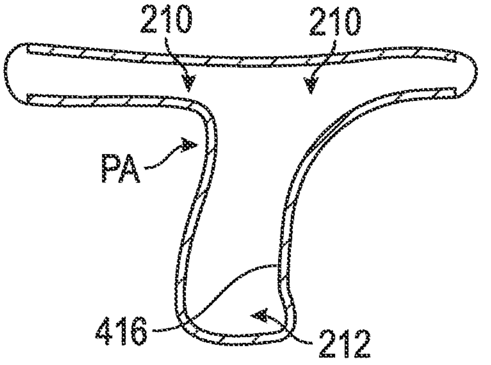
Figure 2C:
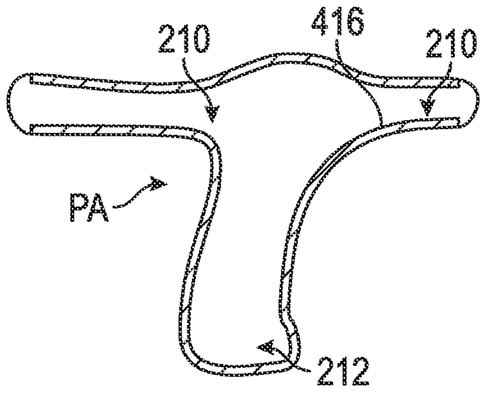
Figure 2D:
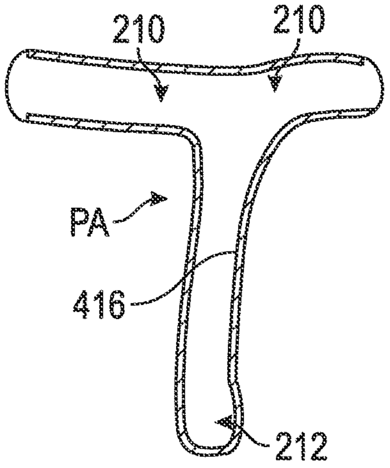
Figure 2E:
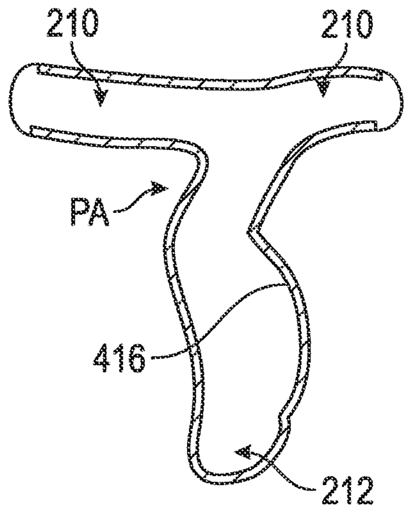
Figure 3A:
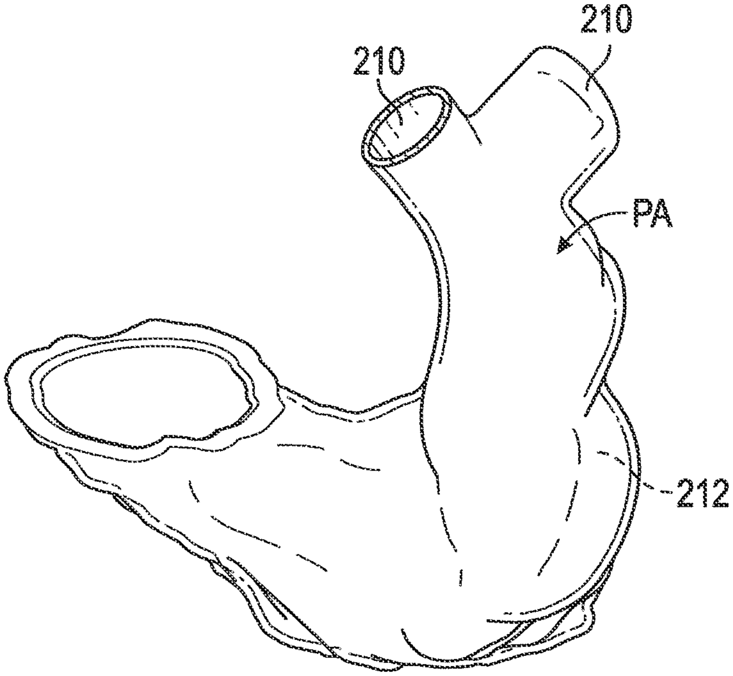
FIGS. 3A-3D are perspective views of pulmonary arteries illustrating that pulmonary arteries can have a variety of different shapes and sizes.
Figure 3B:
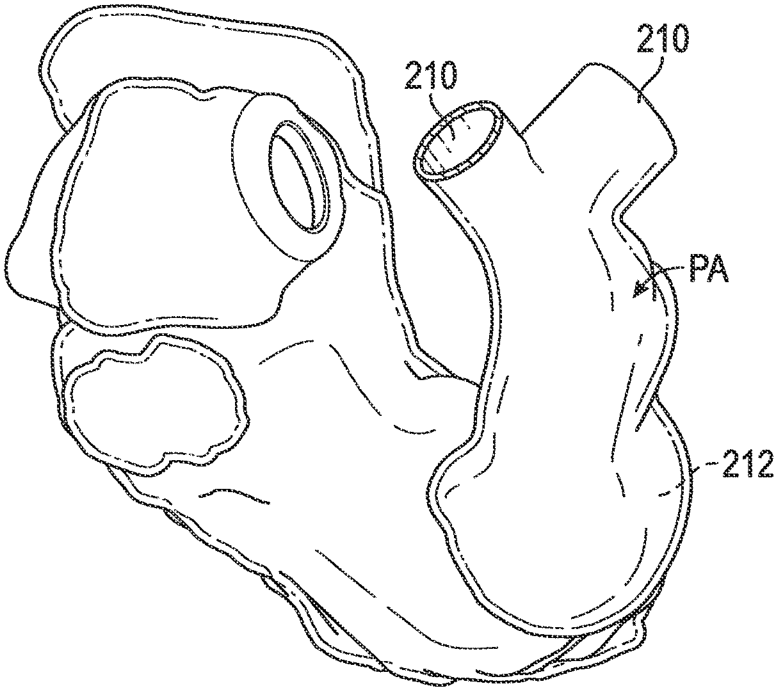
Figure 3C:
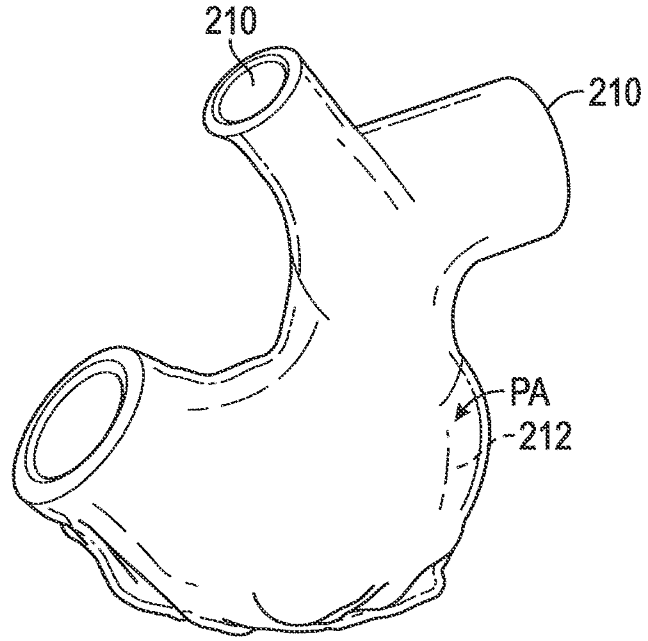
Figure 3D:
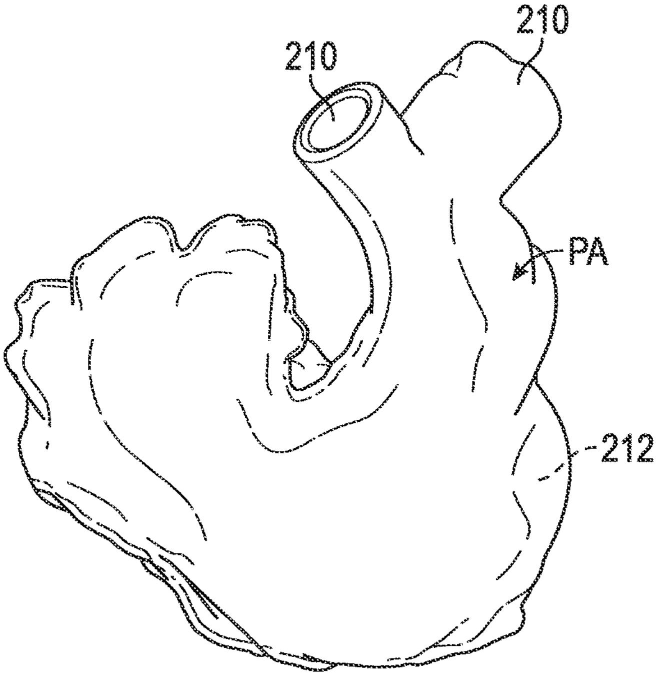

FIGS. 1A and 1B are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery PA. Each of these valves has flexible leaflets extending inward across the respective orifices that come together or "coapt" in the flowstream to form the one-way, fluid-occluding surfaces. The docking stations and valves of the present application are described primarily with respect to the pulmonary valve. Therefore, anatomical structures of the right atrium RA and right ventricle RV will be explained in greater detail. It should be understood that the devices described herein can also be used in other areas, e.g., in the inferior vena cava and/or the superior vena cava as treatment for a regurgitant or otherwise defective tricuspid valve, in the aorta (e.g., an enlarged aorta) as treatment for a defective aortic valve, in other areas of the heart or vasculature, in grafts, etc.

The right atrium RA receives deoxygenated blood from the venous system through the superior vena cava SVC and the inferior vena cava IVC, the former entering the right atrium from above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA enters the tricuspid valve TV by expansion of the right ventricle RV. In the systolic phase, or systole, seen in FIG. 1B, the right ventricle RV contracts to force the venous blood through the pulmonary valve PV and pulmonary artery into the lungs. In one exemplary embodiment, the devices described by the present application are used to replace or supplement the function of a defective pulmonary valve. During systole, the leaflets of the tricuspid valve TV close to prevent the venous blood from regurgitating back into the right atrium RA.

Referring to FIGS. 2A-2E and 3A-3D, the shown, non-exhaustive examples illustrate that the pulmonary artery can have a wide variety of different shapes and sizes. For example, as shown in the sectional views of FIGS. 2A-2E and the perspective views of FIGS. 3A-3D, the length L, diameter, D, and curvature or contour may vary greatly between pulmonary arteries of different patients. Further, the diameter D may vary significantly along the length L of an individual pulmonary artery. These differences can be even more significant in pulmonary arteries that suffer from certain conditions and/or have been compromised by previous surgery. For example, the treatment of Tetralogy of Fallot (TOF) or Transposition of the Great Arteries (TGA) often results in larger and more irregularly shaped pulmonary arteries.

Tetralogy of Fallot (TOF) is a cardiac anomaly that refers to a combination of four related heart defects that commonly occur together. The four defects are ventricular septal defect (VSD), overriding aorta (the aortic valve is enlarged and appears to arise from both the left and right ventricles instead of the left ventricle as in normal hearts), pulmonary stenosis (narrowing of the pulmonary valve and outflow tract or area below the valve that creates an obstruction of blood flow from the right ventricle to the pulmonary artery), and right ventricular hypertrophy (thickening of the muscular walls of the right ventricle, which occurs because the right ventricle is pumping at high pressure).

Transposition of the Great Arteries (TGA) refers to an anomaly where the aorta and the pulmonary artery are "transposed" from their normal position so that the aorta arises from the right ventricle and the pulmonary artery from the left ventricle.

Surgical treatment for some conditions involves a longitudinal incision along the pulmonary artery, up to and along one of the pulmonary branches. This incision can eliminate or significantly impair the function of the pulmonary valve. A trans-annular patch is used to cover the incision after the surgery. The trans-annular patch reduces stenotic or constrained conditions of the pulmonary artery PA, associated with other surgeries. However, the impairment or elimination of the pulmonary valve PV can create significant regurgitation and, prior to the present invention, often required later open-heart surgery to replace the pulmonary valve. The trans-annular patch technique can result in pulmonary arteries having a wide degree of variation in size and shape (See FIGS. 3A-3D)

Referring to FIGS. 4A-4F, in one exemplary embodiment an expandable docking station 10 includes one or more sealing portions 410, a valve seat 18, and one or more retaining portions 414. The sealing portion(s) 410 provide a seal between the docking station 10 and an interior surface 416 of the circulatory system. The valve seat 18 provides a supporting surface for implanting or deploying a valve 29 in the docking station 10 after the docking station 10 is implanted in the circulatory system. The retaining portions 414 help retain the docking station 10 and the valve 29 at the implantation position or deployment site in the circulatory system. Expandable docking station 10 and valve 29 as described in the various embodiments herein are also representative of a variety of docking stations and/or valves that might be known or developed, e.g., a variety of different types of valves could be substituted for and/or used as valve 29 in the various docking stations.

Figure 4A:
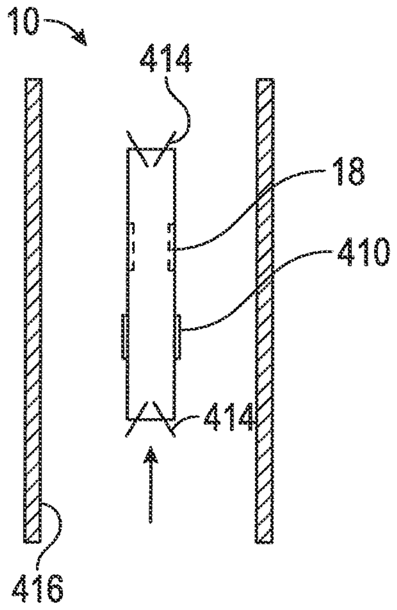
FIG. 4A is a schematic illustration of a compressed docking station being positioned in a circulatory system.
Figure 4B:
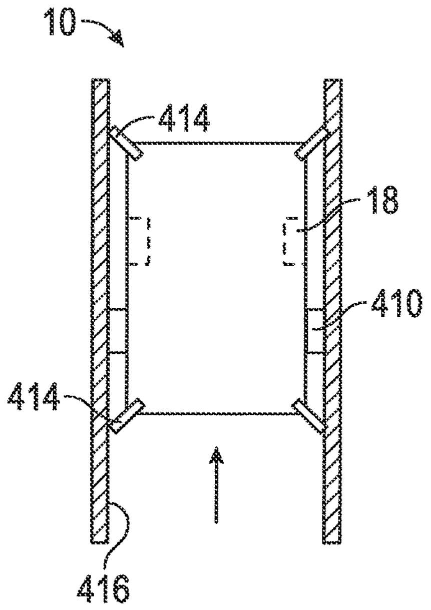
FIG. 4B is a schematic illustration of the docking station of FIG. 4A expanded to set the position of the docking station in the circulatory system.
Figure 4C:
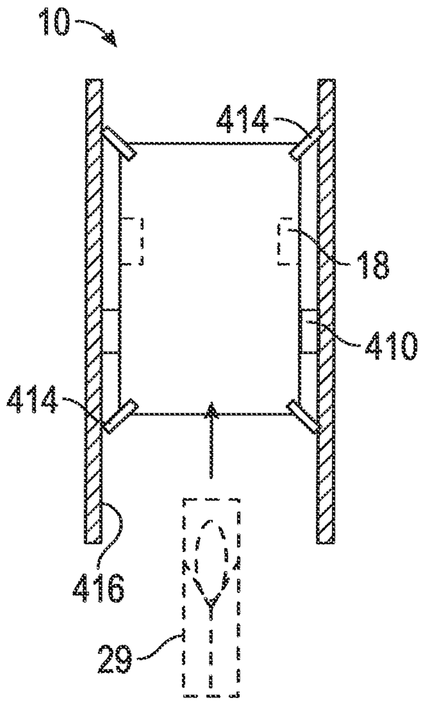
FIG. 4C is a schematic illustration of an expandable transcatheter heart valve being positioned in the docking station illustrated by FIG. 4B.
Figure 4D:
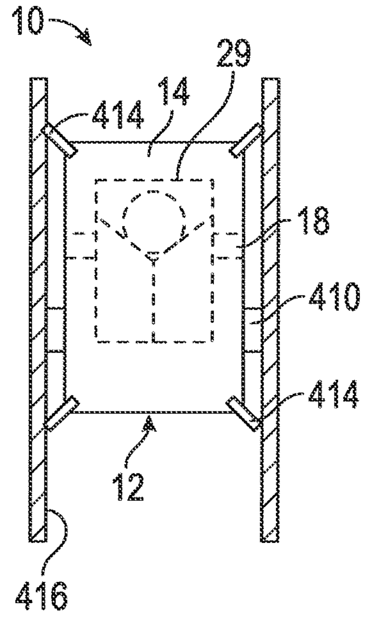
FIG. 4D is a schematic illustration of the transcatheter heart valve of FIG. 4C expanded to set the position of the heart valve in the docking station.

FIGS. 4A-4D schematically illustrate an exemplary deployment of the docking station 10 and valve 29 in the circulatory system. Referring to FIG. 4A, the docking station 10 is in a compressed form/configuration and is introduced to a deployment site in the circulatory system. For example, the docking station 10, can be positioned at a deployment site in a pulmonary artery by a catheter (e.g., catheter 3600 as shown in FIGS. 50A-50D). Referring to FIG. 4B, the docking station 10 is expanded in the circulatory system such that the sealing portion(s) 410 and the retaining portions 414 engage the inside surface 416 of a portion of the circulatory system. Referring to FIG. 4C, after the docking station 10 is deployed, the valve 29 is in a compressed form and is introduced into the valve seat 18 of the docking station 10. Referring to FIG. 4D, the valve 29 is expanded in the docking station, such that the valve 29 engages the valve seat 18. In the examples depicted herein, the docking station 10 is longer than the valve. However, in other embodiments the docking station 10 can be the same length or shorter than the length of the valve 29. Similarly, the valve seat 18 can be longer, shorter, or the same length as the length of the valve 29.

Referring to FIG. 4D, the valve 29 has expanded such that the seat 18 of the docking station supports the valve. The valve 29 only needs to expand against the narrow seat 18, rather than against the wider space within the portion of the circulatory system that the docking station 10 occupies. The docking station 10 allows the valve 29 to operate within the expansion diameter range for which it is designed.

Figure 4E:
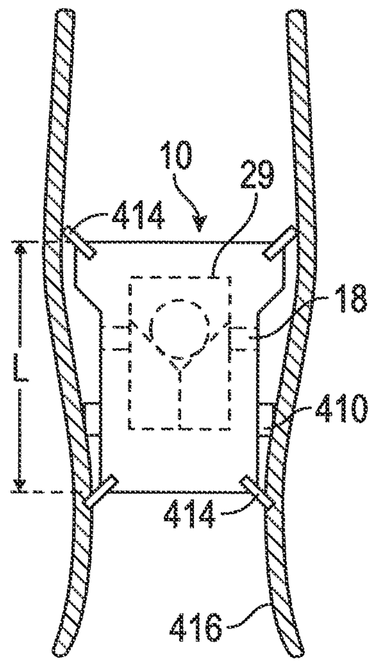
FIG. 4E illustrates the docking station and transcatheter heart valve deployed in an irregularly shaped portion of the circulatory system.

FIG. 4E illustrates that the inner surface 416 of the circulatory system, such as the inner surface of a blood vessel or anatomy of the heart can vary in cross-section size and/or shape along its length. In an exemplary embodiment, the docking station 10 is configured to expand radially outwardly to varying degrees along its length L to conform to shape of the inner surface 416. In one exemplary embodiment, the docking station 10 is configured such that the sealing portion(s) 410 and/or the retaining portion(s) engage the inner surface 416, even though the shape of the blood vessel or anatomy of the heart vary significantly along the length L of the docking station. The docking station can be made from a very resilient or compliant material to accommodate large variations in the anatomy. For example, the docking station can be made from a highly flexible metal, metal alloy, polymer, or an open cell foam. Examples of a metals and metal alloys that can be used include, but are not limited to, nitinol, elgiloy, and stainless steel, but other metals and highly resilient or compliant non-metal materials can be used. For example, the docking station 10 can have a frame or portion of a frame (e.g., a self-expanding frame, retaining portion(s), sealing portion(s), valve seat, etc.) made of these materials, e.g., from shape memory materials, such as nitinol. These materials allow the frame to be compressed to a small size, and then when the compression force is released, the frame will self-expand back to its pre-compressed diameter.

An example of an open cell foam that can be used to form the docking station or a portion of the docking station is a bio-compatible foam, such as a polyurethane foam (e.g., as can be obtained from Biomerix, Rockville, MD). Docking stations described herein can be self-expanding and/or expandable with an inflatable device to cause the docking station to engage an inner surface 416 having a variable shape.

Figure 4F:
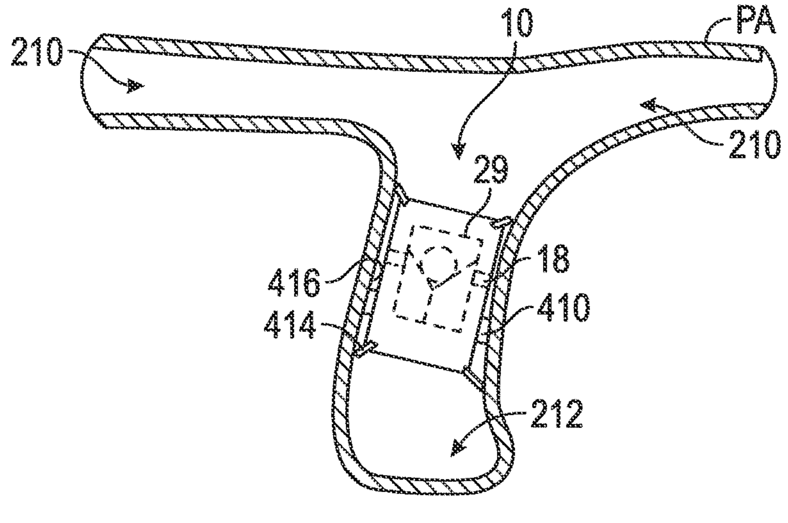
FIG. 4F illustrates the docking station and transcatheter heart valve deployed in a pulmonary artery.

FIG. 4F illustrates the docking station 10 and a valve 29 implanted in a pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA in the same manner as described with respect to FIG. 4E.

Referring to FIGS. 5A-5F, in one exemplary embodiment an expandable docking station 10 is made from an expandable foam material, such as an open cell biocompatible foam. The outer surface 510 of the foam material can serve as the sealing portion 410. In this example, a valve seat 18 can be provided on the inner surface 512 of the foam material as illustrated, or the inner surface 512 can serve as the valve seat. In the example illustrated by FIGS. 5A-5F, the retaining portions 414 are omitted, though retaining portions can be used. In one embodiment, foam material can be used together with an expandable frame (e.g., of metal, shape memory material, etc.). The foam material can cover or extend the full length of the frame or only a portion of the length of the frame.

Figure 5D:
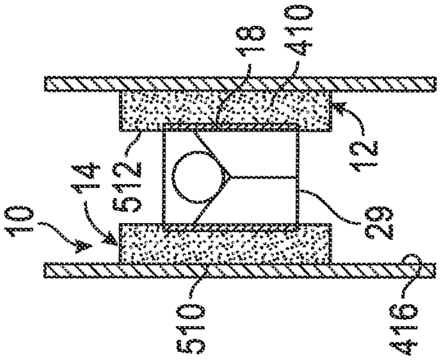
FIG. 5D is a schematic illustration of the transcatheter heart valve of FIG. 5C expanded to set the position of the heart valve in the docking station.
Figure 5F:
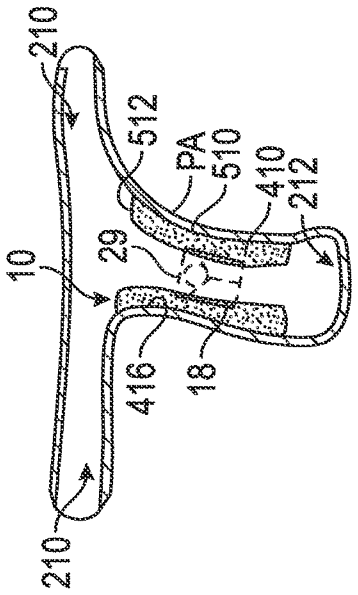
FIG. 5F illustrates the docking station and transcatheter heart valve deployed in a pulmonary artery.
Figure 5C:
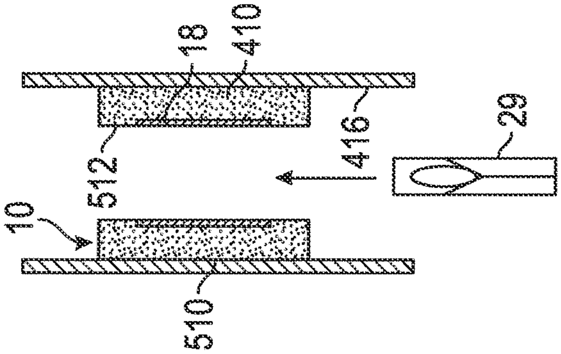
FIG. 5C is a schematic illustration of an expandable transcatheter heart valve being positioned in the docking station illustrated by FIG. 5B.
Figure 5B:
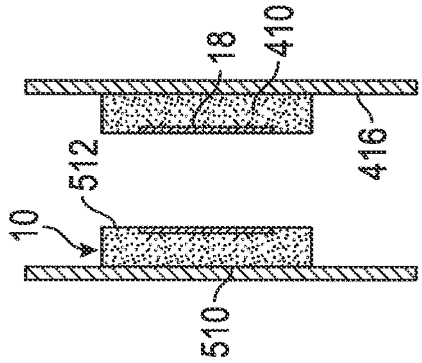
FIG. 5B is a schematic illustration of the docking station of Figure SA expanded to set the position of the docking station in the circulatory system.

FIGS. 5A-5D schematically illustrate deployment of the foam docking station 10 and valve 29 in the circulatory system. Referring to Figure SA, the docking station 10 is in a compressed form and is introduced to a deployment site in the circulatory system. For example, the docking station 10, can be positioned at a deployment site in a pulmonary artery by a catheter (e.g., catheter 3600 shown in FIGS. 50A-50D). Referring to FIG. 5B, the docking station 10 is expanded in the circulatory system such that the sealing portion 410 engage the inside surface 416 of the circulatory system. Referring to FIG. 5C, after the docking station 10 is deployed, the valve 29 is in a compressed form and is introduced into the valve seat 18 or inner surface 512 of the docking station 10. Referring to FIG. 5D, the valve 29 is expanded in the docking station, such that the valve 29 engages the valve seat 18 or inner surface 512 (e.g., where inner surface 512 acts as the valve seat).

Figure 5E:
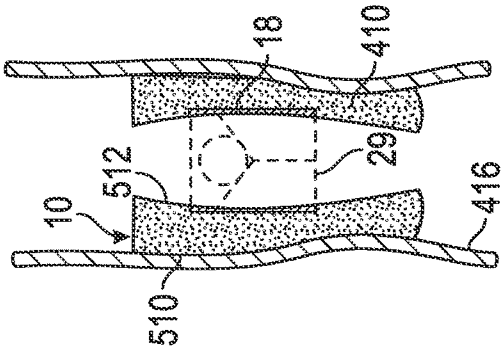
FIG. 5E illustrates the docking station and transcatheter heart valve deployed in an irregularly shaped portion of the circulatory system.
Figure 5A:
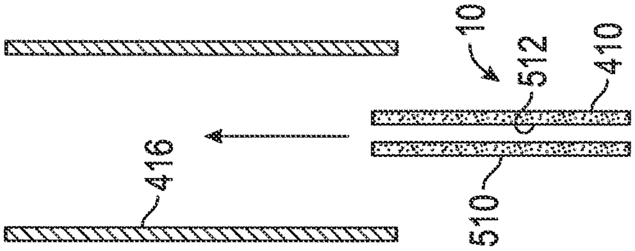
FIG. 5A is a schematic illustration of a compressed docking station being positioned in a circulatory system.

FIG. 5E illustrates that the inner surface 416 of the circulatory system, such as the inner surface of a blood vessel or anatomy of the heart may vary in cross-section along its length. In an exemplary embodiment, the foam docking station 10 is configured to expand radially outwardly to varying degrees along its length L to conform to shape of the inner surface 416.

FIG. 5F illustrates the foam docking station 10 and a valve 29 implanted in a pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA in the same or a similar manner as described with respect to FIG. 4E.

Figure 6A:
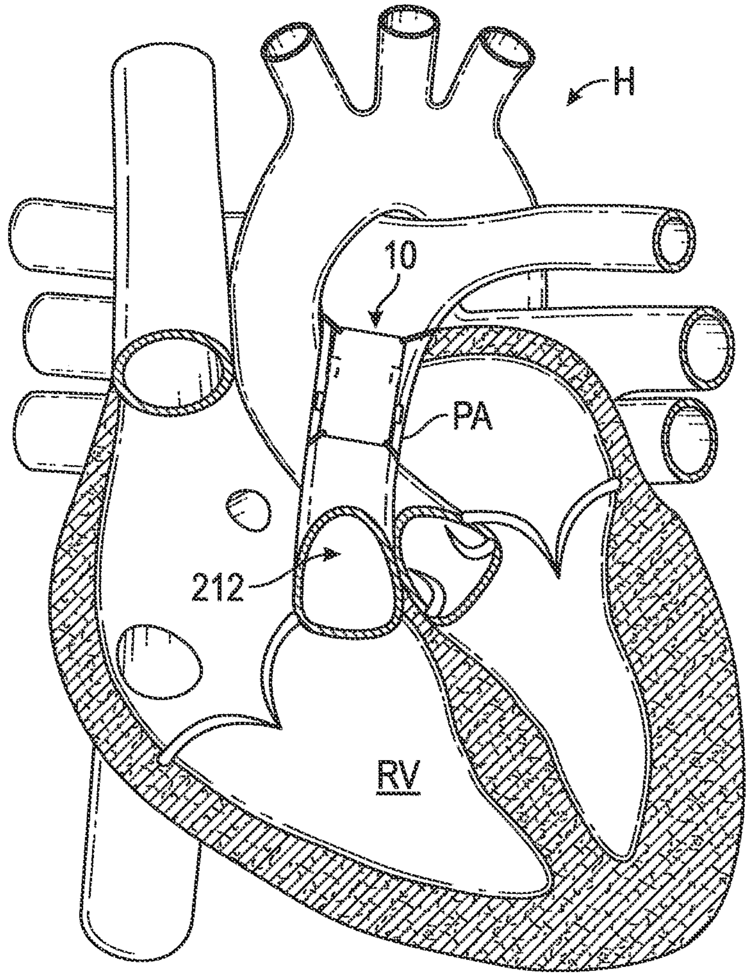
FIG. 6A is a cutaway view of the human heart in a systolic phase with a docking station deployed in a pulmonary artery.
Figure 6B:
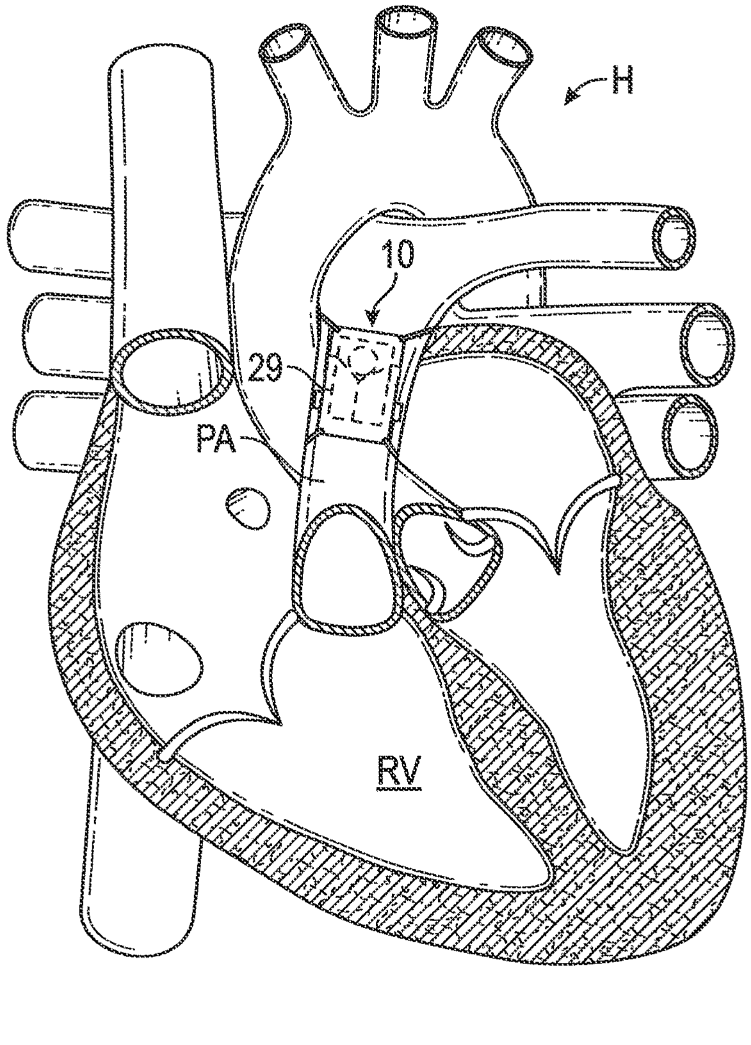
FIG. 6B is a cutaway view of the human heart in a systolic phase with a docking station and transcatheter heart valve deployed in a pulmonary artery.
Figure 7A:
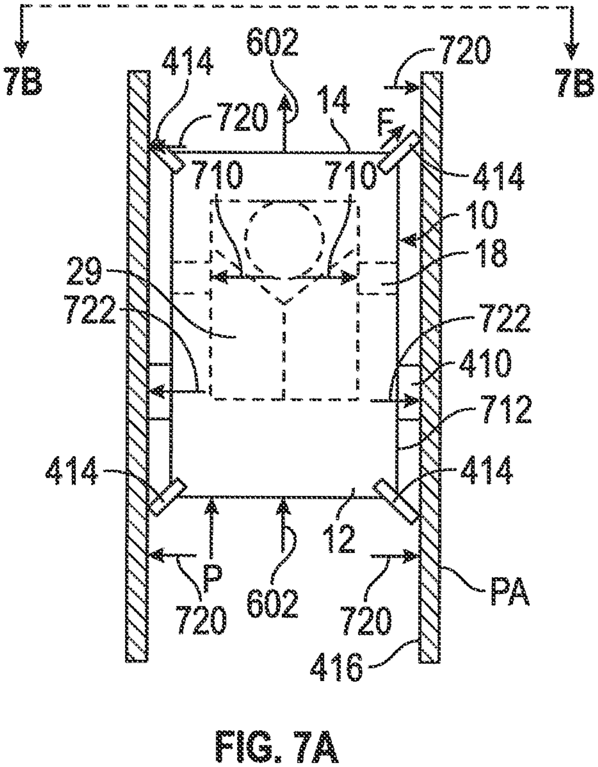
FIG. 7A is an enlarged schematic illustration of the docking station and transcatheter heart valve of FIG. 6B when the heart is in the systolic phase.
Figure 7B:
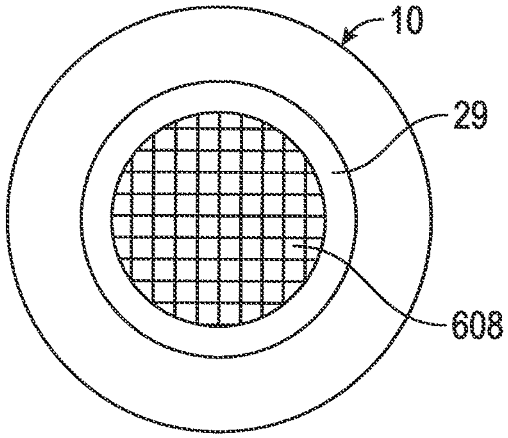
FIG. 7B is a view taken in the direction indicated by lines 7B-7B in FIG. 7A.

Referring to FIG. 6A, a docking station, e.g., a docking station as described with respect to FIGS. 4A-4D, is deployed in the pulmonary artery PA of a heart H. FIG. 6B illustrates a valve 29 deployed in the docking station 10 illustrated by FIG. 6A. In FIGS. 6A and 6B, the heart is in the systolic phase. FIG. 7A is an enlarged representation of the docking station 10 and valve 29 in the pulmonary artery PA of FIG. 6B. When the heart is in the systolic phase, the valve 29 opens. Blood flows from the right ventricle RV and through the pulmonary artery PA, docking station 10, and valve 29 as indicated by arrows 602. FIG. 7B illustrates a blood filled space 608 that represents the valve 29 being open when the heart is in the systolic phase. FIG. 7B does not show the interface between the docking station 10 and the pulmonary artery to simplify the drawing. The cross-hatching in FIG. 7B illustrates blood flow through the open valve. In an exemplary embodiment, blood is prevented from flowing between the pulmonary artery PA and the docking station 10 by the sealing portion(s) 410 and blood is prevented from flowing between the docking station 10 and the valve 29 by seating of the valve 29 in the seat 18 of the docking station 10. In this example, blood is substantially only flowing or only able to flow through the valve 29 when the heart is in the systolic phase.

Figure 8:
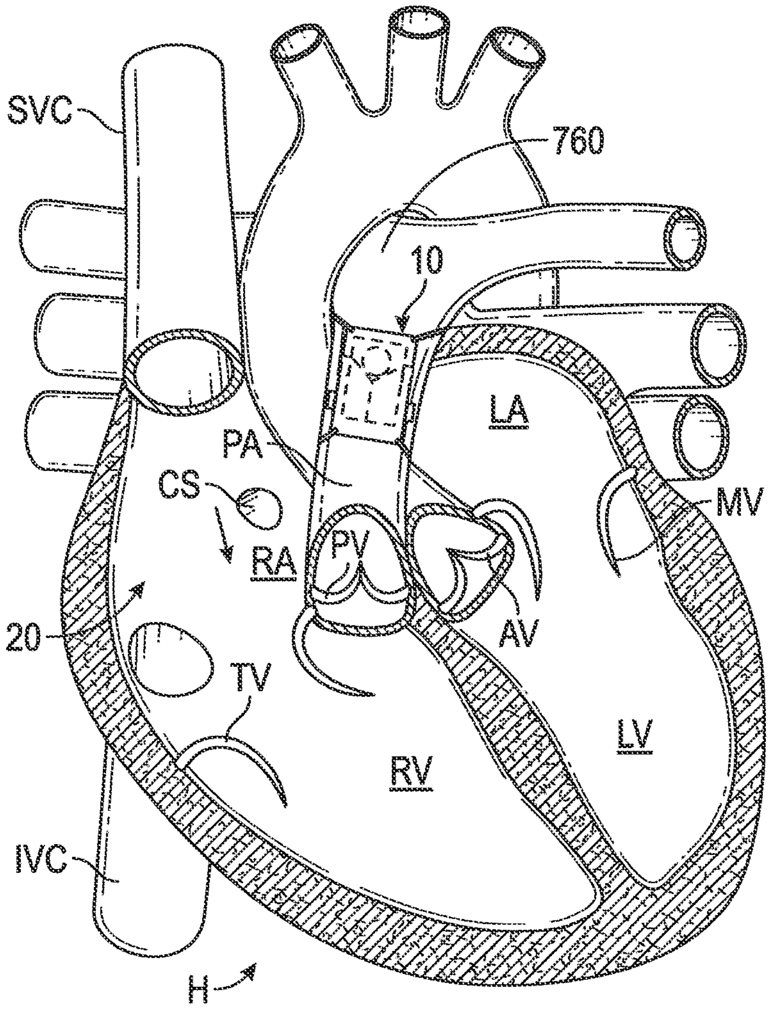
FIG. 8 is a cutaway view of the human heart in a diastolic phase with a docking station and transcatheter heart valve deployed in a pulmonary artery.
Figure 9A:
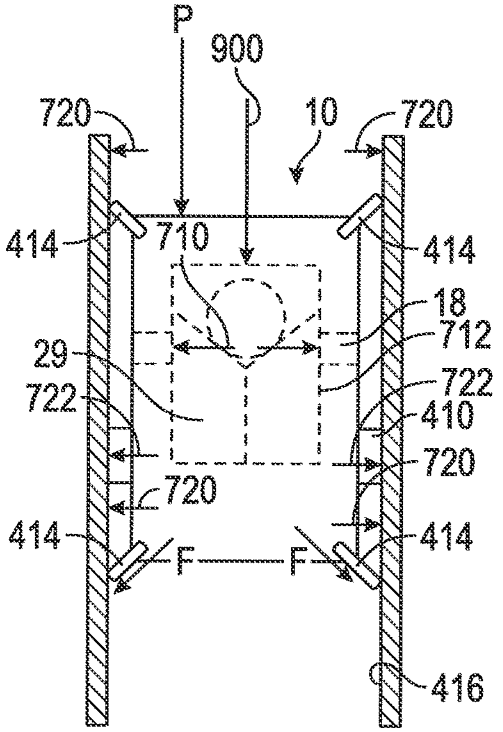
FIG. 9A is an enlarged schematic illustration of the docking station and transcatheter heart valve of FIG. 8 when the heart is in the diastolic phase.
Figure 9B:
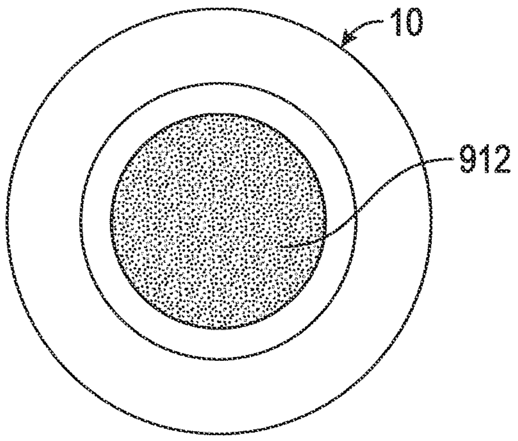
FIG. 9B is a view taken in the direction indicated by lines 9B-9B in FIG. 9A.

FIG. 8 illustrates the valve 29, docking station 10 and heart H illustrated by FIG. 6B, when the heart is in the diastolic phase. Referring to FIGS. 9A and 9B, when the heart is in the diastolic phase, the valve 29 closes. FIG. 9A is an enlarged representation of the docking station 10 and valve 29 in the pulmonary artery of FIG. 8. Blood flow in the pulmonary artery PA above the valve 29 (i.e. in the pulmonary branch 760) is blocked by the valve 29 being closed and blocking blood flow as indicated by arrow 900. The solid area 912 in FIG. 9B represents the valve 29 being closed when the heart is in the diastolic phase.

In one exemplary embodiment, the docking station 10 acts as an isolator that prevents or substantially prevents radial outward forces of the valve 29 from being transferred to the inner surface 416 of the circulatory system. In one embodiment, the docking station 10 includes a valve seat 18 (which is not expanded radially outwardly or is not substantially expanded radially outward by the radially outward force of the THV or valve 29, i.e., the diameter of the valve seat is not increased or is increased by less than 4 mm by the force of the THV), and anchoring/retaining portions 414 and sealing portions 410, which impart only relatively small radially outward forces 720, 722 on the inner surface 416 of the circulatory system (as compared to the radially outward force applied to the valve seat 18 by the valve 29).

When no docking station is used, stents and frames of THVs are held in place in the circulatory system by a relatively high radial outward force 710 of the stent or frame 712 of the THV acting directly on the inside surface 416 of the circulatory system. If a docking station is used, as in the example illustrated by FIG. 7A, the stent or frame 712 of the valve 29 expands radially outward or is expanded radially outward to impart the high force 710 on the valve seat 18 of the docking station 10. This high radially outward force 710 secures the valve 29 to the valve seat 18 of the docking station 10. However, since the valve seat 18 is not expanded or is not substantially expanded by the force 710, the force 710 is isolated from the circulatory system, rather than being used to secure the docking station in the circulatory system.

In an exemplary embodiment, the radially outward force 722 of the sealing portions 410 to the inside surface 416 is substantially smaller than the radially outward force 710 applied by the valve 29 to the valve seat 18. For example, the radially outward sealing force 722 can be less than ½ the radially outward force 710 applied by the valve, less than ⅓ the radially outward force 710 applied by the valve, less than ¼ the radially outward force 710 applied by the valve, less than ⅛, or even less than 1/10 the radially outward force 710 applied by the valve. In one exemplary embodiment, the radially outward force 722 of the sealing portions 410 is selected to provide a seal between the inner surface 416 and the sealing portion 410, but is not sufficient by itself to retain the position of the valve 29 and docking station 10 in the circulatory system.

In an exemplary embodiment, the radially outward force 720 of the anchoring/retaining portions 414 to the inside surface 416 is substantially smaller than the radially outward force 710 applied by the valve 29 to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than 1/10 the radially outward force 710 applied by the valve.

In one exemplary embodiment, the radially outward force 720 of the retaining portions 414 is not sufficient by itself to retain the position of the valve 29 and docking station 10 in the circulatory system. Rather, the pressure of the blood 608 is used to enhance the retention of the retaining portions 414 to the inside surface 416. Referring again to FIG. 6A, when the heart is in the systolic phase, the valve 29 is open and blood flows through the valve as indicated by arrows 602. Since the valve 29 is open and blood flows through the valve 29, the pressure P applied to the docking station 10 and valve 29 by the blood is low as indicated by the small P and arrow in FIG. 7A. Even though small, the pressure P forces the docking station and its upper retaining portions 414 against the surface 416 generally in the direction indicated by arrow F. This blood flow assisted force F applied by the retaining portions F to the surface 416 prevents the docking station 10 and valve 29 from moving in the direction 602 of blood flow in the systolic phase of the heart H.

Referring to FIG. 9A, when the heart is in the diastolic phase, the valve 29 is closed and blood flow is blocked as indicated by arrow 900. Since the valve 29 is closed and the valve 29 and docking station 10 block the flow of blood, the pressure P applied to the docking station 10 and valve 29 by the blood is high as indicated by the large arrow P in FIG. 9A. This large pressure P forces the lower retaining portions 414 against the surface 416 generally in the direction indicated by the large arrows F. This blood flow assisted force F applied by the retaining portions F to the surface 416 prevents the docking station 10 and valve 29 from moving in the direction indicated by arrow 900.

Since the force applied by the upper and lower retaining portions 414 is determined by amount of pressure applied to the valve 29 and docking station 10 by the blood, the force applied to the surface 416 is automatically proportioned. That is, the upper retaining portions are less forcefully pressed against the surface 416 when the heart is in the systolic phase than the lower retaining portions are pressed against the surface 416 when the heart is in the diastolic phase. This is because the pressure against the open valve 29 and docking station 10 in the systolic phase is less than the pressure against the closed valve and docking station in the diastolic phase.

The valve seat 18 and sealing portion 410 can take a wide variety of different forms. For example, the valve seat 18 can be any structure that is not expanded radially outwardly or is not substantially expanded radially outward by the radially outward force of the THV (i.e., the diameter of the valve seat in the deployed position/configuration may not expand or may expand less than 4 mm, e.g., the diameter may only expand 1-4 mm larger when the valve is deployed in the valve seat). For example, the valve seat 18 can comprise a suture or a metal ring that resists or limits expansion. However, in one embodiment, the valve seat 18 (or any valve seat described herein) can be expandable over a larger range, for example, the diameter may expand between 5 mm and 30 mm larger when a valve is deployed in the valve seat. In one embodiment, the diameter might expand from 5 mm or 6 mm in diameter to 20 mm-29 mm, 24 mm, 26 mm, 29 mm, etc. in diameter, or expand from and to different diameters within that range. Even if more expandable, the valve seat can still be restricted in expansion, e.g., restricted to avoid expansion of the valve seat beyond an expanded diameter of a valve to be placed in the valve seat or to avoid expansion beyond a diameter that will securely hold the valve in the valve seat via the forces created therebetween. The valve seat 18 can be part of or define a portion of the body of the docking station 10, or the valve seat 18 can be a separate component that is attached to the body of the docking station. The valve seat 18 can be longer, shorter, or the same length as the valve. The valve seat 18 can be significantly shorter than the valve 29 when the valve seat 18 is defined by a suture or a metal ring. A valve seat 18 formed by a suture or metal ring can form a narrow circumferential seal line between the valve 29 and the docking station.

The sealing portion(s) 410 of various embodiments can take a wide variety of different forms. For example, the sealing portion(s) 410 can be any structure that provides a seal(s) between the docking station 10 and the surface 416 of the circulatory system. For example, the sealing portion(s) 410 can comprise a fabric, a foam, biocompatible tissue, an expandable metal frame, a combination of these, etc. The sealing portion(s) 410 can be part of or define a portion of the body of the docking station 10, and/or the sealing portion(s) 410 can be a separate component that is attached to the body of the docking station. The docking station 10 can include a single sealing portion 410 or two, or more than two sealing portions.

Figure 7C:
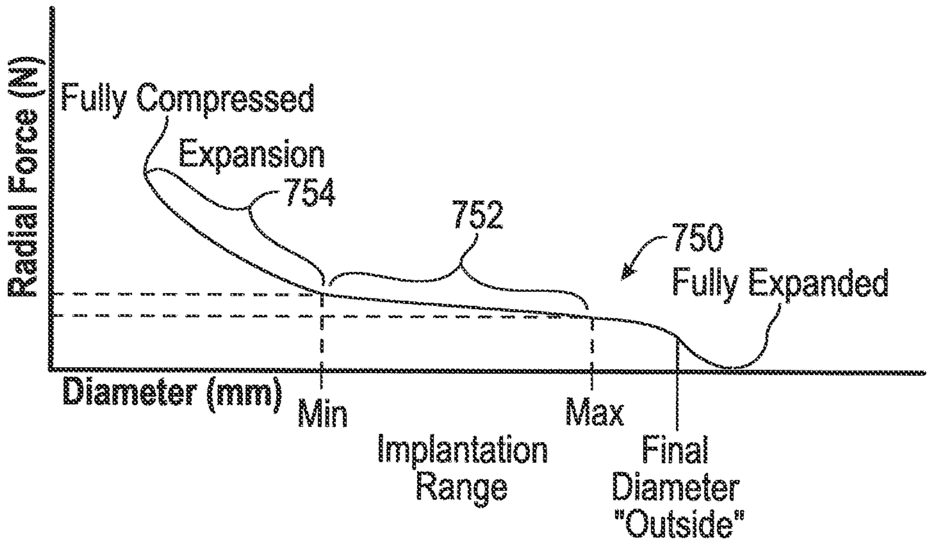
FIG. 7C is a graph showing a relationship between a docking station diameter and a radial outward force applied by the docking station.

As mentioned above, in one exemplary embodiment the sealing portion(s) 410 is configured to apply a low radially outward force to the surface 416. The low radially outward force can be provided in a wide variety of different ways. For example, sealing portion can be made from a very compressible or compliant material. Referring to FIG. 7C, in one exemplary embodiment, the docking station 10 body is made from an elastic or super elastic metal. One such metal is nitinol. When the body of a docking station 10 is made from a lattice of metal struts, the body can have the characteristics of a spring. Referring to FIG. 7C, like a spring, when the body of the docking station is unconstrained and allowed to relax to its largest diameter the body of the docking station applies little or no radially outward force. As the body of the docking station 10 is compressed, like a spring, the radially outward force applied by the docking station increases. As is illustrated by FIG. 7C, in one exemplary embodiment the relationship of the radially outward force of the docking station body to the expanded diameter of the docking station is non-linear, although, in one exemplary embodiment, the relationship could also be linear. In the example illustrated by FIG. 7C, the curve 750 illustrates the relationship between the radially outward force exerted by the docking station 10 and the compressed diameter of the docking station. In the region 752, the curve 750 has a low slope. In this region 752 the radially outward force is low and changes only a small amount. In one exemplary embodiment, the region 752 corresponds to a diameter between 25 mm and 40 mm, such as between 27 mm and 38 mm. The radially outward force is small in the region 752, but is not zero. In the region 754, the curve 750 has a higher slope. In this region 754 the radially outward force increases significantly as the docking station is compressed. In one exemplary embodiment, the body of the stent is constructed to be in the low slope region 752. This allows the sealing portions 410 to apply only a small radially outward force to the inner surface 416 of the circulatory system over a wide range of diameters.

The retaining portions 414 can take a wide variety of different forms. For example, the retaining portion(s) 414 can be any structure that sets the position of the docking station 10 in the circulatory system. For example, the retaining portion(s) 414 can press against or into the inside surface 416 or extend around anatomical structure of the circulatory system to set the position of the docking station 10. The retaining portion(s) 414 can be part of or define a portion of the body of the docking station 10 or the retaining portion(s) 414 can be a separate component that is attached to the body of the docking station. The docking station 10 can include a single retaining portion 414 or two, or more than two retaining portions.

Figure 10A:
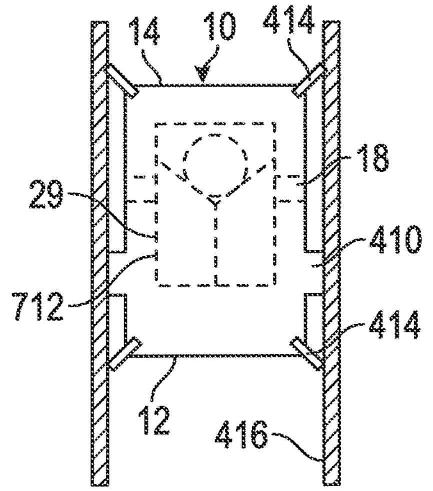
FIG. 10A illustrates an exemplary embodiment of a docking station with a transcatheter heart valve disposed inside the docking station.
Figure 10B:
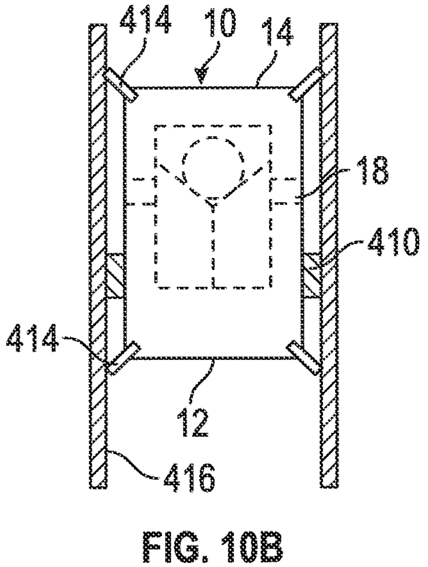
FIG. 10B illustrates an exemplary embodiment of a docking station with a transcatheter heart valve disposed inside the docking station.
Figure 10C:
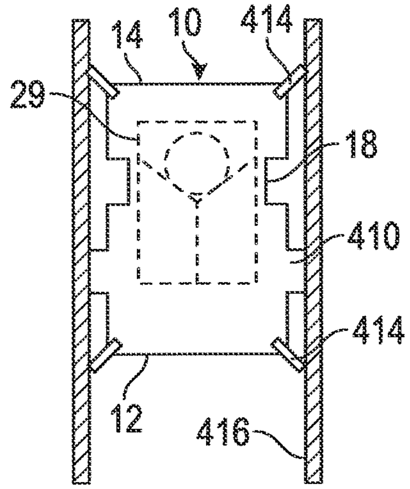
FIG. 10C illustrates an exemplary embodiment of a docking station with a transcatheter heart valve disposed inside the docking station.
Figure 10D:
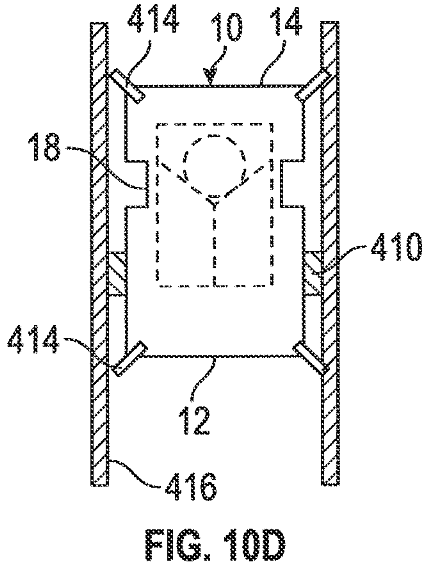
FIG. 10D illustrates an exemplary embodiment of a docking station with a transcatheter heart valve disposed inside the docking station.

FIGS. 10A-10C illustrate that the docking station 10 can have any combination of one or more than one different types of valve seats 18 and sealing portions 410. In the example illustrated by FIG. 10A, the valve seat 18 is a separate component that is attached to the body of the docking station 10 and the sealing portion is integrally formed with the body of the docking station. In the example illustrated by FIG. 10B, the valve seat 18 is a separate component that is attached to the body of the docking station 10 and the sealing portion 410 is a separate component that is attached to the body of the docking station. In the example illustrated by FIG. 10C, the valve seat 18 is integrally formed with the body of the docking station 10 and the sealing portion is integrally formed with the body of the docking station. In the example illustrated by FIG. 10D, the valve seat 18 is integrally formed with the body of the docking station 10 and the sealing portion is a separate component that is attached to the body of the docking station 10.

As mentioned above, the length of the pulmonary artery PA and other anatomical structures of the circulatory system may vary greatly from patient to patient. Referring to FIGS. 11A-11D, in one exemplary embodiment the length of the docking station 10 is adjustable as indicated by arrow 1100. This adjustability 1100 refers to the ability of the implanted/expanded length of the docking station to be adjusted, rather than the inherent change in length that occurs when a stent expands from a compressed state to an expanded state. The length can be adjusted in a wide variety of different ways. In the example illustrated by FIGS. 11A-11D, the docking station 10 includes a first half 1102 and a second half 1104. The use of the word "half" as used herein with respect to two-part docking stations is synonymous with "portion" and does not require the first and second half or first and second portion to be equal in size, i.e., the first half could be larger/longer than the second half and vice versa. In one embodiment, the second half 1104 can be inserted or "telescoped" into the first half 1102. The amount of insertion or "telescoping" sets the length of the docking station 10. Any of the docking stations 10 shown and described in this patent application can be adjustable in length by making the docking stations from two parts that are telescoped together or are otherwise adjustable relative to each other. In one embodiment, a length of a single-piece docking station can be collapsible and expandable. In one embodiment, a docking station can be formed of a material that can change shape to adjust the length. In one embodiment, more than two portions (e.g., 3, 4, or more portions) can be combined in similar ways and include one or more similar features as first half 1102 and second half 1104.

In one exemplary embodiment, the length of the docking station 10 can be adjusted in the pulmonary artery PA by first deploying the first half 1102 of the docking station 10 in the pulmonary artery. For example, the first half 1102 can be positioned and expanded as desired, e.g., such that a distal end 1106 of the first half is aligned with or extends somewhat past the branch of the pulmonary artery. After the first half 1102 is expanded in the pulmonary artery, the compressed second half 1104 can be positioned with a distal end 1110 disposed in the proximal end 1108 of the first half 1102. In one embodiment, the position of the second half 1104 is selected such that the sealing portion 410 and retaining portion 414 will make contact with the pulmonary artery and set the position of the docking station 10 in the pulmonary artery. Once properly positioned, the second half 1104 is expanded. In one embodiment, the distal end of 1110 of the second half 1104 frictionally engages the proximal end 1108 of the first half to secure the two halves 1102, 1104 together. In one embodiment, a lock(s), locking mechanism, suture(s), interlacing, link(s) and/or other attachment device/mechanism can be used to help secure the halves/portions together.

Figure 11A:
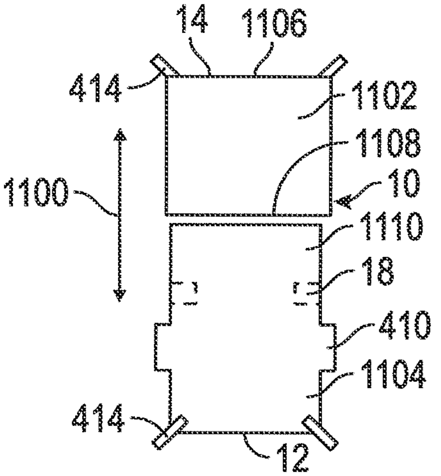
FIG. 11A illustrates an exemplary embodiment of a telescoping docking station.
Figure 11B:
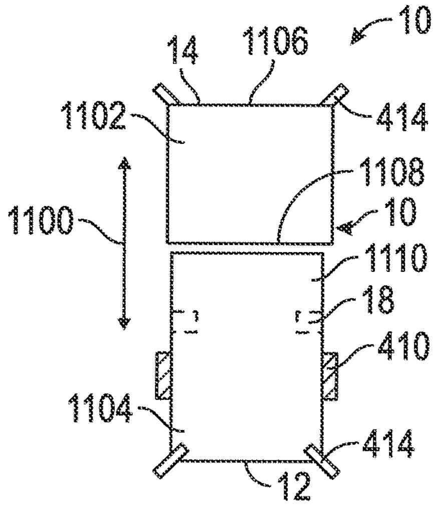
FIG. 11B illustrates an exemplary embodiment of a telescoping docking station.
Figure 11C:
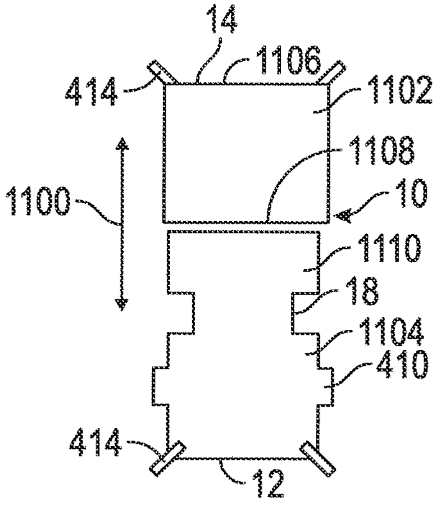
FIG. 11C illustrates an exemplary embodiment of a telescoping docking station.
Figure 11D:
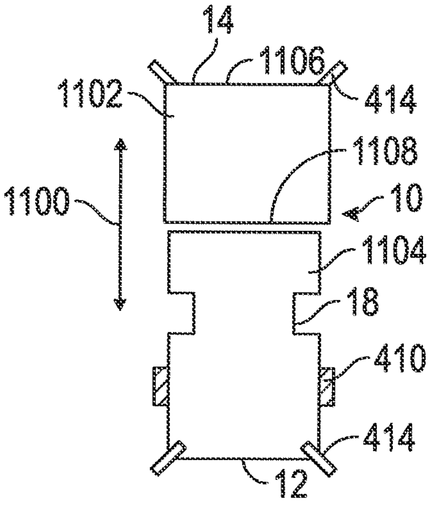
FIG. 11D illustrates an exemplary embodiment of a telescoping docking station.
Figure 12A:
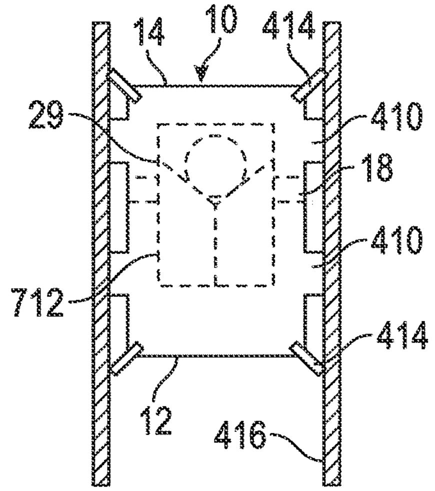
FIG. 12A illustrates an exemplary embodiment of a docking station with a transcatheter heart valve disposed inside the docking station.
Figure 12B:
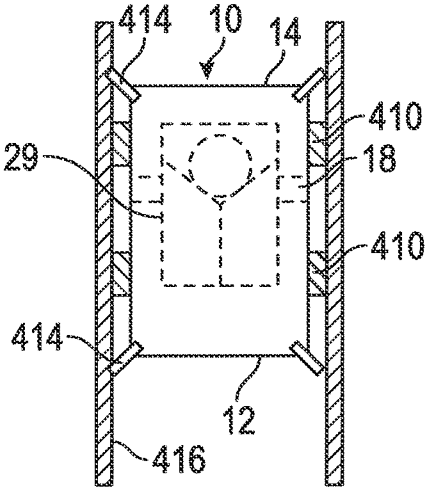
FIG. 12B illustrates an exemplary embodiment of a docking station with a transcatheter heart valve disposed inside the docking station.
Figure 12C:
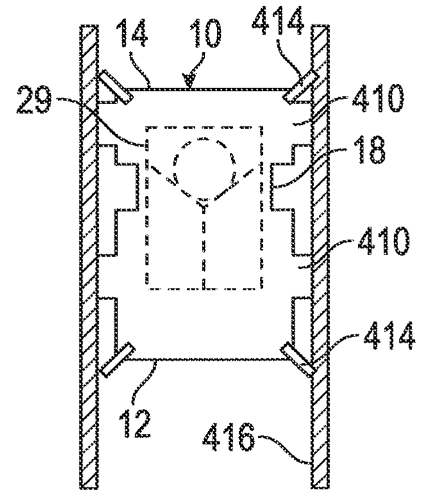
FIG. 12C illustrates an exemplary embodiment of a docking station with a transcatheter heart valve disposed inside the docking station.
Figure 12D:
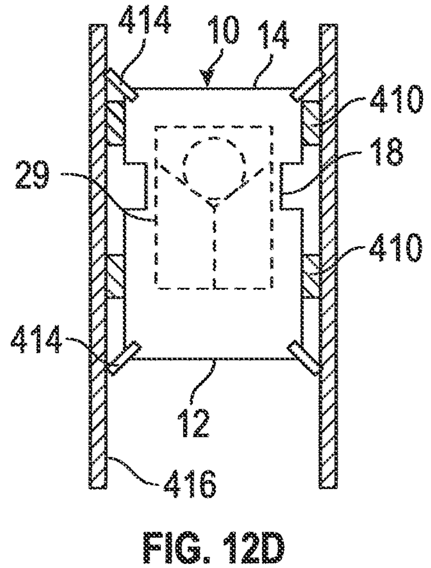
FIG. 12D illustrates an exemplary embodiment of a docking station with a transcatheter heart valve disposed inside the docking station.
Figure 13A:
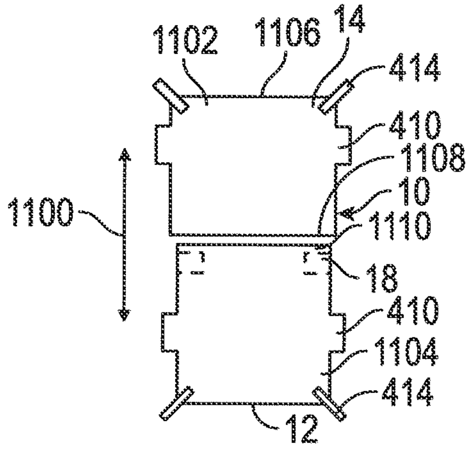
FIG. 13A illustrates an exemplary embodiment of a telescoping docking station.
Figure 13B:
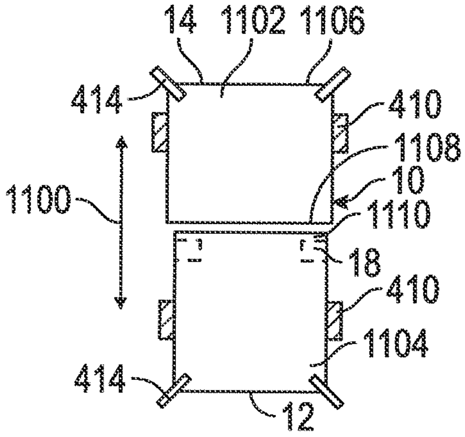
FIG. 13B illustrates an exemplary embodiment of a telescoping docking station.
Figure 13C:
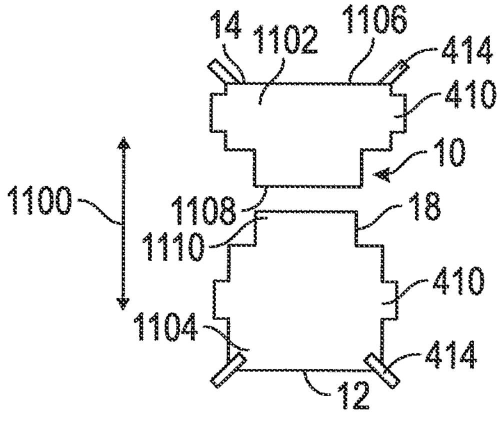
FIG. 13C illustrates an exemplary embodiment of a telescoping docking station.
Figure 13D:
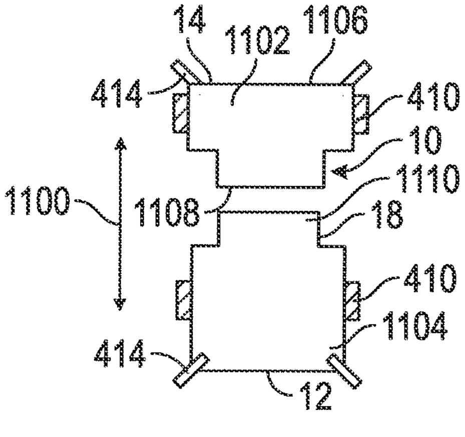
FIG. 13D illustrates an exemplary embodiment of a telescoping docking station.

In the examples illustrated by FIGS. 11A-11D, the seat 18 and the sealing portion 410 are included on the second half 1104 of the docking station 10. However, in other embodiments the seat 18 and/or the sealing portion 410 can be included on the first half 1102. FIGS. 11A-11C illustrate that the halves 1102, 1104 of the docking station 10 can have any combination of different types of valve seats 18 and sealing portions 410. In the example illustrated by FIG. 11A, the valve seat 18 is a separate component that is attached to the body of the docking station half 1104 and the sealing portion is integrally formed with the body of the docking station half 1104. In the example illustrated by FIG. 11B, the valve seat 18 is a separate component that is attached to the body of the docking station half 1104 and the sealing portion 410 is a separate component that is attached to the body of the docking station half 1104. In the example illustrated by FIG. 11C, the valve seat 18 is integrally formed with the body of the docking station half 1104 and the sealing portion is integrally formed with the body of the docking station half 1104. In the example illustrated by FIG. 11D, the valve seat 18 is integrally formed with the body of the docking station half 1104 and the sealing portion 410 is a separate component that is attached to the body of the docking station half 1104.

FIGS. 12A-12D illustrate exemplary embodiments of docking stations 10 with two sealing portions 410. The docking station 10 can have any combination of one or more than one different types of valve seats 18 and sealing portions 410. In the example illustrated by FIG. 12A, the valve seat 18 is a separate component that is attached to the body of the docking station 10 and the sealing portions 410 is integrally formed with the body of the docking station. In the example illustrated by FIG. 12B, the valve seat 18 is a separate component that is attached to the body of the docking station 10 and the sealing portions 410 are separate components that are attached to the body of the docking station. In the example illustrated by FIG. 12C, the valve seat 18 is integrally formed with the body of the docking station 10 and the sealing portions are integrally formed with the body of the docking station. In the example illustrated by FIG. 12D, the valve seat 18 is integrally formed with the body of the docking station 10 and the sealing portions are separate components that are attached to the body of the docking station 10.

FIGS. 13A-13D illustrate that the docking stations illustrated by FIGS. 12A-12D can be two-piece telescoping docking stations. The pieces 1102, 1104 of the docking station 10 can have any combination of one or more than one different types of valve seats 18 and sealing portions 410 on either or both of the two pieces. In the example illustrated by FIG. 13A, the first half 1102 includes an integral sealing portion 410. The second half 1104 includes a valve seat 18 that is a separate component that is attached to the body of the docking station 10 and the sealing portions 410 is integrally formed with the body of the docking station. In the example illustrated by FIG. 13B, the first half 1102 includes a sealing portion 410 that is separate from the body of the first half 102. The valve seat 18 is a separate component that is attached to the body of the docking station 10 and the sealing portion 410 is a separate component that is attached to the body of the docking station. In the example illustrated by FIG. 13C, the first half 1102 includes an integral sealing portion 410. The valve seat 18 is integrally formed with the body of the second half 1104 of the docking station 10 and the sealing portion 410 is integrally formed with the body of the second half 1104. In the example illustrated by FIG. 13D, the first half 1102 includes a sealing portion 410 that is separate from the body of the first half 102. The valve seat 18 is integrally formed with the body of the second half 1104 of the docking station 10 and the sealing portion 410 is a separate component that is attached to the body of the second half 1104.

Referring to FIGS. 14A-14G, in one exemplary embodiment the docking station 10 can include a permeable portion 1400 that blood can flow through as indicated by arrows 1402 and an impermeable portion 1404 that blood cannot flow through. In one exemplary embodiment, the impermeable portion 1404 extends from at least the sealing portion 410 to the valve seat 18 to prevent blood from flowing around the valve 29. In one exemplary embodiment, the permeable portion 1400 allows blood to freely flow through it, so that portions of the docking station that do not seal against the inside surface 416 of the circulatory system or seal against the valve 29 do not block the flow of blood. For example, the docking station 10 can extend into the branch of the pulmonary artery and the portion 1400 of the docking station 10 that extends into the pulmonary artery freely allows blood to flow through the docking station 10. In one exemplary embodiment, the permeable portion 1400 allows blood to freely flow through it, so that areas 1420 between the docking station and the circulatory system are flushed with blood as the heart beats, thereby preventing blood stasis in the areas 1420.

The impermeable portion 1404 can take a wide variety of different forms. The impermeable portion 1404 can be any structure or material that prevents blood to flow through the impermeable portion 1404. For example, the body of the docking station 10 can be formed from wires or a lattice, such as a nitinol wire or lattice, and cells of body are covered by an impermeable material (See FIG. 18). A wide variety of different materials can be used as the impermeable material. For example, the impermeable material can be a blood-impermeable cloth, such as a PET cloth or biocompatible covering material such as a fabric that is treated with a coating that is impermeable to blood, polyester, or a processed biological material, such as pericardium.

Figure 14A:
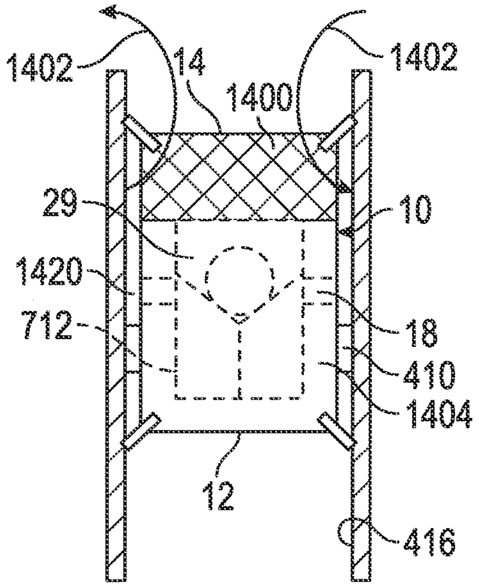
FIG. 14A illustrates an exemplary embodiment of a docking station with a transcatheter heart valve disposed inside the docking station.
Figure 14B:
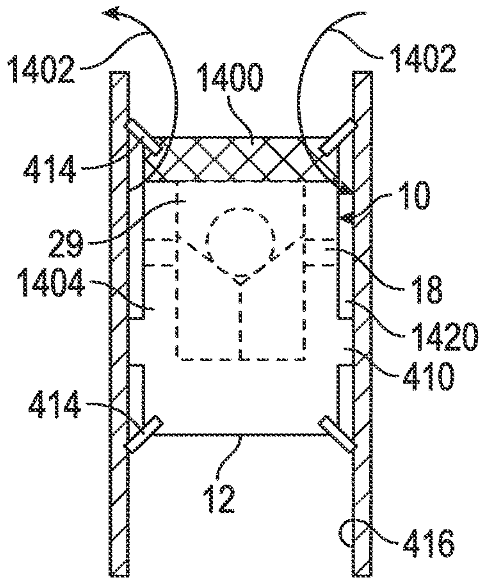
FIG. 14B illustrates an exemplary embodiment of a docking station with a transcatheter heart valve disposed inside the docking station.
Figure 14C:
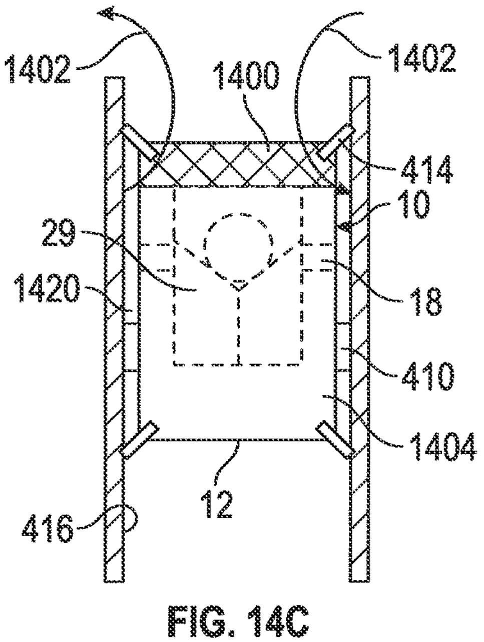
FIG. 14C illustrates an exemplary embodiment of a docking station with a transcatheter heart valve disposed inside the docking station.
Figure 14D:
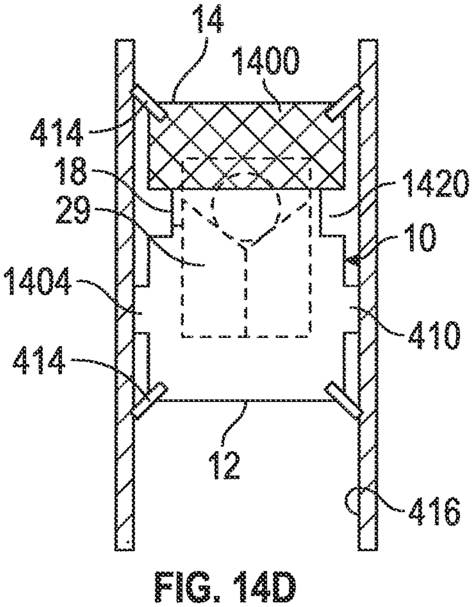
FIG. 14D illustrates an exemplary embodiment of a docking station with a transcatheter heart valve disposed inside the docking station.
Figure 14E:
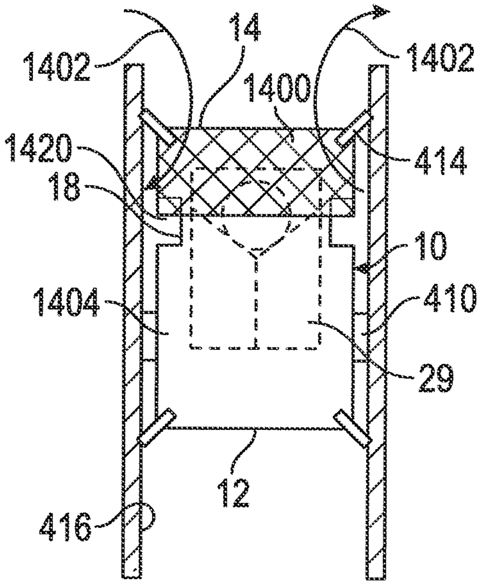
FIG. 14E illustrates an exemplary embodiment of a docking station with a transcatheter heart valve disposed inside the docking station.
Figure 14F:
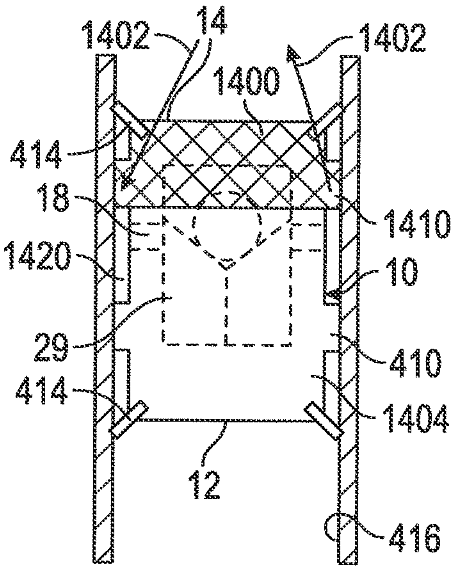
FIG. 14F illustrates an exemplary embodiment of a docking station with a transcatheter heart valve disposed inside the docking station.
Figure 14G:
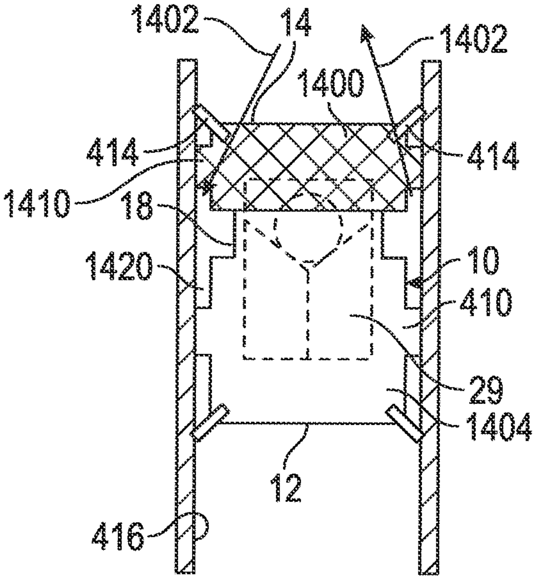
FIG. 14G illustrates an exemplary embodiment of a docking station with a transcatheter heart valve disposed inside the docking station.
Figure 15A:
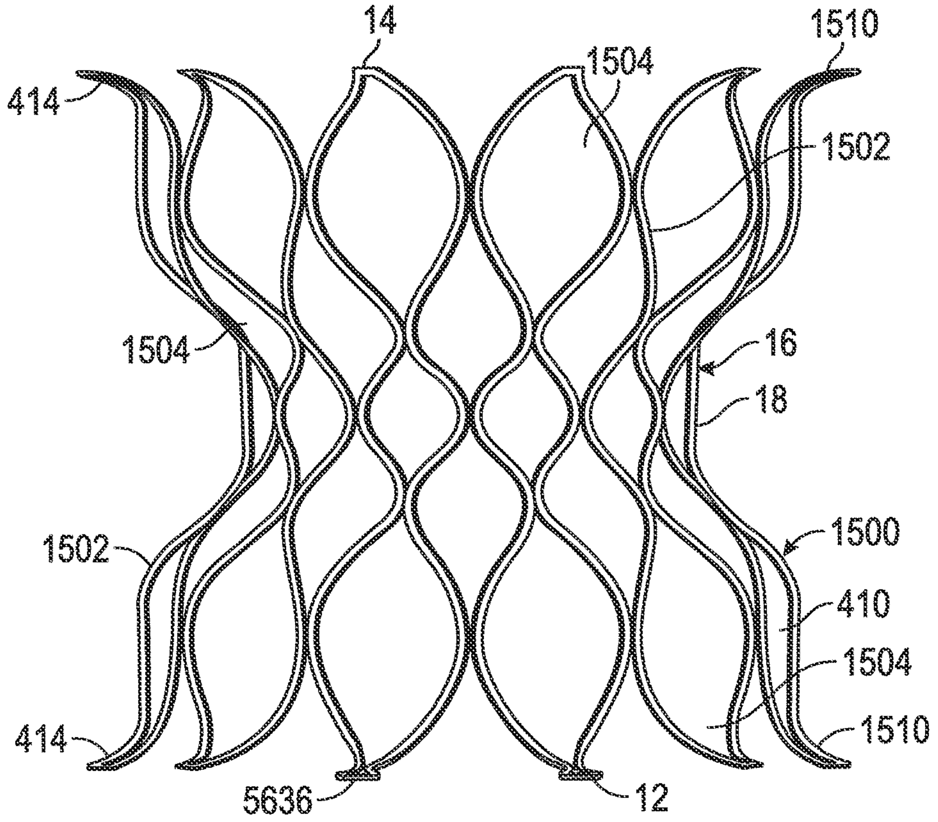
FIG. 15A is a side view of an exemplary embodiment of a frame of a docking station.
Figure 15B:
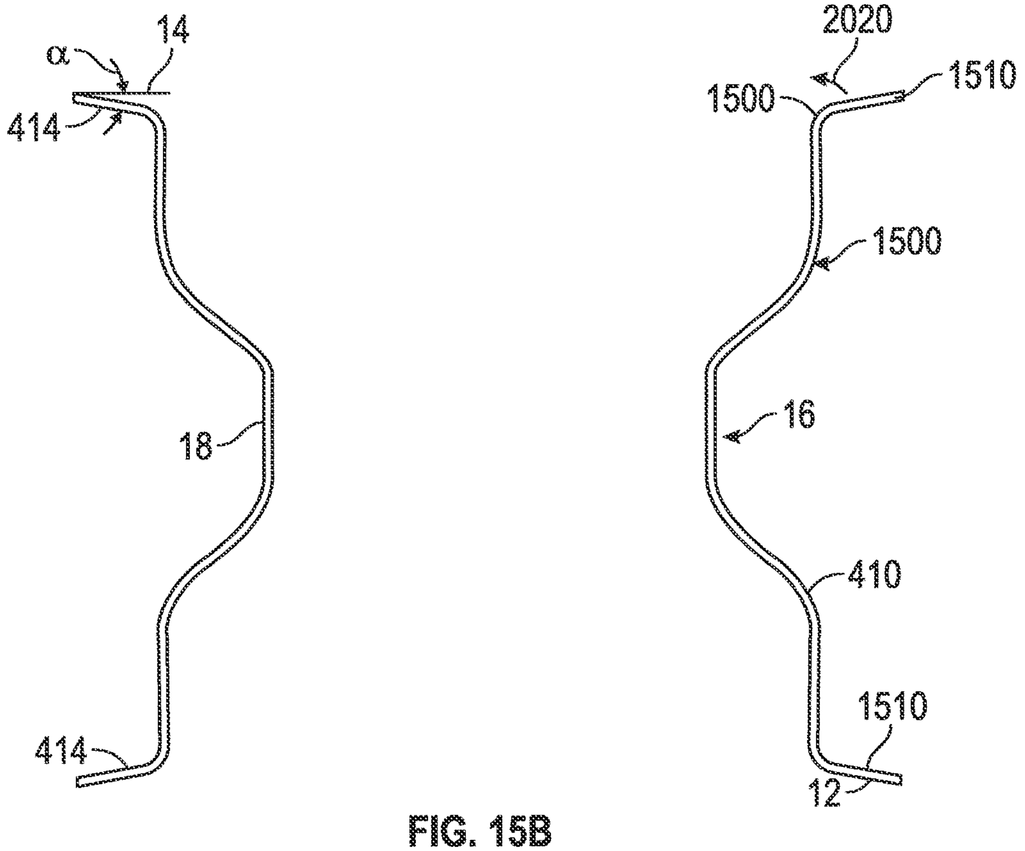
FIG. 15B illustrates a side profile of the frame illustrated by FIG. 15A.

FIGS. 14A-14G illustrate that a wide variety of docking station configurations can be provided with a permeable portion 1400. The sealing portion 410 can be integrally formed with the body of the docking station as illustrated by FIGS. 14B, 14D, and 14F or separate as illustrated by FIGS. 14C, 14E and 14G. In FIGS. 14F and 14G the docking station 10 includes portions 1410. These portions 1410 are similar to the sealing portions 410, but a seal is not formed with the inner surface 416 of the circulatory system, because the portion 1410 is part of the permeable portion 1400. The valve seat 18 can be separately formed from the body of the docking station as illustrated by FIGS. 14A-14C or integrally formed with the body of the docking station 10 as illustrated by FIGS. 14D-14G.

FIGS. 15A, 15B, 16, 17A, and 17B illustrate an exemplary embodiment of a frame 1500 or body of a docking station 10. The frame 1500 or body can take a wide variety of different forms and FIGS. 15A, 15B, 16, 17A, and 17B illustrate just one of the many possible configurations. In the example illustrated by FIGS. 15A, 15B, 16, 17A, 17B, and 18, the docking station 10 has a relatively wider proximal inflow end 12 and distal outflow end 14, and a relatively narrower portion 16 that forms the seat 18 in between the ends 12, 14. In the example illustrated by FIGS. 15A, 15B, 17A, and 17B, the frame 1500 of the docking station 10 is preferably a wide stent comprised of a plurality of metal struts 1502 that form cells 1504. In the example of FIGS. 15A, 15B, 17A, and 17B, the frame 1500 has a generally hourglass-shape that has a narrow portion 16, which forms the valve seat 18 when covered by an impermeable material, in between the proximal and distal ends 12, 14. As described below, the valve 29 expands in the narrow portion 16, which forms the valve seat 18.

Figure 16:
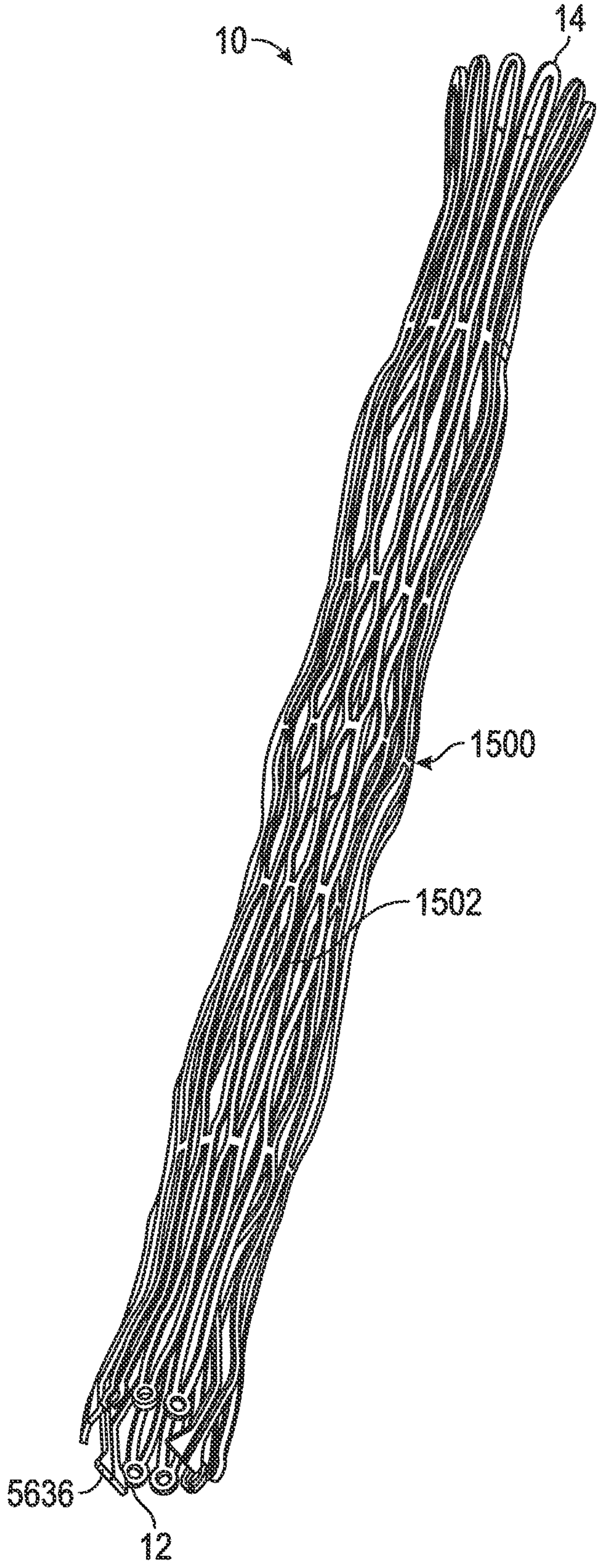
FIG. 16 illustrates the docking station frame of FIG. 15A in a compressed state.
Figure 17A:
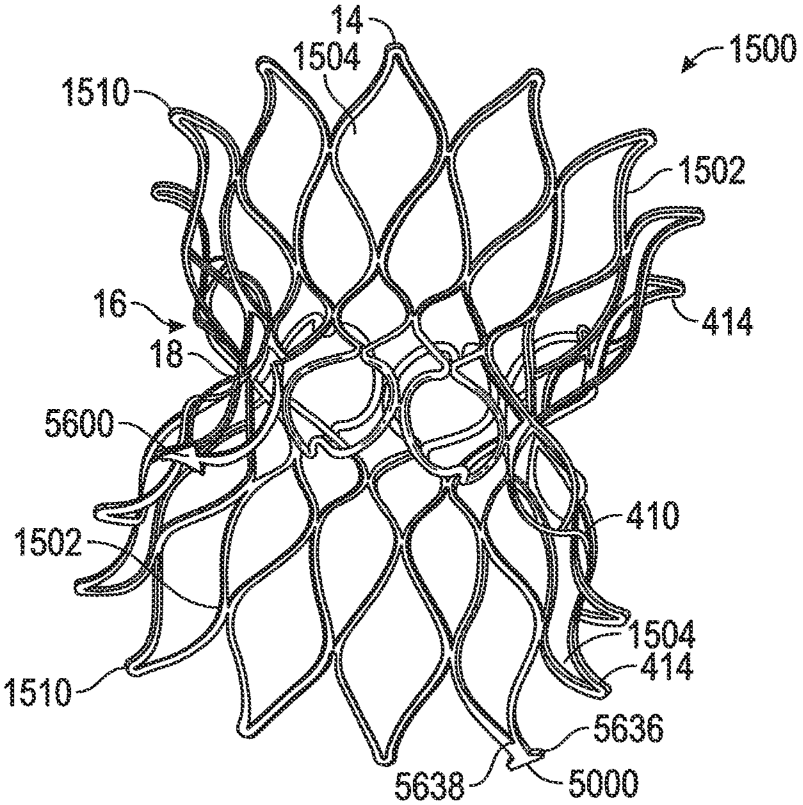
FIG. 17A is a perspective view of the docking station frame of FIG. 15A.
Figure 17B:
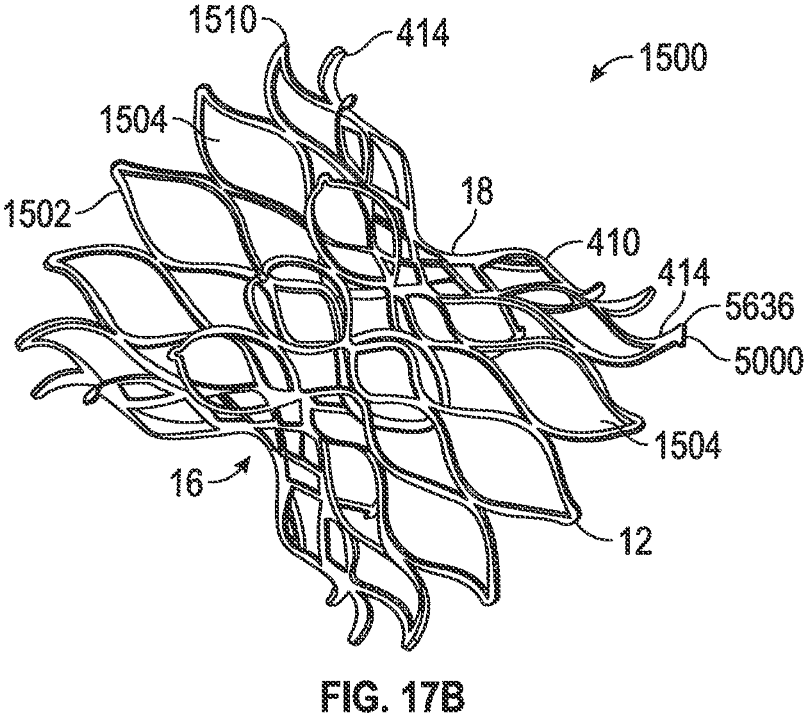
FIG. 17B is a perspective view of the docking station frame of FIG. 15A.

FIGS. 15A, 15B, 17A, and 17B illustrate the frame 1500 in its unconstrained, expanded condition. In this exemplary embodiment, the retaining portions 414 comprise ends or apices 1510 of the metal struts 1502 at the proximal and distal ends 12, 14. The sealing portion 410 is between the retaining portions 414 and the waist 16. In the unconstrained condition, the retaining portions 414 extend generally radially outward and are radially outward of the sealing portion 410. FIG. 16 illustrates the frame in the compressed state for delivery and expansion by a catheter. The docking station can be made from a very resilient or compliant material to accommodate large variations in the anatomy. For example, the docking station can be made from a highly flexible metal, metal alloy, polymer, or an open cell foam. An example of a highly resilient metal is nitinol, but other metals and highly resilient or compliant non-metal materials can be used. The docking station 10 can be self-expanding, manually expandable (e.g., expandable via balloon), or mechanically expandable. A self-expanding docking station 10 can be made of a shape memory material such as, for example, nitinol.

Figure 18:
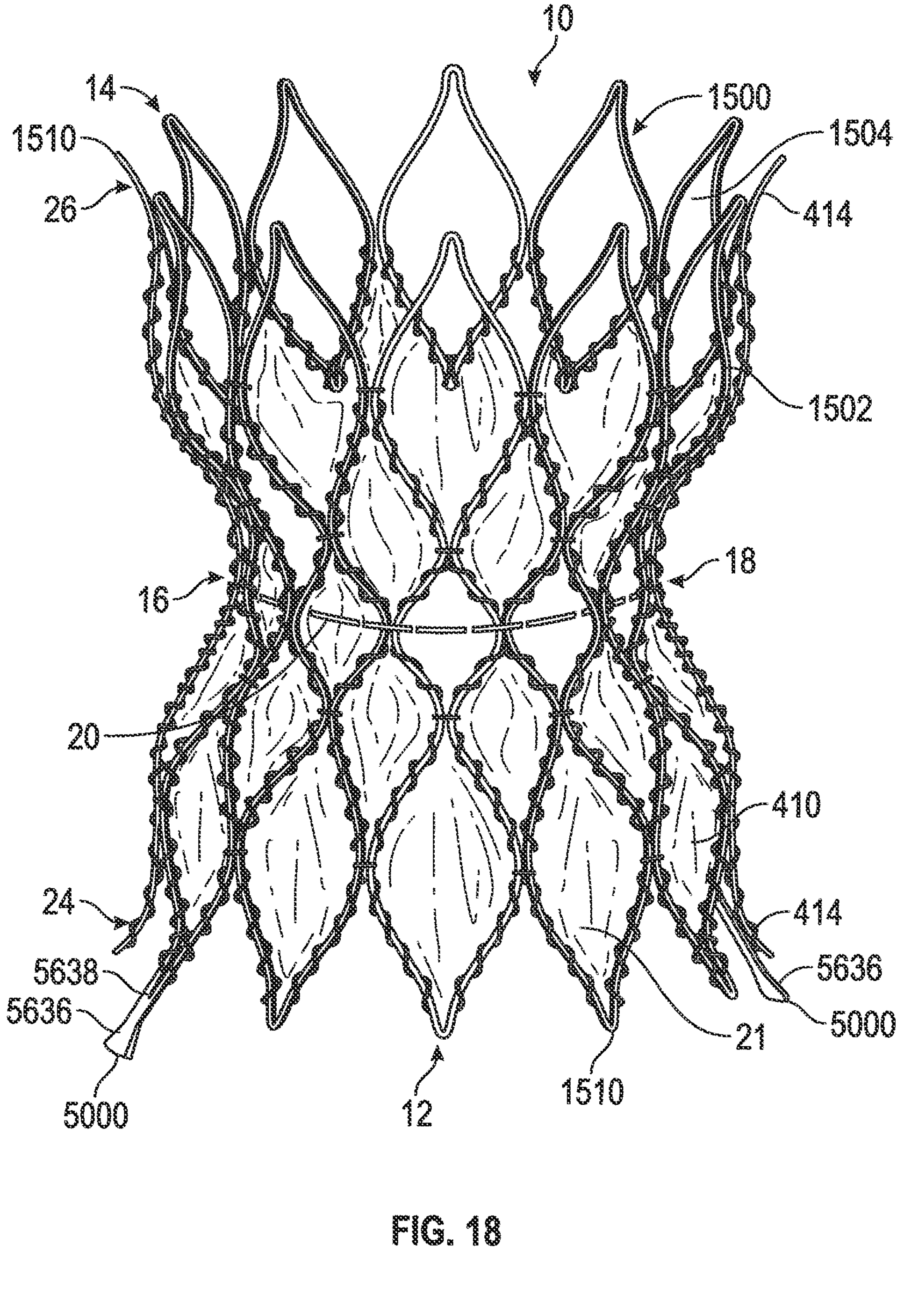
FIG. 18 is a perspective view of an exemplary embodiment of a docking station having a plurality of covered cells and a plurality of open cells.
Figure 19:
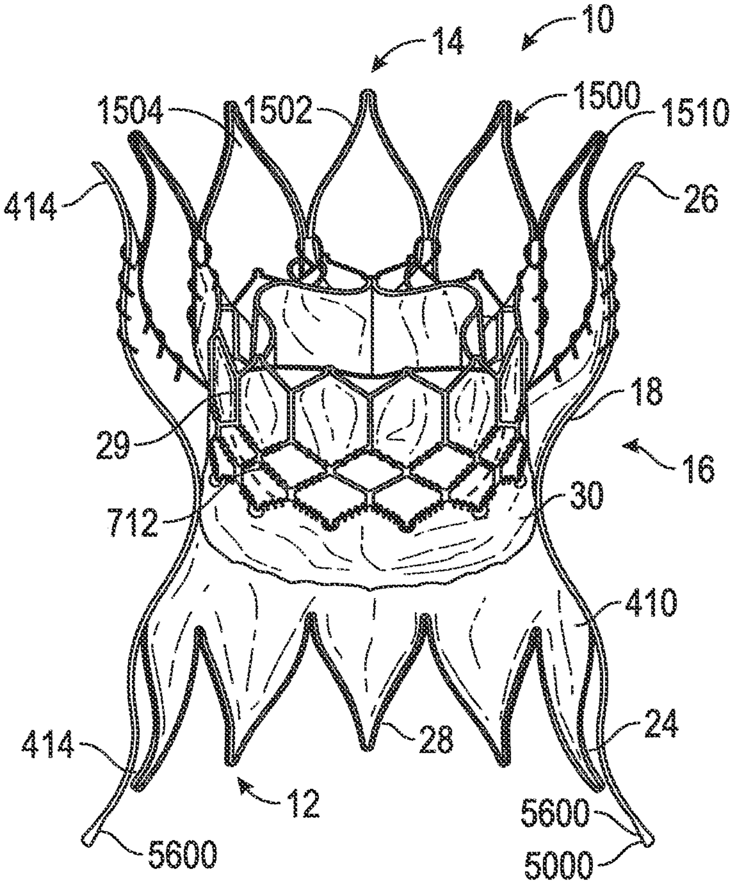
FIG. 19 is a perspective view of the docking station illustrated by FIG. 18 with a portion cut away to illustrate a transcatheter heart valve expanded into place in the docking station.

FIG. 18 illustrates the frame 1500 with impermeable material 21 attached to the frame 1500 to form the docking station 10. Referring to FIG. 18, in one exemplary embodiment a band 20 extends about the waist or narrow portion 16, or is integral to the waist to form an unexpandable or substantially unexpandable valve seat 18. The band 20 stiffens the waist and, once the docking station is deployed and expanded, makes the waist/valve seat relatively unexpandable in its deployed configuration. In the example illustrated by FIG. 19, the valve 29 is secured by expansion of its collapsible frame into the narrow portion 16, which forms the valve seat 18, of the docking station 10. As is explained above, the unexpandable or substantially unexpandable valve seat 18 prevents the radially outward force of the valve 29 from being transferred to the inside surface 416 of the circulatory system. However in another exemplary embodiment, the waist/valve seat of the deployed docking station can optionally expand slightly in an elastic fashion when the valve is deployed against it. This optional elastic expansion of the waist/valve seat 18 can put pressure on the valve 29 to help hold the valve 29 in place within the docking station.

The band can take a wide variety of different forms and can be made from a wide variety of different materials. The band 20 can be made of PET, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 can be narrow, such as the suture band in FIG. 18, or can be wider. The band can be a variety of widths, lengths, and thicknesses. In one non-limiting example, the valve seat 18 is between 27-28 mm wide, although the diameter of the valve seat should be within the operating range of the particular valve 29 that will be secured within the valve seat 18, and can be different than the foregoing example. The valve 29, when docked within the docking station, can optionally expand around either side of the valve seat slightly. This aspect, sometimes referred to as a “dog bone” (e.g., because of the shape it forms around the valve seat or band), can also help hold the valve in place.

Figure 20:
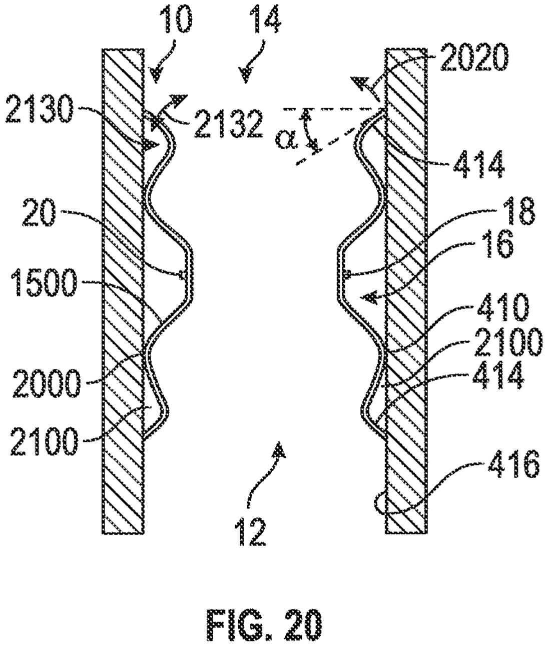
FIG. 20 illustrates a side profile of the docking station illustrated by FIG. 18 when implanted in a vessel of the circulatory system.
Figure 21:
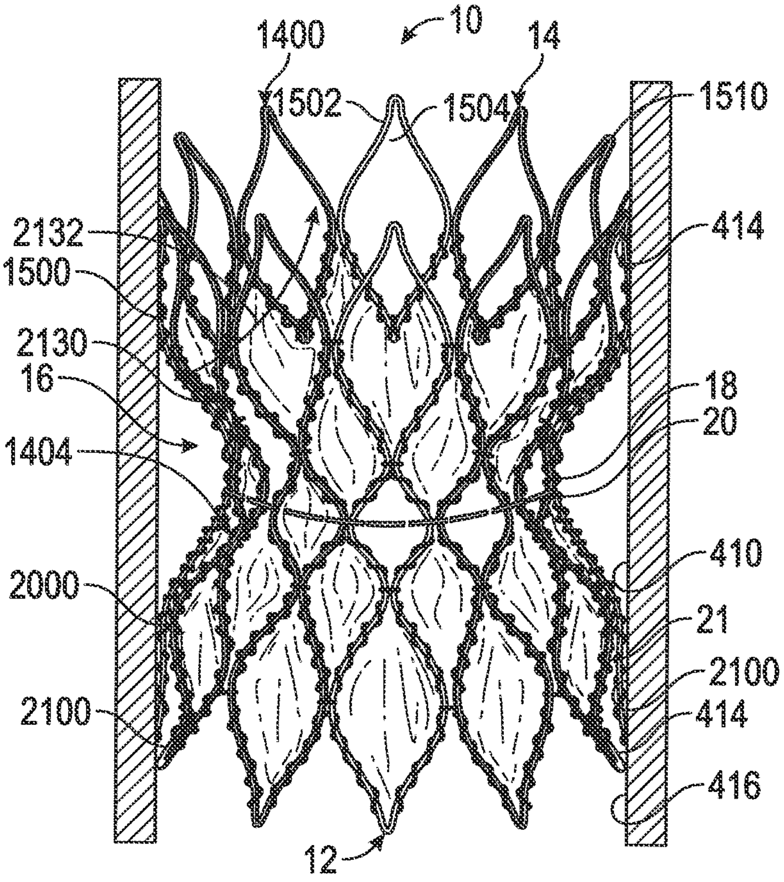
FIG. 21 illustrates a perspective view of the docking station illustrated by FIG. 18 when installed in a vessel of the circulatory system.

FIGS. 20 and 21 illustrate the docking station 10 of FIG. 18 implanted in the circulatory system, such as in the pulmonary artery. The sealing portions 410 provide a seal between the docking station 10 and an interior surface 416 of the circulatory system. In the example of FIGS. 20 and 21, the sealing portion 410 is formed by providing an impermeable material 21 (See FIG. 21) over the frame 1500 or a portion thereof, in particular, the sealing portion 410 can comprise the lower, rounded, radially outward extending portion 2000 of the frame 1500. In an exemplary embodiment, the impermeable material 21 extends from at least the portion 2000 of the frame 1500 to the valve seat 18. This makes the docking station impermeable from the sealing portion 410 to the valve seat 18. As such, all blood flowing in the direction of the inflow end 12 toward the outflow end 14 is directed to the valve seat 18 (and valve 29 once installed or deployed in the valve seat).

In a preferred embodiment of a docking station 10, the inflow portion has walls that are impermeable to blood, but the outflow portion walls are relatively open. In one approach, the inflow end portion 12, the mid-section 16, and a portion of the outflow end portion 14 are covered with a blood-impermeable fabric 21, which can be sewn onto the stent or otherwise attached by a method known in the art. The impermeability of the inflow portion of the stent helps to funnel blood into the docking station 10 and ultimately flow through the valve that is to be expanded and secured within the docking station 10.

From another perspective, this embodiment of a docking station is designed to seal at the proximal inflow section 2000 to create a conduit for blood flow. The distal outflow section, however, is generally left open, thereby allowing the docking station 10 to be placed higher in the pulmonary artery without restricting blood flow. For example, the permeable portion 1400 can extend into the branch of the pulmonary artery and not impede or not significantly impede the flow of blood past the branch. In one embodiment, blood-impermeable cloth, such as a PET cloth for example, or other material covers the proximal inflow section, but the covering does not cover any or at least does not cover a portion of the distal outflow section 14. As one non-limiting example, when the docking station 10 is placed in the pulmonary artery, which is a large vessel, the significant volume of blood flowing through the artery is funneled into the valve 29 by the impermeable material 21. The cloth 21 is fluid impermeable so that blood cannot pass through. Again, a variety of other biocompatible covering materials can be used such as, for example, foam or a fabric that is treated with a coating that is impermeable to blood, polyester, or a processed biological material, such as pericardium.

In the example illustrated by FIG. 21, more of the docking station frame 1500 is provided with the impermeable material 21, forming a relatively large impermeable portion 1404. In the example illustrated by FIG. 21, the impermeable portion 1404 extends from the inflow end 12 and stops one row of cells 1504 before the outflow end. As such, the most distal row of cells 1504 form a permeable portion 1400. However, more rows of cells 1504 can be uncovered by the impermeable material to form a larger permeable portion. The permeable portion 1400 allows blood to flow into and out of the area 2130 as indicated by arrows 2132. That is, blood can flow into and out of the areas 2100 in one exemplary embodiment.

The valve seat 18 can provide a supporting surface for implanting or deploying a valve 29 in the docking station 10. The retaining portions 414 can retain the docking station 10 at the implantation position or deployment site in the circulatory system. The illustrated retaining portions have an outwardly curving flare that helps secure the docking station 10 within the artery. “Outwardly” as used herein means extending away from the central longitudinal axis of the docking station. As can be seen in FIG. 20, when the docking station 10 is compressed by the inside surface 416, the retaining portions 414 engage the surface 416 at an angle $\alpha$ (normal to the surface to the tangent of the midpoint of the surface of the retaining portion 414) that can be between 30 and 60 degrees, such as about 45 degrees, rather than extending substantially radially outward (i.e. a is 0 to 20 degrees or about 10 degrees) as in the uncompressed condition (See FIG. 15B). This inward bending of the retaining portions 414 as indicated by arrow 2020 acts to retain the docking station 10 in the circulatory system. The retaining portions 414 are at the wider inflow end portion 12 and outflow end portion 14 and press against the inner surface 416. The flared retaining portions 414 engage into the surrounding anatomy in the circulatory system, such as the pulmonic space. In one exemplary embodiment, the flares serve as a stop, which locks the device in place. When an axial force is applied to the docking station 10, the flared retaining portions 414 are pushed by the force into the surrounding tissue to resist migration of the stent as described in more detail below. In a specific embodiment, the docking station generally has an hourglass shape, with wider distal and proximal end portions that have the flared retaining portion and a narrow, banded waist in between the ends, into which the valve is expanded.

Figure 22:
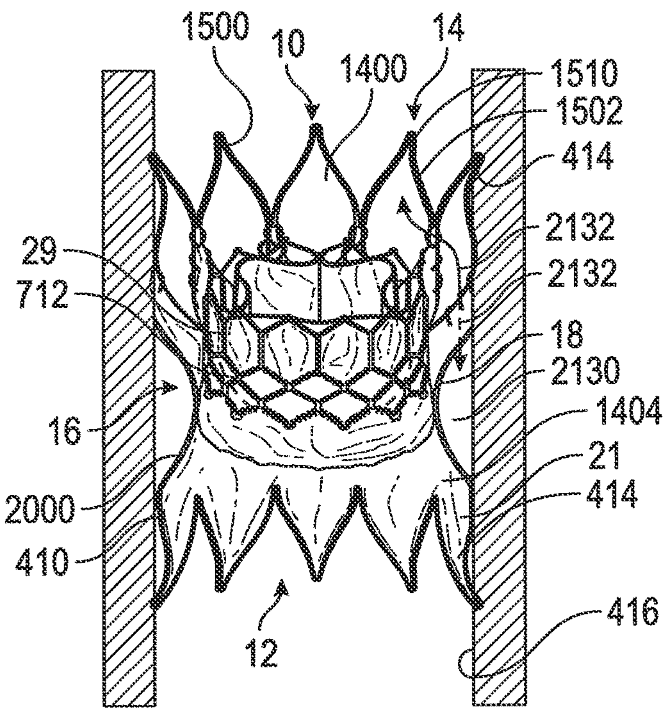
FIG. 22 illustrates a perspective view of the docking station and valve illustrated by FIG. 19 when implanted in a vessel of the circulatory system.

FIG. 22 illustrates the docking station 10 deployed in the circulatory system and a valve 29 deployed in the docking station 10. After the docking station 10 is deployed, the valve 29 is in a compressed form and is introduced into the valve seat 18 of the docking station 10. The valve 29 is expanded in the docking station, such that the valve 29 engages the valve seat 18. In the example illustrated by FIG. 22, the docking station 10 is longer than the valve. However, in one embodiment, the docking station 10 can be the same length or shorter than the length of the valve 29.

The valve 29 can be delivered to the site of the docking station via conventional means, such as by balloon or mechanical expansion or by self-expansion. When the valve 29 is expanded, it nests in the valve seat of the docking station 10. In one embodiment, the banded waist is slightly elastic and exerts an elastic force against the valve 29, to help hold the THV in place.

Figure 23A:
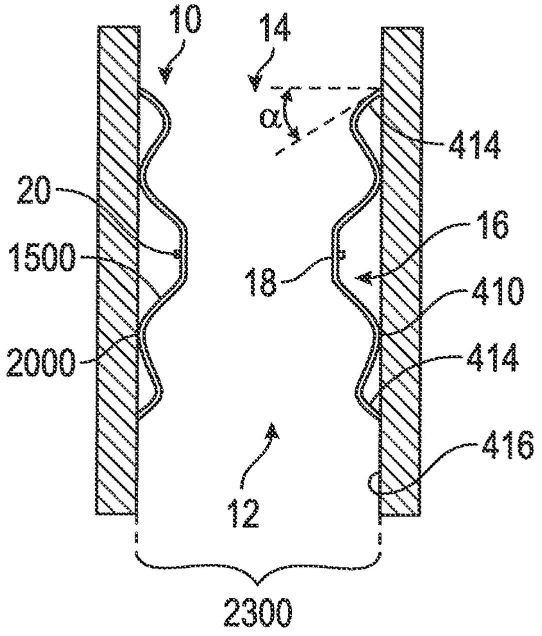
FIGS. 23A and 23B illustrate side profiles of the docking station illustrated by FIG. 18 when implanted in different size vessels of the circulatory system.
Figure 23B:
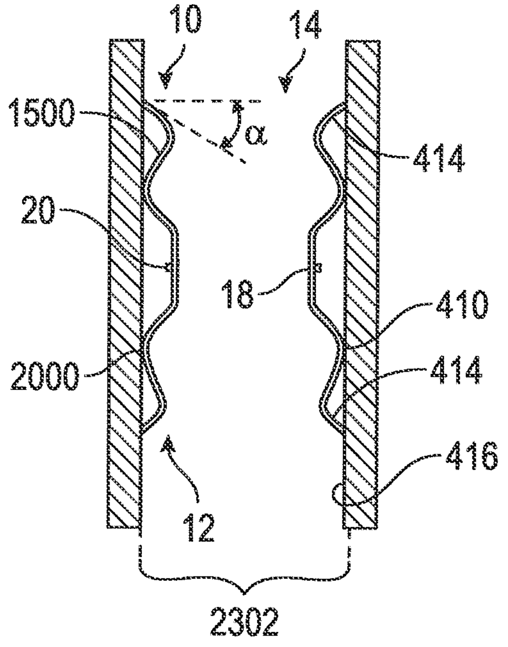

FIGS. 23A and 23B illustrate that the docking station 10 can be used to adapt a variety of different sizes of circulatory system anatomies for implantation of a valve 29 having a consistent size. In the example of FIGS. 23A and 23B, the same size docking station 10 is deployed in two different sized vessels 2300, 2302, such as two differently sized pulmonary arteries PA. In the example, the vessel 2300 illustrated by FIG. 23A has a larger effective diameter than the vessel 2302 illustrated by FIG. 23B. (Note that in this patent application the size of the anatomy of the circulatory system is referred to by the term "diameter" or "effective diameter." The anatomy of the circulatory system is often not circular. The terms "diameter" and "effective diameter" herein refers to the diameter of a circle or disc that could be deformed to fit within the non-circular anatomy.) In the example illustrated by FIGS. 23A and 23B, the sealing portion 410 and the retaining portions 414 conform to contact each vessel 2300, 2302. However, the valve seat 18 remains the same size, even though the sealing portion 410 and the retaining portions 414 are compressed. In this manner, the docking station 10 adapts a wide variety of different anatomical sizes for implantation of a standard or single sized valve. For example, the docking station can conform to vessel diameters of 25 mm and 40 mm, such as 27 mm and 38 mm and provide a constant or substantially constant diameter valve seat of 24 mm to 30 mm, such as 27 mm to 28 mm. However, the valve seat 18 can be adapted for applications where the vessel diameter is larger or smaller than 25 mm to 40 mm and provide valve seats that are larger or smaller than 24 mm to 30 mm.

Referring to FIGS. 23A and 23B, a band 20 maintains a constant or substantially constant diameter of the valve seat 18, even as the proximal and distal ends of the docking station expand to respective diameters necessary to engage with the inside surface 416. The diameter of the pulmonary artery PA can vary considerably from patient to patient, but the valve seat 18 in the deployed configuration consistently has a diameter that is within an acceptable range for the valve 29.

Figure 24:
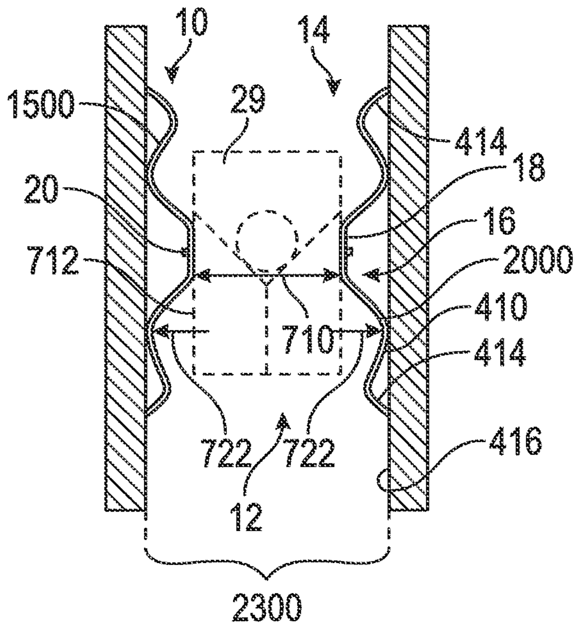
FIGS. 24 and 25 illustrate side profiles of the docking station illustrated by FIG. 18 when implanted in different sized vessels of the circulatory system with a schematically illustrated transcatheter heart valve having the same size installed or deployed in each docking station.
Figure 25:
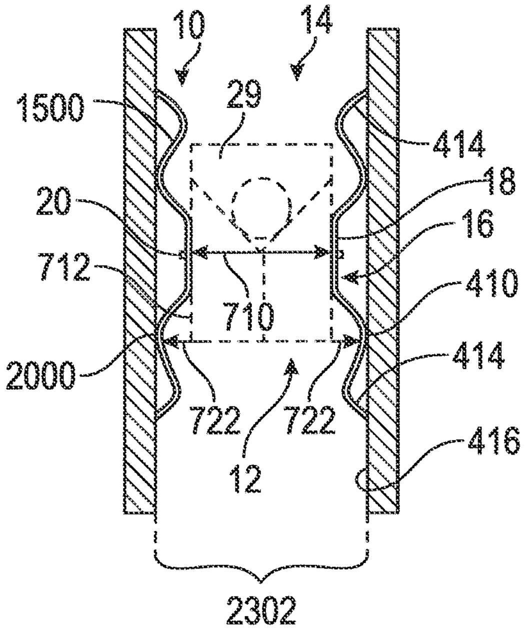

FIGS. 24 and 25 illustrate side profiles of the docking station 10 illustrated by FIG. 18 when implanted in different sized vessels 2300, 2302 of the circulatory system with a schematically illustrated transcatheter heart valve 29 having the same size installed or deployed in each docking station 10. In this example, the docking station 10 both accommodates vessels 2300, 2302 having a variety of different sizes and acts as an isolator that prevents or substantially prevents radial outward forces of the valve 29 from being transferred to the vessels. The valve seat 18 is not expanded radially outwardly or is not substantially expanded radially outward by the radially outward force of the valve 29 and the anchoring/retaining portions 414 and the sealing portions 410 impart only relatively small radially outward force on the vessels 2300, 2302 (as compared to the radially outward force applied to the valve seat 18 by the valve 29), even when the docking station is deployed in a vessel 2302 having a smaller diameter.

In the example illustrated by FIGS. 24 and 25, the stent or frame 712 of the valve 29 expands radially outward or is expanded radially outward to import the high force 710 on the valve seat 18 of the docking station 10. This high radially outward force 710 secures the valve 29 to the valve seat 18 of the docking station 10. However, since the valve seat 18 is not expanded or is not substantially expanded by the force 710, the force 710 is isolated from the circulatory system, rather than being used to secure the docking station in the circulatory system.

In an exemplary embodiment, the radially outward force 722 of the sealing portions 410 to both the larger vessel 2300 and the smaller vessel is substantially smaller than the radially outward force 710 applied by the valve 29 to the valve seat 18. For example, for the smallest vessel to be adapted by the docking station 10 for valve implantation, the radially outward sealing force 722 can be less than ½ the radially outward force 710 applied by the valve, less than ⅓ the radially outward force 710 applied by the valve, less than ¼ the radially outward force 710 applied by the valve, less than ⅛, or even less than ¹⁄₁₀ the radially outward force 710 applied by the valve. In one exemplary embodiment, the radially outward force 722 of the sealing portions 410 is selected to provide a seal between the inner surface 416 and the sealing portion 410, but is not sufficient by itself to retain the position of the valve 29 and docking station 10 in the circulatory system. In one embodiment, the radially outward force 722 is sufficient to retain the position of the valve 29 and docking station 10 in the circulatory system.

In an exemplary embodiment, the docking station 10 illustrated by FIG. 18 also includes anchoring/retaining portions 414 that apply radially outward forces 720 that are substantially smaller than the radially outward force 710 applied by the valve 29 to the valve seat 18. For example, for the smallest vessel to be adapted by the docking station 10 for valve implantation, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than ¹⁄₁₀ the radially outward force 710 applied by the valve. In one embodiment, the radially outward force 720 of the anchoring/retaining portions 414 is not sufficient by itself to retain the position of the valve 29 and docking station 10 in the circulatory system. In one embodiment, the radially outward force 720 is sufficient to retain the position of the valve 29 and docking station 10 in the circulatory system.

In one exemplary embodiment, the docking station 10 frame 1500 is made from an elastic or superelastic material or metal. One such metal is nitinol. When the frame 1500 of the docking station 10 is made from a lattice of metal struts, the body can have the characteristics of a spring. Referring to FIG. 7C, like a spring, when the frame 1500 of the docking station 10 illustrated by FIGS. 24 and 25 is unconstrained and allowed to relax to its largest diameter the frame of the docking station applies little or no radially outward force. As the frame 1500 of the docking station 10 is compressed, like a spring, the radially outward force applied by the docking station increases. As is illustrated by FIG. 7C, in one exemplary embodiment the relationship of the radially outward force of the docking station frame 1500 to the expanded diameter of the docking station is non-linear, though it can also be linear. In the example illustrated by FIG. 7C, the curve 750 illustrates the relationship between the radially outward force exerted by the docking station 10 and the compressed diameter of the docking station. In the region 752, the curve 750 has a low slope. In this region 752 the radially outward force is low and changes only a small amount. In one exemplary embodiment, the region 752 corresponds to a diameter between 25 mm and 40 mm, such as between 27 mm and 38 mm. The radially outward force is small in the region 752, but is not zero. In the region 754, the curve 750 has a higher slope. In this region 754 the radially outward force increases significantly as the docking station is compressed. In one exemplary embodiment, the body of the stent is constructed to be in the low slope region 752 for both a largest vessel 2300 (FIG. 24) accommodated by the docking station 10 and a smallest vessel 2302 (FIG. 25). This allows the sealing portions 410 to apply only a small radially outward force to the inner surface 416 of the circulatory system over a wide range of diameters.

Figure 26B:
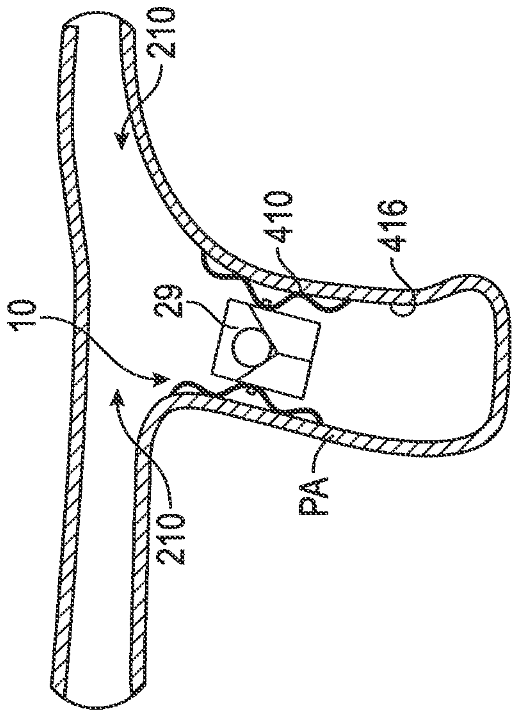
FIG. 26B is a sectional view illustrating a side profile of an exemplary embodiment of a docking station placed in a pulmonary artery and a schematically illustrated valve placed in the docking station.
Figure 26A:
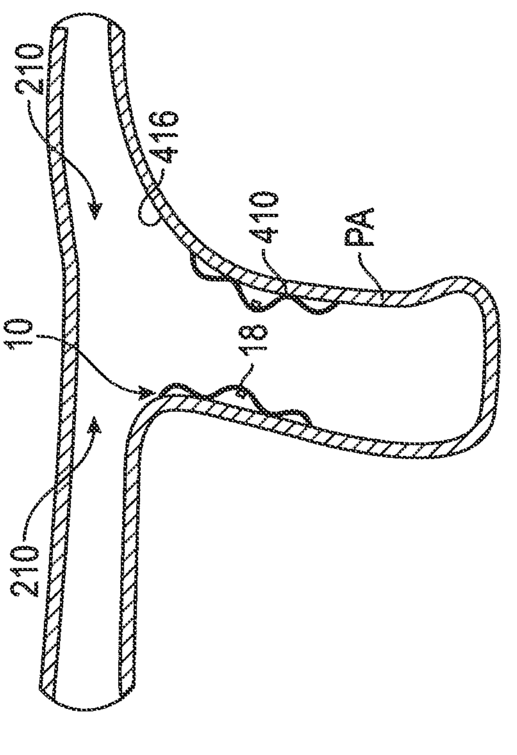
FIG. 26A is a sectional view illustrating a side profile of an exemplary embodiment of a docking station placed in a pulmonary artery.
Figure 26C:
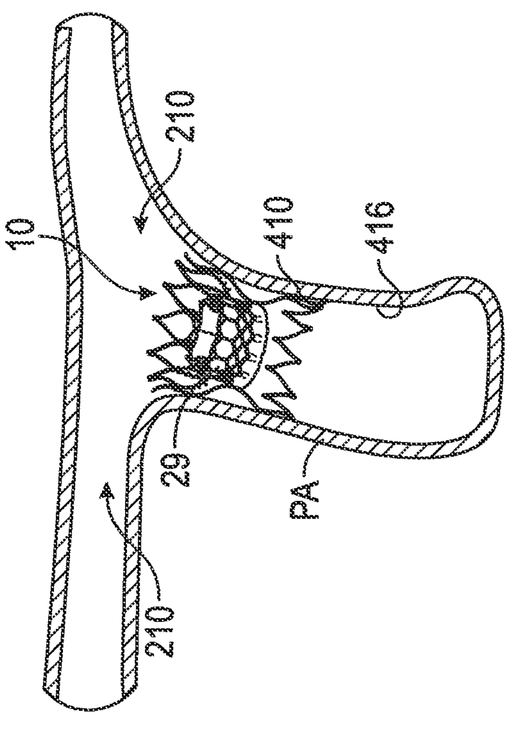
FIG. 26C is a sectional view illustrating an exemplary embodiment of a docking station placed in a pulmonary artery and a valve placed in the docking station.

FIGS. 26A-26C illustrate the docking station 10 of FIG. 18 implanted in a pulmonary artery. FIG. 26A illustrates the profile of the docking station 10 implanted in the pulmonary artery PA. FIG. 26B illustrates the profile of the docking station 10 implanted in the pulmonary artery PA with a schematically illustrated valve 29 installed or deployed in the docking station 10. FIG. 26C illustrates the docking station 10 and valve 29 as depicted in FIG. 22 implanted in the pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA. The docking station 10 is illustrated as being positioned below the pulmonary artery bifurcation or branch. However, often the docking station 10 will be positioned such that the end 14 extends into the pulmonary artery bifurcation 210. When it is contemplated that the docking station 10 will extend into the pulmonary artery bifurcation, the docking station 10 can have a blood permeable portion 1400 (e.g., as shown in FIG. 21).

Figure 27:
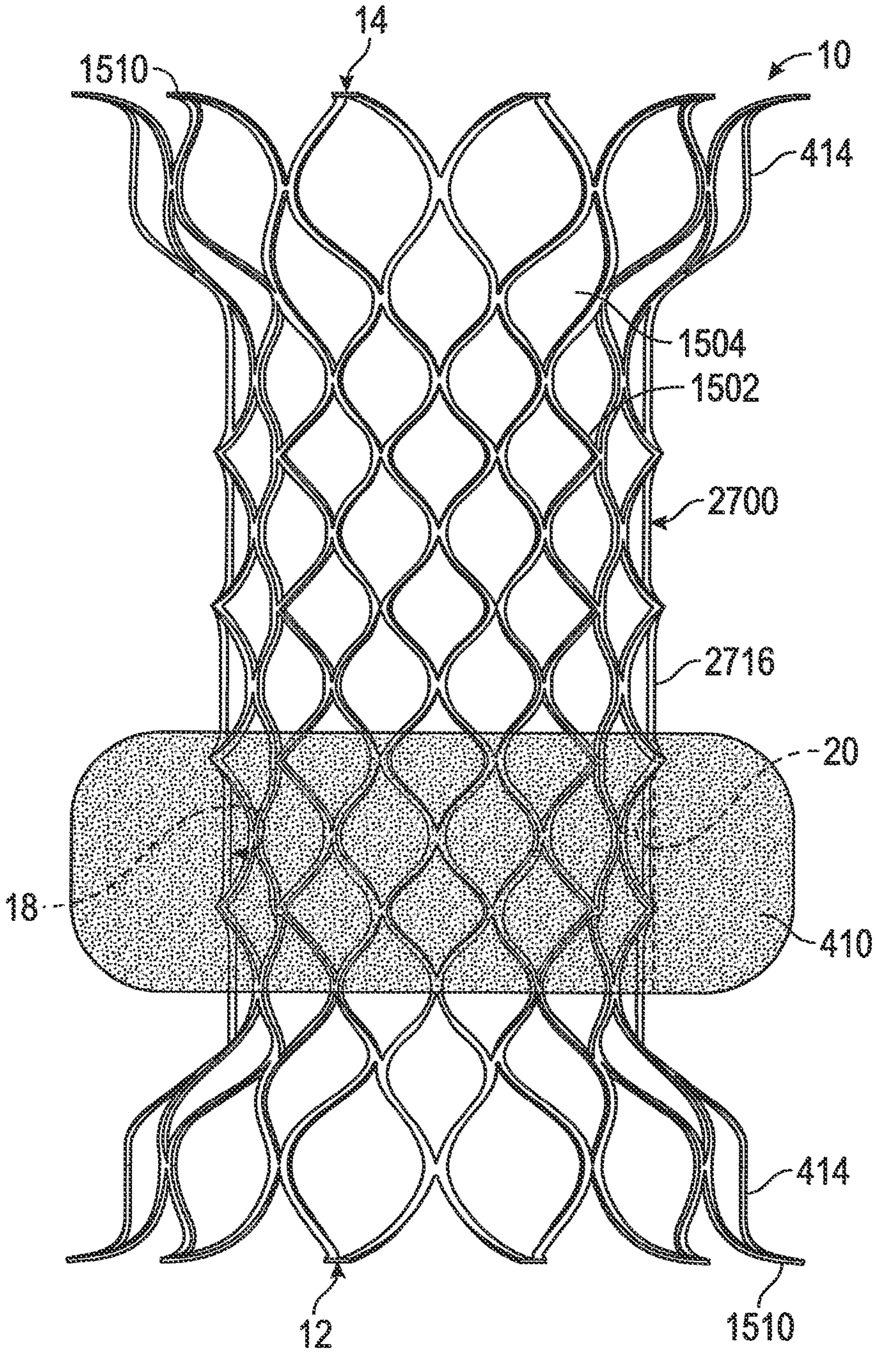
FIG. 27 is a side view of an exemplary embodiment of a docking station.

FIG. 27 illustrates another exemplary embodiment of a docking station 10. The docking station 10 includes a frame 2700 and an external sealing portion 410. The frame 2700 or body can take a wide variety of different forms and FIG. 27 illustrates just one of the many possible configurations. In the example illustrated by FIG. 27 the docking station 10 has a relatively wider proximal inflow end 12 and distal outflow end 14, and an elongated relatively narrower portion 2716. The seat 18 and sealing portion 410 can be provided anywhere along the length of the elongated relatively narrow portion 2716. In the example illustrated by FIG. 27, the frame 2700 of the docking station 10 is preferably a stent comprised of a plurality of metal struts 1502 that form cells 1504. The frame 2700 or portion(s) of the frame can optionally be covered by an impermeable material 21 (e.g., as shown in FIG. 18).

FIG. 27 illustrates the frame 2700 and sealing portion 410 in their unconstrained, expanded condition/configuration or deployed configuration. In this exemplary embodiment, the retaining portions 414 comprise ends or apices 1510 of the metal struts 1502 at the proximal and distal ends 12, 14. The sealing portion 410 can be a separate component that is disposed around the frame 2700 between the retaining portions 414. In the unconstrained condition, the retaining portions 414 extend generally radially outward and can be radially outward of the sealing portion 410.

The docking station 10 illustrated by FIG. 27 can be made from a very resilient or compliant material to accommodate large variations in the anatomy. For example, the docking station can be made from a highly flexible metal (e.g., the frame in the FIG. 27 example) and cloth and/or an open cell foam (e.g., the sealing portion in the FIG. 27 example). An example of a highly resilient metal is nitinol, but other metals and highly resilient or compliant non-metal materials can be used. An example of an open cell foam that can be used is a biocompatible foam, such as a polyurethane foam (e.g., as can be obtained from Biomerix, Rockville, MD). In one embodiment, a foam forming the sealing portion can also form a valve seat on its inner surface.

Still referring to FIG. 27, the frame 2700 and/or the separate sealing portion 410 can include an optional a band 20 to form an unexpandable or substantially unexpandable valve seat 18. In another exemplary embodiment, the frame 2700 can be configured to be substantially unexpandable in the area of the valve seat 18 without the use of a band 20. The optional band 20 stiffens the frame 2700 and/or sealing portion and makes the valve seat relatively unexpandable.

The optional band 20 can take a wide variety of different forms, can be made from a wide variety of different materials, and can be the same as or similar to bands discussed elsewhere in this disclosure. The band 20 can be made of PET, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 can be narrow, such as the suture band in FIG. 18, or can be wider as illustrate by the dashed line in FIG. 27. In one non-limiting example, the valve seat 18 is between 27-28 mm in diameter, although the diameter of the valve seat should be within the operating range of the particular valve 29 that will be secured within the valve seat 18, and can be different than the foregoing example.

Figure 28:
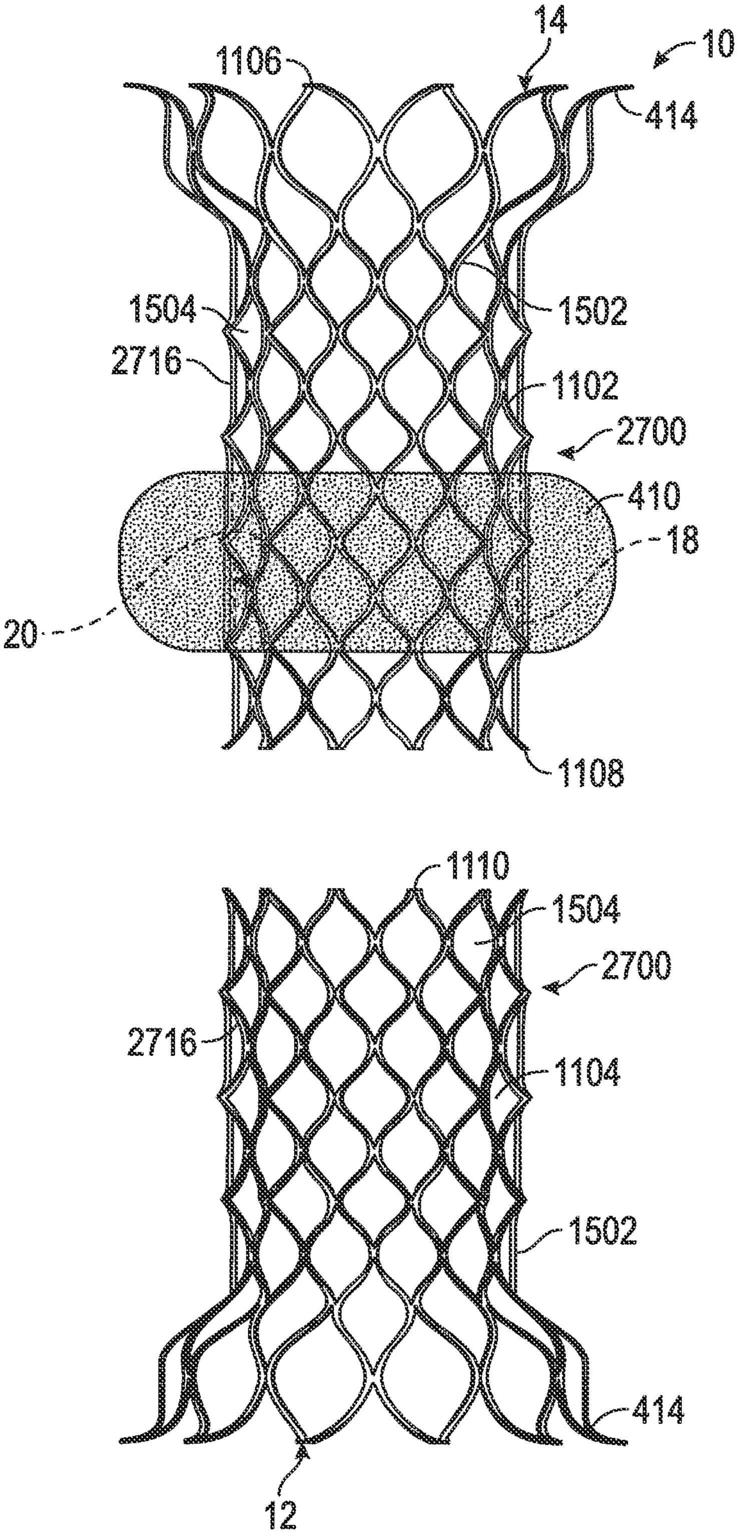
FIG. 28 is a side view of an exemplary embodiment of a telescoping docking station.
Figure 29:
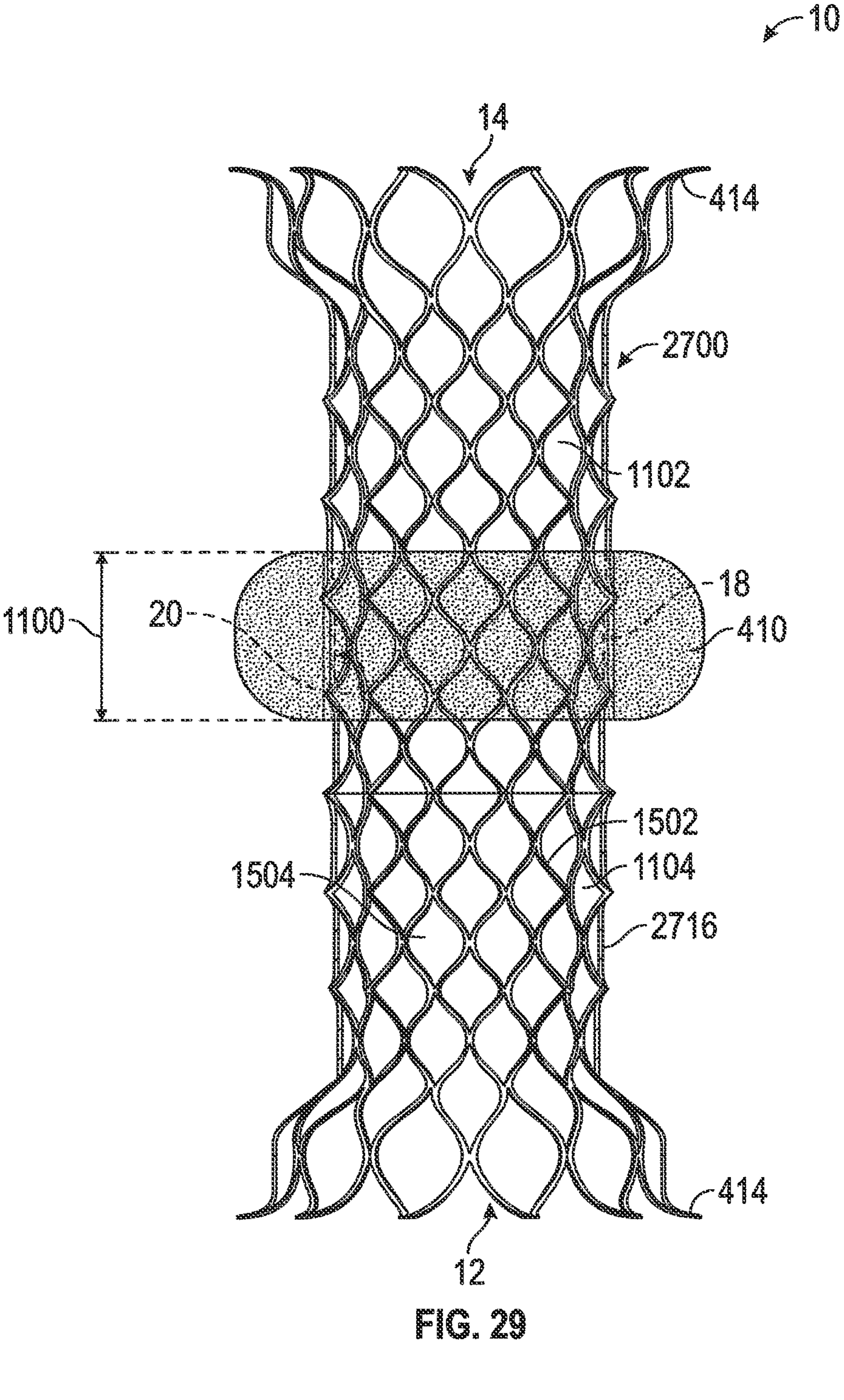
FIG. 29 is a side view of the docking station of FIG. 28 where two parts of the docking station have been telescoped together.

FIGS. 28 and 29 illustrate a modified version of the docking station 10 illustrated by FIG. 27 that is expandable in length. As mentioned above, the length of the pulmonary artery PA and other anatomical structures of the circulatory system can vary greatly from patient to patient. Referring to FIG. 29, in one exemplary embodiment the length of the docking station 10 is adjustable as indicated by arrow 1100. The length can be adjusted in a wide variety of different ways, e.g., it can be adjustable in any of the ways described elsewhere in this disclosure. In the example illustrated by FIGS. 28 and 29, the docking station 10 includes a first half 1102 and a second half 1104. The second half 1104 can be inserted or "telescoped" into the first half 1102. The amount of insertion or "telescoping" sets the length of the docking station 10.

In one exemplary embodiment, the length of the docking station 10 is adjusted in the pulmonary artery PA by first deploying the first half 1102 of the docking station 10 in the pulmonary artery. For example, the first half 1102 can be positioned and expanded such that a distal end 1106 of the first half is aligned with or extends somewhat past the branch of the pulmonary artery. After the first half 1102 is expanded in the pulmonary artery, the compressed second half 1104 is positioned with a distal end 1110 disposed in the proximal end 1108 of the first half 1102. The position of the second half 1104 is selected such that the sealing portion 410 and retaining portion 414 will make contact with the pulmonary artery and set the position of the docking station 10 in the pulmonary artery. Once properly positioned, the second half 1104 is expanded. The distal end of 1110 of the second half 1104 frictionally engages the proximal end 1108 of the first half to secure the two halves 1102, 1104 together. In one embodiment, a lock(s), locking mechanism, suture(s), interlacing, link(s) and/or other attachment device/mechanism can (also or alternatively) be used to secure the two halves together.

In the examples illustrated by FIGS. 28 and 29, the seat 18 and the sealing portion 410 are included on the first half 1102 of the docking station 10. However, in other embodiments the seat 18 and/or the sealing portion(s) 410 can be included on the second half 1104 or in different locations on the first half and/or the second half.

Figure 30:
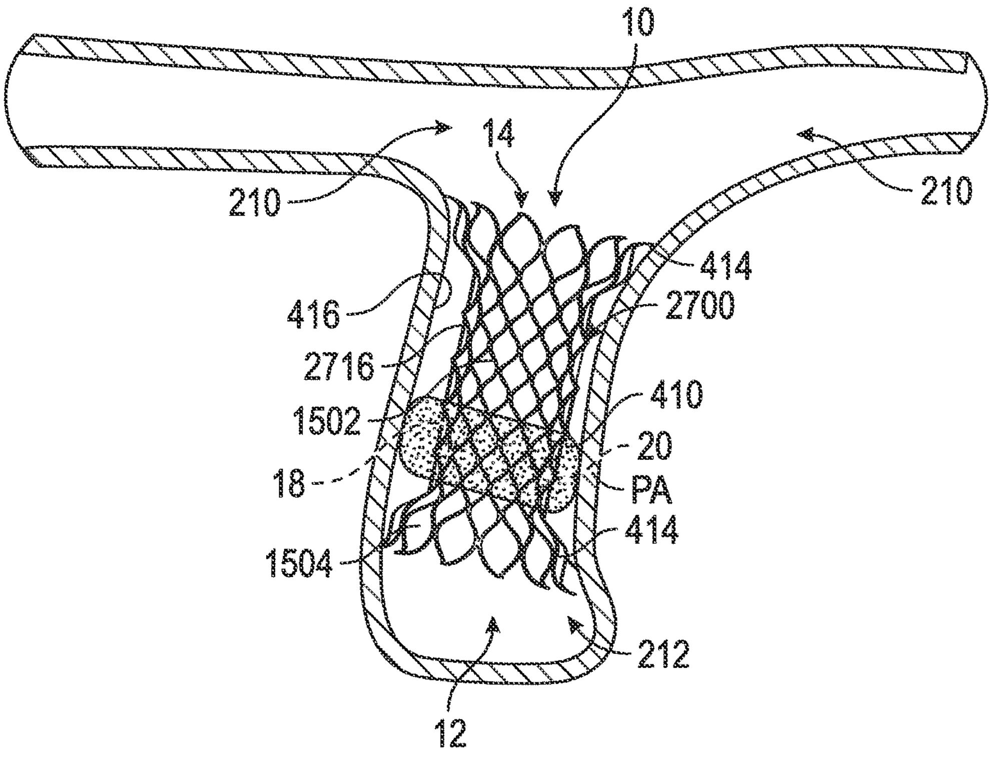
FIG. 30 is a sectional view illustrating a docking station placed in a pulmonary artery.
Figure 31A:
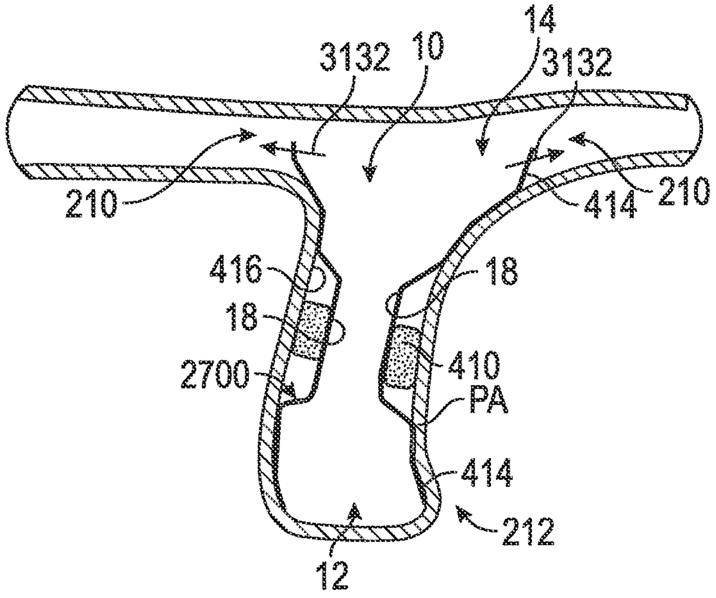
FIG. 31A is a sectional view illustrating a side profile of an exemplary embodiment of a docking station placed in a pulmonary artery.

FIGS. 30 and 31A illustrate the docking station 10 of FIG. 27 of FIGS. 28 and 29 implanted in the circulatory system, such as in the pulmonary artery PA. The sealing portion 410 provides a seal between the docking station 10 and an interior surface 416 of the pulmonary artery PA. In the example of FIGS. 30 and 31A, the sealing portion 410 is an expanding material, such as an expandable open cell foam over the frame 2700. In an exemplary embodiment, the sealing portion 410 coincides or at least overlaps with the valve seat 18. When the sealing portion 410 does not overlap with the valve seat 18, an impermeable material 21 can be provided over a portion of the frame (e.g., from the sealing portion 410 to the valve seat 18 to make the docking station impermeable from the sealing portion 410 to the valve seat 18). Whether the sealing portion 410 overlaps with the valve seat 18 or an impermeable material is provided from the sealing portion 410 to the valve seat 18, all blood flowing in the direction from the inflow end 12 toward the outflow end 14 is directed to the valve seat 18 (and valve 29 once installed or deployed in the valve seat).

In one exemplary embodiment of a docking station 10, at least the outflow portion 14 of the frame 2700 is relatively open. Referring to FIG. 31A, this allows the docking station 10 to be placed higher in the pulmonary artery without restricting blood flow. For example, the open cells 1504 can extend into the branch or bifurcation of the pulmonary artery and not impede or not significantly impede the flow of blood past the branch. The open cells 1504 allow blood to flow through the frame 1500 as indicated by arrows 3132 in FIG. 31A.

In the example illustrated by FIGS. 30 and 31A, the docking station 10 is retained in the pulmonary artery PA by expanding one or more of the retaining portions 414 radially outward into areas 210, 212 of the pulmonary artery PA where the inside surface 416 also extends outward. For example, the retaining portions 414 can be configured to extend radially outward into the pulmonary bifurcation 210 and/or the opening 212 of the pulmonary artery to the right ventricle RV. In one exemplary embodiment, the docking station 10 can be an adjustable docking station. For example, docking station 10 can be a telescoping docking station as illustrated by FIG. 28 and the first portion 1102 is deployed such that the retaining portions 414 extend radially outward into the pulmonary bifurcation 210). The second portion 1104 can then be positioned in the first portion 1102 such that its retaining portions 414 coincide with the opening of the pulmonary artery or another outwardly extending area of the pulmonary artery. Once in position, the second portion 1104 can be expanded to secure the second section 1104 to the first section 1102 and to secure the second section to the pulmonary artery at the opening 212 or other outwardly extending area.

Figure 31B:
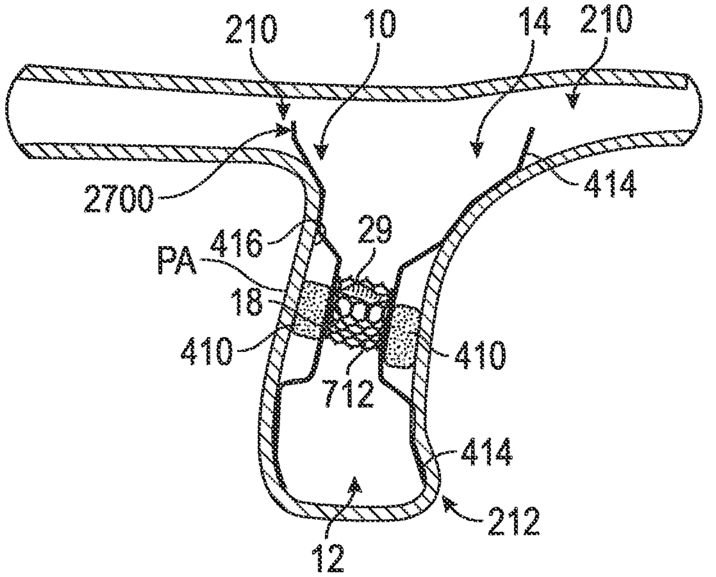
FIG. 31B is a sectional view illustrating a side profile of an exemplary embodiment of a docking station placed in a pulmonary artery and a valve placed in the docking station.

Referring to FIG. 31B, the valve seat 18 provides a supporting surface for installing or deploying a valve 29 in the docking station 10. The valve can be installed or deployed in the valve seat using the steps disclosed here or elsewhere in this disclosure. The anchoring/retaining portions 414 retain the docking station 10 at the implantation or deployed site/position in the circulatory system. After the docking station 10 is deployed, the valve 29 is in a compressed form and can be introduced into the valve seat 18 of the docking station 10. The valve 29 can be expanded in the docking station, such that the valve 29 engages the valve seat 18. The valve 29 can be delivered to the site of the docking station via conventional means, such as by balloon or mechanical expansion or by self-expansion. When the valve 29 is expanded, it nests in the valve seat of the docking station 10.

Figure 32A:
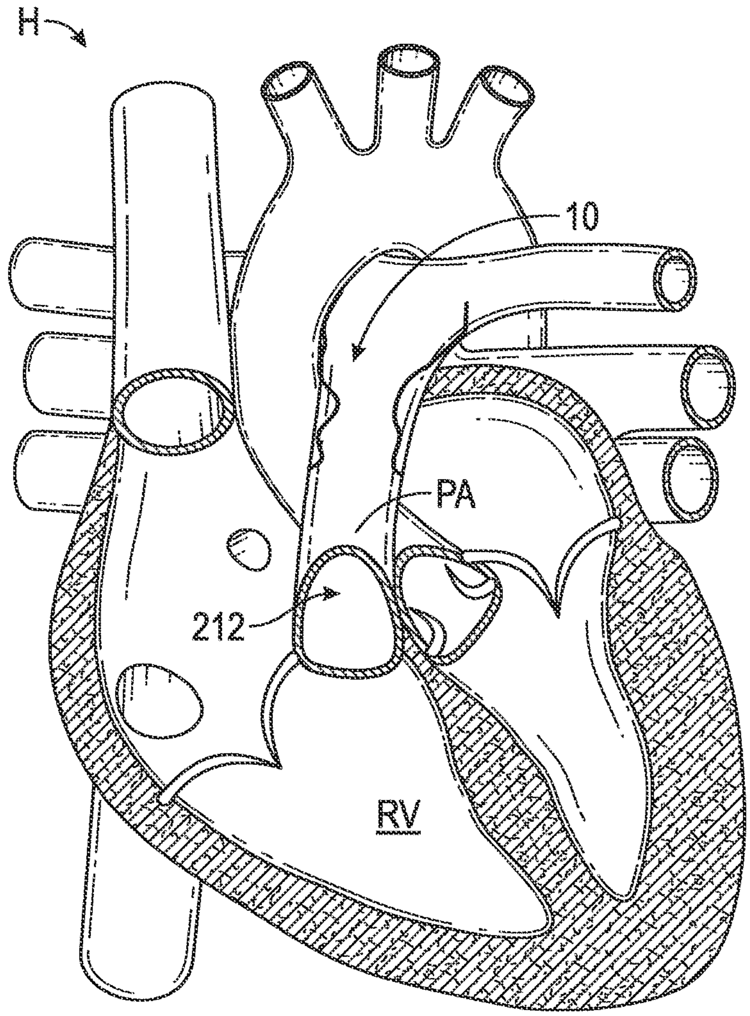
FIG. 32A is a cutaway view of the human heart in a systolic phase with a docking station deployed in a pulmonary artery.
Figure 32B:
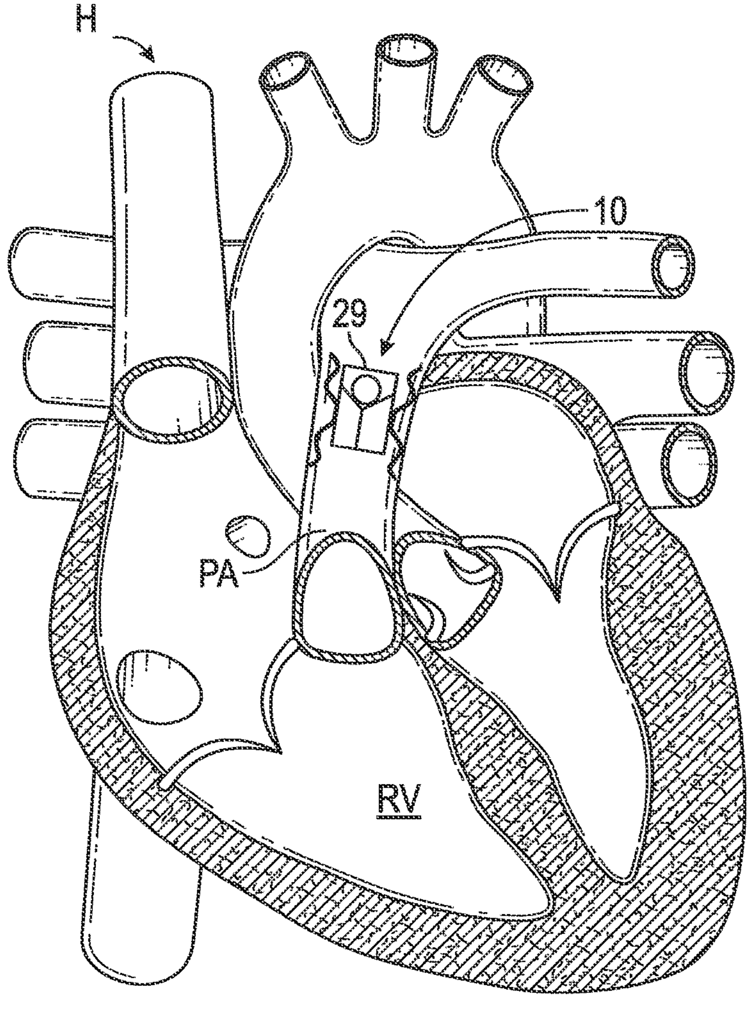
FIG. 32B is a cutaway view of the human heart in a systolic phase with a docking station and transcatheter heart valve deployed in a pulmonary artery.
Figure 33A:
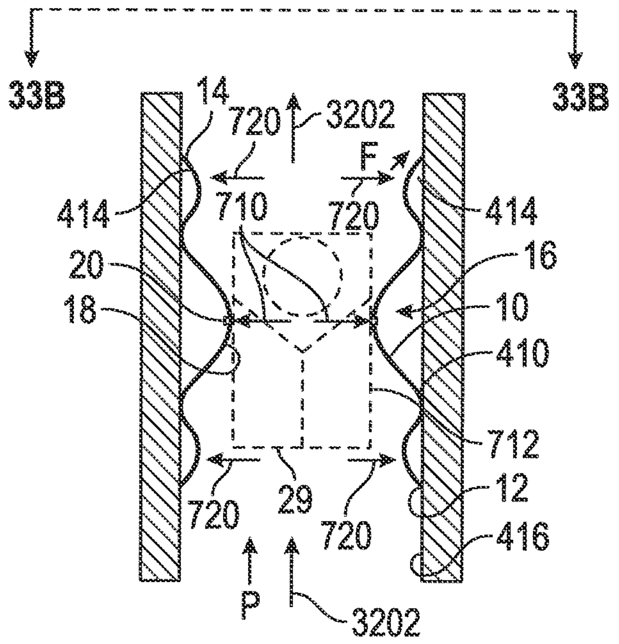
FIG. 33A is an enlarged schematic illustration of the docking station and transcatheter heart valve of FIG. 32B when the heart is in the systolic phase.
Figure 33B:
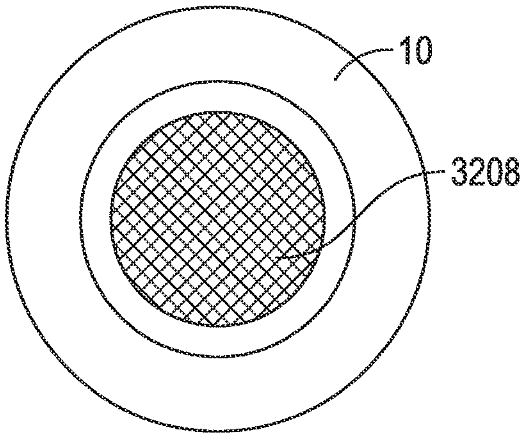
FIG. 33B is a view taken in the direction indicated by lines 33B-33B in FIG. 33A.

Referring to FIG. 32A, the docking station illustrated by FIG. 18 is deployed in the pulmonary artery PA of a heart H. FIG. 32B illustrates a generically illustrated valve 29 deployed in the docking station 10 illustrated by FIG. 32A. In FIGS. 32A and 32B, the heart is in the systolic phase. FIG. 33A is an enlarged representation of the docking station 10 and valve 29 in the pulmonary artery PA of FIG. 32B. When the heart is in the systolic phase, the valve 29 opens. Blood flows from the right ventricle RV and through the pulmonary artery PA, docking station 10, and valve 29 as indicated by arrows 3202. FIG. 33B illustrates space 3208 that represents the valve 29 being open when the heart is in the systolic phase. FIG. 33B does not show the interface between the docking station 10 and the pulmonary artery to simplify the drawing. The cross-hatching in FIG. 33B illustrates blood flow through the open valve. In an exemplary embodiment, blood is prevented from flowing between the pulmonary artery PA and the docking station 10 by the sealing portion 410 and blood is prevented from flowing between the docking station 10 and the valve 29 by seating of the valve 29 in the seat 18 of the docking station 10. In this example, blood is substantially only or only able to flow through the valve 29 when the heart is in the systolic phase.

Figure 34:
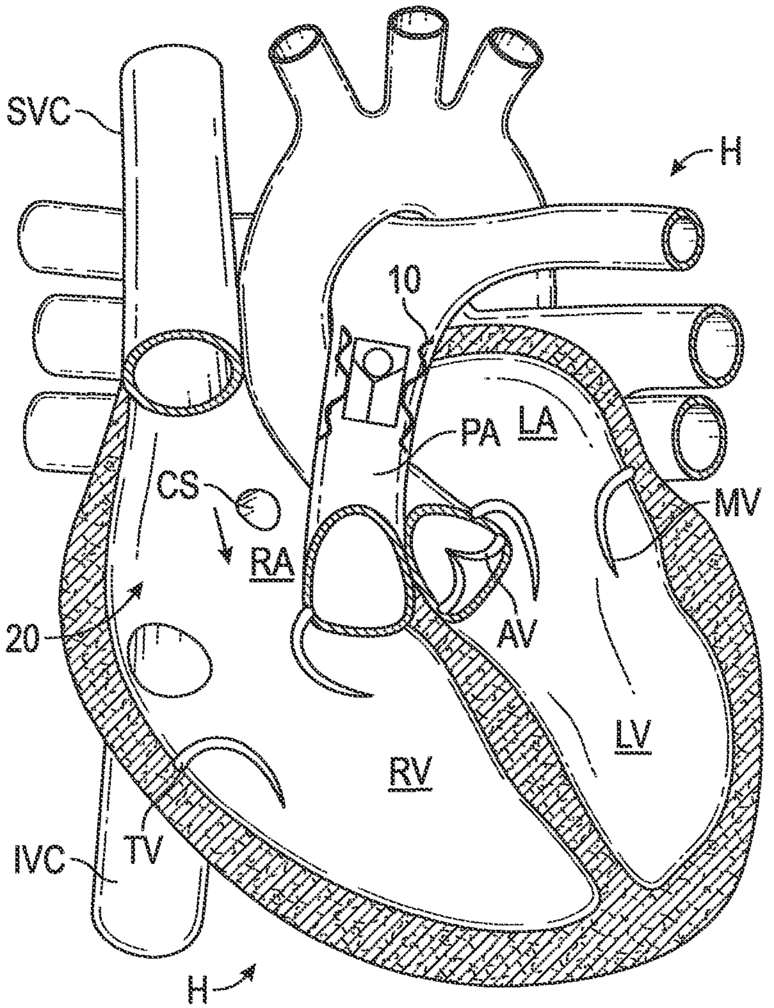
FIG. 34 is a cutaway view of the human heart, docking station, and transcatheter heart valve deployed in the pulmonary artery illustrated by FIG. 32B when the heart is in the diastolic phase.
Figure 35A:
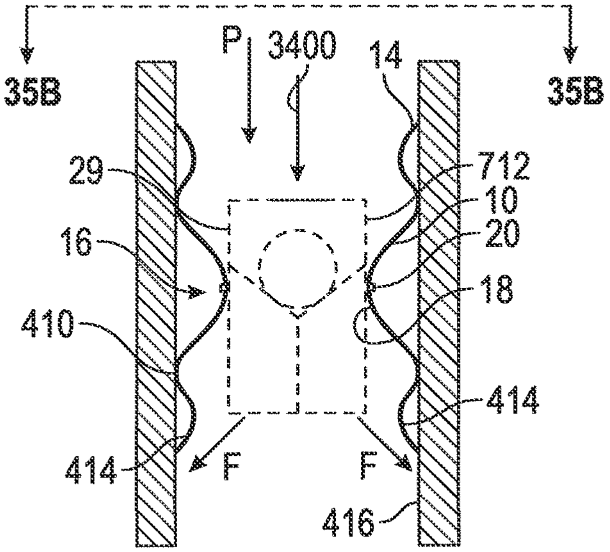
FIG. 35A is an enlarged schematic illustration of the docking station and transcatheter heart valve of FIG. 34 when the heart is in the diastolic phase.
Figure 35B:
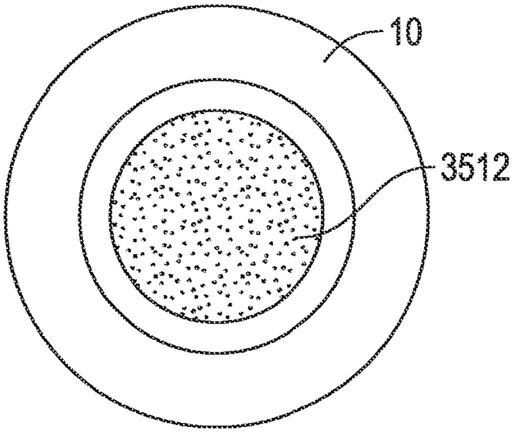
FIG. 35B is a view taken in the direction indicated by lines 35B-35B in FIG. 35A.

FIG. 34 illustrates the valve 29, docking station 10 and heart H illustrated by FIG. 32B, when the heart is in the diastolic phase. Referring to FIGS. 34, when the heart is in the diastolic phase, the valve 29 closes. FIG. 35A is an enlarged representation of the docking station 10 and valve 29 in the pulmonary artery of FIG. 34. Blood flow in the pulmonary artery PA above the valve 29 (i.e. in the pulmonary branch 210) is blocked by the valve 29 being closed and blocking blood flow as indicated by arrow 3400. The solid area 3512 in FIG. 35B represents the valve 29 being closed when the heart is in the diastolic phase.

Referring to FIG. 33A, the radially outward force 720 of the anchoring/retaining portions 414 to the inside surface 416 is substantially smaller than the radially outward force 710 applied by the valve 29 to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than 1/10 the radially outward force 710 applied by the valve.

Referring to FIGS. 33A and 35A, in one exemplary embodiment the radially outward force 720 of the retaining portions 414 is not sufficient by itself to retain the position of the valve 29 and docking station 10 in the circulatory system. Rather, the pressure of the blood in the space 3208 is used to enhance the retention of the retaining portions 414 to the inside surface 416. Referring again to FIG. 33A, when the heart is in the systolic phase, the valve 29 is open and blood flows through the valve as indicated by arrows 3202. Since the valve 29 is open and blood flows through the valve 29, the pressure P applied to the docking station 10 and valve 29 by the blood is low as indicated by the small P and arrow in FIG. 33A. Even though small, the pressure P forces the docking station and its upper retaining portions 414 against the surface 416 generally in the direction indicated by arrow F (the small F represents a relatively low force). This blood flow assisted force F applied by the retaining portions F to the surface 416 prevents the docking station 10 and valve 29 from moving in the direction 3202 of blood flow in the systolic phase of the heart H.

Referring to FIG. 35A, when the heart is in the diastolic phase, the valve 29 is closed and blood flow is blocked as indicated by arrow 3400. Since the valve 29 is closed and the valve 29 and docking station 10 block the flow of blood, the pressure P applied to the docking station 10 and valve 29 by the blood is high as indicated by the large arrow P in FIG. 35A. This large pressure P forces the lower retaining portions 414 against the surface 416 generally in the direction indicated by the large arrows F (the large F represents a relatively larger force). This blood flow assisted force F applied by the retaining portions F to the surface 416 prevents the docking station 10 and valve 29 from moving in the direction indicated by arrow 3400.

Referring to FIGS. 33A and 35A, since the force applied by the upper and lower retaining portions 414 is determined by amount of pressure applied to the valve 29 and docking station 10 by the blood, the force applied to the surface 416 is automatically proportioned. That is, the upper retaining portions are less forcefully pressed against the surface 416 when the heart is in the systolic phase than the lower retaining portions are pressed against the surface 416 when the heart is in the diastolic phase. This is because the pressure against the open valve 29 and docking station 10 in the systolic phase is less than the pressure against the closed valve and docking station in the diastolic phase.

Figure 36A:
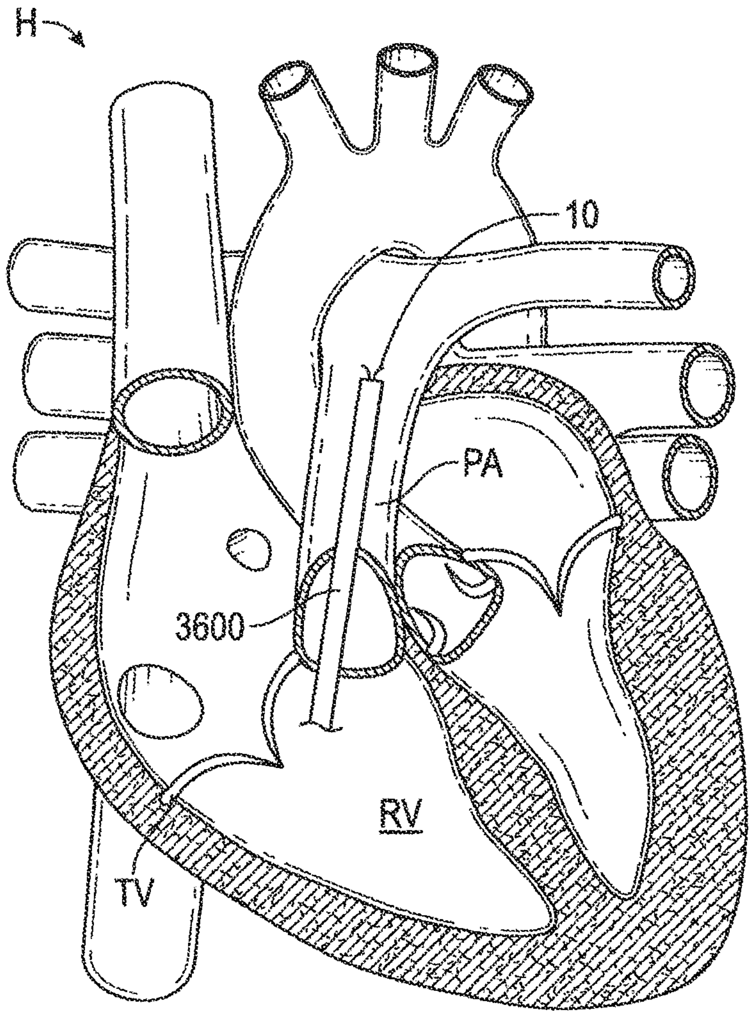
FIG. 36A is a cutaway view of the human heart in a systolic phase with a docking station being deployed in a pulmonary artery.

Methods of treating a subject (e.g., methods of treating heart valve dysfunction/regurgitation/etc.) can include a variety of steps, including steps associated with introducing and deploying a docking station in a desired location/treatment area and introducing and deploying a valve in the docking station. For example, FIG. 36A illustrates the docking station illustrated by FIG. 18 being deployed by a catheter 3600. The docking station 10 can be positioned and deployed in a wide variety of different ways. Access can be gained through the femoral vein or access can be percutaneous. Generally, any vascular path that leads to the pulmonary artery can be used. In one exemplary embodiment, a guidewire followed by a catheter 3600 is advanced to the pulmonary artery PA by way of the femoral vein, inferior vena cava, tricuspid valve and right ventricle RV. The docking station 10 can be placed in the right ventricular outflow tract/pulmonary artery PA to create an artificial conduit and landing zone for a valve (e.g., a transcatheter heart valve) 29.

Figure 36B:
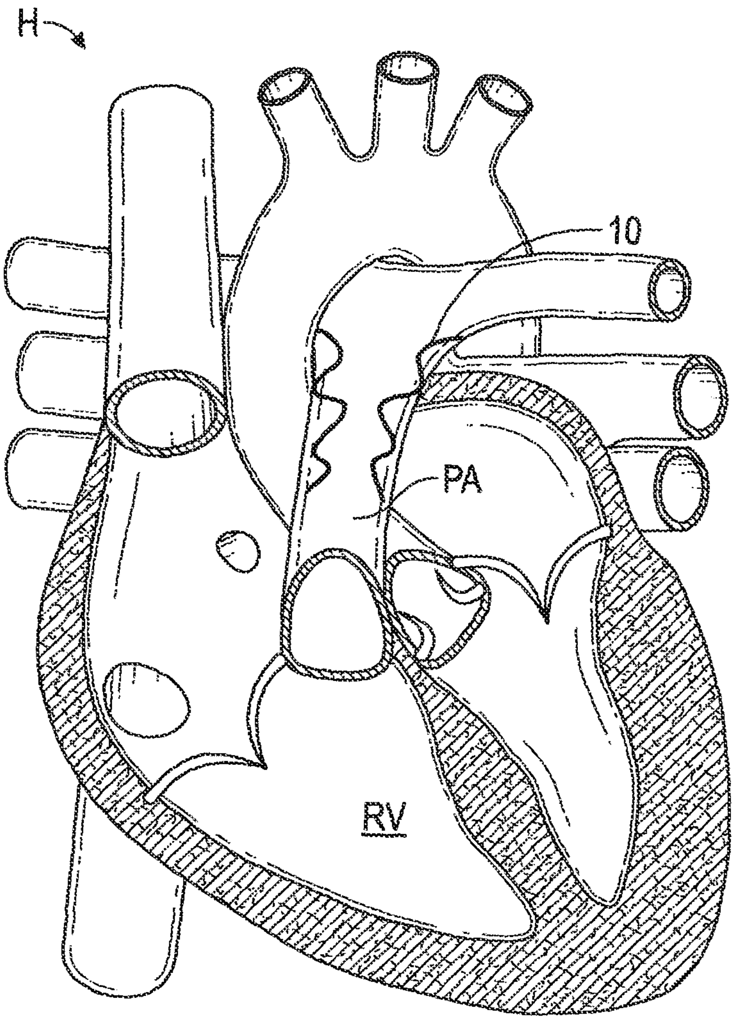
FIG. 36B is a cutaway view of the human heart in a systolic phase with a docking station deployed in a pulmonary artery.
Figure 36C:
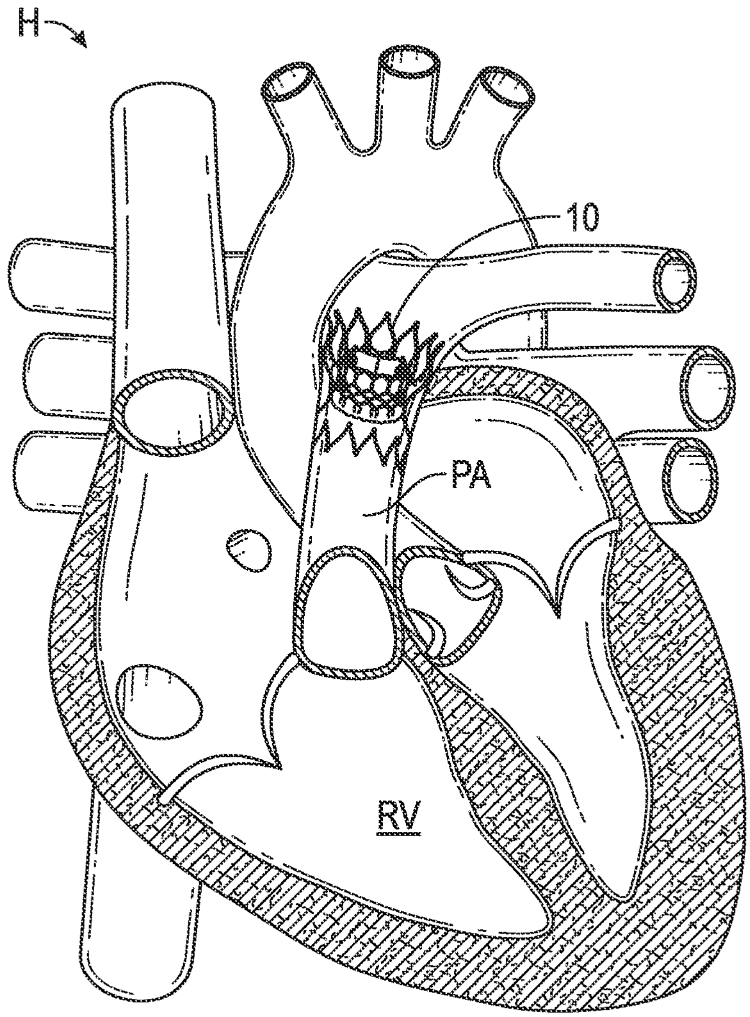
FIG. 36C is a cutaway view of the human heart in a systolic phase with a docking station and transcatheter heart valve deployed in a pulmonary artery.
Figure 37A:
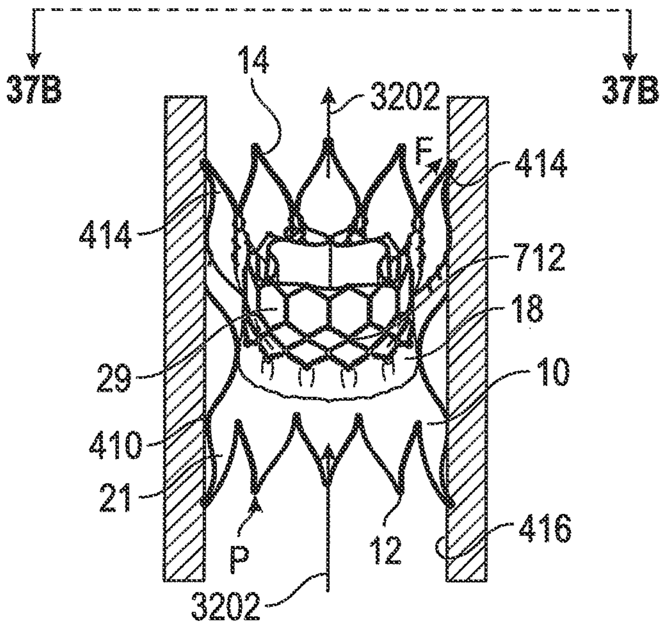
FIG. 37A is an enlarged schematic illustration of the docking station and transcatheter heart valve of FIG. 36C when the heart is in the systolic phase.
Figure 37B:
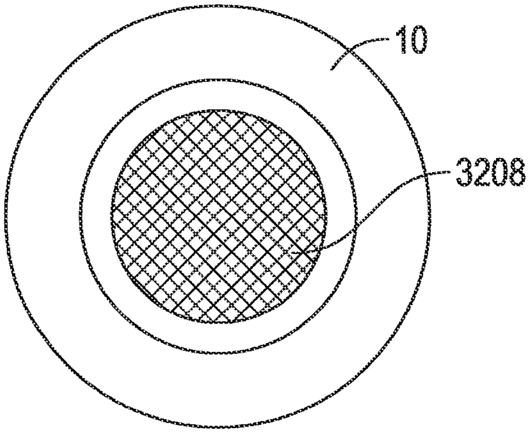
FIG. 37B is a view taken in the direction indicated by lines 37B-37B in FIG. 37A.

Referring to FIG. 36B, the docking station illustrated by FIG. 18 is deployed in the pulmonary artery (PA) of a heart H. FIG. 36C illustrates a valve 29 deployed in the docking station 10 illustrated by FIG. 32A. In the example illustrated by FIGS. 36C, 37A, 38, 39A, and 39B, the valve 29 is depicted as a SAPIEN 3 THV provided by Edwards Lifesciences; however, a variety of other valves can also be used. In FIGS. 36A-36C, the heart is in the systolic phase. FIG. 37A is an enlarged representation of the docking station 10 and valve 29 in the pulmonary artery of FIG. 36C. When the heart is in the systolic phase, the valve (e.g., Sapien 3 valve) is open. Blood flows from the right ventricle RV and through the pulmonary artery PA, docking station 10, and valve as indicated by arrows 3202. FIG. 37B illustrates space 3208 that represents the valve being open when the heart is in the systolic phase. FIG. 37B does not show the interface between the docking station 10 and the pulmonary artery to simplify the drawing. The cross-hatching in FIG. 37B illustrates blood flow through the valve. In an exemplary embodiment, blood is prevented from flowing between the pulmonary artery PA and the docking station 10 by the sealing portion 410 and blood is prevented from flowing between the docking station 10 and the valve by seating of the valve in the seat 18 of the docking station 10. In this example, blood is substantially only or only able to flow through the valve when the heart is in the systolic phase.

Figure 38:
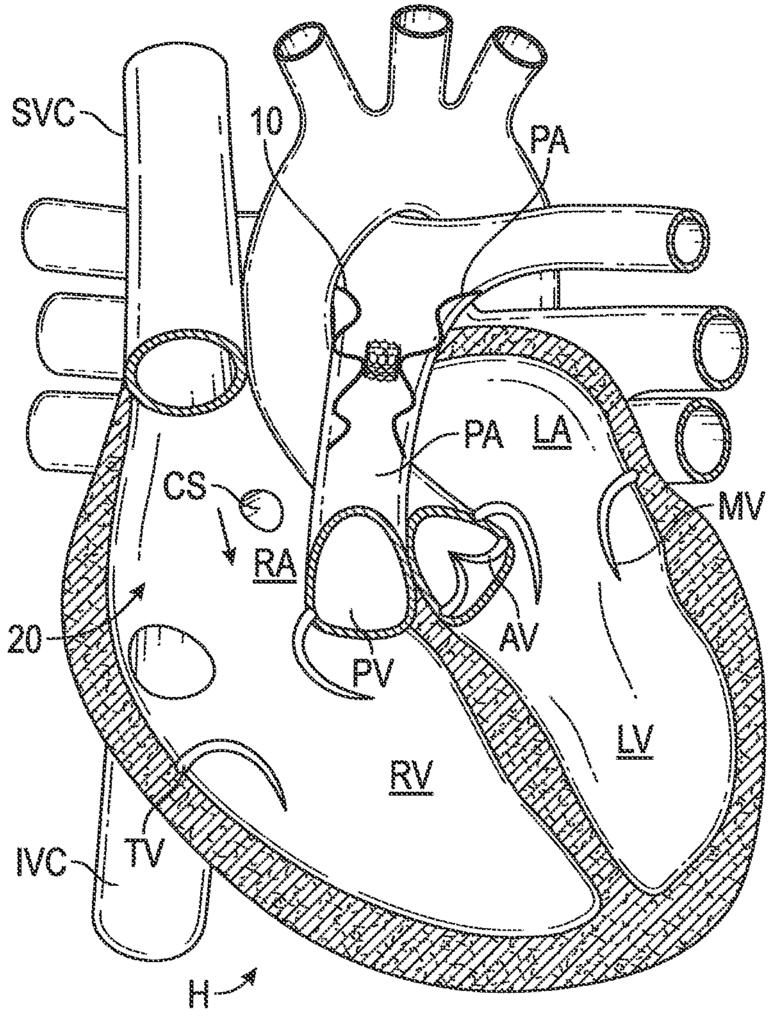
FIG. 38 is a cutaway view of the human heart, docking station, and transcatheter heart valve deployed in the pulmonary artery illustrated by FIG. 36C when the heart is in the diastolic phase.
Figure 39A:
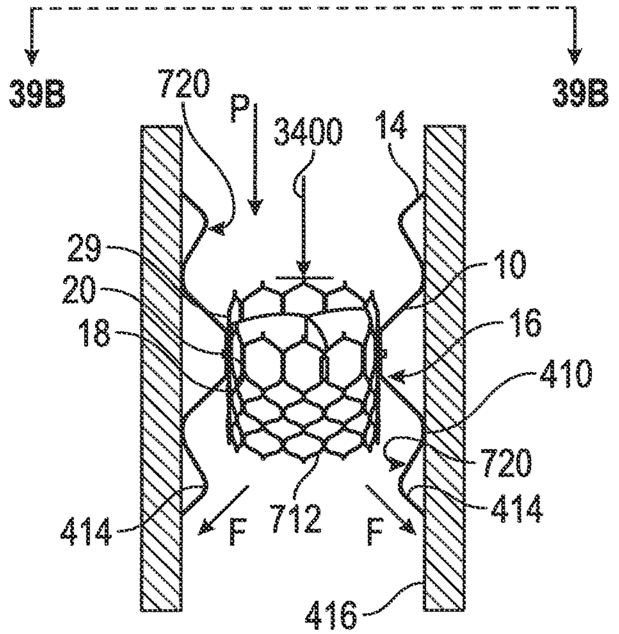
FIG. 39A is an enlarged schematic illustration of the docking station and transcatheter heart valve of FIG. 38 when the heart is in the diastolic phase.
Figure 39B:
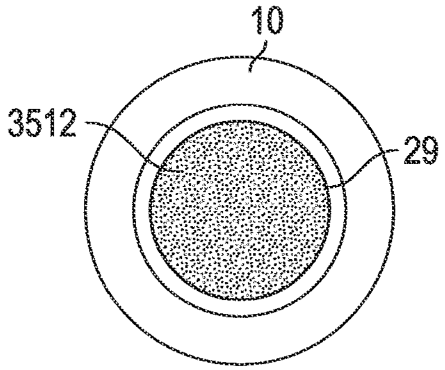
FIG. 39B is a view taken in the direction indicated by lines 39B-39B in FIG. 39A.

FIG. 38 illustrates the valve 29, docking station 10 and heart H illustrated by FIG. 36C, when the heart is in the diastolic phase. Referring to FIGS. 38, when the heart is in the diastolic phase, the valve 29 closes. FIG. 39A is an enlarged representation of the docking station 10 and valve (e.g., Sapien 3 valve) in the pulmonary artery of FIG. 38. Blood flow in the pulmonary artery PA above the valve 29 (i.e. in the pulmonary branch 210) is blocked by the valve 29 being closed and blocking blood flow as indicated by arrow 3400. The solid area 3512 in FIG. 39B represents the valve 29 being closed when the heart is in the diastolic phase.

Referring to FIG. 39A, the radially outward force 720 of the anchoring/retaining portions 414 to the inside surface 416 is substantially smaller than the radially outward force 710 applied by the valve (e.g., Sapien 3 valve) to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than 1/10 the radially outward force 710 applied by the valve. The 29 mm size Sapien 3 valve typically applies radially outward force 710 of about 42 Newtons. In one embodiment, the radially outward force of deployed docking stations described herein, or one or more portions of a deployed docking stations can be between about 4 to 16 Newtons, though other forces are also possible.

Figure 40A:
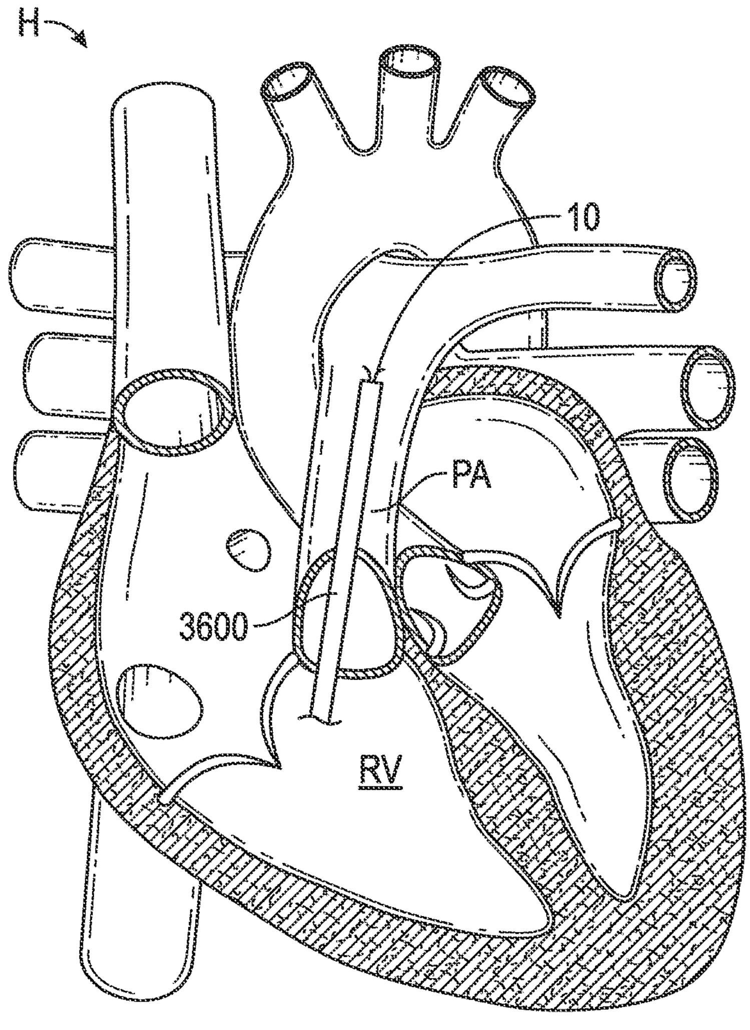
FIG. 40A is a cutaway view of the human heart in a systolic phase with a docking station being deployed in a pulmonary artery.
Figure 40B:
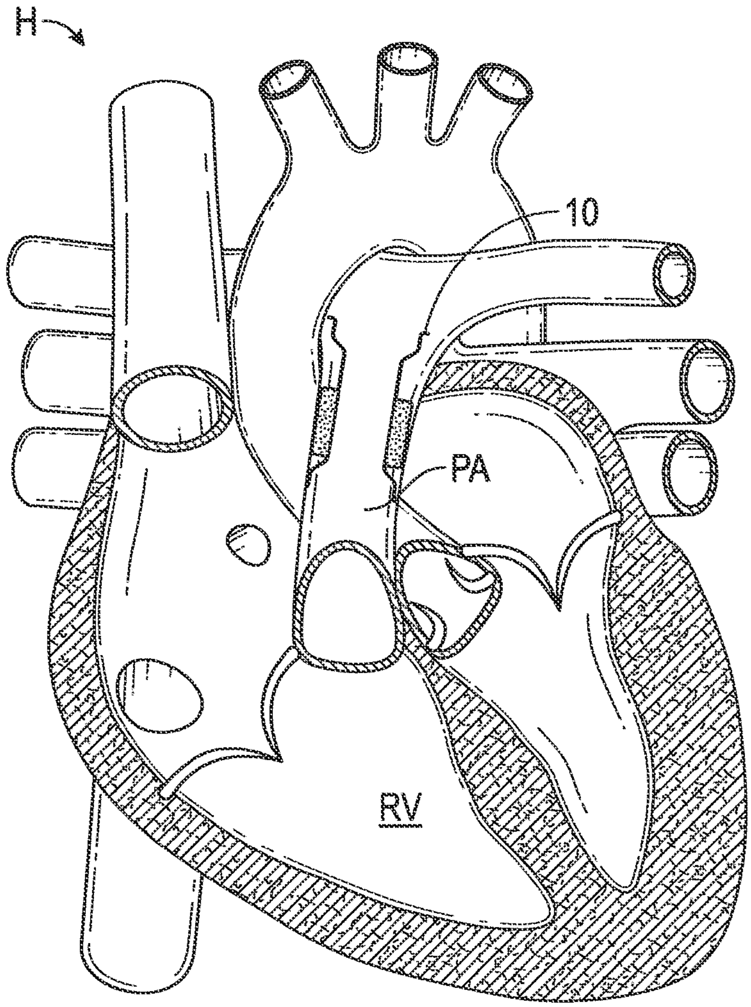
FIG. 40B is a cutaway view of the human heart in a systolic phase with a docking station deployed in the pulmonary artery.
Figure 40C:
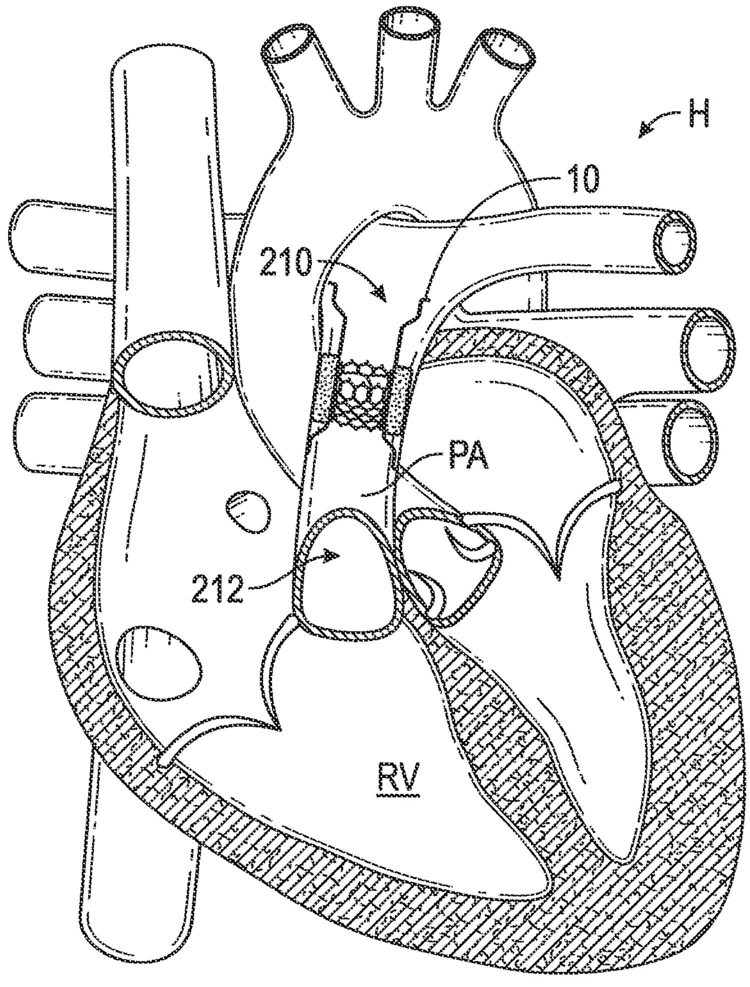
FIG. 40C is a cutaway view of the human heart in a systolic phase with the docking station and a transcatheter heart valve deployed in the pulmonary artery.
Figure 41A:
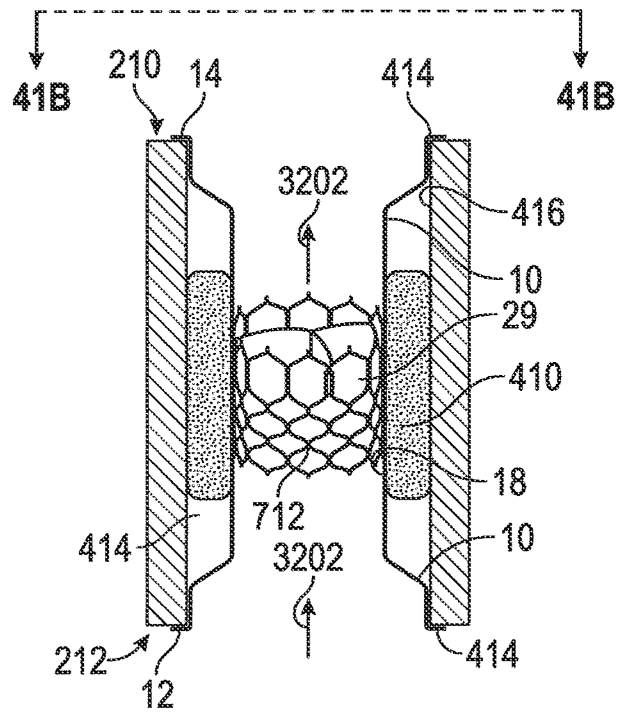
FIG. 41A is an enlarged schematic illustration of the docking station and transcatheter heart valve of FIG. 40C when the heart is in the systolic phase.
Figure 41B:
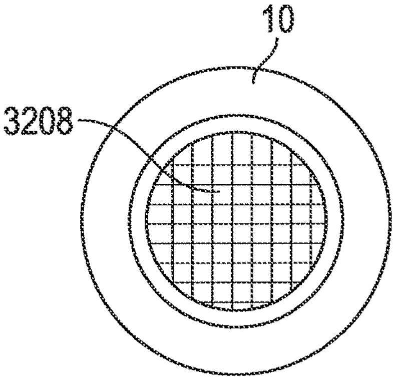
FIG. 41B is a view taken in the direction indicated by lines 41B-41B in FIG. 41A.

FIG. 40A illustrates the docking station illustrated by FIG. 27 or 28 being deployed by a catheter 3600. Referring to FIG. 40B, the docking station illustrated by FIG. 27 or 28 is deployed in the pulmonary artery PA of a heart H. FIG. 40C illustrates a valve 29 deployed in the docking station 10 illustrated by FIG. 40A. In the example illustrated by FIGS. 36C, 37A, 38, 39A, and 39B, the valve 29 is a SAPIEN 3 THV provided by Edwards Lifesciences, though a variety of different valves can be used. In FIGS. 40A-40C, the heart is in the systolic phase. FIG. 41A is an enlarged representation of the docking station 10 and valve 29 in the pulmonary artery of FIG. 40C. When the heart is in the systolic phase, blood flows from the right ventricle RV and through the pulmonary artery PA, docking station 10, and valve 29 as indicated by arrows 3202. FIG. 41B illustrates space 3208 that represents the valve 29 being open when the heart is in the systolic phase. FIG. 41B does not show the interface between the docking station 10 and the pulmonary artery to simplify the drawing. The cross-hatching in FIG. 41B illustrates blood flow through the valve 29. In an exemplary embodiment, blood is prevented from flowing between the pulmonary artery PA and the docking station 10 by the sealing portion 410 and blood is prevented from flowing between the docking station 10 and the valve 29 by seating of the valve in the seat 18 of the docking station 10. In this example, blood is substantially only or only able to flow through the valve when the heart is in the systolic phase.

Figure 42:
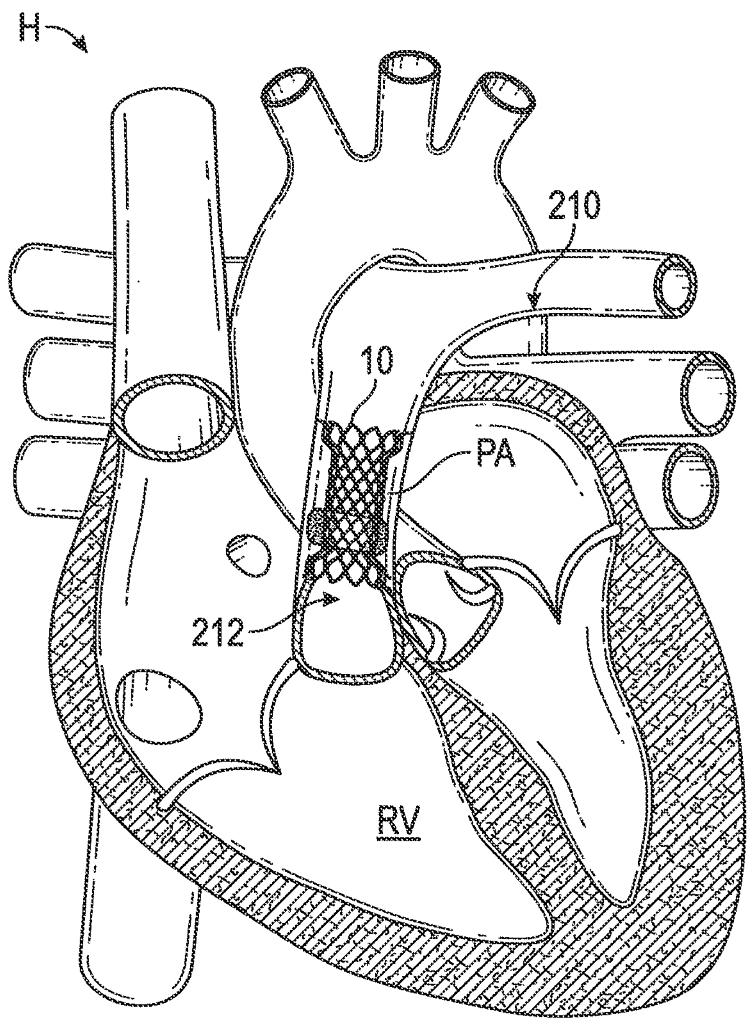
FIG. 42 is a cutaway view of the human heart, docking station, and transcatheter heart valve deployed in the pulmonary artery illustrated by FIG. 40C when the heart is in the diastolic phase.
Figure 43A:
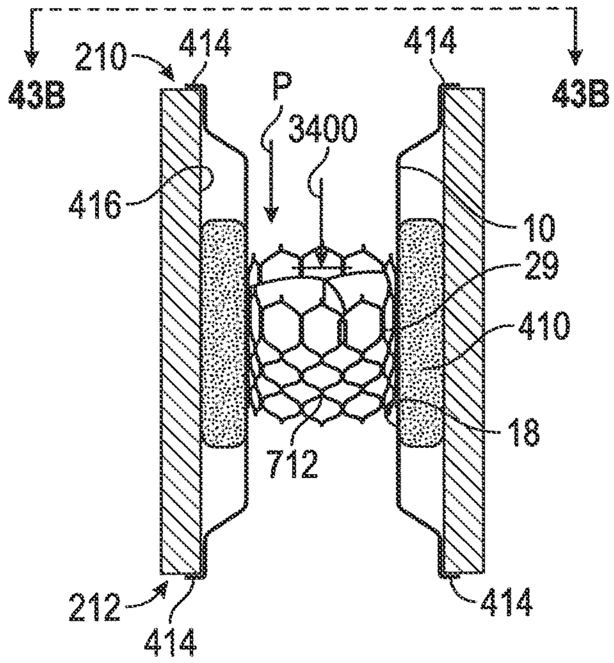
FIG. 43A is an enlarged schematic illustration of the docking station and transcatheter heart valve of FIG. 42 when the heart is in the diastolic phase.
Figure 43B:
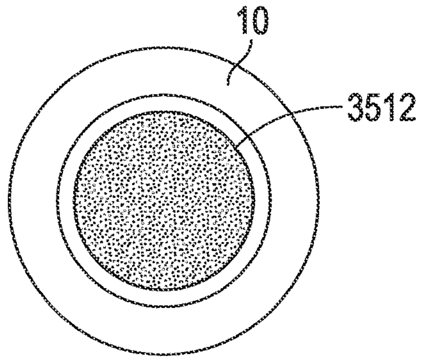
FIG. 43B is a view taken in the direction indicated by lines 43B-43B in FIG. 43A.

FIG. 42 illustrates the valve 29, docking station 10 and heart H illustrated by FIG. 40C, when the heart is in the diastolic phase. Referring to FIG. 42, when the heart is in the diastolic phase, the valve 29 closes. FIG. 43A is an enlarged representation of the docking station 10 and valve 29 in the pulmonary artery of FIG. 42. Blood flow in the pulmonary artery PA above the valve 29 (i.e. in the pulmonary branch 210) is blocked by the valve 29 being closed and blocking blood flow as indicated by arrow 3400. The solid area 3512 in FIG. 43B represents the valve 29 being closed when the heart is in the diastolic phase.

Referring to FIG. 43A, the docking station 10 is retained in the pulmonary artery PA by expanding one or more of the retaining/anchoring portions 414 radially outward into an area 210, 212 of the pulmonary artery PA where the inside surface 416 also extends outward. For example, the retaining portions 414 can be configured to extend radially outward into the pulmonary bifurcation 210 and/or the opening 212 of the pulmonary artery to the right ventricle RV. In one exemplary embodiment, the docking station 10 can be an adjustable and/or multiple component docking station. For example, docking station 10 can be a telescoping docking station as illustrated by FIG. 28 and the first portion 1102 can be deployed such that the retaining portions 414 extend radially outward into the pulmonary bifurcation 210 and the second portion 1104 can be positioned in the first portion 1102 such that its retaining portions 414 coincide with the opening 212 of the pulmonary artery. The extension of the retaining portions 414 into the areas 210, 212 set the position of the docking station 10 in the pulmonary artery PA and help prevent the pressure P shown in FIG. 43A from moving the docking station.

The valve 29 used with the docking station 10 can take a wide variety of different forms. In one exemplary embodiment, the valve 29 is configured to be implanted via a catheter in the heart H. For example, the valve 29 can be expandable and collapsible to facilitate transcatheter application in a heart. However, in other embodiments, the valve 29 can be configured for surgical application. Similarly, the docking stations described herein can be placed using transcatheter application/placement or surgical application/placement.

Figure 44:
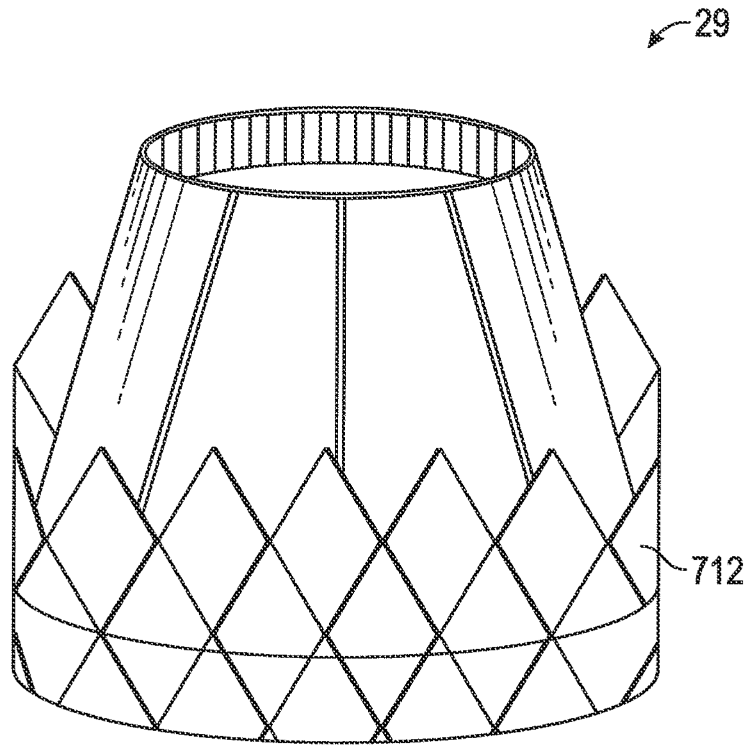
FIGS. 44-47, and 48A-48C illustrate examples of valve types that can be deployed in a docking station, e.g., one of the docking stations described or depicted herein.
Figure 45:
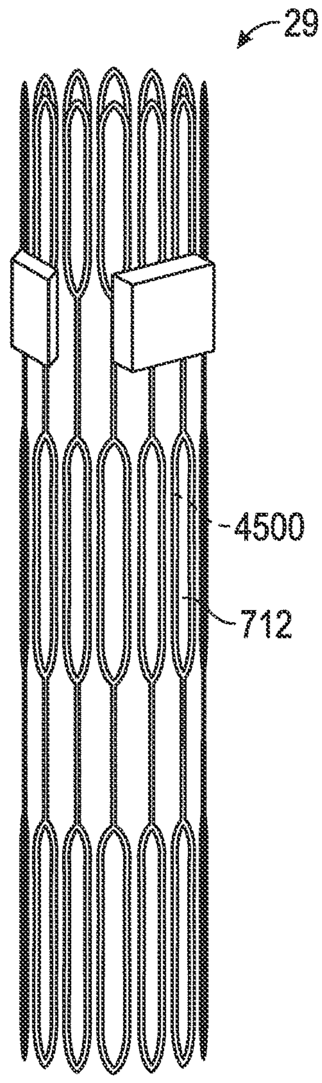
Figure 46:
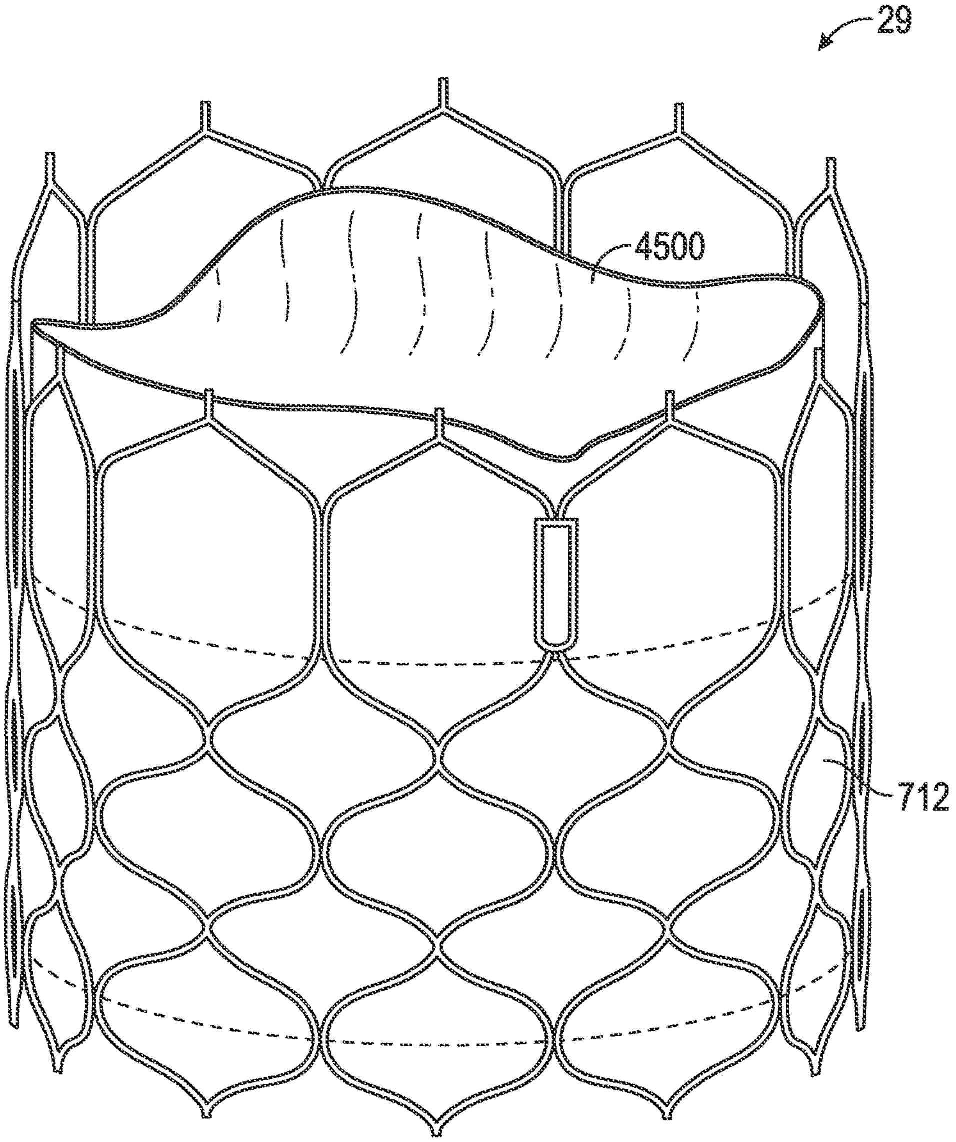
Figure 47:
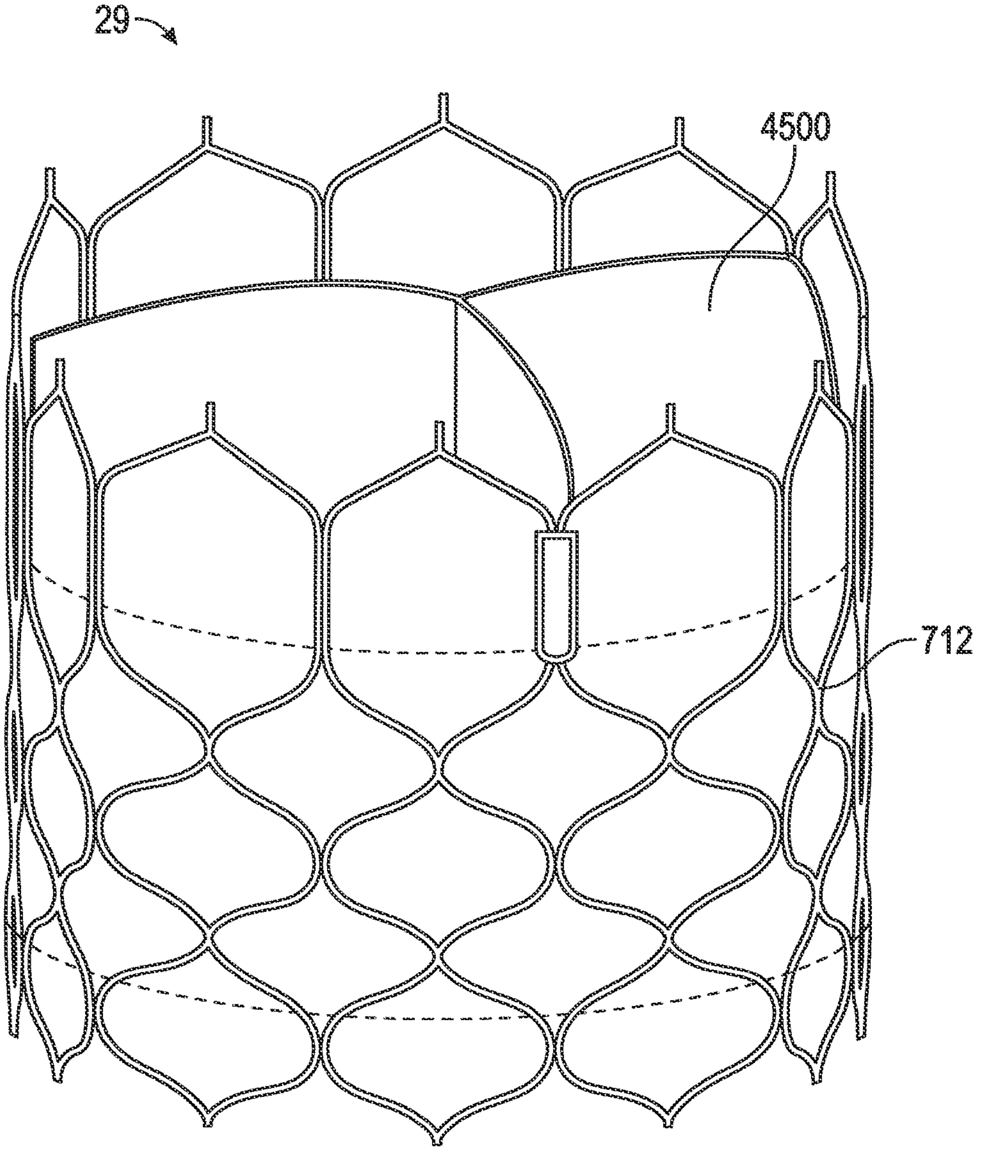
Figure 48A:
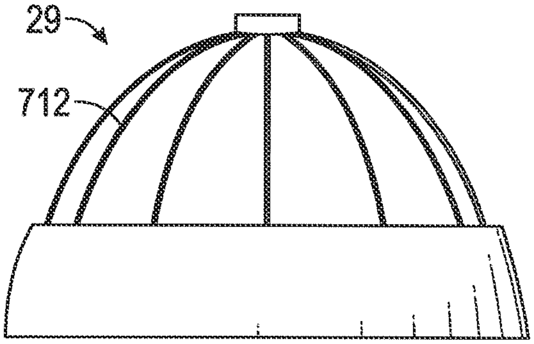
Figure 48B:
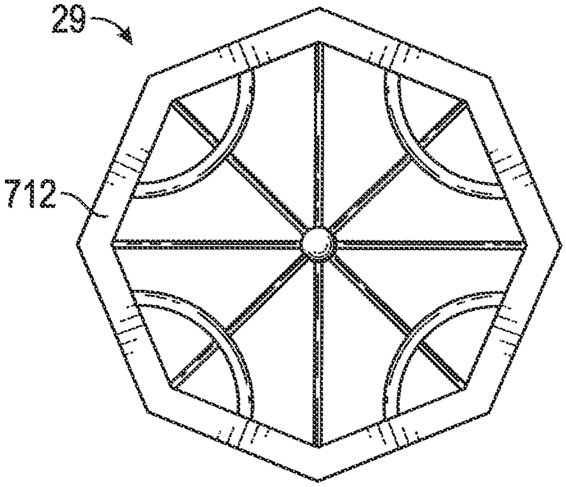
Figure 48C:
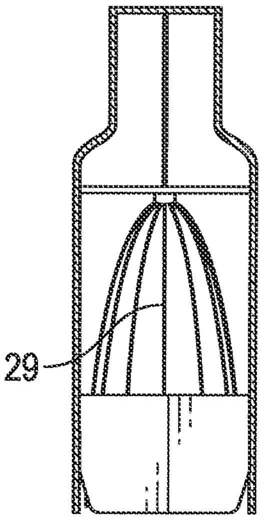

FIGS. 44-48 illustrate a few examples of the many valves or valve configurations that can be used. Any valve type can be used and some valves that are traditionally applied surgically can be modified for transcatheter implantation. FIG. 44 illustrates an expandable valve 29 for transcatheter implantation that is shown and described in U.S. Pat. No. 8,002,825, which is incorporated herein by reference in its entirety. An example of a tri-leaflet valve is shown and described in Published Patent Cooperation Treaty Application No. WO 2000/42950, which is incorporated herein by reference in its entirety. Another example of a tri-leaflet valve is shown and described in U.S. Pat. No. 5,928,281, which is incorporated herein by reference in its entirety. Another example of a tri-leaflet valve is shown and described in U.S. Pat. No. 6,558,418, which is incorporated herein by reference in its entirety. FIGS. 45-47 illustrate an exemplary embodiment of an expandable tri-leaflet valve 29, such as the Edwards SAPIEN Transcatheter Heart Valve. Referring to FIG. 45, in one exemplary embodiment the valve 29 comprises a frame 712 that contains a tri-leaflet valve 4500 (See FIG. 46) compressed inside the frame 712. FIG. 46 illustrates the frame 712 expanded and the valve 29 in an open condition. FIG. 47 illustrates the frame 712 expanded and the valve 29 in a closed condition. FIGS. 48A, 48B, and 48C illustrate an example of an expandable valve 29 that is shown and described in U.S. Pat. No. 6,540,782, which is incorporated herein by reference in its entirety. An example of a valve is shown and described in U.S. Pat. No. 3,365,728, which is incorporated herein by reference in its entirety. Another example of a valve is shown and described in U.S. Pat. No. 3,824,629, which is incorporated herein by reference in its entirety. Another example of a valve is shown and described in U.S. Pat. No. 5,814,099, which is incorporated herein by reference in its entirety. Any of these or other valves can be used as valve 29 in the various embodiments disclosed herein.

FIGS. 49A, 49B and 50A-50D illustrate a distal portion of an exemplary embodiment of a catheter 3600 for delivering and deploying the docking station 10. The catheter 3600 can take a wide variety of different forms. In the illustrated example, the catheter 3600 includes an outer tube/sleeve 4910, an inner tube/sleeve 4912, a docking station connector 4914 that is connected to the inner tube 4912, and an elongated nosecone 28 that is connected to the docking station connector 4914 by a connecting tube 4916.

Figure 49A:
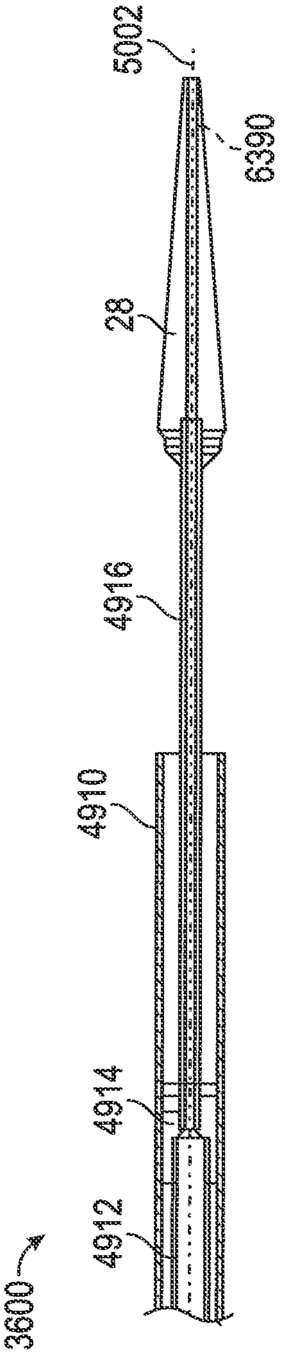
FIG. 49A is a sectional view of an exemplary embodiment of a catheter.
Figure 49B:
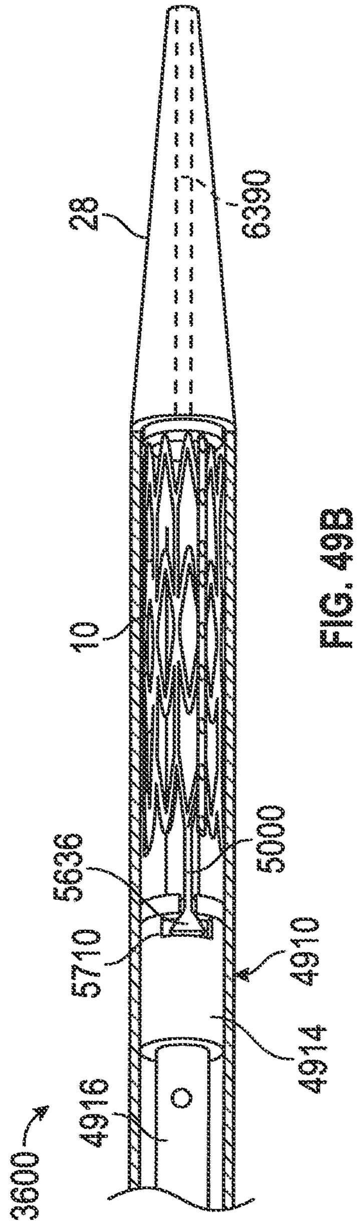
FIG. 49B is a sectional view of an exemplary embodiment of a catheter with a docking station crimped and loaded in the catheter.

The docking station 10 can be disposed in the outer tube/sleeve 4910 (See FIG. 49B). Elongated legs 5000 can connect the docking station 10 to the docking station connector 4914 (See FIG. 49B). The elongated legs 5000 can be retaining portions that are longer than the remainder of the retaining portions 414. The catheter 3600 can be routed over a guidewire 5002 to position the docking station 10 at the delivery site.

Figure 50A:
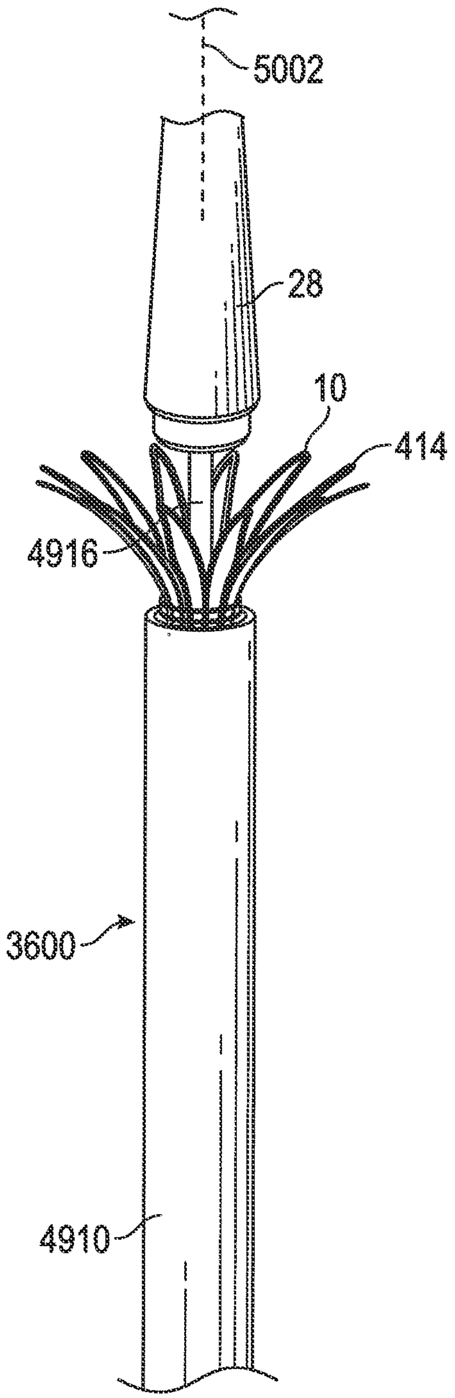
FIGS. 50A-50D illustrate deployment of a docking station from a catheter.
Figure 50B:
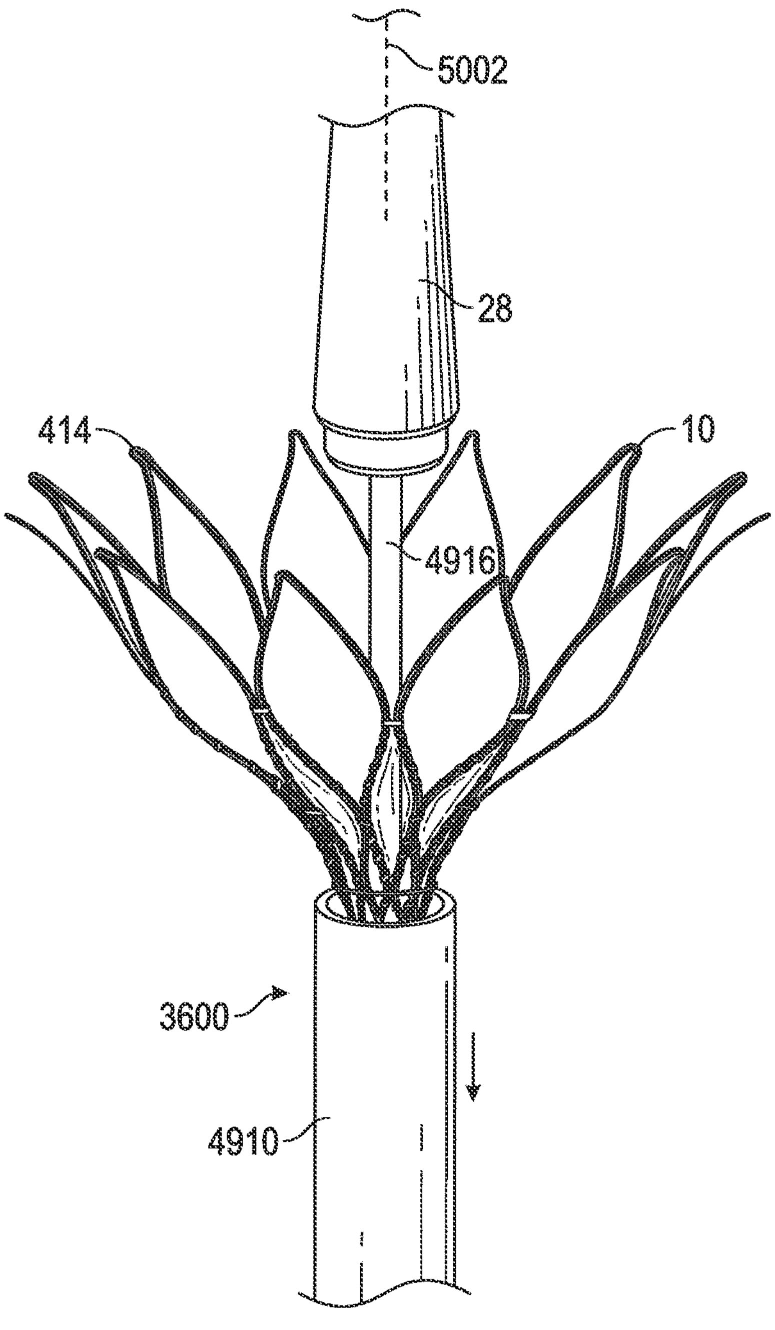
Figure 50C:
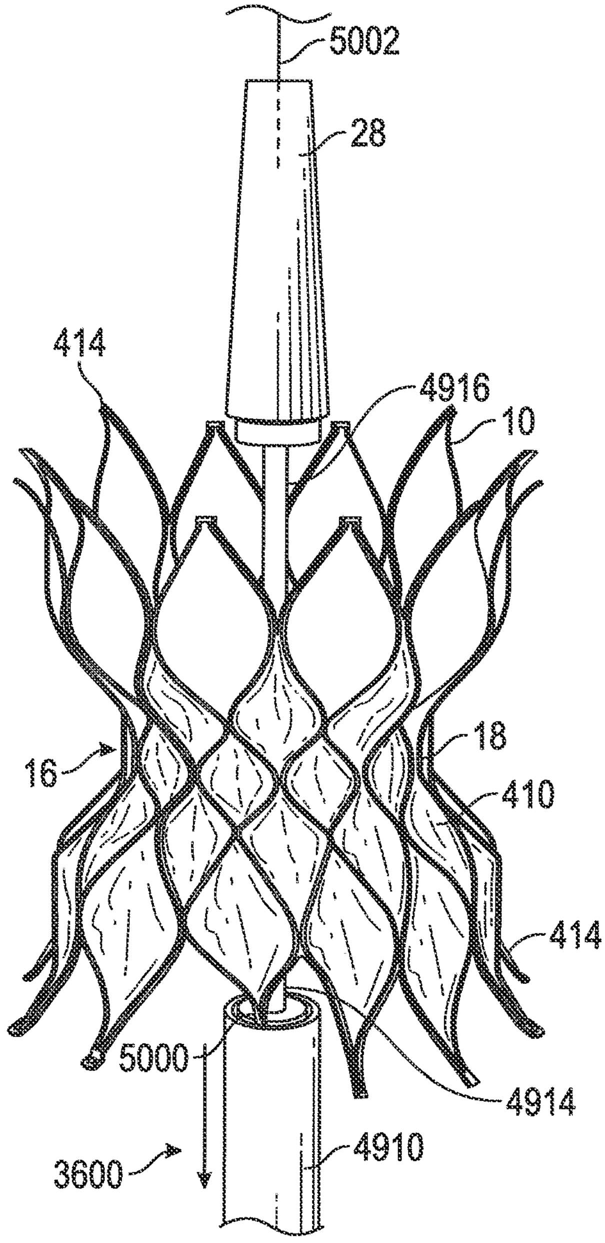
Figure 50D:
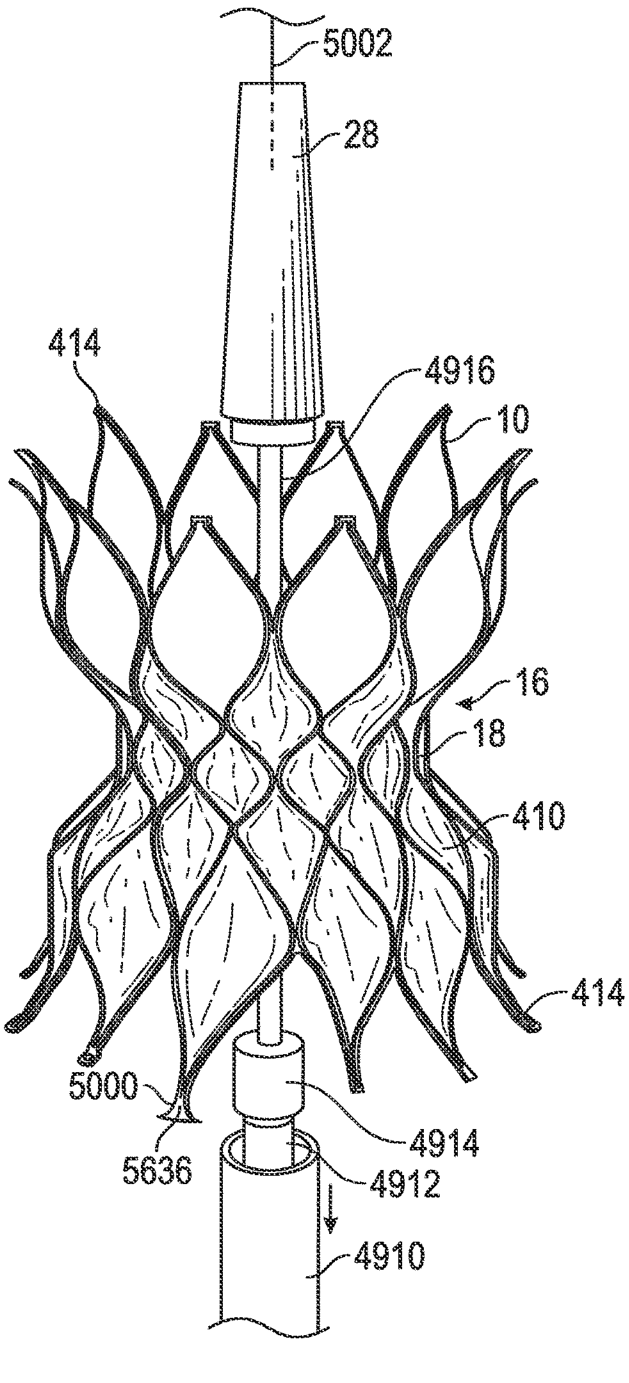

Referring to FIGS. 50A-50D, the outer tube 4910 is progressively retracted with respect to inner tube 4912, the docking station connector 4914, and the elongated nosecone 28 to deploy the docking station 10. In FIG. 50A, the docking station 10 begins to expand from the outer tube 4910. In FIG. 50B, a distal end 14 of the docking station 10 expands from the outer tube 4910. In FIG. 50C, the docking station 10 is expanded out of the outer tube, except the elongated legs 5000 remain retained by the docking station connector 4914 in the outer tube 4910. In FIG. 50D, docking station connector 4914 extends from the outer tube 4910 to release the legs 5000, thereby fully deploying the docking station. During deployment of a docking station in the circulatory system, similar steps can be used, and the docking station can be deployed in a similar way.

Figure 51:
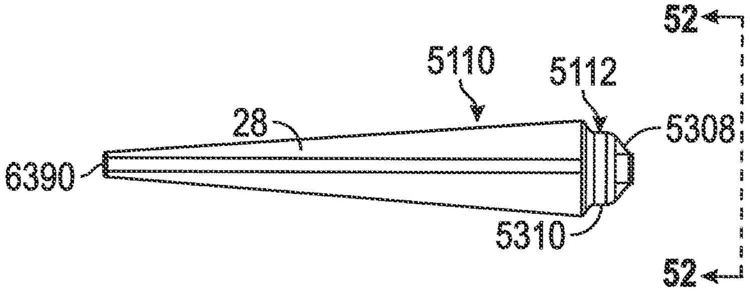
FIG. 51 is a side view of an exemplary embodiment of a nosecone of a catheter.
Figure 52:
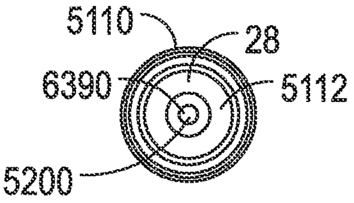
FIG. 52 is a view taken as indicated by lines 52-52 in FIG. 51.
Figure 54:
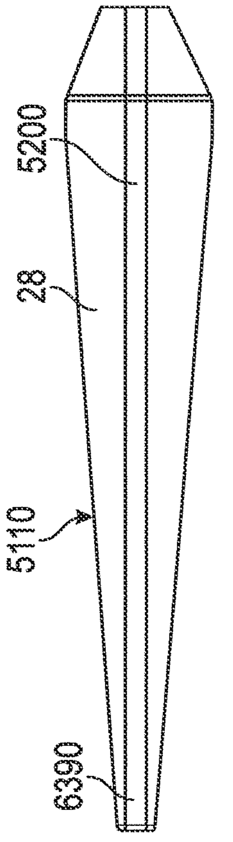
FIG. 54 is a side view of an exemplary embodiment of a nosecone of a catheter.

FIGS. 51 and 54 illustrate exemplary embodiments of the nosecone 28. In one exemplary embodiment, the nosecone 28 is an elongated flexible tip or distal end 5110 on a catheter used to assist feeding the catheter 3600 into the heart. In the illustrated examples, nosecone 28 is a long, gradually-tapering cone, with the narrow, distal end of the cone being relatively flexible. In one non-limiting embodiment, a nosecone has a length of 1.5 inches, with an inner lumen 5200 of the nosecone 28 having an inner diameter of 0.04 inches to accommodate the guidewire 5002. In one embodiment, as the diameter of the nosecone 100 increases from the narrow distal end to the wider proximal end, the cone becomes gradually stiffer. This can be due to the increase in thickness and/or the nosecone can be constructed from different materials having different durometers. Optionally, the stiffness of the nose cone at the point it connects with the outer tube 4910 can be approximately the same as the stiffness of the outer tube 4910, in order to prevent a sudden change in stiffness. In the examples illustrated by FIGS. 51 and 54, the elongated distal ends 5110 of the nosecone 28 are the same. In one embodiment, the taper of the nosecone 28 extends the full length or only a portion of the length of the nosecone 28 from end to end. To form the taper an outer diameter of the nosecone 28 can increase in a distal to proximal direction. The taper can take a variety of shapes and the outer surface of the taper can be at a variety of angles with respect to a longitudinal axis of the nosecone 28.

In one exemplary embodiment, a longer distal end 5110 of the nosecone 28 assists in navigating around a bend or curve in the subject's vasculature. Because of the increased length of the nosecone 28 more of the tip gets around the bend, and creates a "follow-the-leader" effect with the remainder of the nose cone.

Figure 53:
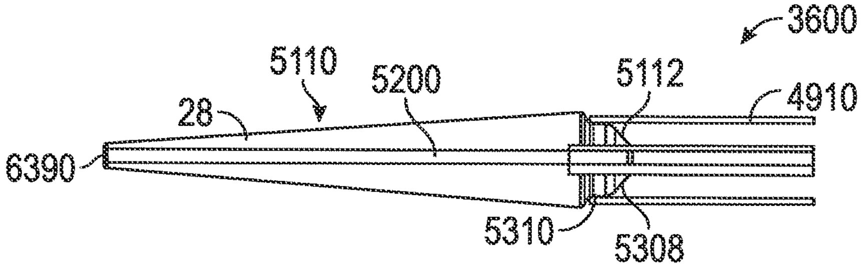
FIG. 53 is a sectional view of an exemplary embodiment of a distal portion of a catheter.

In the example illustrated by FIG. 51, the base or proximal end 5112 of the nosecone 28 has a proximal angled portion 5308 adjacent to a shelf 5310. The proximal angled portion 5308 does not catch on the docking station 10 that has been implanted in the heart, when the delivery catheter is retrieved. Thus, the proximal base portion 5112 allows for easier removal of the delivery system. Referring to FIG. 53, as the angled portion 5308 (or "ramp") of the base portion 5112 is retracted into the outer tube 4910, the ramp 5308 enters the delivery catheter first, followed by the shelf 5310. When the nose cone 28 engages with the outer sleeve/tube 4910, the inner diameter of the outer sleeve rides up the ramp 5308, and then rests on the shelf 5310 (which can be flat or substantially flat, e.g., 180° or 180°±5° with respect to a longitudinal axis of the nosecone 28). The inner diameter of the outer sleeve/tube 4910 can be slightly less than the diameter of the shelf 5310, to ensure a snug fit.

In one non-limiting example, the shelf 5310 of the nosecone 28 fits snugly into a lumen or outer lumen of the catheter assembly 3600 which, in one non-limiting example, can have a diameter of approximately 0.2 inches or between 0.1 inches and 0.4 inches. In one embodiment, the outer diameter of the largest portion of the nosecone 28 can be 0.27 inches or between 0.2 inches and 0.4 inches, with a diameter at the distal tip of the nosecone of 0.069 inches or between 0.03 inches and 0.1 inches. Again, these dimensions are for illustrative purposes only. For example, the outer diameter or largest outer diameter of the nosecone 28 can be larger than the outer diameter of the outer tube 4910 (e.g., slightly larger as illustrated), the outer diameter of the nosecone 28 can be the same as the outer diameter of the outer tube 4910, or the outer diameter of the nosecone 28 can be smaller (e.g., slightly smaller) than the outer diameter of the outer tube 4910.

Figure 55:
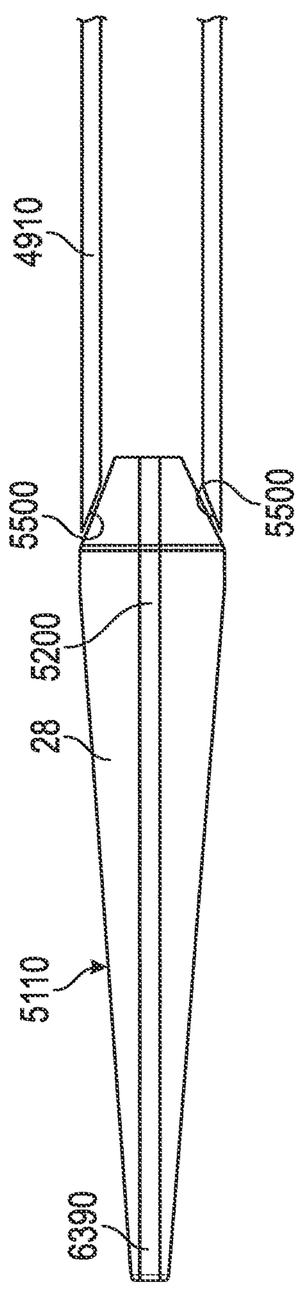
FIG. 55 is a sectional view of an exemplary embodiment of a distal portion of a catheter.

In the example illustrated by FIG. 54, the entire base or proximal end/portion 5112 of the nosecone 28 is angled. The continuously angled proximal end 5112 does not catch on the docking station 10 that has been implanted in the heart, when the delivery catheter is retrieved. Thus, the base portion 5112 allows for easier removal of the delivery system. Referring to FIG. 55, the outer tube 4910 can include a chamfer 5500 to accept and mate with the continuously angled proximal end 5112.

In one non-limiting example, the continuously angled proximal end 5112 of the nosecone 28 fits snugly into the outer tube/sleeve 4910 (which can optionally be chamfered) of the catheter assembly 3600. The outer diameter or largest outer diameter of the nosecone 28 can be larger (e.g., slightly larger) than the outer diameter of the outer tube 4910, the outer diameter of the nosecone 28 can be the same as the outer diameter of the outer tube 4910 as illustrated, or the outer diameter of the nosecone 28 can be smaller (e.g., slightly smaller) than the outer diameter of the outer tube 4910.

The docking station 10 can be coupled to the catheter assembly, or a docking station connector 4914 of the catheter assembly, in a wide variety of different ways. For example, the docking station 10 could be coupled with the catheter assembly with a lock(s), locking mechanism, suture (s) (e.g., one or more sutures releasably attached, tied, or woven through one or more portion of the docking station), interlocking device(s), a combination of these, or other attachment mechanisms. Some of these coupling or attachment mechanisms can be configured to allow for the docking station to be retracted back into the catheter assembly without causing the docking station to catch on edges of the catheter assembly, e.g., by constraining the proximal end of the docking station to a smaller profile or collapsed configuration, to allow for adjustment, removal, replacement, etc. of the docking station. FIGS. 56, 57, 57A, and 57B illustrate one non-limiting example of how docking station 10 can be coupled to the docking station connector 4914. As is illustrated by FIGS. 50A-50D, when the docking station 10 is pushed out of the outer tube, it self-expands in one exemplary embodiment. One approach to controlling expansion of the docking station 10 is to anchor at least one end, such as the proximal end 12, of the stent to the docking station connector 4914. This approach allows a distal end 14 of the stent to expand first, without the proximal end expanding (See FIG. 50B). Then when the stent is moved relatively forward with respect to the outer tube 4910, the proximal end 12 disengages from the docking station connector 4914, and the proximal end 12 of the docking station is permitted to expand (See FIG. 50D).

One way of accomplishing this approach is to include one or more extensions 5000 on at least the proximal end 12 of the stent. In the illustrated examples, two extensions are included. However, any number of extensions 5000, such as two, three, four, etc. can be included. The extensions 5000 can take a wide variety of different forms. The extensions 5000 can engage with the docking station connector 4914 within the outer tube 4910. In one exemplary embodiment, the docking station connector 4914 can engage an inner face 5600 of the extensions 5000. In one exemplary embodiment, other than possible engagement of an inner face 5600 (See FIG. 57A) of the extensions 5000 with the docking station connector 4914, the extensions 5000 and docking station connector 4914 are configured to limit the retaining engagement therebetween to two points when the distal portion of the catheter assembly and/or docking station are in a straight or substantially straight configuration, but these could similarly be configured to limit the retaining engagement another number of points, e.g., three to six points. In one exemplary embodiment, the inner face 5600 of the extensions 5000 do not contact with the docking station connector 4914 when the distal portion of the catheter assembly and/or the docking station is in a straight or substantially straight configuration, due to the radially outward biasing force of the compressed extensions. In this embodiment, the inner face 5600 of the extensions 5000 could contact the docking station connector 4914 due to bending of the catheter assembly 3600 and/or the docking station. The extensions 5000 can include heads 5636 with sides 5640 that extend away from a straight portion 5638 at an angle β (See FIG. 57A), such as between 30 and 60 degrees. Such heads 5636 can be generally triangular as illustrated or the angularly extending sides 5640 can be connected together by another shape, such as a rounded shape, a rectangular shape, pyramidal shape, or another shape. That is, the heads 5636 can function in the same manner as the illustrated triangular head, without being triangular.

Figure 57:
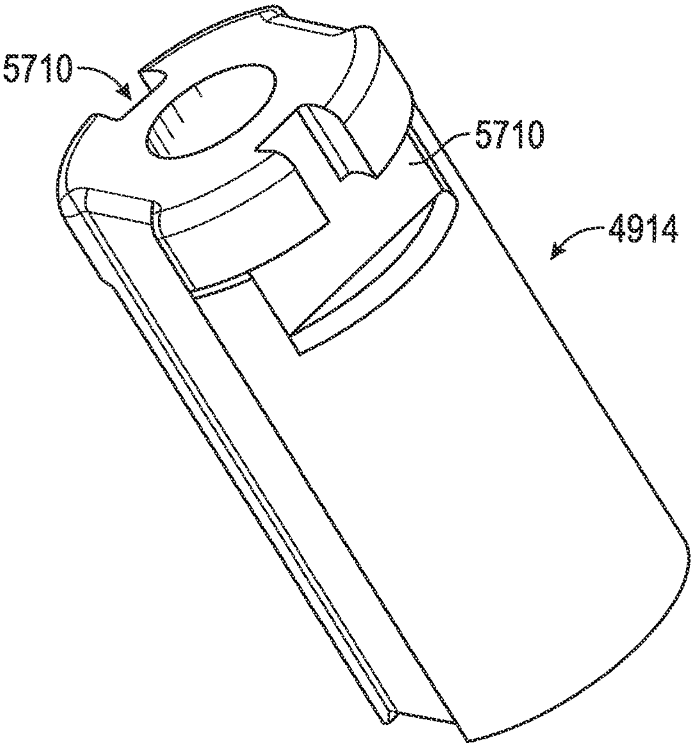
FIG. 57 is a perspective view of a holder for retaining a docking station in a catheter.
Figure 57B:
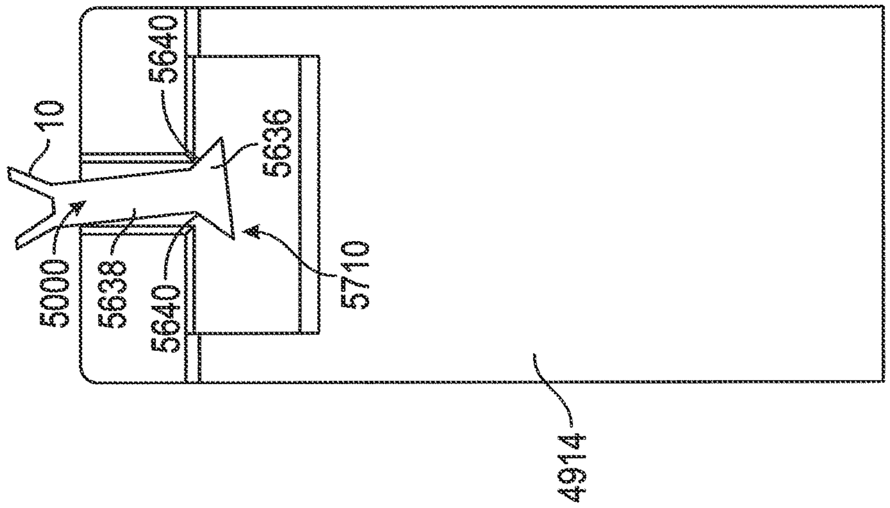
FIGS. 57A and 57B illustrate side views of extensions of a docking station disposed in the holder.
Figure 57A:
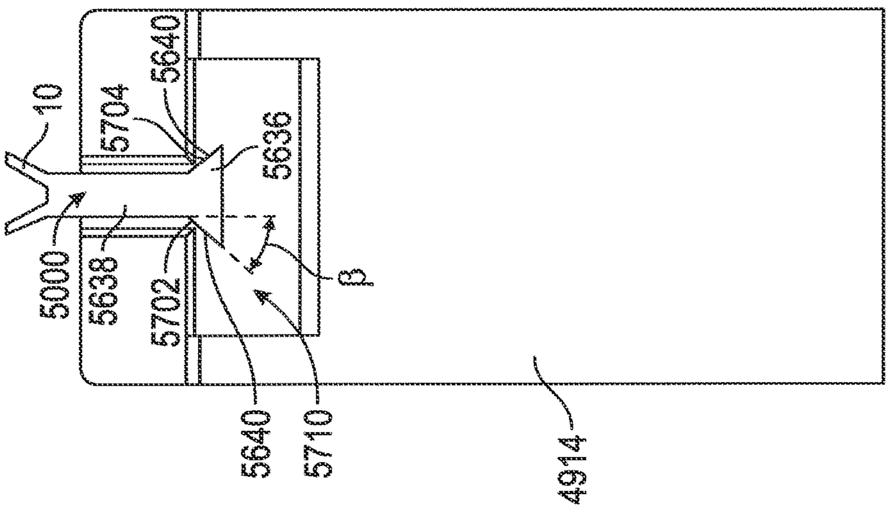
Figure 58:
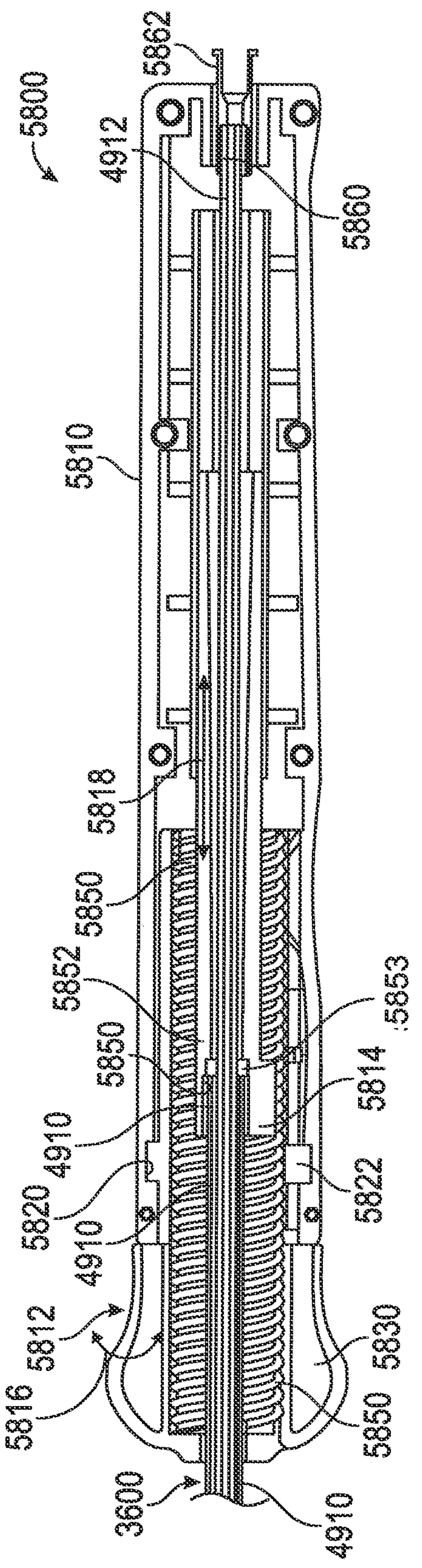
FIG. 58 is a sectional view of an exemplary embodiment of a handle for a docking station catheter.

The delivery catheter 3600 constantly bends and curves as it moved through the vasculature of the subject. A head 5636 that transitions directly from a straight portion 5638 of the extension 5000 to a T-shape, curved T-shaped, circular or spherical shape will generally have more than two point retaining contact with its holder (other than possible engagement of an inner face 5600 (See FIG. 17A) of the extension 5000 with the docking station connector 4914). Referring to FIGS. 57A and 57B, a head 5636 with sides 5640 that extend away from one another at an angle β, such as a triangular head, results in the head 5636 only touching the docking station connector 4914 at two points 5702, 5704. In the example illustrated by FIG. 57A, the two points are corners formed by a T-shaped recess 5710. As shown in FIG. 57B, the extension 5000 can tilt as the catheter 3600 and docking station 10 moves through the body during delivery. In one exemplary embodiment, this tilting can also result in only two-point contact between the extension 5000 and the docking station connector 4914 as illustrated by FIG. 57B (other than possible engagement of an inner face 5600 (See FIG. 17A) of the extension 5000 with the docking station connector 4914). As such, the extension 5000 can tilt during delivery, increasing the flexibility of the catheter 3600 in the area of the docking station 10, while the two-point contact prevents binding between the extension 5000 and the connector 4914.

Figure 56:
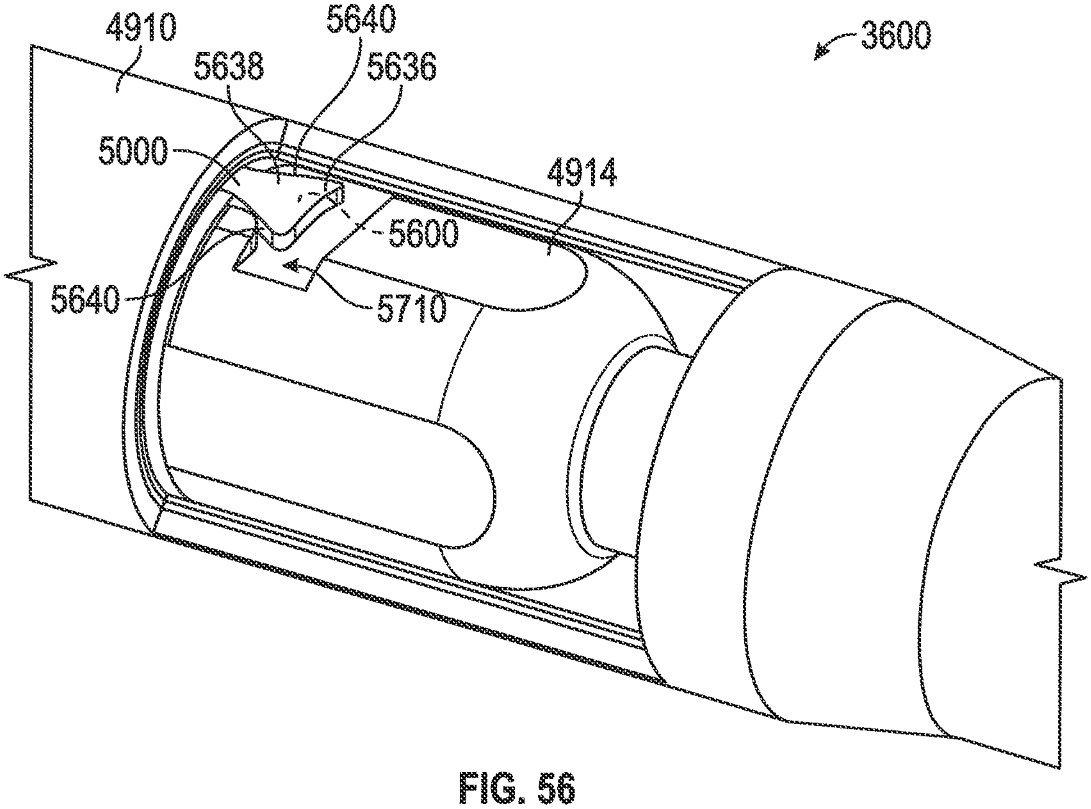
FIG. 56 is a perspective view of a holder for retaining a docking station in a catheter.

Referring to FIGS. 56, 57, 57A, and 57B, the heads 5636 fit into the T-shaped recesses 5710 in a holder to holds the proximal end 12 of the docking station while the distal end self-expands within the body. The docking station connector 4914 remains in the delivery catheter until moved relatively out of the catheter (i.e. by retracting the outer tube/sleeve 4910 or by advancing the connector 4914, See Figure SOD). Referring to FIG. 56, the outer tube/sleeve 4910 of the catheter 3600 can be closely disposed over the connector 4914, such that the heads 5636 are captured in the recesses 5710, between the outer tube/sleeve 4910 and the body of the connector 4914. This capturing in the recesses 5710 holds the end of the docking station 10 as the docking station expands. In this manner, delivery of the docking station 10 is controlled.

Referring back to Figure SOD, at the end of the expansion of the docking station 10—when the distal end of the stent has already expanded—the connector 4914 is moved relatively out of the outer sleeve. The heads 5636 are then free to move radially outward and disengage with the respective recesses 5710 (see FIG. 56).

In one embodiment, all of the extensions 5000 are the same length. As the connector is moved relatively out of the outer tube/sleeve 4910, the recesses 5710 are simultaneously relatively moved out of the outer sleeve 4910. Since the extensions 5000 are all the same length, the recesses 5710 with the heads 5636 will all emerge from the delivery outer sleeve 4910 at the same time. Consequently, the heads 5636 of the docking station will move radially outward and release all at once.

In an alternative embodiment, the docking station 10 is provided with extensions 5000 having heads 5636, but at least some of the extensions 5000 are longer than others. That way, as the connector 4914 is gradually moved relatively out of the outer sleeve 4910, the shortest extensions 5000 are released first from their respective recess(es) 5710. Then, as the connector 4914 is moved relatively further out of the outer sleeve 4910, the longer of the extensions 5000 are released from the respective recess(es) 5710. As is described above, in one exemplary embodiment the docking station 10 can be deployed with a catheter/catheter assembly 3600. The catheter/catheter assembly 3600 is advanced in the circulatory system to a delivery site or treatment area. Once at the delivery site, the docking station 10 is deployed by moving an outer sleeve or tube 4910 relative to an inner sleeve or tube 4912 and attached connector 4914 and docking station 10 (See FIGS. 50A-50D). The outer sleeve 4910 can be moved relative to the inner sleeve 4912 in a wide variety of different ways. FIGS. 58-61 and 62-73 illustrate examples of tools or handles 5800, 6200 that can be used for moving a catheter 3600 in the circulatory system and relatively moving an outer sleeve 4910 relative to an inner sleeve 4912 of the catheter 3600, e.g., to deploy/place a docking station.

Figure 59:
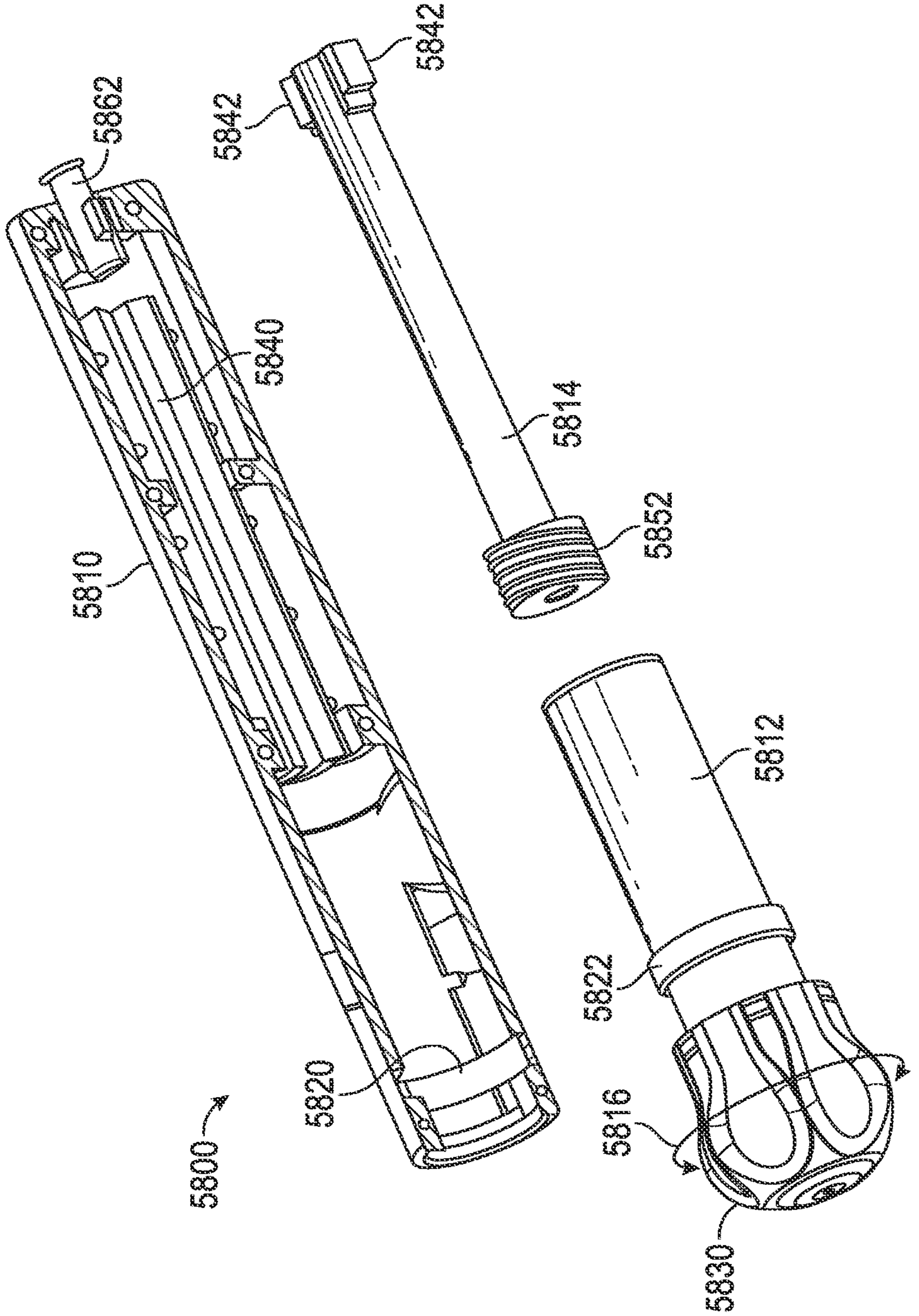
FIG. 59 is an exploded perspective view of parts of the handle of FIG. 58.
Figure 60:
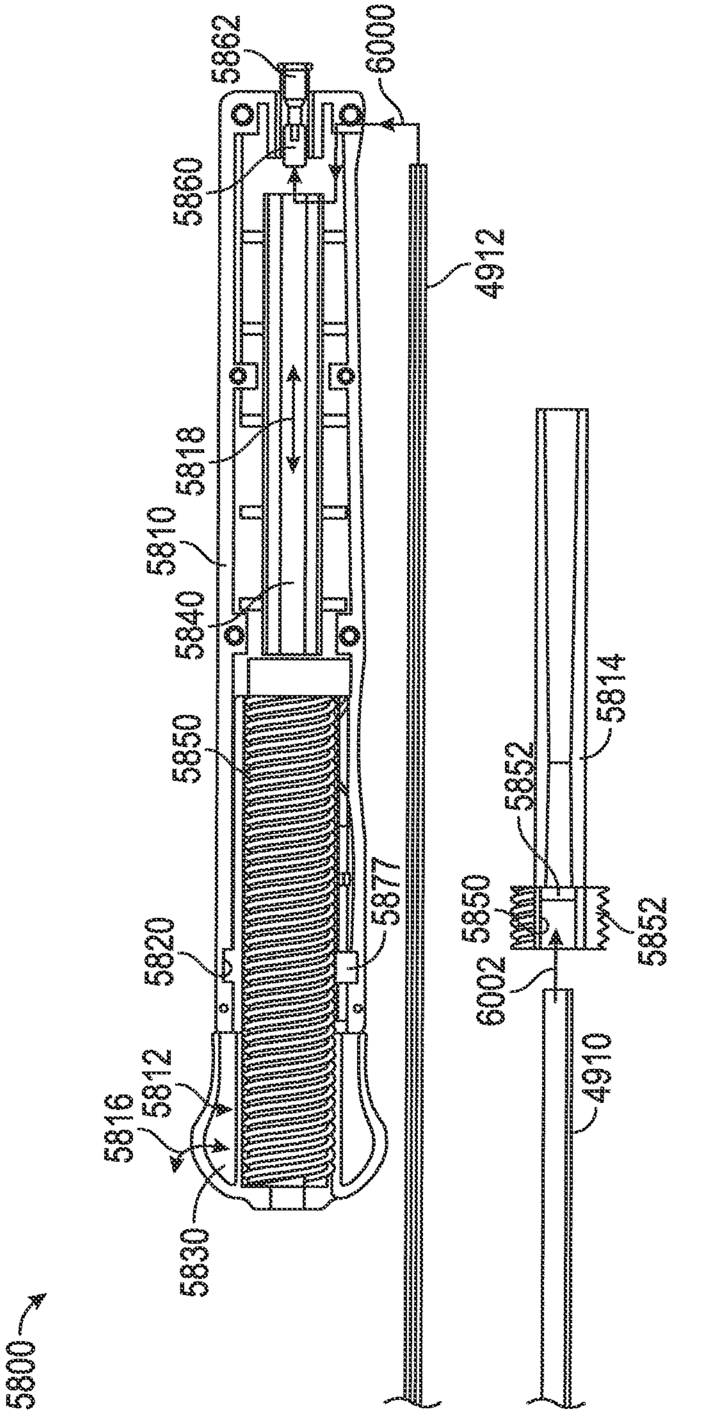
FIG. 60 is an exploded sectional view of parts of the handle of FIG. 58.
Figure 61:
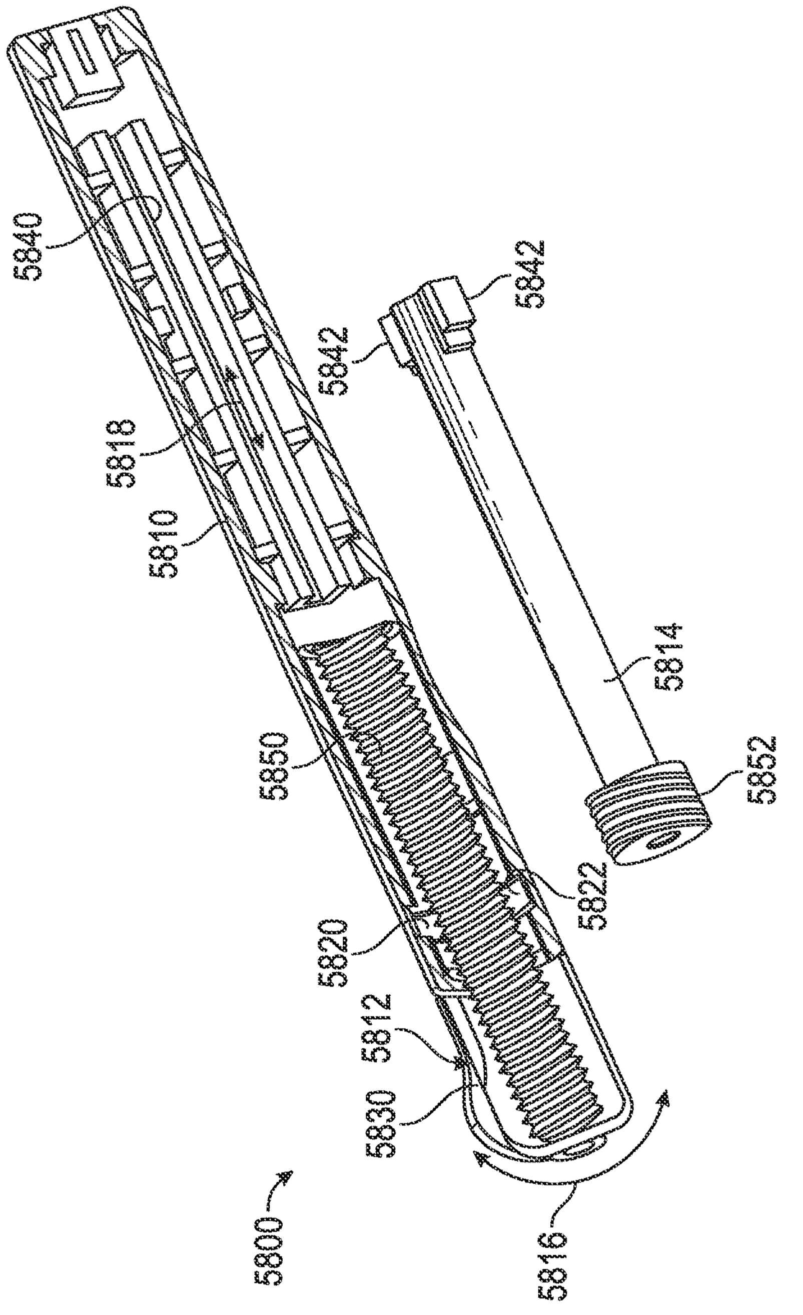
FIG. 61 is an exploded perspective sectional view of parts of the handle of FIG. 58.

In the example illustrated by FIGS. 58-61, the handle 5800 includes a housing 5810, a drive member 5812, and a driven shaft 5814. In the illustrated example, rotation of the drive member 5812 as indicated by arrow 5816 relative to the housing 5810 moves the driven shaft 5814 linearly as indicated by arrow 5818. Referring to FIG. 60, the inner sleeve 4912 is fixedly connected to the housing 5810 as indicated by arrow 6000 and the outer sleeve 4910 is fixedly connected to the driven shaft 5814 as indicated by arrow 6002. As such, rotating the drive member 5812 in a first direction retracts the outer sleeve 4910 relative to the inner sleeve 4912 and rotating the drive member 5812 in the opposite direction advances the outer sleeve 4910 relative to the inner sleeve 4912.

In the example illustrated by FIGS. 58-61, the housing 5810 includes an annular recess 5820. The drive member 5812 includes an annular projection 5822. The annular projection 5822 fits within the annular recess to rotatably couple the drive member 5812 to the housing 5810. The drive member 5812 includes an engagement portion 5830 that extends from the housing to allow a user to rotate the drive member 5812 relative to the housing 5810.

In the example illustrated by FIGS. 58-61, the housing 5810 includes a linear recess 5840 or groove (See FIG. 59). The driven shaft 5814 includes a linear projection 5842. The linear projection 5842 fits within the linear recess 5840 to slidably couple the driven shaft 5814 to the housing 5810.

In the example illustrated by FIGS. 58-61, the drive member 5812 includes internal threads 5850. The driven shaft 5814 includes an externally threaded portion 5852. The externally threaded portion 5852 mates with the internal threads 5850 to operationally couple the drive member 5812 to the driven shaft 5814. That is, when the drive member 5812 is rotated relative to the housing 5810 as indicated by arrow 5816, the driven shaft 5814 is prevented from rotating due to the linear projection 5842 that fits within the linear recess 5840. As such, rotation of the drive member 5812 in the housing 5810 causes the driven shaft 5814 to linearly slide as indicated by arrow 5818 along the linear recess 5840 due to the engagement of the externally threaded portion 5852 mates with the internal threads 5850. Since the outer shaft/tube 4910 is connected to the driven shaft 5814 and the inner shaft/tube 4912 is connected to the housing 5810, the outer shaft/tube 4910 is advanced and retracted relative to the inner shaft/tube 4912 by rotation of the drive member 5812.

In the example illustrated by FIGS. 58-61, the outer shaft/tube 4910 is fixedly connected in a recess, such as by threads 5850, in the driven shaft 5814 and an optional seal 5853 is provided between the outer shaft/tube 4910 and the inner shaft/tube 4912 and/or between the outer shaft/tube 4910 and the driven shaft 5814. A luer port 5862 is fixedly connected to the housing 5810, e.g., a proximal end of the housing 5810 as shown. The inner shaft/tube 4912 is fixedly connected in a recess 5860 in the luer port 5862. The luer port 5862 is configured to accept a guide wire 5002 (See FIG. 49) that extends through the inner shaft/tube 4912.

Figure 62:
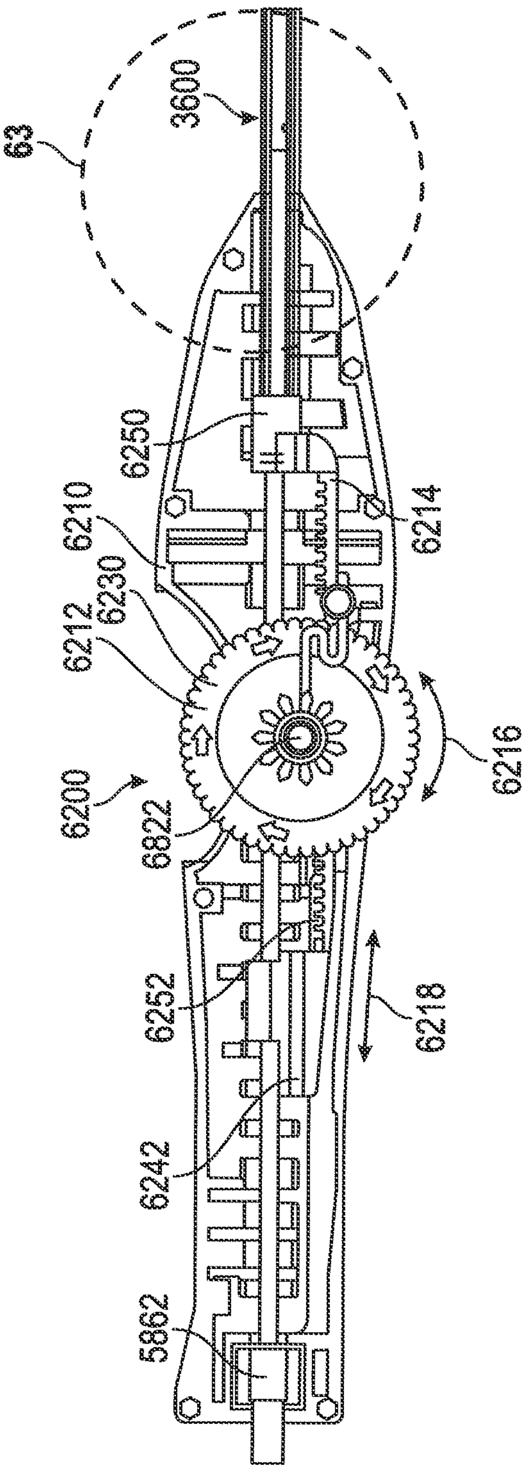
FIG. 62 is a view of an exemplary embodiment of a handle for a docking station catheter with a side cover removed.

In the example illustrated by FIG. 62-67, the handle 6200 includes a housing 6210, a drive wheel 6212, and a driven member 6214. In the illustrated example, rotation of the drive wheel 6212 as indicated by arrow 6216 relative to the housing 6210 moves the driven member 6214 linearly as indicated by arrow 6218 (compare the position of the driven member 6214 in FIGS. 64A and 64B). Referring to FIG. 62, the inner sleeve/tube 4912 is fixedly connected to the housing 6210 and the outer sleeve/tube 4910 is fixedly connected to the driven member 6214. As such, rotating the drive wheel 6212 in a first direction retracts the outer sleeve 4910 relative to the inner sleeve 4910 and rotating the drive wheel 6212 in the opposite direction advances the outer sleeve/tube 4910 relative to the inner sleeve/tube 4912. Although, in the various embodiments shown in FIGS. 58-73, the inner sleeve/tube 4912 is shown and described as being connected unmovably relative to the handle or a proximal end of the handle while the outer sleeve/tube 4910 is movable relative to the handle or a proximal end of the handle, in one embodiment using similar concepts, the inner sleeve/tube 4912 could be moveable relative to the handle or a proximal end of the handle while the outer sleeve/tube 4910 is connected unmovably relative to the handle or a proximal end of the handle, or both the inner sleeve/tube 4912 and outer sleeve/tube 4910 can be configured to be movable relative to each other and relative to the handle or proximal end of the handle.

In the example illustrated by FIGS. 62-67, the housing rotatably accepts an axle 6822 of the drive wheel 6212 to rotatably couple the drive wheel to the housing 6210. The drive wheel 6212 includes an engagement portion 6230 that extends from the housing 6210 to allow a user to rotate the drive wheel 6212 relative to the housing 6210.

Figure 66:
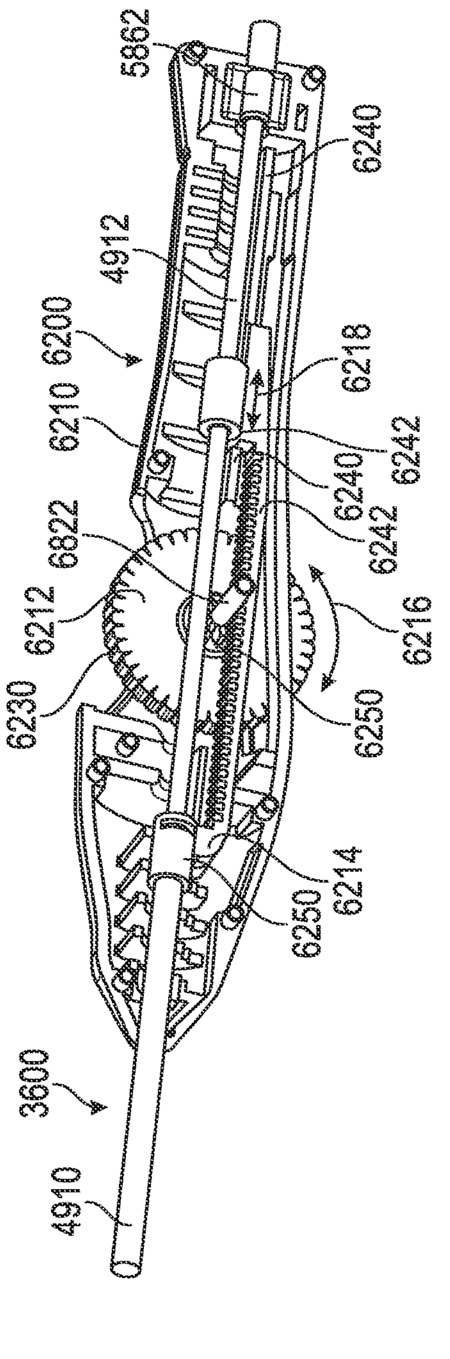
FIG. 66 is a perspective view of the handle illustrated by FIG. 62 with the opposite side cover removed
Figure 67:
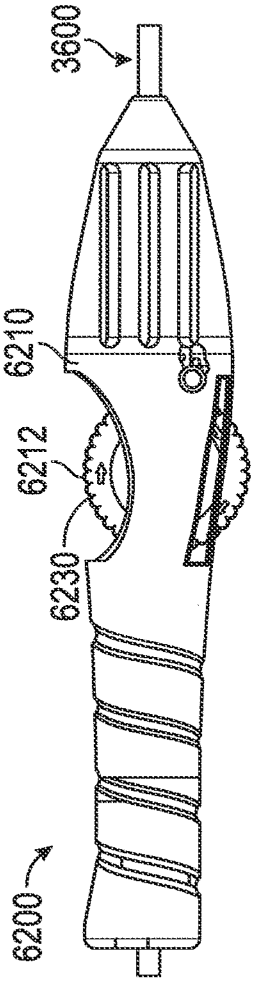
FIG. 67 is a side view of the handle illustrated by FIG. 62.
Figure 68:
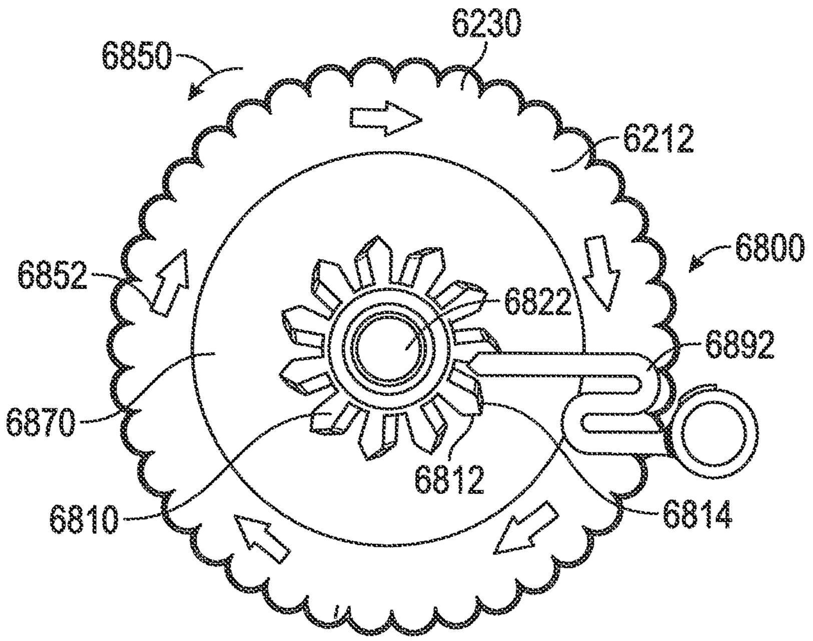
FIG. 68 is a side view of an indexing wheel of the handle illustrated by FIG. 62 in a ratcheting state.
Figure 69:
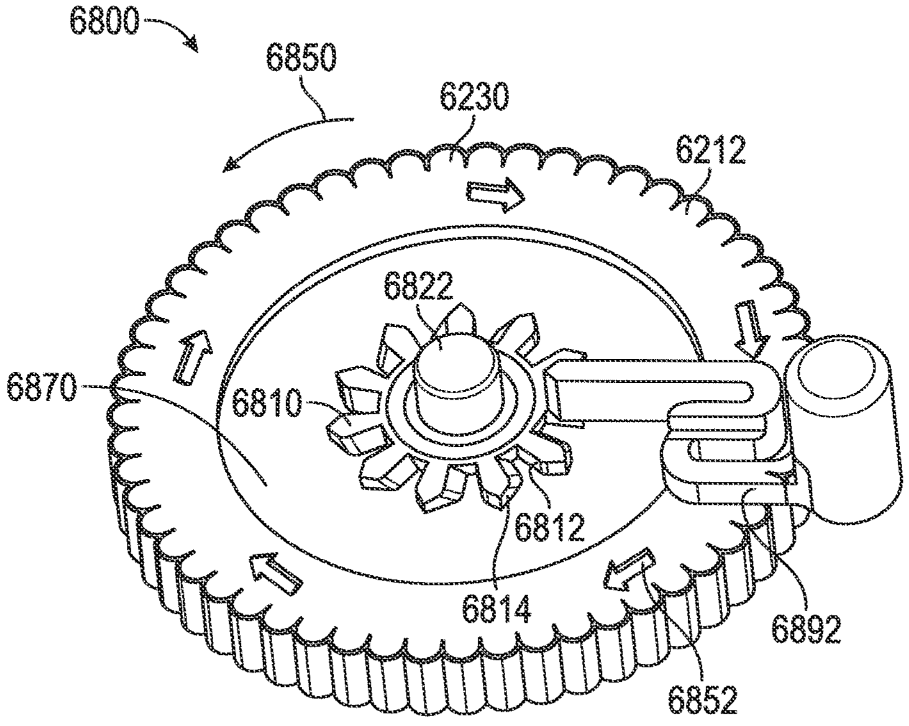
FIG. 69 is a perspective view of the indexing wheel of FIG. 68 in the ratcheting state.
Figure 70:
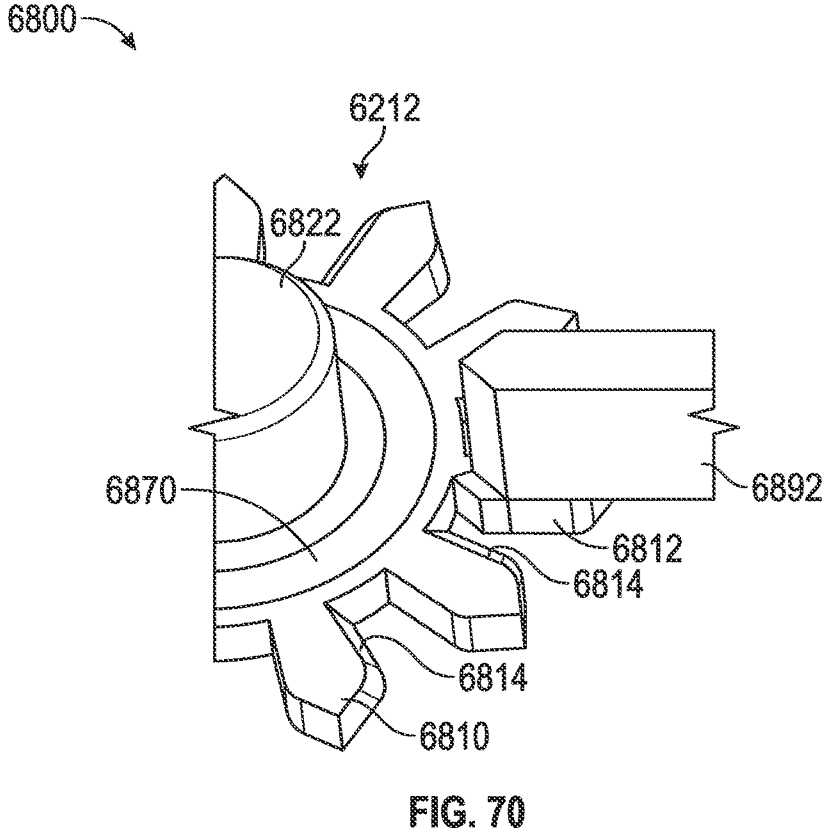
FIG. 70 is an enlarged portion of FIG. 69.

In the example illustrated by FIGS. 62-67, the housing 6210 includes a linear projection 6240 (See FIG. 66). The driven member 6214 includes a linear groove 6242 (See FIGS. 62, 66) that the projection 6240 fits within to slidably couple the driven member 6214 to the housing 6210.

In the example illustrated by FIGS. 62-67, the drive member 6212 includes a pinion gear 6250. The driven member 6214 includes a gear rack portion 6252. The pinion gear 6250 meshes with the gear rack portion 6252 to operationally couple the drive wheel 6212 to the driven member 6214. That is, when the drive wheel 6212 is rotated relative to the housing 6210 as indicated by arrow 6216, the driven member 6214 slides relative to the housing 6210 due to the linear projection 6240 that fits within the linear groove or recess 6242. As such, rotation of the drive member 6212 relative to the housing 6210 causes the pinion gear 6250 to drive the gear rack portion 6252 to cause the driven member 6214 to linearly slide as indicated by arrow 6218 relative to the housing 6210. Since the outer shaft/tube 4910 is connected to the driven member 6214 and the inner shaft/tube 4912 is connected to the housing 5810, the outer shaft/tube 4910 is advanced and retracted relative to the inner shaft/tube 4912 by rotation of the drive wheel 6212.

In the example illustrated by FIGS. 62-67, the outer shaft/tube 4910 is fixedly connected in a support portion that extends from the gear rack portion 6252 of the driven member 6214 and an optional seal (not shown) is provided between the outer shaft/tube 4910 and the inner shaft/tube 4912 and/or between the outer shaft/tube 4910 and the driven member 6214. A luer port 5862 is fixedly connected to the housing 6210, e.g., at a proximal end of the housing 6210. The inner shaft/tube 4912 is fixedly connected in a recess 5860 in the luer port 5862. The luer port 5862 is configured to accept a guide wire 5002 (See FIG. 49) that extends through the inner shaft/tube 4912.

Figure 63:
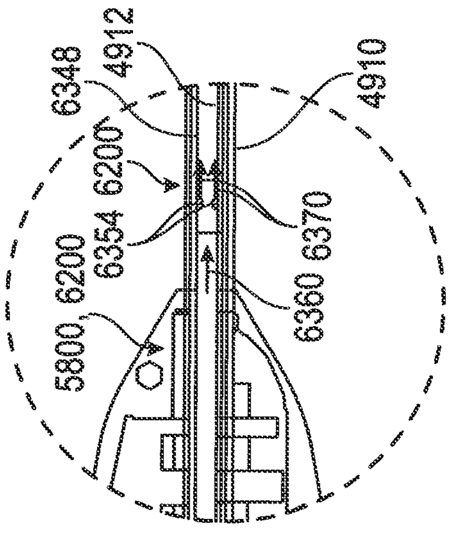
FIG. 63 is an enlarged portion of FIG. 62 illustrating a flushing system of a catheter.
Figure 64A:
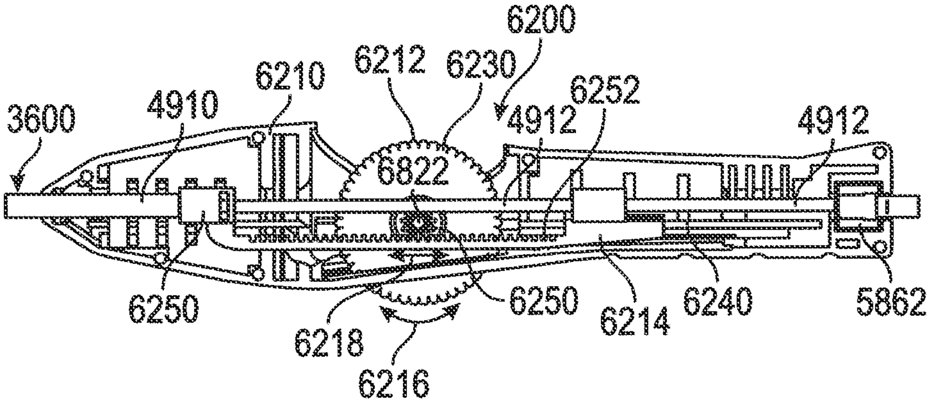
FIGS. 64A and 64B are views of the handle illustrated by FIG. 62 with an opposite side cover removed to illustrate extension and retraction of an outer sleeve of a docking station catheter.
Figure 64B:
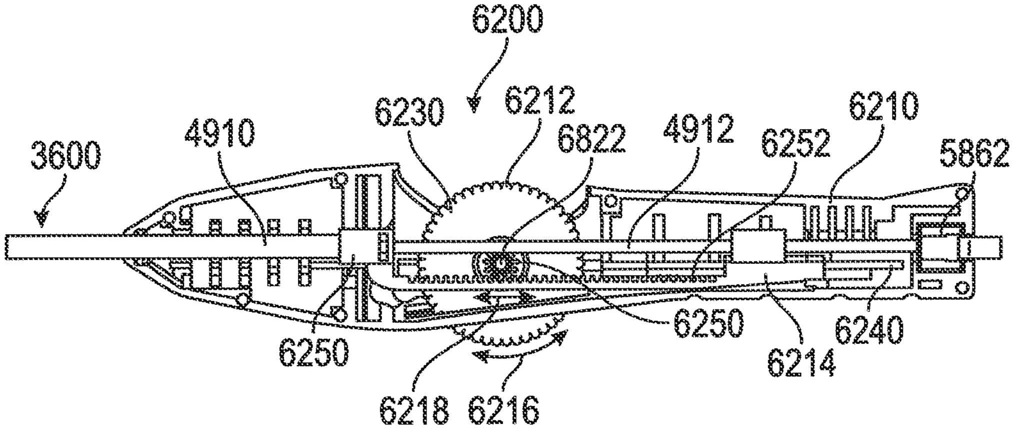
Figure 65:
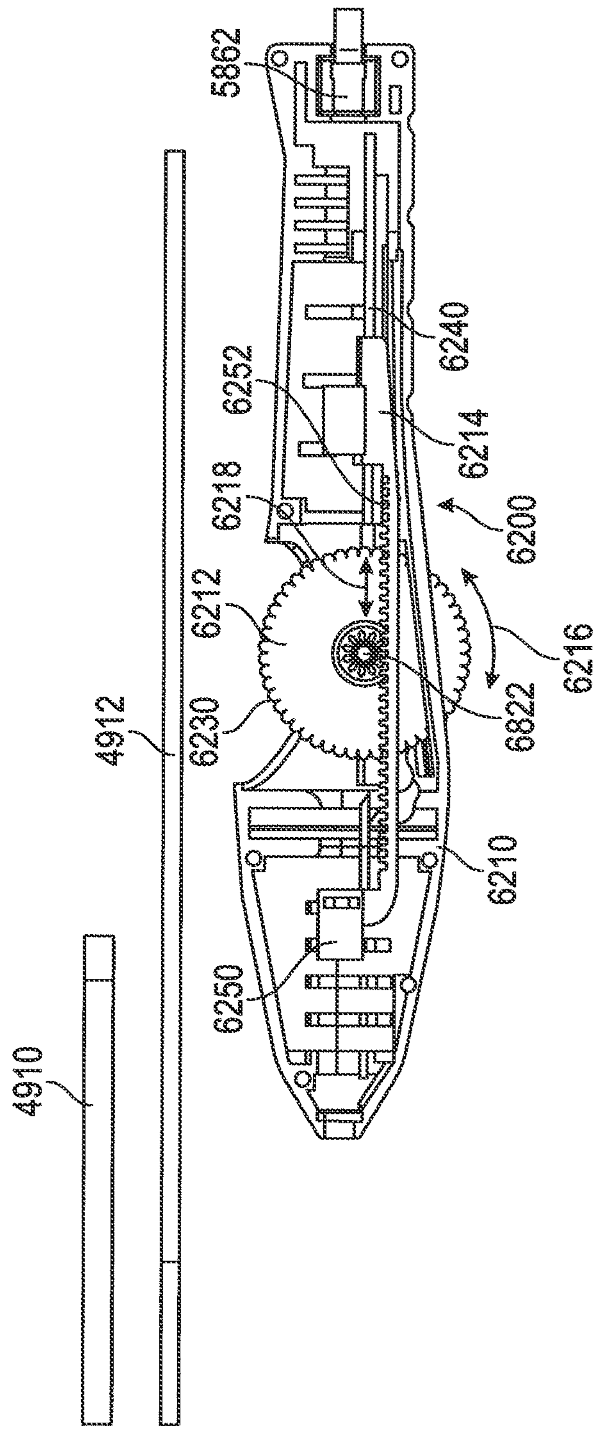
FIG. 65 is an exploded view of the handle of FIG. 62.

Referring to FIG. 63, in one exemplary embodiment, the catheter 3600 can be flushed by applying a fluid to the inner tube 4912, such as to the inner tube via the luer port 5862. As is described above, the delivery catheter 3600 includes an outer lumen formed within an outer tube/sleeve 4910 and an inner lumen formed within an inner tube/sleeve 4912, and the inner lumen and inner tube 4912 are longitudinally co-axial with the outer lumen and outer tube 4910. An annular lumen/gap/space 6348 in between the inner tube 4912 and outer tube 4910 that may result from, for example, the need to provide space for a crimped stent to travel through the catheter 3600. This gap/space 6348 can initially be filled with air, which can be subsequently expelled and replaced with a liquid, e.g., a saline solution. Flushing in this way can be done with the various handle embodiments shown in FIGS. 58-73.

In one exemplary embodiment, a fluid such as saline or another suitable fluid, flows from the luer port 5862 and through the inner lumen of inner tube 4912 as indicated by arrow 6360. In this embodiment, the inner tube 4912 is provided with one or more flushing apertures 6354. The fluid flows through the inside of the inner tube 4912, out the apertures 6354 as indicated by arrows 6370 and into the gap/space 6348.

As the gap/space 6348 fills with fluid, air is pushed out of the delivery catheter through the distal end of the outer tube 4910. In one exemplary embodiment, the nosecone 28 is disengaged from the distal end of the outer tube 4910 to allow the air to flow out of the outer tube and out of the catheter 3600. Fluid also flows through the inner lumen of the inner tube 4912 to push air out of the inner lumen. In one exemplary embodiment, the air is forced out of the inner lumen through the opening 6390 in the end of the nosecone 28 (See FIGS. 49A and 49B). This flushing procedure is performed before the delivery catheter 3600 is introduced into the body. The device and method of this approach saves space as compared to, for example, providing a side port on the outer tube 4910 for introducing a flushing fluid into the delivery catheter assembly or gap/space 6348.

Referring to FIGS. 68-73, in one exemplary embodiment, the handle 6200 illustrated by FIGS. 62-67 can be provided with a ratchet mechanism 6800. The ratchet mechanism 6800 can take a wide variety of different forms and can be used with the handle 6200 in a variety of different ways. In one exemplary embodiment, the ratchet mechanism 6800 is used during a "recapture" of the docking station 10 to pull it back into the delivery catheter 3600. The force required to recapture the docking station can be significant. As such, the ratchet mechanism 6800 can be configured such that, when the ratchet mechanism is engaged (FIGS. 68-71), the drive wheel 6212 can only be rotated in the direction that draws the docking station 10 back into the outer tube/sleeve 4910. That is, the spring force of the docking station 10 is prevented from pulling the docking station back out of the outer tube by the ratchet mechanism 6800. The operator can recapture the docking station 10 sequentially, without the docking station slipping back if the operator lets go of the drive wheel 6212, for instance.

Referring to FIGS. 68-71, one exemplary ratchet system uses projections 6810 with stop surfaces 6812 on one side of the projections and ramp surfaces 6814 on the other side of the projections. FIGS. 68-71 illustrate an engaged condition where a ratchet arm 6892 is positioned to engage with the projections 6810 to permit the drive wheel 6212 to rotate in one direction, and to prevent the drive wheel from turning in the opposite direction. For example, the ratchet arm 6892 can be configured to ride over the ramped surfaces 6814 to allow movement of the drive wheel 6212 in the retracting direction 6850. For example, the ratchet arm 6892 can flex to ride over the inclined ramped surfaces 6814. The stop surfaces 6812 are configured to engage the ratchet arm 6892 and prevent rotation of the drive wheel in the advancing direction 6852. For example, the stop surfaces 6812 can be substantially orthogonal to a side surface 6870 of the drive wheel 6212 to prevent the ratchet arm from moving over the projection 6810.

Figure 72:
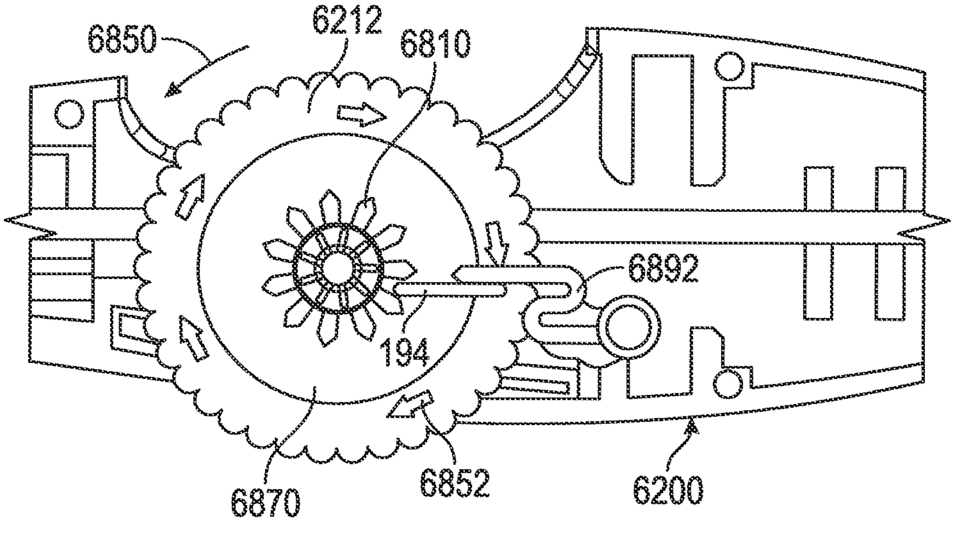
FIG. 72 is a view that is similar to FIG. 71 in a disengaged state.
Figure 73:
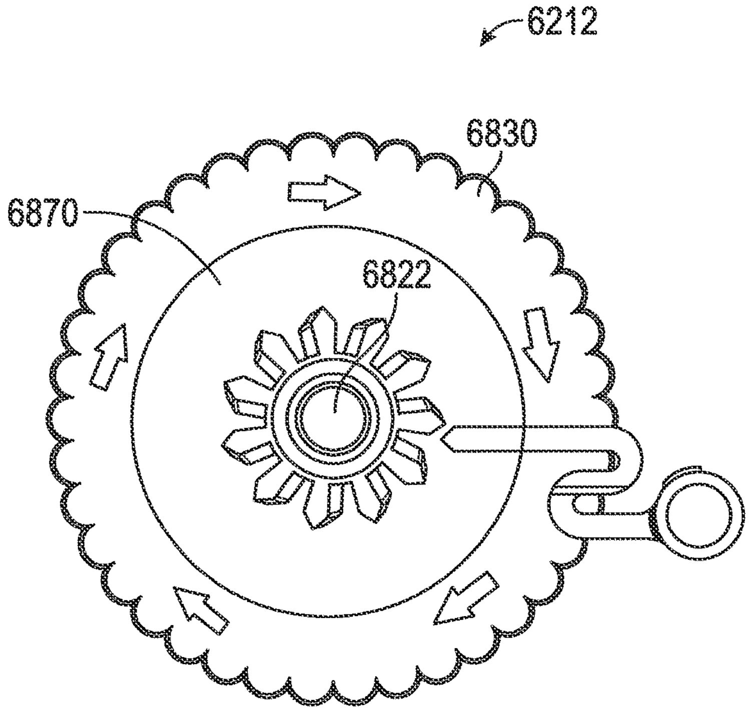
FIG. 73 is a side view of an indexing wheel of the handle illustrated by FIG. 62 in the disengaged state.

FIGS. 72 and 73 illustrate the ratchet mechanism 6800 with the ratchet arm 6892 moved out of engagement with the projections 6810. This allows the drive wheel 6212 to be turned in either direction. For example, the ratchet mechanism 6800 can be placed in the disengaged condition to allow the drive wheel 6212 to be turned in either direction as the docking station 10 is being deployed.

In ratchet systems, it is common to place the ratchet teeth on the outer perimeter of the wheel. By putting the teeth on the face of the wheel, the radial diameter of the wheel can be reduced, saving space. It also allows the outer perimeter of the wheel to be used as a grip for the thumb rather than, for example, having a second wheel for gripping that is in engagement with a first wheel. The wheel itself is also allowed to be thinner. The wheel can be made of any suitable material, such as polycarbonate.

Figure 71:
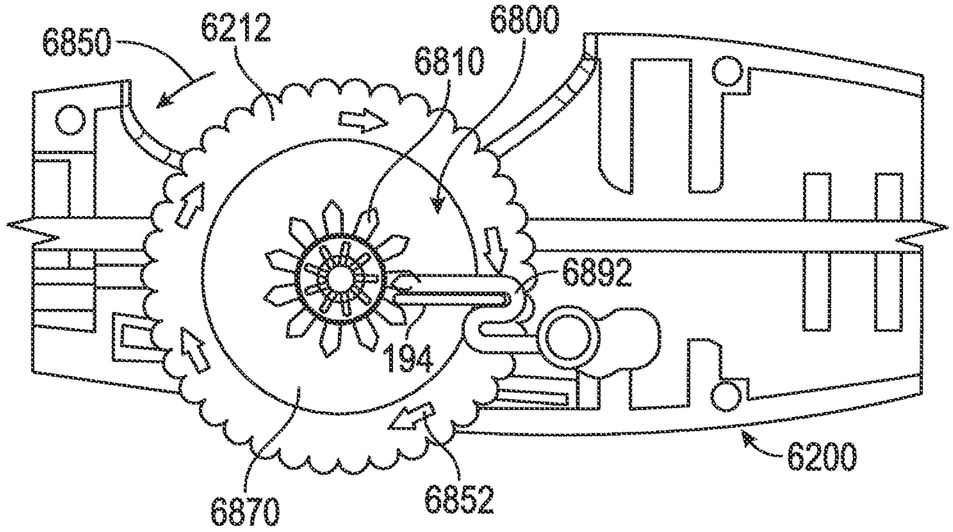
FIG. 71 is a partial sectional view of the indexing wheel illustrated by FIG. 68 disposed in a handle housing.

Referring to FIG. 71, in one embodiment the ratchet arm 6892 can be bent so that a portion of the arm can rest on a stabilizing bar 194 extending from a housing wall or otherwise located within the housing, to prevent the arm 6892 from twisting as force from movement of the wheel is applied to the arm.

FIGS. 74 through 90C show additional embodiments of docking stations 10 and frames 1500 for docking stations. Any combination or sub-combination of features, or any individual feature of the embodiments of FIGS. 74 through 90C can be used/combined with any combination or sub-combination of features, or any individual feature of the embodiments of FIGS. 4A through 73. Commonly owned U.S. Pat. No. 10,363,130 and Patent Cooperation Treaty Application No. PCT/US2017/016587 are incorporated herein by reference in their entireties.

Referring now to FIGS. 74 through 78B, the frame 1500 of the docking station 10 can be sized, shaped, and/or otherwise configured to fit pulmonary arteries of varying sizes, shapes, diameters, and geometries. The frame 1500 of the docking station 10 can have any number of struts 1502, any number of cells 1504, or any number of apices 1510, or the struts 1502 or the cells 1504 can have any shape to fit pulmonary arteries of varying sizes, shapes, and geometries.

The struts 1502 can have any size, shape, thickness, or configuration to retain the valve 29 in the pulmonary artery PA. Additionally, the proximal end 12 of the frame 1500 can have a different size, shape, and/or configuration from the distal end 14 of the frame 1500.

The frame 1500 of the docking station 10 can include a lattice of struts 1502 which extend from the proximal end 12 to the distal end 14 and define the valve seat 18. The struts 1502 each extend from the apices 1510 at the proximal end 12 to the nearest junction 1503, extend between adjacent junctions 1503, and extend from the apices 1510 at the distal end 14 to the nearest junction 1503. As such, each strut 1502 connects with one or more other struts 1502 at a junction 1503 and/or apex 1510. The space enclosed by the junctions 1503, apices 1510, and connected struts 1502 define the cells 1504. The struts 1502 can connect at the proximal and distal ends 12, 14 to form a plurality of apices 1510. The apices 1510 can serve as or connect to the retaining portions 414. Rungs 1506 are a circumferential row of the struts 1502 that extend from the apices 1510 at the proximal end 12 to the nearest junction 1503, circumferential row(s) of the struts 1502 that extend between adjacent junctions 1503, and/or a circumferential row of struts 1502 that extends from the apices 1510 at the distal end 14 to the nearest junction 1503. In the example illustrated by FIG. 74, the frame 1500 comprises four rungs. The struts 1502 alternate between converging with the junctions 1503 pointed toward the proximal end 12 and converging with the junctions 1503 pointed toward the distal end 14, such that the cells 1504 are generally diamond shaped. Additionally or alternatively, one or more struts 1502 in one rung 1506 can be continuous with one or more struts 1502 in the successive rung 1506. That is, one or more of the struts 1502 can be formed from a continuous strip of material that is simply connected to an adjacent strut at the junctions 1503, rather than each strut 1502 terminating on one side of a junction 1503 with a discrete strut starting on the other side of the junction.

Figure 74:
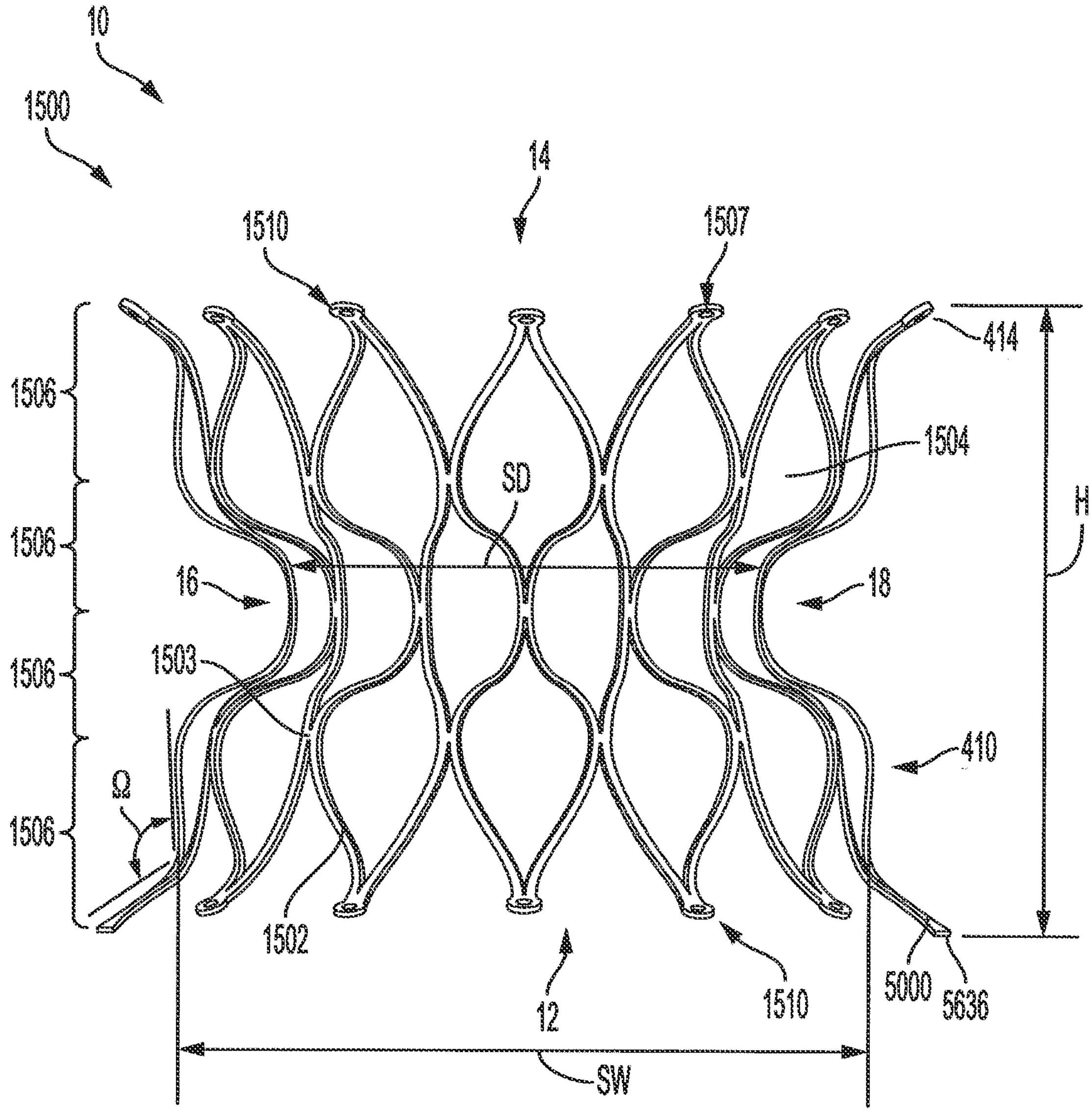
Figure 75:
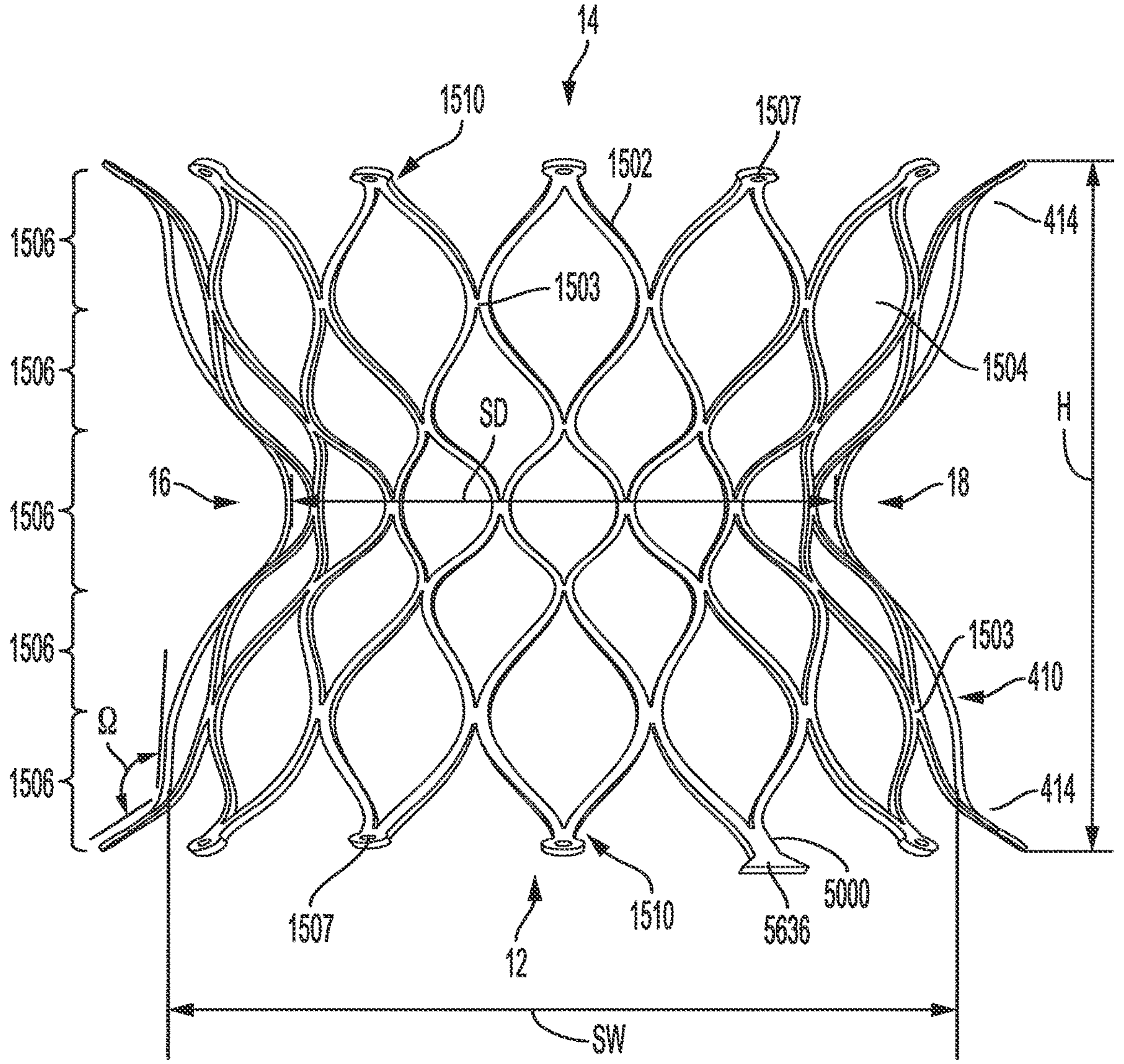

As shown in FIGS. 74-75, the frame 1500 can have a height H extending from the proximal end 12 to the distal end 14 of the frame and a seat diameter SD which is the diameter of the valve seat 18. The frame 1500 can also have a seal width SW which is the width of the sealing portion 410 at the point between the proximal end 12 and the valve seat 18 where the docking station 10 seals with the pulmonary artery.

Referring to FIGS. 74 and 75, the frame 1500 of the docking station 10 can have different numbers of rungs 1506. The number and configuration of rungs 1506 can be determined to provide a better securement, fit, or apposition of the docking station 10 in the pulmonary artery PA. For example, the docking station 10 can include more rungs 1506 for longer pulmonary arteries PA or where more radial force is beneficial.

As shown in FIG. 74, the frame 1500 of the docking station 10 can be configured for wide pulmonary arteries PA. For example, the frame 1500 of the docking station 10 can be configured for pulmonary arteries PA that are short and wide. The frame 1500 of the docking station 10 can have four rungs 1506 and can have three rows of cells 1504. The frame 1500 can have a height H between 30 mm and 40 mm, such as between 32 mm and 38 mm, such as 35 mm. The frame 1500 can have a seat diameter SD between 24 mm and 31 mm, such as between 26 mm and 29 mm, such as 27 mm. The frame 1500 can have a seal width SW between 36 mm and 46 mm, such as between 38 mm and 44 mm, such as 41 mm.

The frame 1500 of the docking station 10 can also be configured to fit a longer and/or wider pulmonary artery. For example, the frame 1500 of the docking station 10 can be longer and wider. As shown in FIG. 75, the frame 1500 of the docking station 10 can have six rungs 1506 and can have five rows of cells 1504. The frame 1500 of the docking station 10 can have a height H between 43 mm and 53 mm, such as between 45 mm and 51 mm, such as 48 mm. The frame 1500 can have a seat diameter SD between 24 mm and 31 mm, such as between 26 mm and 29 mm, such as 27 mm. The frame 1500 can have a seal width SW between 44 mm and 54 mm, such as between 46 mm and 52 mm, such as 48 mm and 50 mm.

While the frame 1500 has been described as having either four or six rungs 1506, the frame 1500 can have any suitable number of rungs 1506 and any suitable number of rows of cells 1504. For example, the frame 1500 can have three, five, or seven or more rungs 1506 and two, four, or six or more rows of cells 1504. The frame 1500 can also have alternative configurations or geometries such that the frame 1500 does not have diamond-shaped cells 1504 or not all the cells 1504 are diamond-shaped.

Referring to FIGS. 76A through 78B, the docking station 10 can be shaped or otherwise configured to better secure in pulmonary arteries of varying sizes, shapes, diameters, and geometries. As shown in FIGS. 76A through 77C, the frame 1500 of the docking station 10 can include different number of apices 1510 at the proximal and/or distal ends 12, 14. The number of apices 1510 can be determined to provide a better securement, fit, or apposition of the docking station 10 in the pulmonary artery PA. For example, the docking station 10 can include more apices 1510 in pulmonary arteries with larger diameters or varying geometries.

Figure 76A:
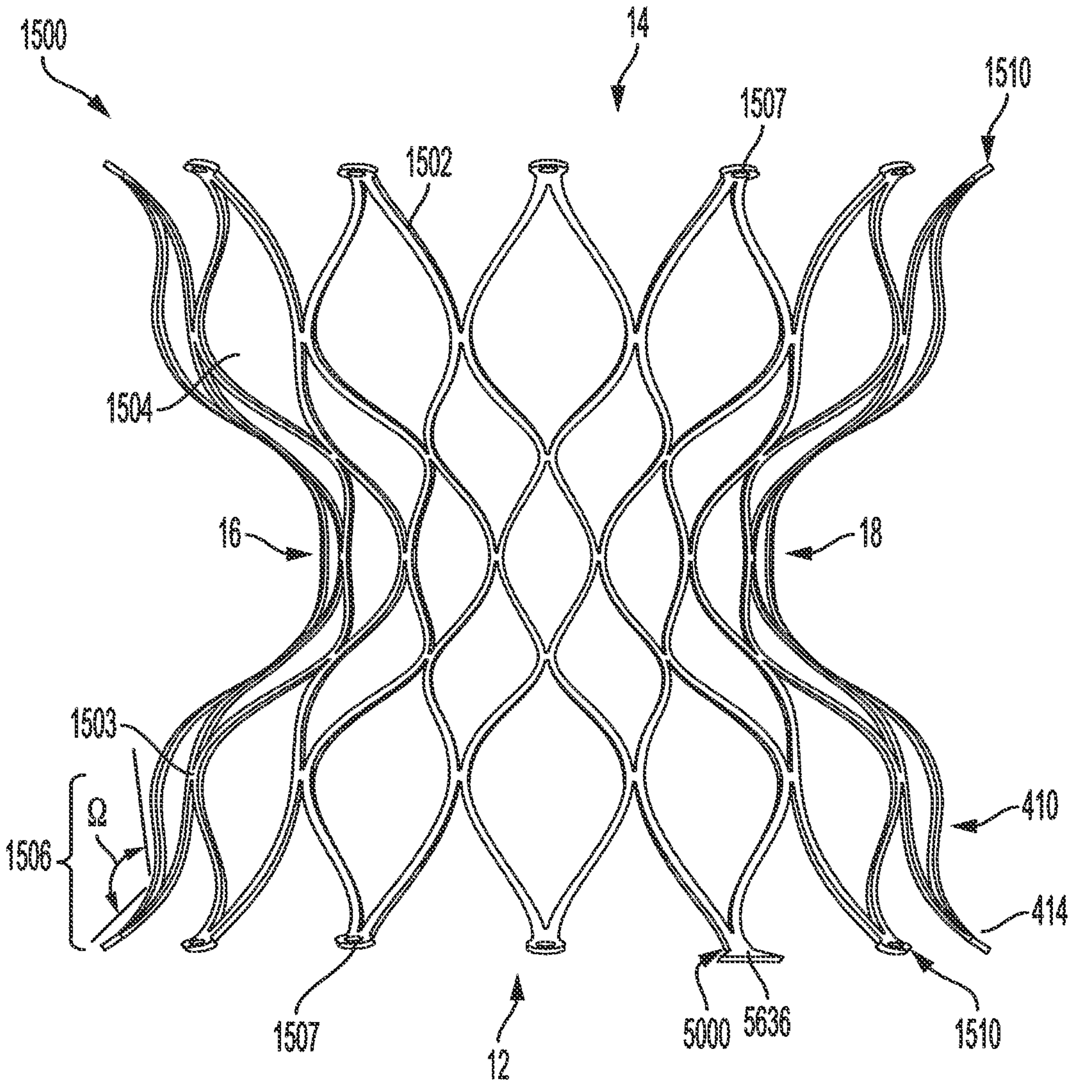
Figure 76B:
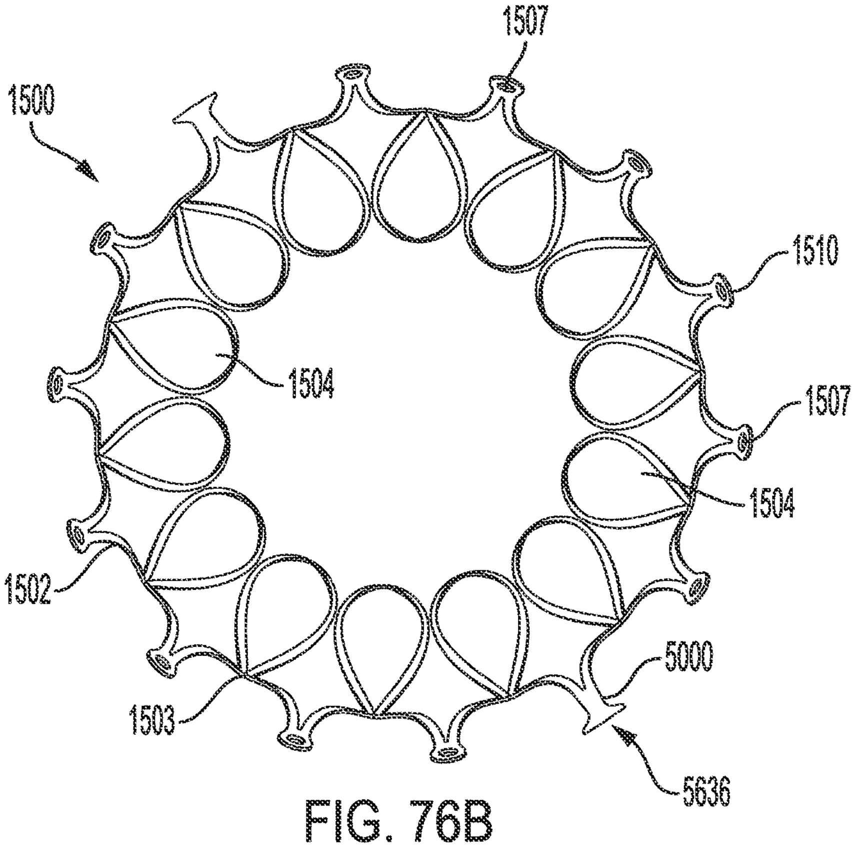
Figure 76C:
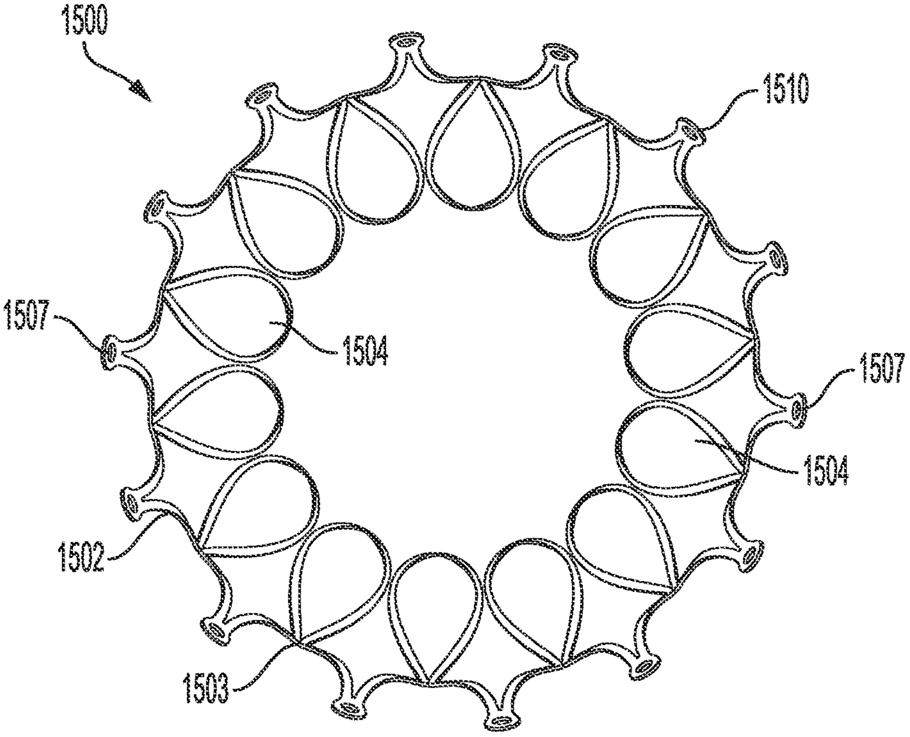
Figure 77A:
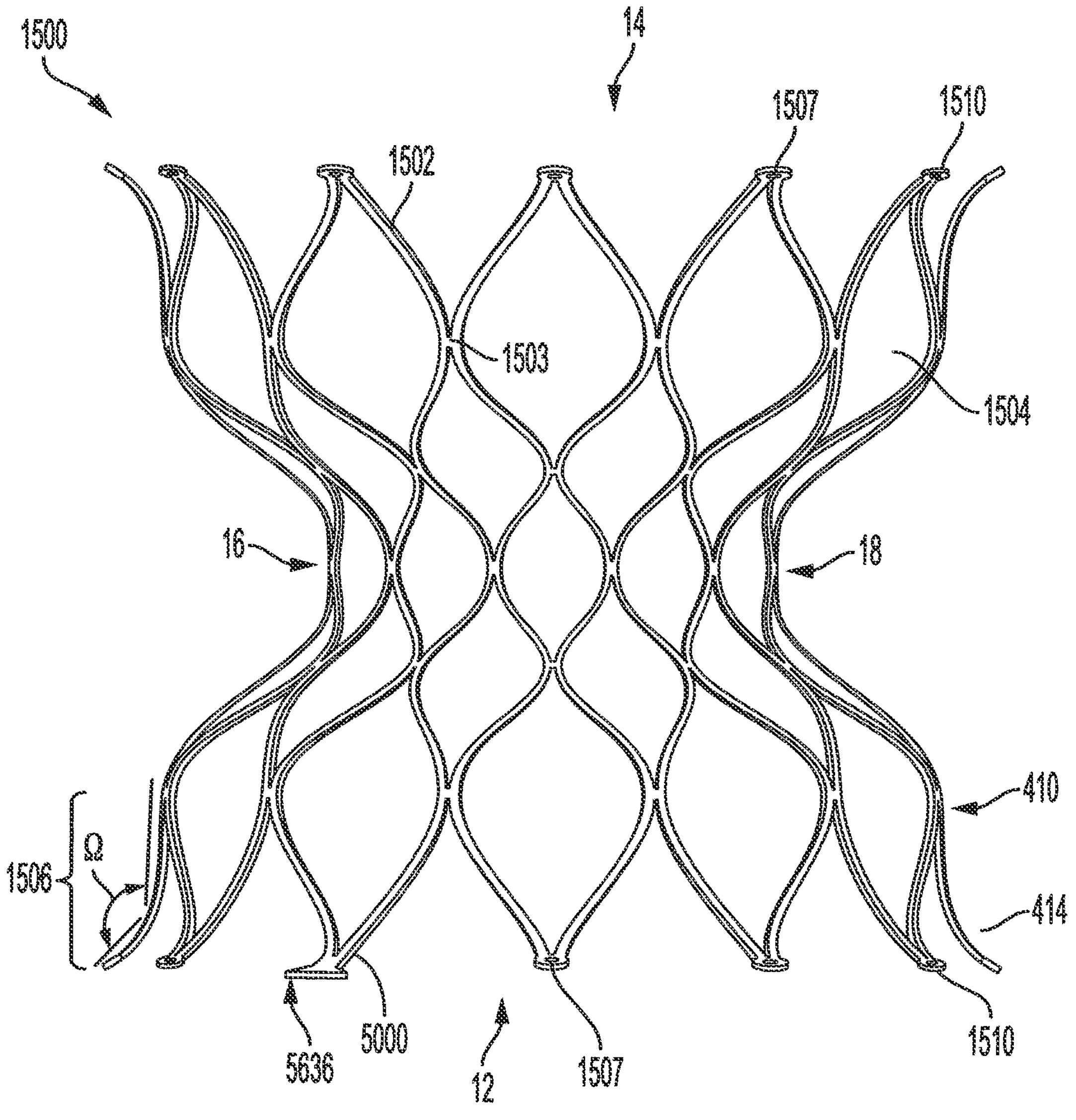
Figure 77B:
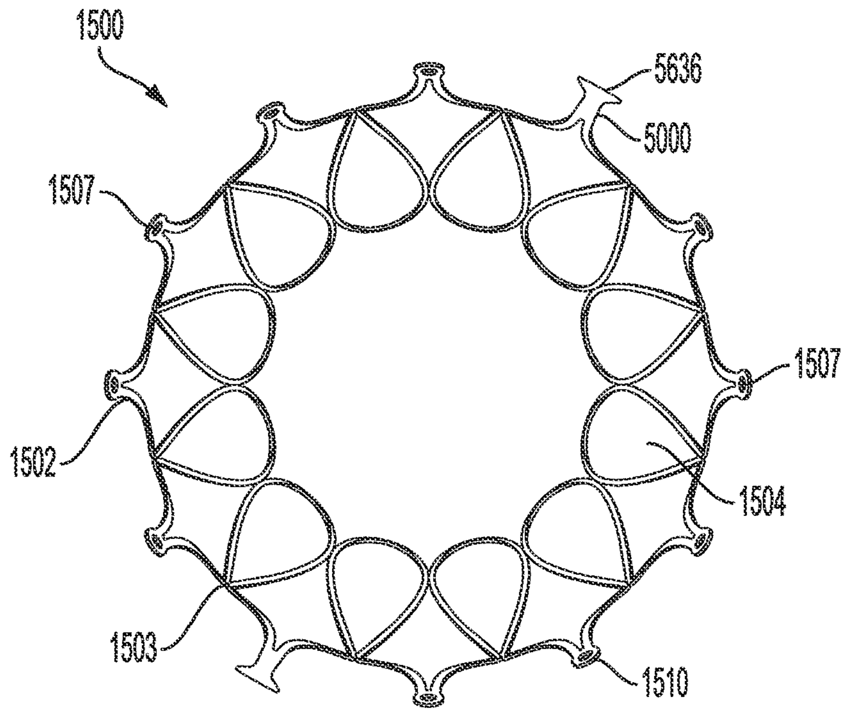
Figure 77C:
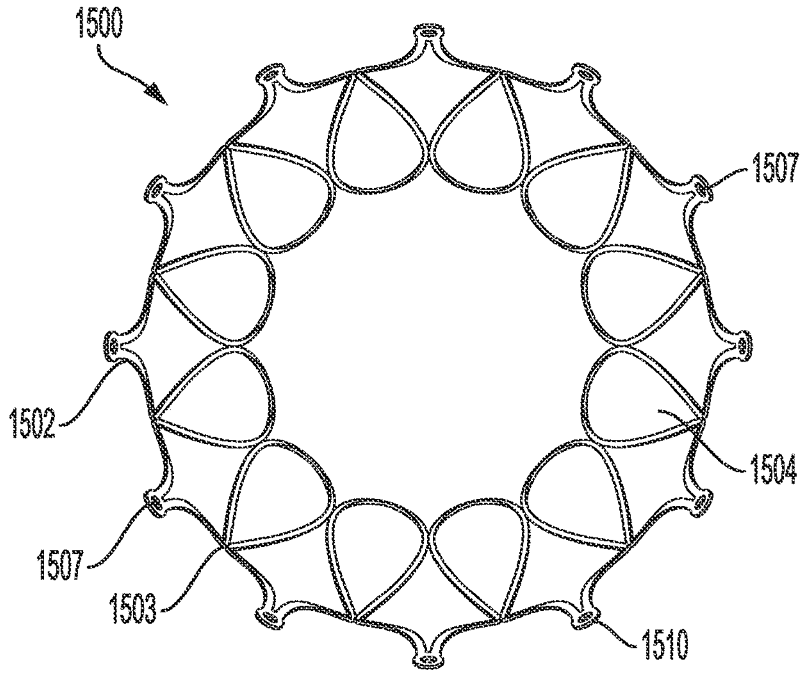

As shown in FIGS. 76A through 76C, the frame 1500 can be configured to include apices 1510 at the proximal end 12 and 14 apices 1510 at the distal end 14 which can provide better apposition in the anatomy of the pulmonary artery PA. As shown in FIGS. 77A through 77C, the frame 1500 can be configured to include apices 1510 at the proximal end 12 and 12 apices 1510 at the distal end 14 which can lower the force required to crimp the docking station 10 to fit a delivery device such as a catheter (e.g., catheter 3600 as shown in FIGS. 50A-50D) or can reduce the outward radial force exerted by the docking station 10 onto the pulmonary artery PA. While the docking station 10 has been described as having either 12 or 14 apices 1510, the docking station 10 can include any number of apices 1510. For example, the docking station 10 can have 8-11 apices 1510, such as 10 apices 1510, 13 apices, 15 or more apices 1510, such as 16 apices 1510, or any other number of apices 1510. Additionally, the docking station 10 can be configured such that the proximal and distal ends 12, 14 have different numbers of apices 1510 to fit pulmonary arteries PA of varying shapes, sizes, and diameters.

The docking station 10 can also be configured to decrease or prevent additional trauma to the pulmonary artery. For example, the apices 1510 of the frame 1500 can contain a shallow angle between the sealing portions 410 and the retaining portions 414 to decrease traumatization of the tissue of the pulmonary artery while still permitting retention of the docking station 10 within the pulmonary artery PA. For example, an angle Ω at the transition between the sealing portions 410 and the retaining portions 414 can be between 120 degrees and 140 degrees, such as between 125 and 135 degrees, such as about 130 degrees. The struts 1502 which define the proximal and distal apices 1510 can be curved, bent, or otherwise shaped such that the apices 1510 are flared radially outward to a position that will maintain the docking station 10 in the pulmonary artery when the docking station 10 is deployed and will decrease or minimize trauma caused to the tissue of the pulmonary artery.

The frame 1500 of the docking station 10 can include one or more eyelets 1507 at the apices 1510. The eyelets 1507 can be circular or rounded passages or apertures extending through the frame 1500 at the proximal and/or distal ends 12, 14. As detailed below, the eyelets 1507 can be used to secure or attach the impermeable material 21 to the frame 1500. In the illustrated embodiment, the frame 1500 includes eyelets 1507 at the proximal and distal ends 12, 14. However, one or more apices 1510 at either the proximal end 12 or the distal end 14 may not have an eyelet 1507 and the apex 1510 can be generally solid and rounded. For example, the apices 1510 at the distal end 14 may not include eyelets 1507 in embodiments where the impermeable member 21 does not extend to the distal end 14, as detailed below.

The frame 1500 can also include one or more elongated legs or extensions 5000 and one or more heads 5636, as described above. The one or more elongated legs or extensions 5000 and one or more heads 5636 can facilitate the deployment, recapture, and redeployment of the docking station 10. In the illustrated embodiments, each frame 1500 includes two extensions 5000 and two heads 5636 at opposite sides of the proximal end 12. However, the frame 1500 can include extensions 5000 and heads 5636 in any number and in any suitable configuration. For example, the frame 1500 can include extensions 5000 and heads 5636 at the distal end 14 and/or the frame 1500 can have one or three or more heads 5636 at one or both of the ends 12, 14. The extensions 5000 and/or the heads 5636 can be longer than the apices 1510, while still being short enough to control the frame 1500 during deployment from the delivery device. For example, the extensions 5000 and/or the heads 5636 can be between 0.5 mm and 3.0 mm longer than the apices 1510 (or any particular length or subrange between 0.5 mm and 3.0 mm), such as between 0.8 mm and 1.8 mm (or any particular length or subrange between 0.8 mm and 1.8 mm) longer than the apices 1510, such as 1.3 mm longer than the apices.

Figure 78A:
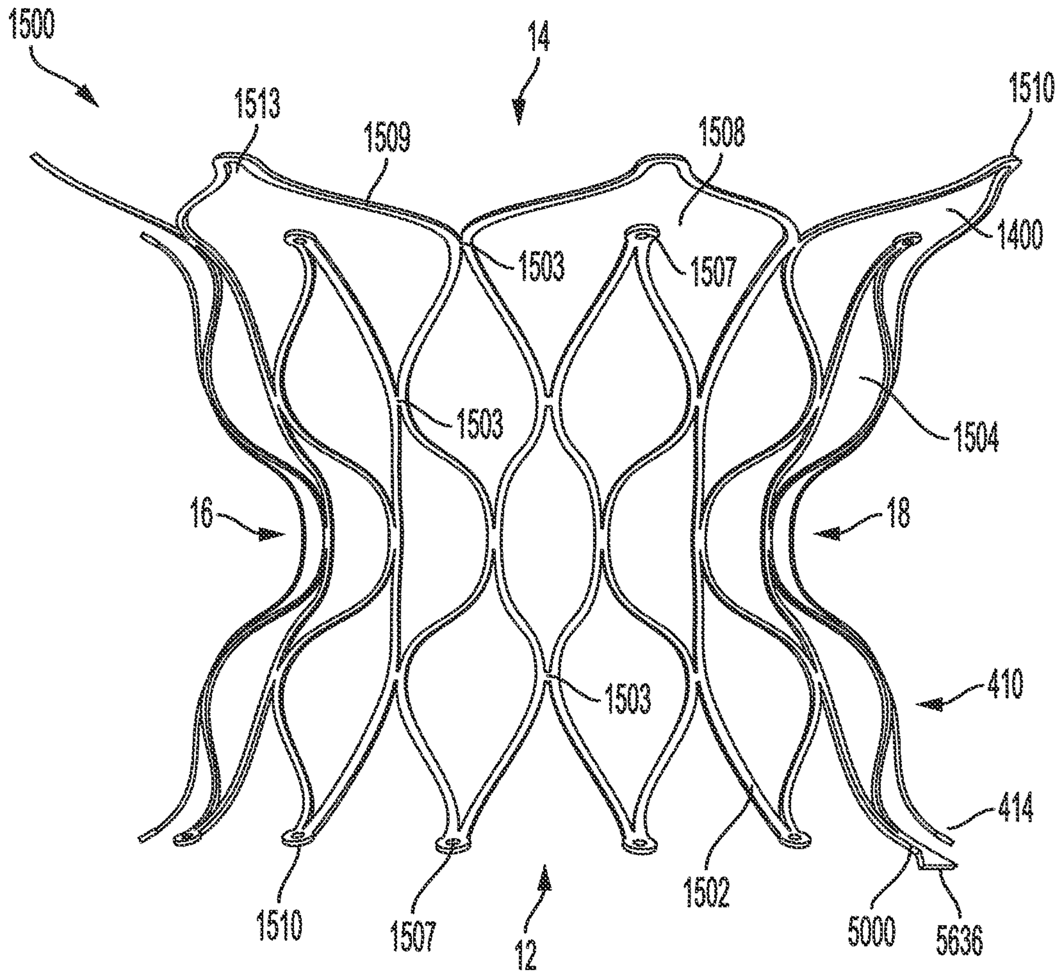
Figure 78B:
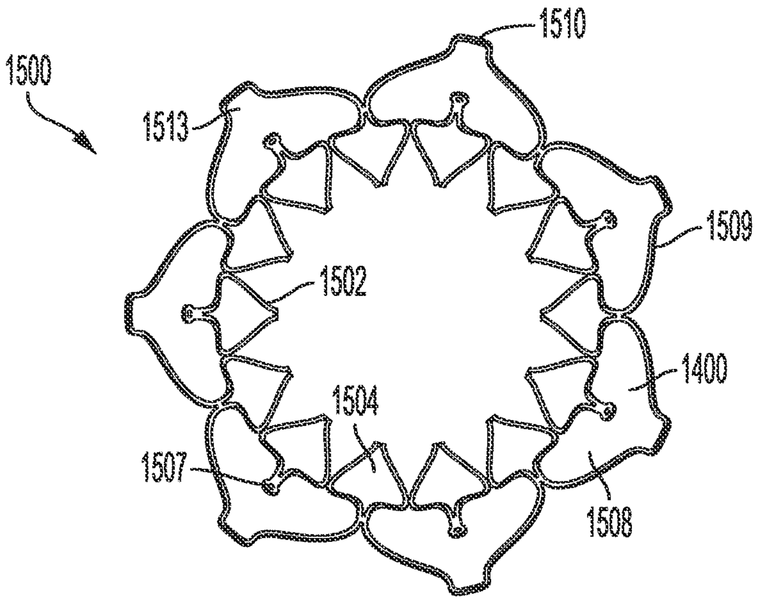

As shown in FIGS. 78A and 78B, the frame 1500 of the docking station 10 can be configured to include a plurality of outflow cells 1508 at the distal end 14 of the frame 1500 that facilitate blood flow through the docking station 10 when the docking station 10 is deployed. The outflow cells 1508 can extend into the pulmonary artery bifurcation or branch when the docking station 10 is placed higher in the pulmonary artery. At least a portion of the outflow cells 1508 may not be covered by the impermeable material 21 and the outflow cells 1508 can form at least part of the permeable portion 1400. The outflow cells 1508 can be larger than the other cells 1504 of the frame 1500. Each outflow cell 1508 can be defined by one or more outflow struts 1509. The one or more outflow struts 1509 defining the outflow cell 1508 can be shaped or otherwise configured to define one of the distal ends or apices 1510. The outflow struts 1509 of each outflow cell 1508 can extend distally from two of the distal-most junctions 1503 of the cells 1504. The outflow cells 1508 can increase the width and the stability of the frame 1500 when deployed without significantly increasing the height of the frame 1500. For example, the outflow cells can increase the height of the frame by less than $1/8^{th}$ of the height of the remainder of the frame, increase the height of the frame by less than $1/12^{th}$ of the height of the remainder of the frame, increase the height of the frame by less than $1/16^{th}$ of the height of the remainder of the frame, increase the height of the frame by less than $1/20^{th}$ of the height of the remainder of the frame, or not increase the height of the frame at all.

In the illustrated embodiments, the outflow cells 1508 are each partially defined by one outflow strut 1509 which is bent to define one of the distal ends 1510. The ends of the outflow strut 1509 are each attached to the distal most junction 1503 between two of the distal most cells 1504 with one cell 1504 in between the two cells 1504. In such an embodiment, the frame 1500 can include eyelets 1507 at the distal most junction 1503 of the cells 1504 to which the outflow struts 1509 do not attach. In such an embodiment, each outflow cell 1508 is defined by one outflow strut 1509 and four struts 1502.

As shown in FIGS. 78A and 78B, the outflow strut 1509 can be bent, pinched, or otherwise shaped such that the distal portion of the outflow cells 1508 define a narrow end 1513. The narrow ends 1513 can help secure the deployed docking station 10 in the pulmonary artery and can be used to help crimp the docking station 10 into a delivery device such as a catheter (e.g., catheter 3600 as shown in FIGS. 50A-50D).

In the illustrated embodiments, the outflow cells 1508 comprise the distal most row of cells. However, the frame 1500 can include outflow cells 1508 in any suitable configuration. For example, some but not all of the cells in the distal most row can be outflow cells 1508 or the outflow cells 1508 can constitute two or more rows of cells.

Figure 79:
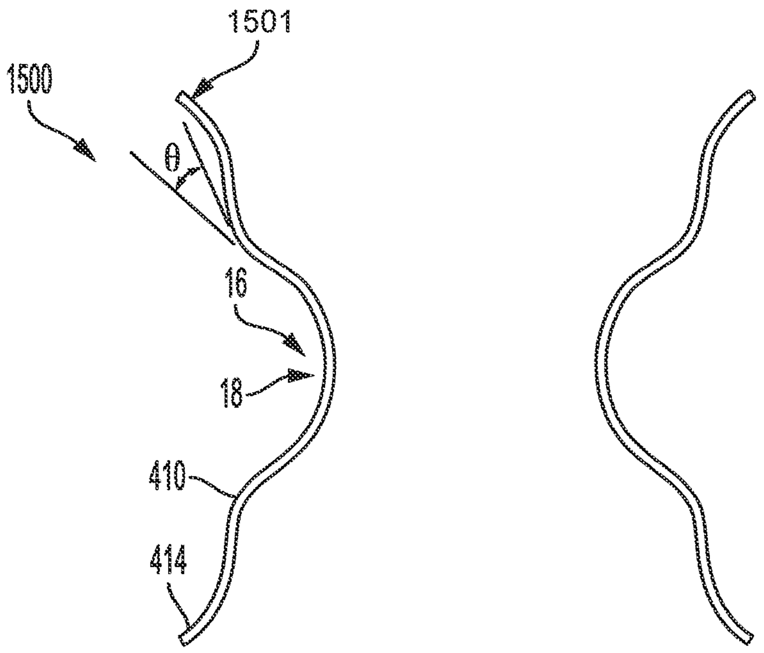

Referring now to FIG. 79, any of the frames 1500 described herein can be configured such that the frame 1500 is easier to deploy, recapture, and/or redeploy. For example, the frame 1500 can be configured to reduce the amount of force required to recapture frame 1500. As shown in FIG. 79, any of the frames 1500 described herein can have a side profile with a maximum transition angle θ at any location along the frame 1500. The maximum transition angle θ defines the maximum angle between tangent lines at close points along the frame 1500. For example, the maximum transition angle can be measured as the angle between tangents of any two points that are 0.1 mm apart along the profile of the frame. The frame 1500 can be shaped and configured and the maximum transition angle θ set such that the docking station 10 can be easily deployed, recaptured, and redeployed. The frame 1500 can be configured such that the maximum transition angle θ is minimized and large internal forces within the frame 1500 required to compress the frame back into the catheter do not prevent the frame 1500 from being recaptured or redeployed. For example, the side profile 1501 is shaped and configured such that the maximum transition angle θ is less than 60°, such as less than 55°, such as less than 50°, such as 45°.

Referring now to FIGS. 80A, 80B, and 80C, the struts 1502 of the docking station 10 can be configured to provide a more resilient valve seat 18 or to provide more radial force against the valve 29 when the valve 29 is deployed in the valve seat 18. In some exemplary embodiments, the frame 1500 can be configured such that the band 20 (see FIG. 18) can be omitted. Additionally or alternatively, the frame can be configured such that the impermeable member 21 does not include additional stitching which can increase the radial resistance as described below. As shown in FIGS. 80A-80C, the struts 1502 in the rungs 1506 near the valve seat 18 can be thicker or have an increased cross-sectional width or diameter in relation to the struts 1502 of other portions of the frame 1500. In the illustrated embodiments, the struts 1502 of the two rungs 1506 in the middle of the frame 1500 (i.e. in the area of the valve seat 18) are thicker than the struts 1502 of the other rungs 1506. However, the frame 1500 of the docking station 10 can have a variety of other configurations to provide a more resilient valve seat 18 or to provide more radial force against the valve 29 when the valve 29 deployed in the valve seat 18. For example, the struts 1502 of any other rung 1506 can also have an increased cross-sectional width or diameter or not all of the struts 1502 of the middle two rungs 1506 can have an increased cross-sectional width or diameter.

While the docking station 10 has been described as having thicker struts 1502 or struts 1502 with an increased cross-sectional width or diameter to provide a more resilient valve seat 18 and/or to assert more radial force against the deployed valve 29, the docking station 10 can be configured in other ways to provide the same effect. For example, the portions of the struts 1502 and/or frame 1500 near the valve seat 18 can comprise a stronger, less elastic, and/or more resilient metal or material, the junctions 1503 near the valve seat 18 can be stronger and/or thicker, or the lattice structure of the frame 1500 can be stronger near the valve seat 18, such as by increasing the number and decreasing the length of the struts 1502 in the rungs 1506 near the valve seat 18.

Referring now to FIGS. 81A through 81D, the cloth or impermeable material 21 can be cut, configured, or otherwise shaped such that the impermeable material 21 does not bunch and/or tear when the docking station 10 is compressed or deployed. The impermeable material 21 can be cut, configured, or otherwise shaped such that the impermeable material 21 does not cover at least a portion of the frame 1500 near the proximal end 12 and/or the distal end 14. The impermeable material 21 can be cut or shaped such that the impermeable material 21 does not cover at least a portion of the space not defined by one of the cells 1504 near the proximal and/or distal ends 12, 14. The impermeable material 21 can be configured or cut to the desired shape before the impermeable material 21 is attached to the frame 1500 or the impermeable material 21 can be attached to the frame 1500 and then cut to the desired shape.

At the proximal and distal ends 12, 14, the frame 1500 can include a plurality of openings 1511 between the struts 1502 and the apices 1510 in the portions of the frame 1500 which are not defined by the cells 1504. The openings 1511 are generally triangular in shape and are partially defined by two struts 1502, two apices 1510, and a junction 1503. The impermeable material 21 can be cut or shaped such that the impermeable material 21 does not cover at least a portion of the openings 1511 at the proximal and/or distal ends 12, 14.

The impermeable material 21 can be cut, configured, or otherwise shaped in a wide variety of ways such that the impermeable material 21 does not bunch or tear when the docking station 10 is compressed or deployed. The impermeable material 21 can be cut or shaped such that the impermeable material 21 can be attached to or disposed on the frame 1500 such that the impermeable material 21 can cover at least a portion of the cells 1504 but not cover at least a portion of the openings 1511 at the proximal and/or distal ends 12, 14.

As shown in FIG. 81A, the impermeable material 21 can be shaped or cut such that the impermeable material 21 substantially covers each cell 1504, substantially covers one-half of each opening 1511 at the proximal end 12, and substantially covers one-half of each opening 1511 at the distal end 14. However, the impermeable material 21 can be shaped or cut such that the impermeable material 21 substantially covers each cell 1504, substantially covers one-fourth, one-third, two-third, three-fourths, or any other suitable amount of each opening 1511 at the proximal end 12, and substantially covers one-fourth, one-third, two-third, three-fourths, or any other suitable amount of each opening 1511 at the distal end 14. Referring back to FIGS. 23A and 23B, the docking stations 10 can be used in differently sized circulatory system anatomies. By removing a portion of the material 21 in the opening 1511 at the proximal and/or distal end, the material 21 in the opening will not bunch up or the bunching up will be reduced when the docking station is used in a smaller circulatory system anatomy (e.g. FIG. 23B).

As shown in FIG. 81B, the impermeable material 21 substantially covers each cell 1504, substantially covers three-fourths of each opening 1511, at the proximal end 12 and generally does not cover the openings 1511 at the distal end 14.

As shown in FIG. 81C, the impermeable material 21 substantially covers each cell 1504, substantially covers the openings 1511 at the proximal end 12, and generally does not cover the openings 1511 at the distal end 14.

In each of the illustrated embodiments, the impermeable material 21 is cut horizontally or straight across. However, the impermeable material 21 can be cut or shaped in any suitable direction or pattern. For example, the impermeable material 21 can be cut or shaped in a rounded or sinusoidal pattern. Additionally, the impermeable material 21 has been described as covering each of the openings 1511 at the proximal end 12 in a uniform manner and covering each of the openings 1511 at the distal end 14 in a uniform manner. However, the impermeable material 21 can be cut or shaped such that the openings 1511 at each end 12, 14 are not covered in a uniform manner. For example, each of the openings 1511 at either end 12, 14 can be covered in a different manner or amount than the other openings 1511. Further, the impermeable material 21 can be cut or shaped larger than desired such that the impermeable material 21 can be disposed on or affixed to the struts 1502, as detailed below.

The impermeable material 21 can also be cut or otherwise shaped such that the impermeable material 21 does not cover at least a portion of the distal most cells 1504 or the outflow cells 1508. In such an embodiment, a portion of the distal most cells 1504 or the outflow cells 1508 and the openings 1511 can form the permeable portion 1400. As shown in FIG. 81D, the impermeable material 21 can be cut or shaped such that the impermeable material 21 substantially covers the proximal most cells 1504, generally does not cover the openings 1511 at the proximal end 12, substantially covers one-half of each of the distal most cells 1504, and generally does not cover the openings 1511 at the distal end 14. The impermeable material 21 can be cut or otherwise shaped such that the impermeable material 21 extends horizontally across at a point substantially equivalent to the location of the distal most junctions 1503.

In the embodiment illustrated by FIG. 81D, the impermeable cover 21 substantially covers one-half of the distal most cells 1504. However, the impermeable cover 21 can cover any amount of the distal most cells 1504. For example, the impermeable cover 21 can be cut or shaped to cover one-fourth, one-third, two-third, three-fourths, or any other suitable amount of the distal most cells 1504. In the illustrated embodiment, the impermeable material 21 generally does not cover the openings 1511 at the proximal end 12. However, the impermeable material 21 can cover the openings 1511 at the proximal end 12 in any amount or manner, such as the ways depicted and described in FIGS. 81A, 81B, and 81C. Additionally, while the impermeable material 21 is depicted as extending horizontally across the distal most junctions, the impermeable material 21 can have any other suitable shape extending across the distal most cells 1504 and junctions 1503. For example, the impermeable material 21 can have a rounded, curved, sinusoidal, or any other cut or shape extending across the distal most cells 1504 and junctions 1503.

While the various configurations of the impermeable material 21 have been described and illustrated as being used with the four rung 1506 frame 1500 of FIG. 74, the various configurations of the impermeable material 21 can be applied with any other docking station 10 described herein. For example, the various configurations of the impermeable material 21 can be used with the six rung 1506 frame 1500 of FIGS. 75-77C, with the frame 1500 having outflow cells 1508 of FIGS. 78A and 78B, the frame 1500 with thicker struts 1502 of FIGS. 80A-80C, or any other frame 1500 described herein.

Referring now to FIGS. 82A to 85E, the impermeable material 21 can be attached to, secured around, or otherwise affixed to the frame 1500 of the docking station 10 in a variety of ways. For example, the impermeable material can be affixed to the frame 1500 using sewing or electrospinning or the impermeable material 21 can be made from a sutureless material.

Figure 84A:
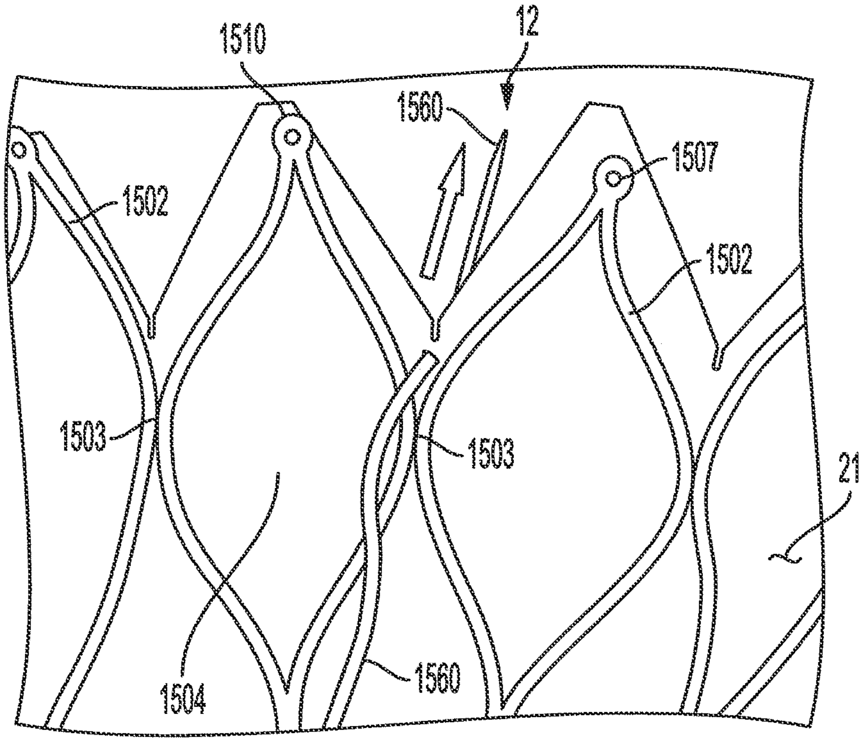
Figure 84B:
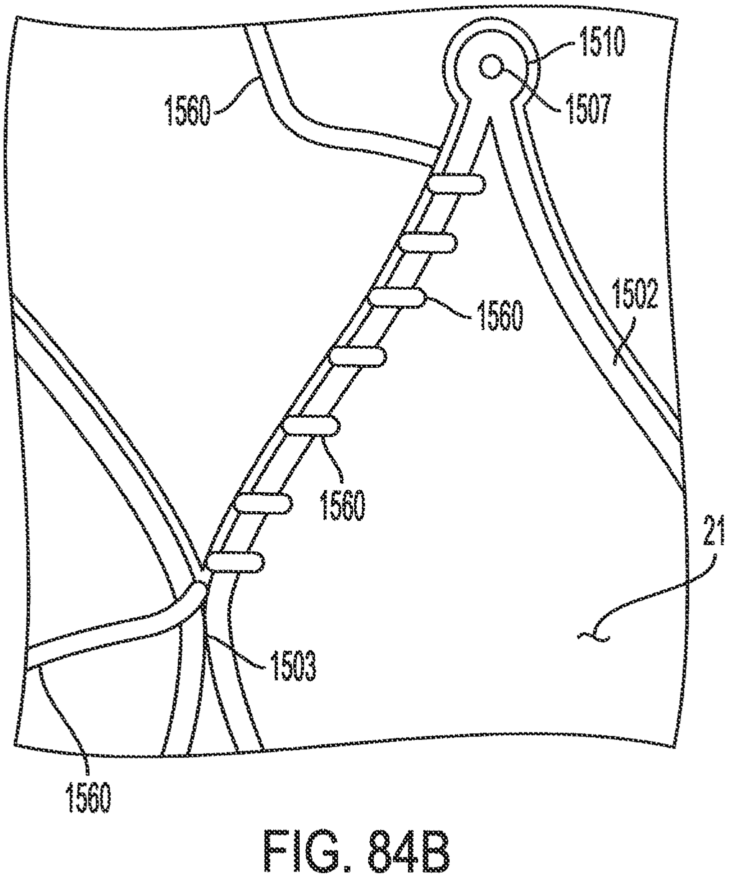
Figure 84C:
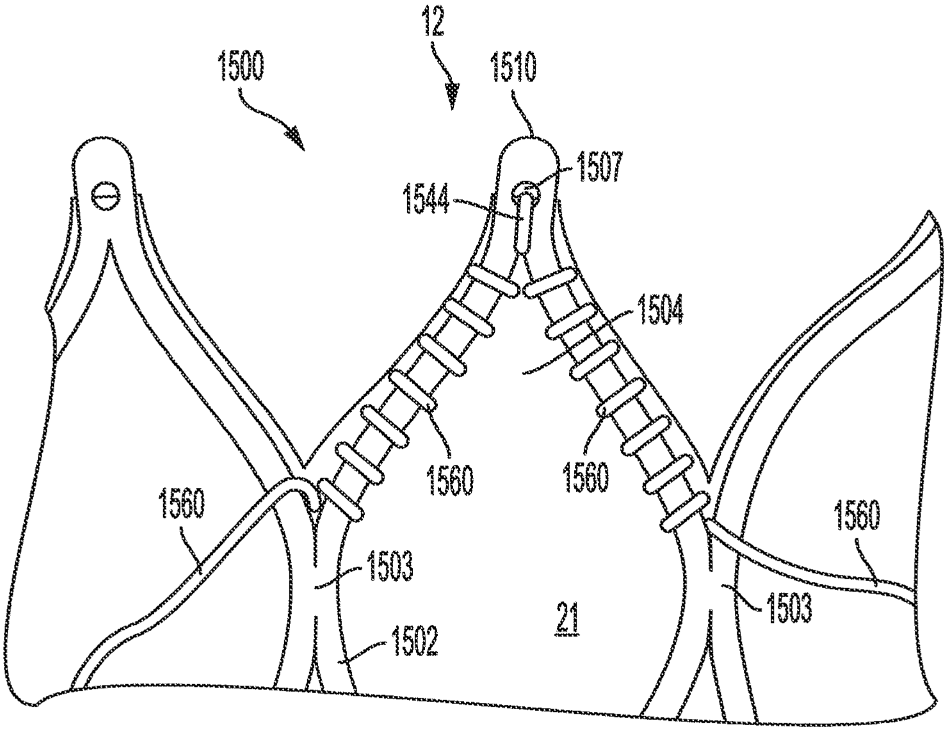
Figure 84D:
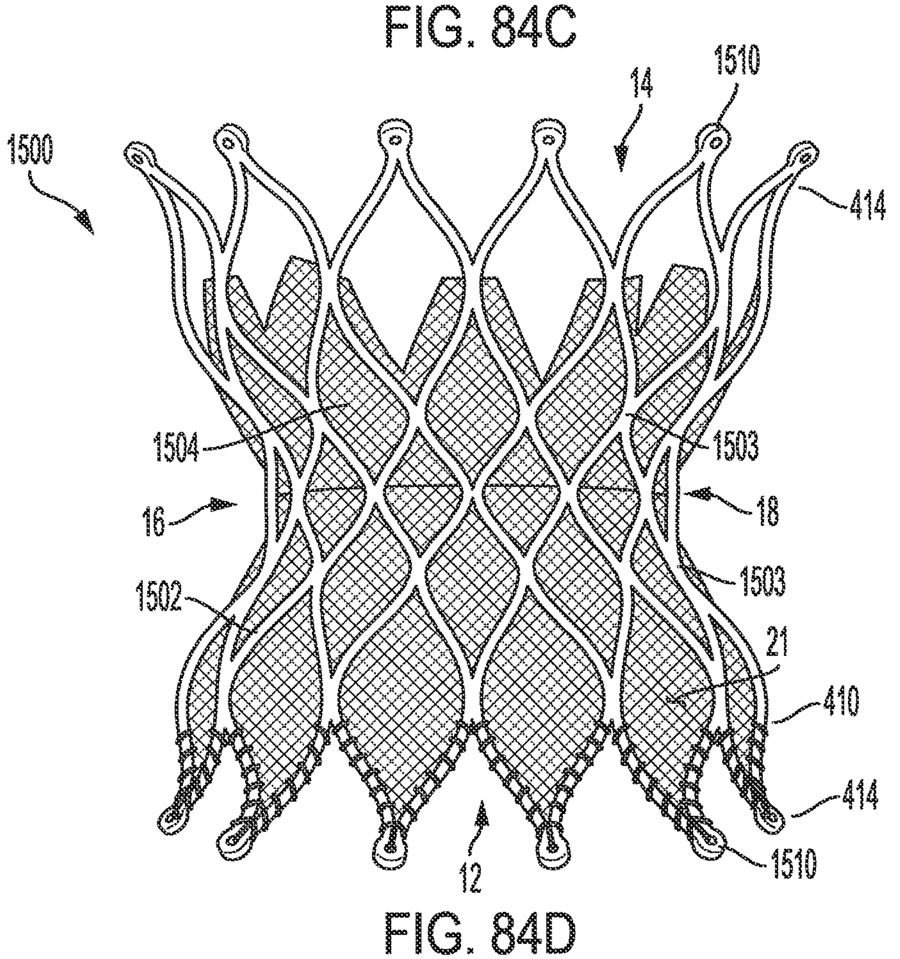
Figure 84E:
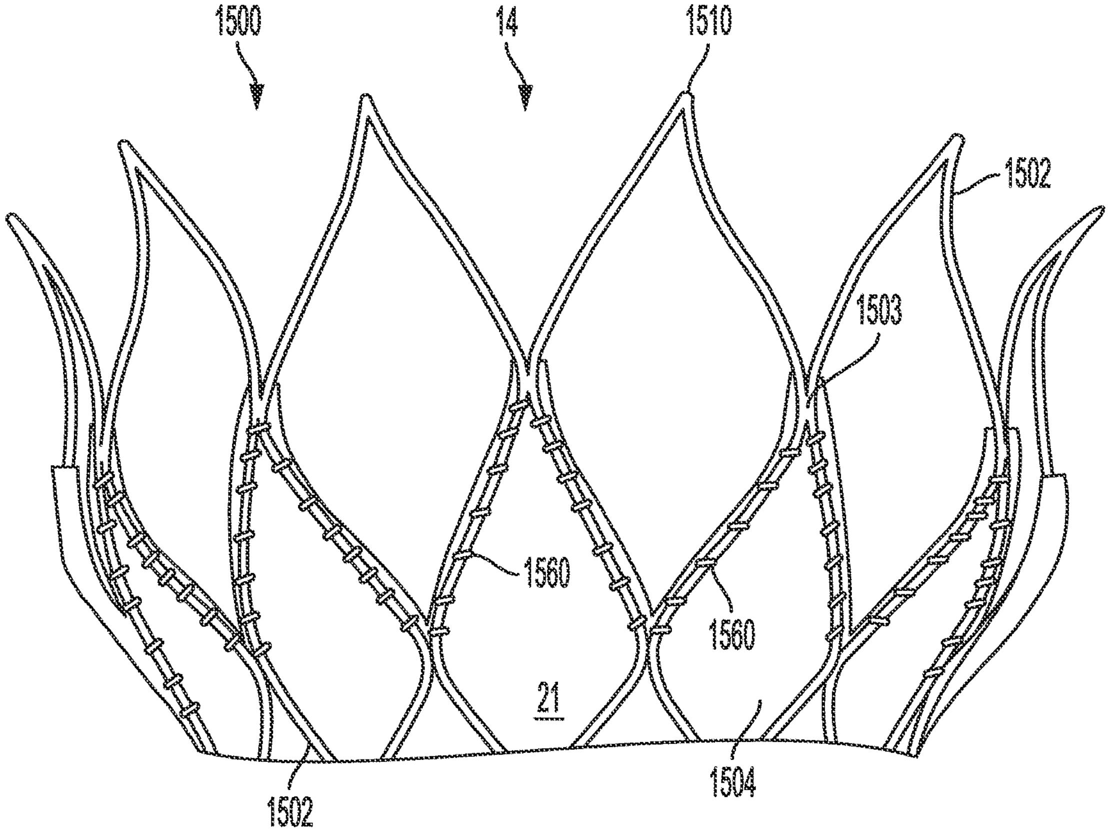
Figure 84F:
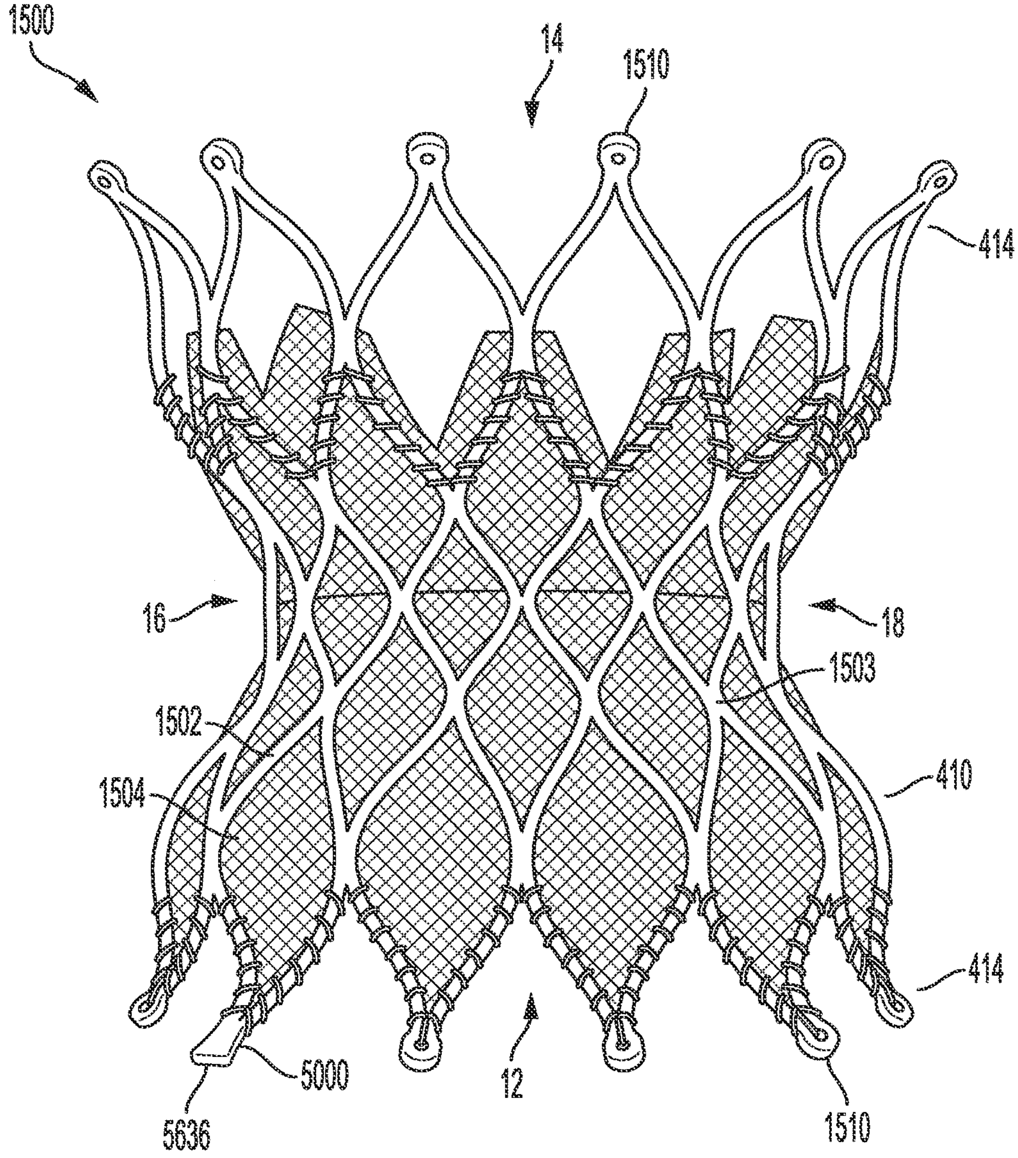
Figure 84G:
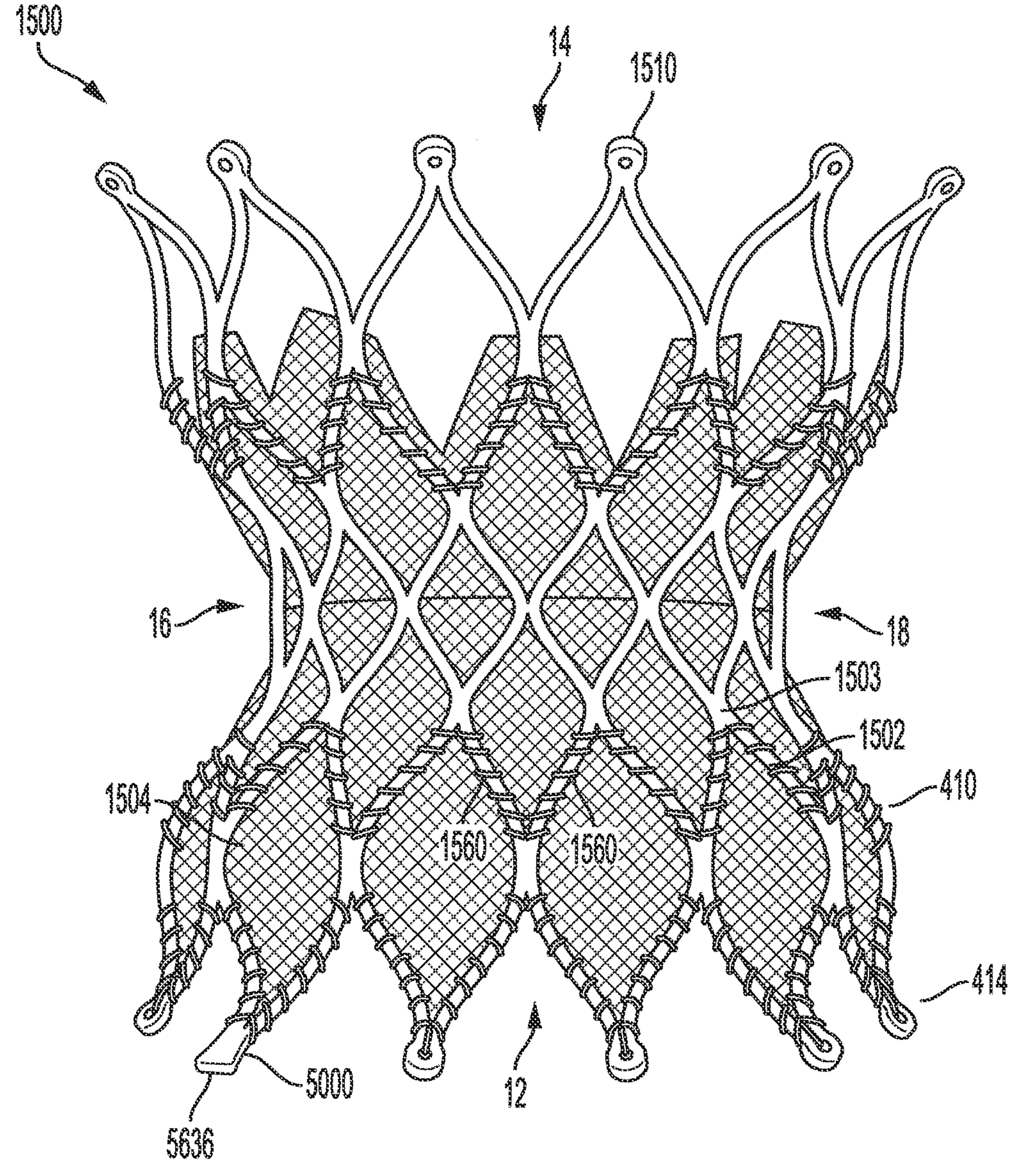
Figure 84H:
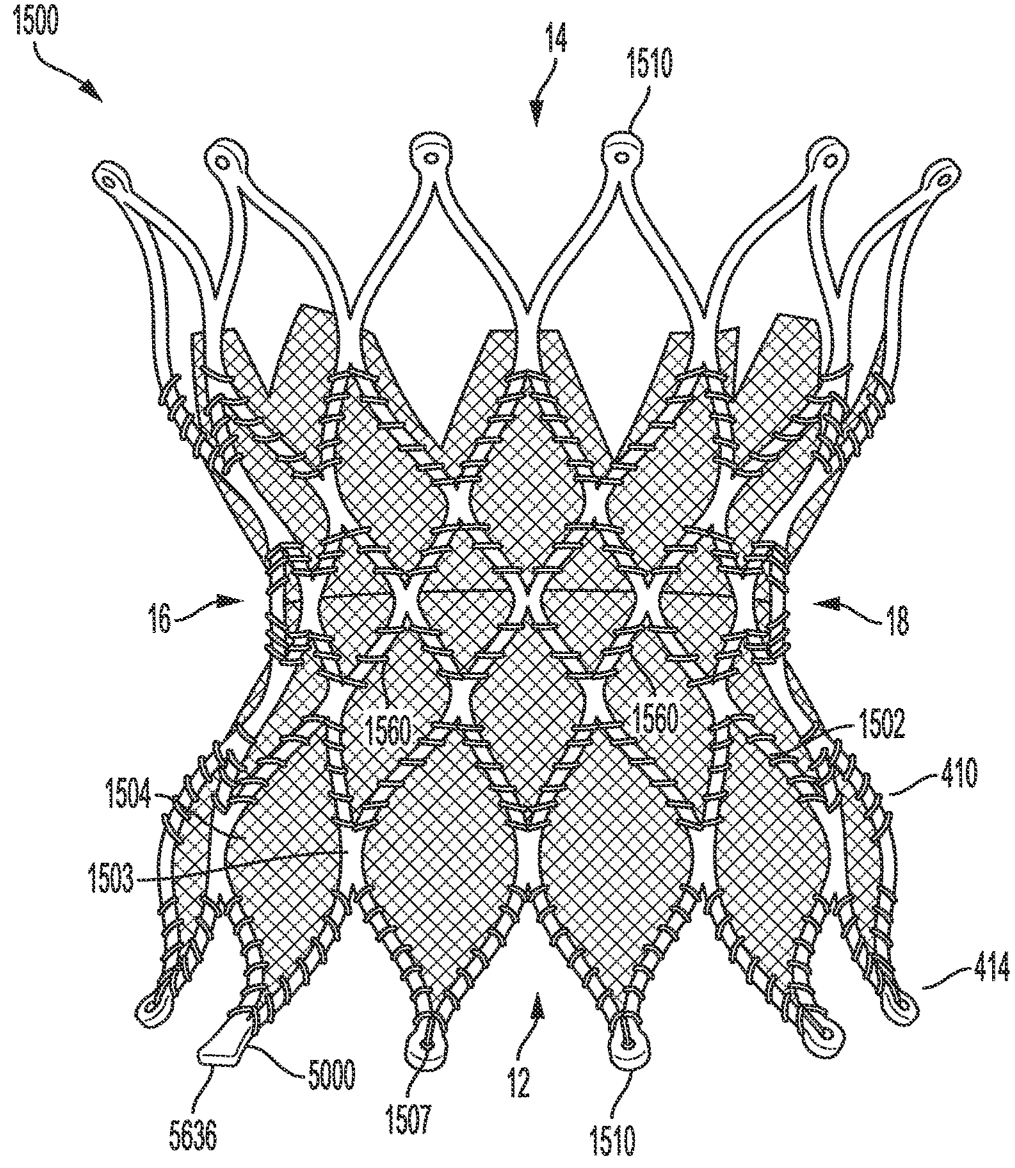
Figure 84I:
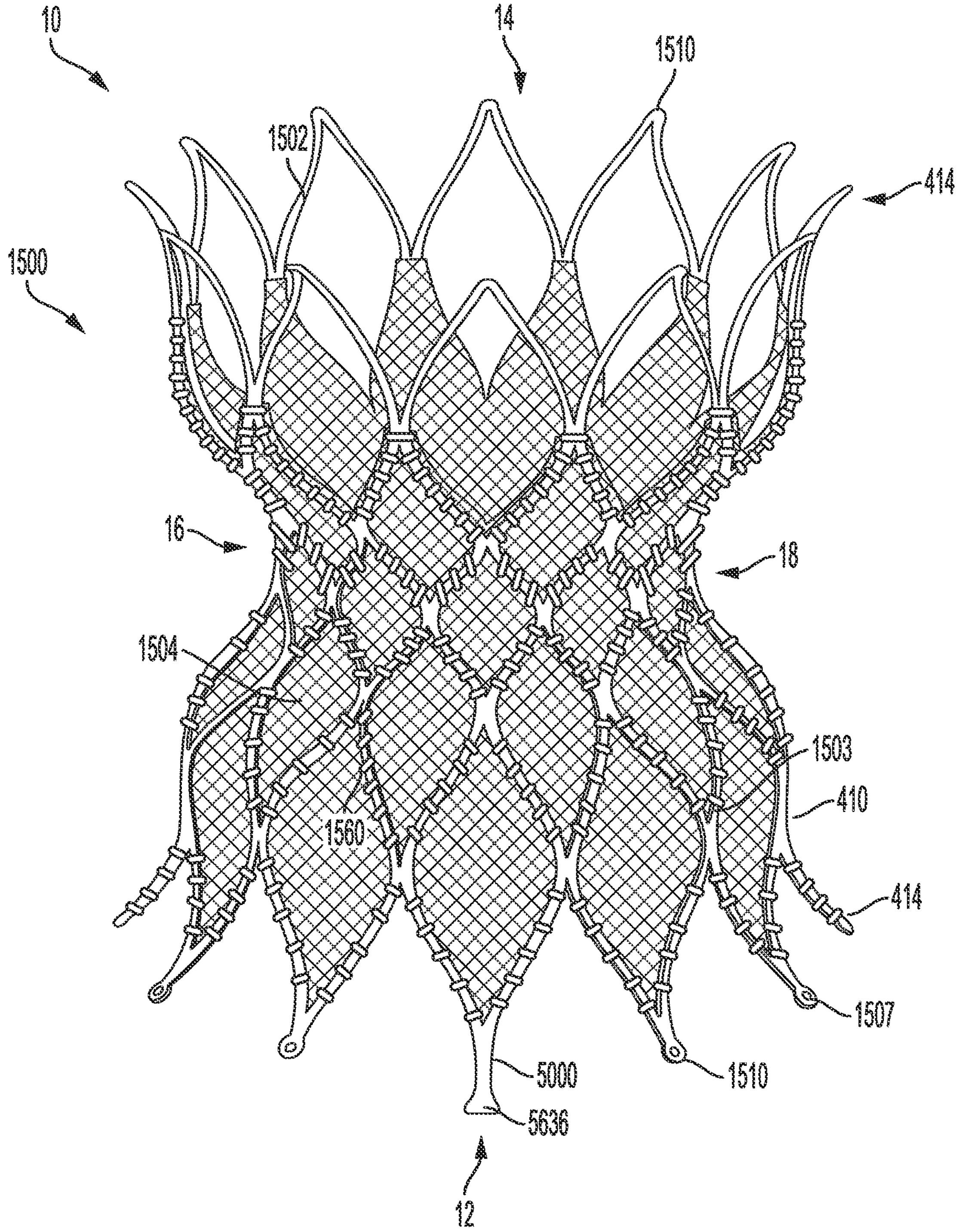

As shown in FIGS. 82A through 84I, the impermeable material 21 can be affixed to the frame 1500 by sewing one or more pieces of impermeable material 21 together and then onto the frame 1500. As shown in FIGS. 83 through 84I, the frame 1500 can include one or more eyelets 1507 at the apices 1510 which can facilitate attaching the impermeable material 21 to the frame 1500. In the illustrated embodiment, each apex 1510 that does not include an elongated leg 5000 includes an eyelet 1507. However, the number of eyelets 1507 can vary and each apex 1510 may not include either an elongated leg 5000 or an eyelet 1507. For example, the apices 1510 at the distal end 14 may not have any eyelets 1507 or elongated legs 5000.

As shown in FIGS. 82A through 82I, the impermeable cover 21 can have a proximal portion 1520 and a distal portion 1530. The proximal portion 1520 can be sized and shaped to cover the desired portion of the frame 1500 between the valve seat 18 and the proximal end 12. The distal portion 1530 can be sized and shaped to cover the desired portion of the frame 1500 between the valve seat 18 and the distal end 14. In the illustrated embodiment, the impermeable member 21 has two portions 1520, 1530. However, the impermeable member 21 can have any number of portions which are secured together form the impermeable member 21. For example, the impermeable member can be made from a single piece or have three, four, five, or more portions.

The proximal portion 1520 has a first edge 1522, a second edge 1524, a first end 1526, and a second end 1528 and the distal portion 1530 has a first edge 1532, a second edge 1534, a first end 1536, and a second end 1538. As detailed below, the first edges 1522, 1532 can be sized and shaped to fit the valve seat 18 of the frame 1500, the second edge 1524 of the proximal portion 1520 can be sized and shaped to fit the frame 1500 at the desired position between the valve seat 18 and the proximal end 12, and the second edge 1534 of the distal portion 1530 can be sized and shaped to fit the frame 1500 at the desired position between the valve seat 18 and the distal end 14. In the illustrated embodiment, the proximal and distal portions 1520, 1530 are shaped such that first ends 1526, 1536 are generally in the shape of the apices 1510. However, the proximal and distal portions 1520, 1530 can be shaped in a wide variety of ways. For example, the proximal and distal portions 1520, 1530 can be shaped or otherwise configured such that the impermeable material 21 has any of the shapes or configurations illustrated and described in FIGS. 81A-81D.

As shown in FIGS. 82B and 82C, the first end 1526 of the proximal portion 1520 can be folded or looped around and secured to the second end 1528 of the proximal portion 1520 to form a proximal portion joint 1525.

As shown in FIG. 82D, the first end 1536 of the distal portion 1530 can be folded or looped around and secured to the second end 1538 of the distal portion 1530 to form a distal portion joint 1535. The first ends 1526, 1536 can be secured to the second ends 1528, 1538 in any suitable manner. For example, the first ends 1526, 1536 can be secured to the second ends 1528, 1538 by sewing a thread or suture, by an adhesive, by a fastener, or by any other suitable means.

As shown in FIGS. 82E through 82I, the proximal portion 1520 can be secured to the distal portion 1530 such that the second edge 1524 of the proximal portion 1520 is opposite the second edge 1534 of the distal portion 1530. The first edge 1522 of the proximal portion 1520 can overlap the first edge 1532 of the distal portion 1530 and can create a medial joint 1542. In one embodiment, the proximal portion joint 1525 is not aligned with the distal portion joint 1535 when the proximal and distal portions 1520, 1530 are secured. Offsetting the proximal and distal portion joints 1525, 1535 can increase the ease of manufacture of the impermeable member 21 and/or increase the strength and resilience of the impermeable member 21. The proximal portion joint 1525 can be offset from the distal portion joint 1535 such that the proximal portion joint 1525 aligns with one of the apices 1510 and/or junctions 1503 and the distal portion joint 1535 aligns with another one of the apices 1510 and/or junctions 1503. For example, the proximal portion joint 1525 and distal portion joints 1535 can be offset so that the proximal and distal portion joints 1525, 1535 can each run along one of the junctions 1503 when the impermeable member 21 is attached to the frame 1500.

The proximal portion 1520 can be secured to the distal portion 1530 in any suitable manner. For example, the first edge 1522 of the proximal portion 1520 can be secured to the first edge 1532 of the distal portion 1530 by sewing a thread or suture, by an adhesive, by a fastener, or by any other suitable means.

In one embodiment, the proximal and distal portions 1520, 1530 each include a plurality of apertures 1540 along the first edge 1522, 1532, the first end 1526, 1536, and the second end 1528, 1538. The apertures 1540 may facilitate the assembly of the impermeable material 21, such as by serving as guides for a suture or thread to be sewn therethrough. The apertures 1540 can be formed by any suitable process, such as cutting or laser drilling.

As shown in FIGS. 82E through 82I, the proximal portion 1520 can be attached to the distal portion 1530 near the medial joint 1542 by an interlocking stitch which provides radial force against the valve 29 when the valve 29 is deployed in the valve seat 18. The proximal portion 1520 can be positioned in line with or on top of the distal portion 1530 such that the first edges 1522, 1532 overlap. A suture 1560 can be passed through (radially inwardly) the proximal and distal portions 1520, 1530 between the first edges 1522, 1532 at a first point 1543*a*. The suture 1560 can then be passed back through (radially outwardly) the proximal and distal portions 1520, 1530 in the opposite direction at a second point 1543*b* circumferentially spaced apart from the first point 1543*a*. The suture 1560 can then be repeatedly passed in and out through the proximal and distal portions 1520, 1530 at other points 1543 until the suture 1560 substantially spans the circumference of the proximal and distal portions 1520, 1530.

Once the suture 1560 has been passed substantially around the circumference of the proximal and distal portions 1520, 1530, the suture 1560 can be passed back through the proximal and distal portions 1520, 1530 in the opposite direction. When the suture 1560 is passed back through the proximal and distal portions 1520, 1530 in the opposite direction, the suture 1560 can be passed through the proximal and distal portions 1520, 1530 at the same points 1543 such that the suture 1560 fills the spaces between the previous stitches of the suture 1560 along or near the medial joint 1542. As such, a circumferential portion of the impermeable material 21 at or near the medial joint 1542 can be substantially covered by the suture 1560 on both sides of the impermeable material 21.

As shown in FIGS. 82J and 82K, the proximal portion 1520 and the distal portion 1530 can be cut, shaped, or otherwise formed from one or more pieces of cloth 23. The cloth 23 can include fibers 24 generally disposed vertically and horizontally when the cloth 23 is oriented vertically. In the illustrated embodiment, the proximal portion 1520 and the distal portion 1530 are cut from the same cloth 23. However, the proximal portion 1520 can be cut from a first cloth 23 and the distal portion 1530 can be cut from a second cloth 23.

The proximal portion 1520 can be cut from the cloth 23 such that an angle β is formed between the horizontally oriented fibers 24 and a line normal to the center of the first edge 1522 of the proximal portion 1520. Or, a cloth can be selected that has fibers that are oriented with the angle β. The proximal portion 1520 can be cut (or fiber orientation can be selected) in a manner that increases the strength and resiliency of the proximal portion 1520 and/or facilitates the assembly of the impermeable member 21 and the attachment of the impermeable member 21 to the frame 1500. In one embodiment, as shown in FIG. 82J, the proximal portion 1520 can be cut such that the angle β is approximately 90°. In another embodiment, as shown in FIG. 82K, the proximal portion 1520 can be cut such that the angle β is between 20° and 70°, such as between 30° and 50°, such as 45°.

The distal portion 1530 can be cut from the cloth 23 such that an angle Δ is formed between the horizontally oriented fibers 24 and a line normal to the center of the first edge 1532 of the distal portion 1530. Or, a cloth can be selected that has fibers that are oriented with the angle Δ. The distal portion 1530 can be cut (or fiber orientation can be selected) in a manner that increases the strength and resiliency of the distal portion 1530 and/or facilitates the assembly of the impermeable member 21 and the attachment of the impermeable member 21 to the frame 1500. In one embodiment, as shown in FIG. 82J, the distal portion 1530 can be cut such that the angle Δ is approximately 90°. In another embodiment, as shown in FIG. 82K, the proximal portion 1520 can be cut such that the angle Δ is between 90° and 20° and 70°, such as between 30° and 50°, such as 45°.

Forming the proximal and distal portions 1520, 1530 with the fibers 24 of the cloth 23 at an angle can improve the strength or resiliency of the impermeable member 21 and/or can facilitate the assembly of the impermeable member 21. In the illustrated embodiments, the angle β and the angle Δ are substantially the same. However, the angle β and the angle Δ can be substantially different.

As shown in FIG. 83, the impermeable material 21 can be properly positioned or disposed within the frame 1500. The impermeable material 21 can be positioned such that the medial joint 1542 is substantially aligned in the middle of the valve seat 18 of the frame 1500. The impermeable material 21 can also be positioned such that the second edge 1524 of the proximal portion 1520 is substantially aligned with the desired struts 1502, junctions 1503, and/or apices 1510 near the proximal end 12 and the second edge 1534 of the distal portion 1530 is substantially aligned with the desired struts 1502, junctions 1503, and/or apices 1510 near the distal end 14. In the illustrated embodiment, the impermeable material 21 extends from the proximal end 12 of the frame 1500 toward the distal end 14 and does not extend to the distal most row of cells 1504. The impermeable material 21 can also be configured such that the impermeable material 21 does not cover the openings 1511 at the proximal end 12. However, the impermeable material 21 can be sized and shaped in any suitable configuration. For example, the impermeable material 21 can extend to the distal end 14 of the frame 1500 and the impermeable material 21 can cover the cells 1504 and openings 1511 near the ends 12, 14 in any amount or configuration, such as the configurations depicted and described in FIGS. 81A-81D.

Optionally, the impermeable member 21 can be configured and/or positioned such that the proximal portion joint 1525 and distal portion joint 1535 increase the strength or resiliency of the docking station 10 or facilitate the attachment of the impermeable member 21 to the frame 1500. As shown by the dotted lines in FIG. 83, the impermeable member 21 can be configured and/or positioned such that the proximal portion joint 1525 is aligned with one of the apices 1510 and/or one or more junction 1503. The impermeable member 21 can also be configured and/or positioned such that the distal portion joint 1535 is aligned with one of the apices 1510 and/or one or more junction 1503. The proximal portion joint 1525 can be aligned with different apices 1510 and/or junctions 1503 than the distal portion joint 1535. For example, the proximal portion joint 1525 can be offset from the distal portion joint 1535 by one junction 1503. In the illustrated embodiment, the proximal and distal portion joints 1525, 1535 are aligned with junctions 1503 and not with any apices 1510. However, the proximal and distal portion joints 1525, 1535 can be arranged and/or configured in a variety of ways. For example, one of or both of the proximal and distal portion joints 1525, 1535 can be respectively aligned with one of the apices 1510.

Referring now to FIGS. 84A through 84I, the impermeable material 21 can be affixed to the frame 1500 by one or more threads or sutures 1560. As shown in FIGS. 84A through 84D, the impermeable material 21 can be affixed to the proximal end 12 of the frame 1500. The impermeable material 21 can be positioned such that the proximal portion of the impermeable material 21 aligns with the desired proximal rung 1506, apices 1510, or junctions 1503. The one or more threads or sutures 1560 can be sewn or looped around the struts 1502 of the proximal most rung 1506. At a point near the proximal most junction 1503 to which the impermeable material 21 extends, the suture 1560 can be passed through the impermeable material 21, looped around the strut 1502, and passed back through the impermeable material 21 on the other side of the strut 1502. This stitch can be repeated until the suture 1560 substantially extends the length of the strut 1502. Near the apex 1510, the stitch can be repeated such that the suture 1560 descends down the subsequent strut 1502 in the rung until the suture 1560 substantially extends to the junction 1503. This stitch can be repeated until the suture 1560 substantially extends along each strut 1502 in the proximal most rung 1506 and the suture 1560 substantially extends circumferentially around the frame 1500.

As shown in FIGS. 84E and 84F, the impermeable material 21 can be affixed near the distal end 14 of the frame 1500. The impermeable material 21 can be positioned such that the distal portion of the impermeable material 21 aligns with the desired distal rung 1506, apices 1510, or junctions 1503. In the illustrated embodiment, at a point near the junction 1503 that defines the proximal end of the distal most cell 1504, the suture 1560 can be passed through the impermeable material 21, looped around the strut 1502, and passed back through the impermeable material 21 on the other side of the strut 1502. This stitch can be repeated until the suture 1560 substantially extends the length of the strut 1502. Near the distal most junction 1503 to which the impermeable material 21 extends, the stitch can be repeated such that the suture 1560 descends down the subsequent strut 1502 in the rung 1506 until the suture 1560 substantially extends to the junction 1503. This stitch can be repeated until the suture 1560 substantially extends along each strut 1502 in the distal most rung 1506 to which the impermeable material 21 extends and the suture 1560 substantially extends circumferentially around the frame 1500.

As shown in FIGS. 84G through 84I, similar stitches to the stitches described in FIGS. 84A through 84F can be used to secure the impermeable material 21 to the remaining rungs 1506 by one or more sutures 1560. The stitches can be at any angle in relation to the struts 1502 of the frame. For example, the stitches can form an angle with the struts 1502 between 45° and 90°. In the illustrated embodiment, one or more sutures 1560 secures the impermeable material 21 to each strut 1502 of each rung 1506 which the impermeable material 21 covers. However, the impermeable material 21 may not be secured to each strut 1502 of each rung 1506 which the impermeable material 21 covers. For example, the impermeable material 21 may not be secured or attached to each strut 1502 in each covered rung 1506 and/or the impermeable material 21 may not be secured or attached to some of the rungs 1506.

As shown in FIG. 84C, the impermeable material 21 can be additionally secured to the frame 1500 with one or more vertical stitches 1544. After the suture 1560 has been stitched around one of the struts 1502 in the proximal most rung 1506 and the suture 1560 substantially extends from the junction 1503 to the apex 1510, the suture 1560 can be passed through the impermeable material 21, through the eyelet 1507, and back through the impermeable material 21 to form the vertical stitch 1544. The suture 1560 can then be stitched around the descending strut 1502 toward the junction 1503. While the vertical stitch 1544 has only been depicted as securing the impermeable material 21 to the eyelets 1507 at the apices 1510 at the proximal end 12, the vertical stitch 1544 can be used at other locations of the frame 1500. For example, vertical stitches 1544 can be used in embodiments where the impermeable material 21 extends to the apices 1510 at the distal end 14 or in embodiments where the frame 1500 includes outflow cells 1508 and the impermeable material 21 extends to apices 1510 near the distal end 14. However, the impermeable material 21 may not be secured to the frame 1500 with one or more vertical stitches (e.g., FIG. 84I).

Referring now to FIGS. 85A through 85E, in another exemplary embodiment the impermeable material 21 can be affixed to the frame 1500 by a coating and/or adhesive material 1570. The coating and/or adhesive material can take a wide variety of different forms. For example, the coating and/or adhesive material can be a liquid, solids, hot melt, etc. material. The coating and/or adhesive material can adhere to the impermeable material 21 and/or the frame 1500. In one exemplary embodiment, the adhesive material 1570 surrounds or coats the frame 1500, but does not adhere to the frame 1500, and adheres to and coats the frame 1500.

In one exemplary embodiment, the coating and/or adhesive material is a fiber material. In one exemplary embodiment, the coating and/or adhesive material 1570 can be applied by electrospinning or otherwise depositing an adhesive fiber material 1570 to adhere the impermeable material 21 to the frame 1500. This can be done instead of some or all of the stitching described above. In one exemplary embodiment, the electrospinning or other depositing of an adhesive fiber material 1570 replaces all of the stitches of the docking station. The coating and/or adhesive 1570 can be polymer fibers, nanofibers, or threads, such as polytetrafluoroethylene (PTFE), or expanded PTFE (ePTFE), polyetherkeytone (PEEK), Polysulfones (PSU, PPSU), and Polyethylene (HDPE, UHMWPE).

Figure 85A:
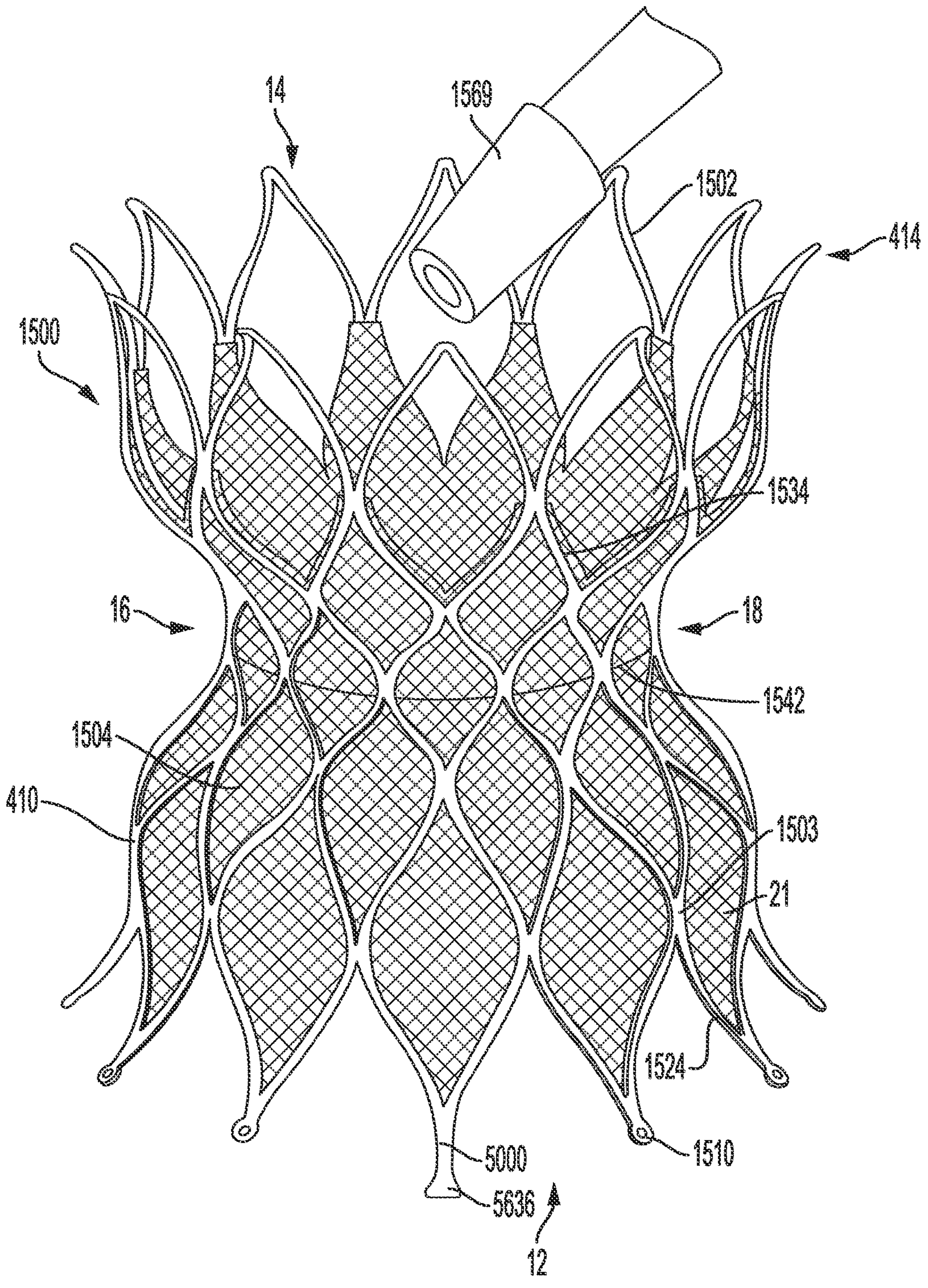

As shown in FIG. 85A, the impermeable material 21 can be disposed around or within the frame 1500 and positioned such that the impermeable material 21 is in the desired location and substantially in contact with one or more struts 1502 of the frame 1500. For example, the impermeable material 21 can be positioned such that the medial joint 1542 is substantially aligned in the middle of the valve seat 18 of the frame 1500. The impermeable material 21 can also be positioned such that the second edge 1524 of the proximal portion 1520 is aligned with the desired struts 1502, junctions 1503, and/or apices 1510 near the proximal end 12 and the second edge 1534 of the distal portion 1530 is aligned with the desired struts 1502, junctions 1503, and/or apices 1510 near the distal end 14. A nozzle 1569 can be positioned above and facing the impermeable material 21 and one or more struts 1502. The nozzle 1569 can be positioned on the outside or the inside of the frame 1500 facing the impermeable material 21 and one or more struts 1502. In embodiments where the impermeable material 21 is affixed to the inside of the frame 1500, the nozzle 1569 can be positioned on the outside of the frame 1500, and in embodiments where the impermeable material 21 is affixed to the outside of the frame 1500, the nozzle 1569 can be positioned on the inside of the frame 1500.

Figure 85B:
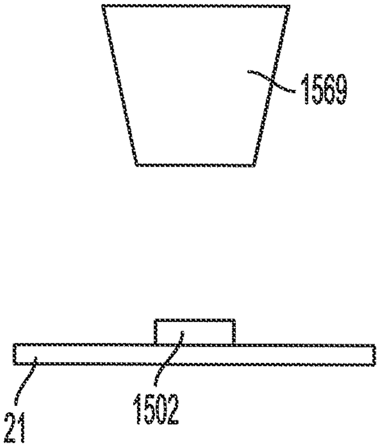
Figure 85D:
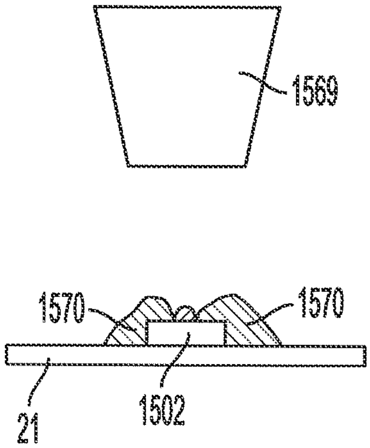
Figure 85C:
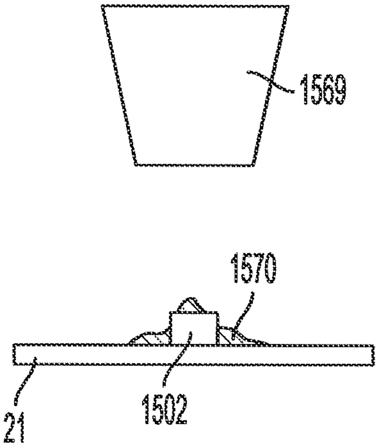
Figure 85E:
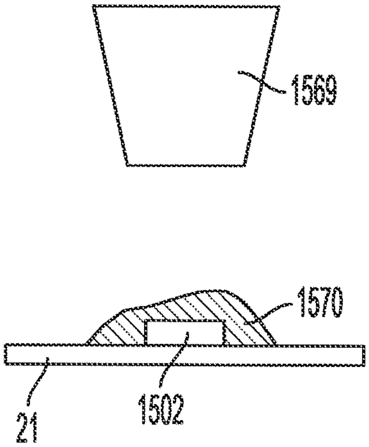

As shown in FIG. 85B, the nozzle 1569 can be positioned above the strut 1502 and the impermeable material 21 such that an opening of the nozzle 1569 is directed toward the strut 1502 and the impermeable material 21. As shown in FIG. 85C, the coating and/or adhesive 1570 can be sprayed or otherwise deposited from the nozzle 1569 onto the impermeable material 21 and the strut 1502. The nozzle 1569 can coat both the impermeable material 21 and the strut 1502 with the coating and/or adhesive 1570. As shown in FIG. 85D, additional coating and/or adhesive 1570 can be deposited onto the impermeable material 21 and the strut 1502 such that coating and/or adhesive 1570 builds up along the sides of the struts 1502. As shown in FIG. 85E, more coating and/or adhesive 1570 is deposited onto the impermeable material 21 and the strut 1502 such that the coating and/or adhesive 1570 extends from the impermeable material 21 on one side of the strut 1502, over the strut 1502, and to the impermeable material 21 on the other side of the strut 1502, substantially encasing the strut 1502 in fiber material. The coating and/or adhesive 1570 can then be allowed to dry, harden, or otherwise set, thereby substantially securing the impermeable material 21 to the frame 1500.

The coating and/or adhesive 1570 can be sprayed or otherwise deposited onto one or more struts 1502 until the impermeable material 21 is sufficiently attached to the frame 1500. In the illustrated embodiment, the coating and/or adhesive 1570 is deposited along the rungs 1506 that align with the second edges 1524, 1534 of the impermeable material 21. However, the coating and/or adhesive 1570 can be deposited to secure the impermeable material 21 to the frame 1500 in any suitable manner. For example, the coating and/or adhesive 1570 can be deposited only at particular locations along the rungs 1506, such as only at the junctions 1503 and apices 1510.

Referring now to FIGS. 86A through 89D, the docking station 10 can include one or more radiopaque markers 1580 which can assist with deployment of the docking station 10 as well as placement of the valve 29 into the valve seat 18. The one or more radiopaque markers 1580 can be radiopaque or have a higher radiopacity such that the one or more radiopaque markers 1580 can be identified under fluoroscopy or a similar imaging process. The one or more radiopaque markers 1580 can be disposed on, attached to, or otherwise affixed to the docking station 10 in a wide variety of ways, such as the ways detailed below. The one or more radiopaque markers 1580 can comprise any material or combination of materials that are radiopaque or increase the radiopacity of at least a portion of the valve seat 18. For example, the one or more radiopaque markers 1580 can comprise barium sulfate, bismuth, tungsten, tantalum, platinum-iridium, gold or any other material which is opaque to fluoroscopy, X-rays, or similar radiation or any combination thereof. As illustrated in FIGS. 86A-86D, the radiopaque markers 1580 are disc-shaped and circular or octagonal. However, the one or more radiopaque markers 1580 can be configured to reduce axial motion and can be any suitable shape. For example, the one or more radiopaque markers 1580 can be hexagonal, triangular, rectangular, elliptical, 3D, or any other shape or configuration. The radiopaque markers 1580 can also include an aperture 1582 extending through a central portion of the marker 1580. The aperture 1582 can be sized such that a suture can pass therethrough.

As shown in FIGS. 87A through 90C, one or more radiopaque markers 1580 can be affixed to the frame 1500 of the docking station 10. In certain implementations, the radiopaque markers 1580 can be attached or affixed to the struts 1502 or junctions 1503 in the valve seat 18 of the frame 1500, with the radiopaque markers 1580 affixed to the frame 1500 in any suitable manner. For example, the radiopaque markers 1580 can be affixed to the frame 1500 by an adhesive, a suture, press fit, snap fit, or any other suitable means. The frame 1500 can include three or more radiopaque markers 1580 spaced circumferentially around the valve seat 18 to establish an annular plane through the valve seat 18 of the docking station 10. However, the frame 1500 can include fewer than three radiopaque markers 1580. In other implementations, the radiopaque markers 1580 can be attached or affixed to the impermeable material 21 as further described elsewhere in this disclosure, with the radiopaque markers 1580 attached or affixed at or near the struts 1502 or junctions 1503 of the frame 1500 or attached or affixed remotely from the struts 1502 and junctions 1503 of the frame 1500.

As shown in FIGS. 87A, 87B, and 87C, the frame 1500 can include one or more marker settings 1584 at one or more junctions 1503 in the valve seat 18. The one or more marker settings 1584 can be sized and shaped to receive one of the radiopaque markers 1580. The one or more marker settings 1584 can be an opening defined by one or more struts 1502 or can be an indentation in the frame 1500 which can receive one of the radiopaque markers 1580.

As shown in FIG. 88, the one or more radiopaque markers 1580 can be disposed on the one or more marker settings 1584 and secured by any suitable means. For example, the one or more radiopaque markers 1580 can be secured in the one or more marker settings 1584 by press fit, snap fit, adhesive, fasteners, or any other suitable manner.

Additionally or alternatively, as shown in FIG. 89A through 89D, one or more radiopaque markers 1580 can be included with the impermeable material 21 such that the one or more radiopaque markers 1580 are disposed within the valve seat 18 when the impermeable material 21 is attached to the frame 1500. The one or more radiopaque markers 1580 can be sewn onto, sewn into, encased by a pocket, or otherwise attached to the impermeable material 21 such that, when the impermeable material 21 is disposed on the frame 1500, the one or more radiopaque markers 1580 are disposed around the valve seat 18.

The radiopaque markers 1580 can be attached or affixed to the impermeable material 21 in various positions relative to the struts 1502 and junctions 1503 of the frame. In some implementations, the radiopaque markers 1580 can be attached or affixed at or near the struts 1502 or junctions 1503 of the frame 1500. In certain implementations, the radiopaque markers 1580 can be attached or affixed remotely from the struts 1502 and junctions 1503 of the frame 1500, such as a location in the central portions of cells 1504 of the frame. Positioning the radiopaque markers 1580 in the central portion of cells 1504 can provide certain technical advantages. One technical advantage is that the crimped profile of frame 1500 can be reduced as overlaps between the radiopaque marker 1580 with its associated attachment materials and the struts 1502 and junctions 1503 of the frame 1500 can be minimized Another technical advantage is that physical contact between the radiopaque marker 1580 and the frame 1500 can be minimized, which can avoid material fatigue, degradation, and/or corrosion. A further technical advantage is that placement in the central portion of a cell 1504 can allow the radiopaque marker 1580 to move radially outwards to accommodate an expanding valve 29 within the frame 1500, which can reduce the physical contact between the valve 29 frame 712 and the frame 1500 and avoid interference with the proper function of the valve 29.

As shown in FIG. 89A, the one or more radiopaque markers 1580 can be sewn into the impermeable material 21 at or near the optional medial joint 1542 when the proximal portion 1520 is attached to the distal portion 1530. For example, the suture 1560 can be passed through the aperture 1582 to attach the radiopaque marker 1580 to the impermeable material 21. The one or more radiopaque markers 1580 can also be sewn onto the impermeable material 21 at or near the medial joint 1542 after the proximal portion 1520 has been attached to the distal portion 1530 or if the proximal portion 1520 is integrally formed with the distal portion 1530. The one or more radiopaque markers 1580 can be affixed to the outside of the impermeable material 21 such that the radiopaque markers do not interfere with the valve 29 when the valve 29 is deployed in the valve seat 18. However, the one or more radiopaque markers 1580 can also be affixed to the inside of the impermeable material 21.

As shown in FIGS. 89B through 89D, the one or more radiopaque markers 1580 can also be disposed in one or more pockets 1586 in or on the impermeable material 21. The one or more pockets can take a wide variety of different forms. The pockets can be formed from a patch of material or by any other manner of forming a pocket. For example, any manner that pockets are formed in clothing can be used on the impermeable material 21.

The one or more pockets 1586 can be sized and shaped to receive one of the radiopaque markers 1580. The pockets 1586 can be generally rectangular or diamond shaped. However, the pockets 1586 can also be triangular, circular, elliptical, or any other suitable shape. In one embodiment, the pockets 1586 extend radially outwardly from the remainder of the impermeable member 21. However, the pockets 1586 can alternatively extend radially inwardly from the remainder of the impermeable material 21. The pockets 1586 can be a part of or near the medial joint 1542 of the impermeable material 21. For example, the proximal and distal portions 1520, 1530 can be sized and shaped such that the pockets 1586 are formed when the proximal portion 1520 is attached to the distal portion 1530. The pockets 1586 can be formed from additional material or patch added to the proximal portion 1520 and/or the distal portion 1530 or can be formed from additional impermeable material 21 attached to an area defined by the proximal and/or distal portions 1520, 1530. The one or more pockets 1586 can be spaced around the impermeable material 21 at or near the medial joint 1542 such that the pockets 1586 are disposed around the circumference of the valve seat 18 of the docking station 10 when the impermeable material 21 is attached to the frame 1500.

The radiopaque markers 1580 can be disposed and secured in the pockets 1586. In one embodiment, the radiopaque markers 1580 are disposed in the pockets 1586 before the impermeable material 21 is attached to the frame 1500. The pockets 1586 can then be covered by one or more pocket coverings 1588, the pocket can be stitched closed, and/or a stitch can be passed through the radiopaque marker to secure the marker in the pocket. The optional pocket coverings 1588 can be sized and shaped to cover the opening of the pockets 1586 and can comprise the same material as the impermeable material 21. The pocket coverings 1588 can be attached to the impermeable material 21 on the side of the impermeable material 21 opposite the frame 1500. The pocket coverings 1588 can be attached to the impermeable material 21 by one or more sutures 1560. The pockets 1586 can alternatively be formed by attaching the pocket coverings 1588 to the impermeable material 21 and thereby defining the pocket 1586 as the space between the pocket covering 1588 and the impermeable member 21.

Referring to FIGS. 89C and 89D, a suture 1560 can attach the pocket coverings 1588 to the impermeable material 21 around the outside of the pocket covering 1588 and can include a support stitch 1589 extending across the pocket covering 1588. The support stitch 1589 can provide radial force against the valve 29 when the valve 29 is deployed in the valve seat 18. The support stitch 1589 can be in line with or parallel to the medial joint 1542 (FIG. 89C) or can be perpendicular to the medial joint 1542 (FIG. 89D).

Referring to FIGS. 89E through 89N, the radiopaque markers 1580 with optional apertures 1582 can be disposed and secured in the pockets 1586 (not pictured, as the pocket 1586 is formed between the pocket covering 1588 and the impermeable member 21) of the impermeable member 21. The radiopaque markers 1580 can be secured in the pockets 1586 in a manner that can increase the securement of the radiopaque markers 1580 and can decrease the translational and rotational movement of the radiopaque markers 1580. As shown in FIGS. 89E and 89F, the pocket covering 1588 can be disposed on the impermeable material 21 and partially secured to the impermeable material 21 by a suture

1560. The suture 1560 can be stitched around a portion of the pocket covering 1588 to partially secure the pocket covering 1588 to the impermeable member 21 such that a portion of pocket covering 1588 is not secured to the impermeable member 21. The suture 1560 can be passed through the pocket covering 1588 and the impermeable member 21 at a plurality of through points 1591. The through points 1591 can be near the edges of the pocket covering 1588 and can substantially surround the perimeter of the pocket covering 1588. For example, the suture 1560 can be passed through the through points 1591 to surround three-fourths of the perimeter of the pocket covering 1588. In the illustrated embodiment, the suture 1560 is stitched through the through points 1591 by an in and out stitch. However, the suture 1560 can be stitched through the through points 1591 by any suitable stitch.

As shown in FIG. 89G, the radiopaque marker 1580 can then be placed in the pocket 1586 formed between the impermeable material 21 and the pocket covering 1588. The radiopaque marker 1580 can be positioned or oriented such that the aperture 1582 extends between the pocket covering 1588 and the impermeable member 21. As shown in FIG. 89H, the remainder of the pocket covering 1588 can be secured to the impermeable member 21 by the suture 1560. The suture 1560 can be passed through an additional through point 1591 such that the suture 1560 substantially surrounds the radiopaque marker 1580 near the edges of the pocket covering 1588. The suture 1560 can be passed through the pocket covering 1588 and the impermeable member 21 such that the suture 1560 passes through the initial through point 1591. Optionally, as shown in FIG. 89H, the suture 1560 can be stitched back through the through points 1591 to create an interlocking stitch 1590, similar to the stitch described in FIGS. 82E through 82I.

While the pocket covering 1588 has been described as partially stitched to the impermeable member 21 before the radiopaque marker 1580 is placed in the pocket 1586 the pocket covering 1588 can be attached to the impermeable member 21 in other ways. For example, the radiopaque marker 1580 can be disposed between the pocket covering 1588 and the impermeable member 21 and the pocket covering 1588 can then be stitched to the impermeable member 21.

Referring to FIGS. 89I through 89L, the radiopaque marker 1580 can be further secured in the pocket 1586 with a cross stitch. The suture 1560 can be stitched from one of the through points 1591 to a through point 1591 on the opposite side of the pocket covering 1588 and can also pass through a through point 1591 in the center of the pocket covering 1588. The center through point 1591 can be aligned with the aperture 1582 of the radiopaque marker 1580 such that the suture 1560 extends through the aperture 1582 of the radiopaque marker 1580. The additional stitch can be configured such that the suture 1560 extends vertically across the pocket covering 1588 (as shown in FIG. 89I), such that the suture 1560 extends horizontally across the pocket covering 1588 (as shown in FIG. 89J), and/or such that the suture 1560 extends diagonally across the pocket covering 1588 (as shown in FIGS. 89K and 89L).

As shown in FIGS. 89M and 89N, the radiopaque marker 1580 can be still further secured in the pocket 1586 with a second cross stitch. The second cross stitch of the suture 1560 can extend from one of the through points 1591 to a through point 1591 on the opposite side of the pocket covering 1588 and can also pass through the through point 1591 in the center of the pocket covering 1588. This second stitch through the center through point 1591 can be substantially perpendicular to the first cross stitch across the pocket covering 1588 which extends through the center through point 1591. As such, the suture 1560 can form a "+" or "X" shape across the pocket covering 1588. However, the suture 1560 can be stitched in any shape to secure the radiopaque marker 1580 in the pocket 1586 and can include more than two stitches extending through the center through point 1591.

As shown in FIGS. 90A through 90C, instead of being separate pieces which are affixed to the frame 1500 or the impermeable material 21, the one or more radiopaque markers 1580 be included in the frame 1500. The radiopaque markers 1580 can be built into the frame 1500 or the radiopaque markers 1580 can be thicker frame junctions 1503 in the valve seat 18 of the frame 1500 which increases the radiopacity or radiodensity of one or more portions of the valve seat 18. For example, in embodiments where the frame 1500 comprises nitinol, additional nitinol can be deposited at frame junctions 1503 in the valve seat 18 to increase the radiopacity or radiodensity of the valve seat 18. However, the radiopacity or radiodensity of the frame junctions 1503 in the valve seat 18 can be increased in a variety of other ways, such as by depositing additional and/or different radiopaque materials at one or more frame junctions 1503 in the valve seat 18.

Additionally or alternatively, the radiopacity of the valve seat 18 can be increased with the use of a radiopaque or radiopacity increasing material in the impermeable material 21. For example, the proximal portion 1520 can include a radiopaque or radiopacity increasing material near the first edge 1522 and/or the distal portion 1530 can include a radiopaque or radiopacity increasing material near the first edge 1532 such that the radiopacity of the impermeable material 21 is increased at or near the medial joint 1542. Further, the suture 1560 used to join the proximal portion 1520 to the distal portion 1530 can include a radiopaque or radiopacity increasing material such that the radiopacity of the medial joint 1542 is increased. As such, the radiopacity of the valve seat 18 of the docking station 10 can be increased when the impermeable material 21 is affixed to the frame 1500.

The radiopaque markers 1580 or portions of increased radiopacity or radiodensity, such as by the inclusion of additional radiopaque materials, can be used to facilitate the deployment of any of the docking stations 10, docking station frames 1500, and/or THVs or valves 29 described herein. As shown in FIG. 91, the radiopaque markers 1580 or portions of increased radiopacity or radiodensity of the frame 1500 can be used such that the THV or valve 29 can be properly deployed in the docking station 10 or the docking station frame 1500, such as in the valve seat 18. The valve 29 can be deployed such that a middle or central portion of the valve 29 is aligned with the radiopaque markers 1580 of the frame 1500. The radiopaque markers 1580 can be any of the radiopaque markers described herein and can be affixed to the frame 1500 at junctions 1503 (FIG. 90A), disposed in marker settings 1584 (FIG. 88), affixed to the impermeable material (FIG. 89A), disposed in pockets 1586 disposed in the impermeable material 21 (FIG. 89B), or in any other suitable manner. The valve 29 can be deployed under fluoroscopy or a similar imaging process such that the radiopaque markers 1580 of the deployed frame 1500 are visible. The valve 29 can be composed or configured such that it is also visible under fluoroscopy or a similar imaging process. Additionally or alternatively, the valve 29 can include radiopaque markers or portions of increased radiopacity or radiodensity similar to the radiopaque markers 1580 of the frame 1500 described above. For example, the valve 29 can include radiopaque markers disposed on a central or middle portion of the valve 29.

During deployment, the valve 29 can be positioned or repositioned such that a central or middle portion of the valve 29 is situated between and aligned with the radiopaque markers 1580 of the frame 1500. For example, the valve 29 can be positioned or repositioned such that radiopaque markers in the central or middle portion of the valve 29 are aligned with the radiopaque markers 1580 of the frame. When the central or middle portion of the valve 29 is substantially aligned with the radiopaque markers 1580 in the valve seat 18 of the frame 1500, the valve 29 can be released or deployed such that the valve 29 is deployed in the valve seat 18 of the docking station frame 1500. This alignment of the valve 29 with the valve seat 18 of the docking station frame 1500 can prevent leakage between the valve 29 and the frame 1500.

While the frame 1500 has been described as including radiopaque markers 1580 to position and reposition the valve 29 for deployment in the valve seat 18 of the frame 1500, the positioning of the valve 29 within the frame 1500 can be done by any other suitable manner for positional identification. For example, the frame 1500 can include portions in the valve seat 18 with increased radiopacity or radiodensity, such as by including thicker frame junctions 1503 in the valve seat 18, including additional nitinol at the frame junctions 1503, depositing additional and/or different radiopaque materials at one or more frame junctions 1503 in the valve seat 18, or any other suitable manner.

Referring to FIGS. 91 through 96B, radiopaque markers or portions of increased radiopacity or radiodensity can also be used in the deployment of the docking station 10 or frame 1500 from a delivery device such as a catheter. As shown in FIGS. 92A through 96B, portions of the delivery catheter 3600 can include radiopaque markers or portions of increased radiopacity or radiodensity which can be viewable under fluoroscopy or similar imaging process and which can be used in the deployment, positioning, recapturing, and/or redeployment of the frame 1500. The elongated nosecone 28 can have increased radiopacity or radiodensity such that at least a portion of the elongated nosecone 28 can be identified under fluoroscopy or similar imaging process. For example, the elongated nosecone 28 can at least partially include barium sulfate to increase the radiopacity of the nosecone 28. However, any material that provides radiopacity can be used.

As shown in FIGS. 92A through 92C, the outer tube 4910 of the delivery catheter 3600 has a terminal or distal end 4911 near the nosecone 28 when the delivery catheter 3600 is in the compact or undeployed state and from which the frame 1500 can be deployed, as described below. The outer tube 4910 can include one or more radiopaque markers 4920 disposed at or near the distal end 4911 to increase the radiopacity or radiodensity at or near the distal end 4911. The radiopaque markers 4920 can be any suitable size, shape, configuration, or composition, such as the size, shape, configuration, and compositions of any of the radiopaque markers previously described herein. The radiopaque markers 4920 can be configured and positioned to indicate an amount the frame 1500 has been deployed, as detailed below. Optionally, the outer tube 4910 can include an end cap 4913 disposed at the end of the outer tube 4910. The end cap 4913 can be a ring, such as a plastic ring, at the end of the outer tube 4910 and the one or more radiopaque markers 4920 can be disposed on, as a part of, or in the end cap 4913. Additionally or alternatively, the end cap 4913 can be constructed of material with increased radiopacity or radiodensity such that the end cap 4913 is visible or identifiable under fluoroscopy or similar imaging process. As shown in FIG. 92B, the proximal end of the nosecone 28 can at least partially extend into the end cap 4913.

As shown in FIGS. 92A and 92B, the radiopaque marker 4920 can be a single band which extends around the outer tube 4910. The band can be continuous (i.e. extend 360° around the tube) or partial (i.e. extend less than 360°). The band can be attached to the outer tube 4910 in a variety of different ways. For example, the band can be embedded in the tube, bonded to tube surface, or otherwise attached to the tube. The radiopaque marker 4920 can comprise any suitable material of increased radiopacity or radiodensity, such as platinum-iridium, and can be embedded in the end cap 4913. However, the radiopaque marker 4920 can have any suitable size, shape, or configuration. For example, the radiopaque marker 4920 can be disposed around the end cap 4913 or can be disposed radially inside of the end cap 4913.

As shown in FIG. 92C, the outer tube 4910 can include a plurality of radiopaque markers 4920 disposed circumferentially around the outside of the outer tube 4910 near the distal end 4911. The radiopaque markers 4920 can be solid, cylindrical disks disposed equidistantly around the outer surface of the end cap 4913. However, the one or more radiopaque markers 4920 can be any suitable size, shape, or configuration. For example, the radiopaque markers 4920 can be any of the configurations of the radiopaque markers 1580 shown in FIGS. 86A-86D. Additionally, the radiopaque markers 4920 can be disposed on or in the optional end cap 4913 or the outer tube 4910 in any suitable manner. For example, the radiopaque markers 4920 can be embedded within the end cap 4913 or can be disposed radially inside of the end cap 4913.

While the radiopacity or radiodensity near the distal end 4911 of the outer tube 4910 has been described as being increased by the inclusion of one or more radiopaque markers 4920, the radiopacity or radiodensity can be increased in other ways. For example, the end cap 4913 can at least partially comprise a material with increased radiopacity or radiodensity or additional and/or different materials can be deposited around the distal end 4911 to increase the radiopacity or radiodensity.

As shown in FIGS. 93A-93C, the outer tube 4910 can be retracted proximally from the nosecone 28. As the outer tube 4910 is retracted, the connecting tube 4916 is exposed. The connecting tube 4916 is disposed between the nosecone 28 and the docking station connector 4914 and is sized to be disposed and moveable within the outer tube 4910. In the illustrated embodiment, the outer tube 4910 includes an end cap 4913 with an embedded radiopaque marker 4920 (not pictured). However, the outer tube 4910 can include any radiopaque markers or manners of increased radiopacity or radiodensity. For example, the outer tube 4910 can include multiple radiopaque markers 4920 disposed near the distal end 4911 as shown in FIG. 92C.

The connecting tube 4916 can include one or more radiopaque markers 4922 disposed along the length of the connecting tube 4916 to increase the radiopacity or radiodensity. The one or more radiopaque markers 4922 can be spaced along the connecting tube 4916 at fixed or predetermined distances from the nosecone 28 and/or the docking station connector 4914 to provide positioning and/or deployment information. The location or positioning of the radiopaque markers 4922 can be selected to indicate or identify an amount of deployment of the frame 1500, as detailed below. In one exemplary embodiment, the outer tube 4910 includes one or more radiopaque markers, but the connecting tube does not include any radiopaque markers. In one exemplary embodiment, the connecting tube 4916 includes one or more radiopaque markers, but the outer tube 4910 does not include any radiopaque markers. In one exemplary embodiment, the connecting tube 4916 includes one or more radiopaque markers and the outer tube 4910 includes one or more radiopaque markers. Any combination of the nosecone, outer tube, connecting tube, docking station, and valve can include one or more radiopaque marker to assist in deployment of the docking station and/or the valve.

Referring to the embodiment illustrated by FIGS. 93A-93C, the connecting tube 4916 includes one radiopaque marker 4922 as a band disposed around the connecting tube 4916. However, the connecting tube 4916 can have any number, positioning, or configuration of radiopaque markers 4922. For example, the connecting tube 4916 can have two radiopaque markers 4922 (FIG. 94) or three or more radiopaque markers 4922 disposed at different lengths along the connecting tube 4916, and the radiopaque markers 4922 can be similar to the radiopaque markers 1580 described in FIGS. 86A-86D. Additionally or alternatively, the connecting tube 4916 can increase the radiopacity or radiodensity by other suitable means. For example, the radiopacity or radiodensity of portions of the connecting tube 4916 can be achieved by depositing additional and/or different radiopaque materials along the connecting tube 4916 or by at least partially constructing portions of the connecting tube 4916 out of a radiopaque or radio-dense material.

As shown in FIG. 94, the frame 1500 can be disposed in the compressed or undeployed state along and around the connecting tube 4916 between the nosecone 28 and the docking station connector 4914. The outer tube 4910 can be retracted with respect to the nosecone 28, the connecting tube 4916, the docking station connector 4914, the inner tube 4912, and the frame 1500 to deploy the frame 1500. The frame 1500 can be coupled to the catheter assembly, or a docking station connector 4914 of the catheter assembly, in a wide variety of different ways. For example, the frame 1500 could be coupled with the catheter assembly with a lock(s), locking mechanism, suture(s) (e.g., one or more sutures releasably attached, tied, or woven through one or more portion of the docking station), interlocking device(s), a combination of these, or other attachment mechanisms. Some of these coupling or attachment mechanisms can be configured to allow for the frame to be retracted back into the catheter assembly without causing the frame to catch on edges of the catheter assembly, e.g., by constraining the proximal end of the docking station to a smaller profile or collapsed configuration, to allow for adjustment, removal, replacement, etc. of the docking station.

In one exemplary embodiment, a docking station connector 4914 can be configured to at least partially secure or control the frame 1500 during deployment. In the illustrated embodiment, the frame 1500 includes elongated legs 5000 which can connect the frame 1500 to the docking station connector 4914. The elongated legs 5000 can be retaining portions on the proximal end 12 of the frame 1500 that are longer than the remainder of the retaining portions 414. The illustrated elongated legs 5000 include heads 5636 which can be retained in the T-shaped recess 5710 of the docking station connector 4914 to at least partially connect the frame 1500 to the delivery catheter assembly during deployment of the frame 1500. The head 5636 of the elongated leg 5000 can be secured in the T-shaped recess 5710 when the outer tube 4910 is withdrawn and the remainder of the frame 1500 expands. Once the remainder of the frame 1500 has been deployed, the head 5636 of the elongated leg 5000 can be released from the T-shaped recess 5710. However, the frame 1500 can be connected, coupled, or otherwise secured to the delivery catheter assembly in any other way, such as any other way previously described herein.

As shown in FIG. 94, the frame 1500 can be disposed within the outer tube 4910 and around the connecting tube 4916 with the radiopaque markers 4922 of the connecting tube 4916 disposed along the length of the frame 1500. The radiopaque markers 4922 can be disposed along the connecting tube 4916 to correspond to predetermined points of the frame 1500. The radiopaque markers 4922 can be positioned along the connecting tube 4916 to correspond to various amounts of deployment of the frame 1500, as described below. In the illustrated embodiment, the connecting tube 4916 includes two spaced-apart radiopaque markers 4922 disposed along the length of the shaft. However, the connecting tube 4916 can have any number, shape, size, or configuration of radiopaque markers 4922. For example, the connecting tube 4916 can have one radiopaque marker 4922, three or more radiopaque markers 4922, or a single radiopaque marker 4922 extending a longer distance along the length of the connecting tube 4916.

As shown in FIGS. 95A-95C, the outer tube 4910 can be retracted from the remainder of the delivery catheter assembly to expose the frame 1500 for deployment. In the illustrated example, the frame 1500 includes an impermeable member 21 and one or more radiopaque markers 1580 in the valve seat 18 which are exposed as the outer tube 4910 is retracted and the frame 1500 is deployed. The impermeable member 21 can be any suitable covering for the frame 1500. For example, the impermeable member 21 can be similar to any of the impermeable members 21 described herein. The radiopaque markers 1580 of the frame 1500 can be visible under fluoroscopy or similar image processing while the radiopaque markers 1580 are disposed within the outer tube 4910. The radiopaque markers 1580 can be disposed on or affixed to the frame 1500 in any manner described herein. For example, the radiopaque markers 1580 can be disposed on the junctions 1503 of the frame 1500, such as by being disposed in marker settings 1584 (FIG. 88), affixed to the impermeable material (FIGS. 89A, 95C), disposed in pockets 1586 located in the impermeable member 21 (FIG. 89B), or in any other suitable manner. Alternatively, the radiopacity or radiodensity of one or more portions of the valve seat 18 can be increased in any other suitable manner. For example, the frame 1500 can include portions in the valve seat 18 with increased radiopacity or radiodensity, such as by including thicker frame junctions 1503 in the valve seat 18, including additional nitinol at the frame junctions 1503, depositing additional and/or different radiopaque materials at one or more frame junctions 1503 in the valve seat 18, or any other suitable manner.

The radiopaque markers 1580 of the frame 1500, the one or more radiopaque markers 4920 of the outer tube 4910, the one or more radiopaque markers 4922 of the connecting tube 4916, and/or the radiopaque nosecone 28 can be used to facilitate the deployment of the docking station frame 1500 in the proper position, such as a proper position in the pulmonary artery, a proper position in the mitral valve, a proper position in the tricuspid valve, or a proper position of any portion of the vasculature.

As shown in FIG. 95A, the outer tube 4910 can be retracted or withdrawn from the remainder of the delivery catheter assembly such that the distal end 14 of the frame 1500 is no longer contained by the outer tube 4910. The exposed portions of the frame 1500 begin to expand out of the outer tube 4910. As the distal portions of the frame 1500 begin to expand out of the distal end 4911 of the outer tube 4910, the radiopaque markers 1580 of the frame 1500 and the one or more radiopaque markers 4922 of the connecting tube 4916 move relatively toward the distal end of the outer tube. but are still be disposed within the outer tube 4910. The frame 1500 also remains coupled to the delivery catheter assembly. For example, the head 5636 of one or more elongated legs 5000 of the frame 1500 can be retained by the docking station connector 4914. In such a position, the deployed portions of the frame 1500 can be recaptured into the outer tube 4910 by distally advancing the outer tube 4910 or retracing the remainder of the delivery catheter assembly into the outer tube 4910.

As shown in FIG. 95B, the outer tube 4910 can be retracted or withdrawn farther from the remainder of the delivery catheter assembly such that the radiopaque markers 1580 in the valve seat 18 of the frame 1500 are substantially aligned with the radiopaque marker 4920 at the distal end 4911 of the outer tube 4910. In such position, the frame 1500 can be about 50% or half deployed from the outer tube 4910. The one or more radiopaque markers 4922 on the connecting tube 4916 can still be disposed within the outer tube 4910. The frame 1500 can remain coupled to the delivery catheter assembly, such as with the head 5636 of one or more elongated legs 5000 being retained by the docking station connector 4914. In such a position, either the outer tube 4910 can be distally advanced or the remainder of the delivery catheter assembly can be retracted into the outer tube 4910 such that the deployed portions of the frame 1500 are recaptured into the outer tube 4910. The alignment of the radiopaque markers 1580 of the frame 1500 with the one or more radiopaque markers 4920 of the outer tube 4910 can indicate a point at which the frame 1500 should either be deployed in its entirety or recaptured into the outer tube 4910, repositioned, and redeployed from the outer tube 4910. That is, the radiopaque markers 1580 of the frame 1500 and the one or more radiopaque markers 4920 of the outer tube 4910 can be used to determine whether the frame 1500 is correctly positioned before fully deploying and releasing the frame 1500.

As shown in FIG. 95C, the outer tube 4910 can be retracted or withdrawn even farther from the remainder of the delivery catheter assembly. The docking station frame 1500 is expanded out of the outer tube 4910 except one or more elongated leg 5000 can be retained by the docking station connector 4914 in the outer tube 4910. In such a position, the frame 1500 it may not be possible to recapture the frame 1500 into the outer tube 4910 but the frame 1500 can be repositioned before the frame 1500 is released from the delivery catheter assembly.

Once the frame 1500 is in the desired position, the frame 1500 can be released from the delivery catheter assembly, such as by retracting the outer tube 4910 farther to release the engagement between the elongated leg 5000 and the docking station connector 4914. In the illustrated embodiment, the outer tube 4910 is retracted such that the radiopaque marker 4920 at the distal end 4911 of the outer tube 4910 is proximal to the one or more radiopaque markers 4922 of the connecting tube 4916 such that the radiopaque markers 4922 of the connecting tube 4916 are deployed.

The radiopaque markers 4922 of the connecting tube 4916 and/or the one or more radiopaque markers 4920 of the outer tube 4910 can be spaced or positioned in any suitable manner. For example, the radiopaque markers 4922 of the connecting tube 4916 can be spaced such that, in such position, one of the radiopaque markers 4922 of the connecting tube 4916 can be positioned on the connecting tube 4916 to substantially align with the radiopaque marker 4920 of the outer tube 4910 (i.e. at a position between the positions illustrated by FIGS. 95B and 95C). For example, when viewed under fluoroscopy or similar imaging process, the alignment of one of the radiopaque markers 4922 of the connecting tube 4916 with one of the radiopaque markers 4920 of the outer tube 4910 can indicate a final position where the frame 1500 can be brought back into the outer tube 4910.

As shown in FIGS. 96A and 96B, the radiopaque nosecone 28, the one or more radiopaque markers 4920 of the outer tube 4910, the radiopaque markers 1580 of the frame 1500, and the one or more radiopaque markers 4922 of the connecting tube 4916 can be visible under fluoroscopy or other imaging process and monitored during the deployment of the frame 1500. The frame 1500, the connecting tube 4916, the docking station connector 4914, and the inner tube 4912 can optionally be visible under fluoroscopy or similar imaging process, but not as clearly as the radiopaque markers. In FIGS. 96A and 96B, the frame 1500 is illustrated in dashed lines to show the position of the frame in the drawing, but to indicate that the frame may not be visible under fluoroscopy or is difficult to see under fluoroscopy.

The positioning of the radiopaque markers 1580, 4920, 4922 can be monitored to indicate the amount the frame 1500 has been expanded or deployed. For example, the radiopaque markers 1580, 4920 can be used to position and deploy the frame at the desired location in the vasculature. In addition, the radiopaque markers 4920, 4922 can be used to monitor when the frame 1500 is still able to be moved back into the outer tube (i.e. when the marker 4922 has not moved distally past the marker 4920). For example, the amount of frame 1500 deployment indicated by alignment of the markers 4920, 4922 can represent the amount or extent of deployment corresponding to the maximum amount of deployment before the frame 1500 can no longer no longer be recaptured by the outer tube 4910.

As shown in FIG. 96A, while the delivery catheter assembly is in the undeployed state (FIG. 94) before the docking station frame 1500 is deployed from the outer tube 4910, the elongated nosecone 28 can be disposed distally to the one or more radiopaque markers 4920 of the outer tube 4910. Before deployment, the radiopaque markers 4920 of the outer tube 4910 can be disposed at or near the proximal end of the elongated nosecone 28. The radiopaque markers 1580 of the frame 1500 can be disposed proximally to the radiopaque markers 4920 of the outer tube 4910, and the one or more radiopaque markers 4922 of the connecting tube 4916 can be disposed proximally to the radiopaque markers 1580 of the frame 1500. The one or more radiopaque markers 4922 of the connecting tube 4916 can be disposed distally to the docking station connector 4914.

During deployment of the frame 1500, the positions of the radiopaque markers 1580 of the frame 1500, the one or more radiopaque markers 4920 of the outer tube 4910, the one or more radiopaque markers 4922 of the connecting tube 4916, and the radiopaque nosecone 28 can be monitored and compared to indicate the extent of deployment of the frame 1500, such as to determine when the frame 1500 is properly expanded and deployed in the desired position. For example, the distal marker 4920 of the outer tube can be positioned substantially at the desired deployment location of the waist of the frame and the docking station frame 1500 can be deployed from the delivery catheter assembly (such as by retracting the outer tube 4910) until the radiopaque markers 1580 in the valve seat 18 of the frame 1500 are substantially aligned with the one or more radiopaque markers 4920 of the outer tube 4910. This positions the waist of the frame, indicated by markers 1580, at the desired deployment location. In the illustrated example, this alignment causes the frame 1500 to be about half or 50% deployed from the outer tube 4910. At such a point, the operator can determine either that the frame 1500 is being deployed in the proper position and continue with the deployment of the frame 1500 or that the frame 1500 should be recaptured into the outer tube 4910, repositioned, and redeployed from the outer tube 4910.

As shown in FIG. 96B, the outer tube 4910 (not shown under fluoroscopy) can be retracted until the one or more radiopaque markers 4920 is substantially aligned with one of the radiopaque markers 4922 of the connecting tube 4916. The radiopaque markers 1580 of the frame 1500 can be disposed between the nosecone 28 and the radiopaque marker 4920 of the outer tube 4910 and the frame 1500 can be more than half deployed. The position of the radiopaque marker(s) 1580 at the waist of the frame 1500 can be checked to confirm that the frame is in the desired deployment position in the vasculature. The alignment of the radiopaque marker 4920 of the outer tube 4910 and the radiopaque marker 4922 of the connecting tube 4916 can provide an indication to an operator as to the amount the frame 1500 is deployed. The alignment of the radiopaque marker 4920 of the outer tube 4910 and the radiopaque marker 4922 of the connecting tube 4916 can provide an indication of the desired and/or maximum amount the frame 1500 can be expanded or deployed and still be recaptured into the delivery catheter assembly, such as by advancing the outer tube 4910 distally. This can provide an indication to the operator that the frame 1500 should either be deployed or recaptured by the outer tube 4910, such as to reposition the frame 1500 for redeployment. For example, the alignment of the radiopaque marker 4920 of the outer tube 4910 and the radiopaque marker 4922 of the connecting tube 4916 can indicate that the frame 1500 is 50% to 75% deployed, such as 60% deployed. Additionally or alternatively, the alignment of one of the radiopaque markers 4920 of the outer tube 4910 and one of the radiopaque markers 4922 of the connecting tube 4916 can indicate when the frame 1500 is fully deployed from the outer tube 4910 except for the elongated leg 5000 attached to the docking station connector 4914 and/or the desired position at which the frame 1500 should be released from the delivery catheter assembly.

While the frame 1500 has been described as having radiopaque markers 1580 disposed in the valve seat 18, the outer tube 4910 has been described as having radiopaque markers 4920 near the distal end 4911 of the outer tube 4910, and the connecting tube 4916 has been described as having radiopaque markers 4922 disposed along the shaft of the connecting tube 4916 for indicating the deployment of the frame 1500, the outer tube 4910, connecting tube 4916, frame 1500, and/or any other components of the delivery system can have any suitable configuration of portions of increased radiopacity or radiodensity which can provide an indication as to the amount of frame 1500 expansion or deployment prior to the release of the frame 1500. For example, the frame 1500 can include radiopaque markers 1580 at junctions 1503 distal to the valve seat 18 which, when aligned with the radiopaque markers 4920 of the catheter 3600 during deployment of the frame 1500, indicate the desired or maximum amount of frame 1500 expansion and/or deployment before the frame 1500 is released from the catheter 3600.

The foregoing primarily describes embodiments of docking stations that are self-expanding. But the docking stations and/or delivery devices shown and described herein can be modified for delivery of balloon-expandable and/or mechanically-expandable docking devices, within the scope of the present disclosure. That is to say, delivering balloon-expandable and/or mechanically-expandable docking stations to an implantation location can be performed percutaneously using modified versions of the delivery devices of the present disclosure. In general terms, this includes providing a transcatheter assembly that can include a delivery sheath and/or additional sheaths as described above. In the case of balloon-expandable docking stations, the devices generally further include a delivery catheter, a balloon catheter, and/or a guide wire. A delivery catheter used in a balloon-expandable type of delivery device can define a lumen within which the balloon catheter is received. The balloon catheter, in turn, defines a lumen within which the guide wire is slidably disposed. Further, the balloon catheter includes a balloon that is fluidly connected to an inflation source. With the docking station mounted on the balloon, the transcatheter assembly is delivered through a percutaneous opening in the subject via the delivery device. Once the docking station is properly positioned, the balloon catheter is operated to inflate the balloon, thus transitioning the docking station to an expanded arrangement.

EXAMPLES

In view of the above described implementations of the disclosed subject matter, this disclosure provides additional examples enumerated below. It should be noted that one feature of an example in isolation or more than one feature of the example taken in combination and, optionally, in combination with one or more features of one or more further examples are further examples also falling within the disclosure of this application.

Example 1. A docking station for a medical device, the docking station comprising: a frame having a plurality of struts extending from a proximal end to a distal end and defining a plurality of cells and a valve seat; a plurality of radiopaque markers disposed around the valve seat; and an impermeable material attached to the frame.

Example 2. The docking station of any example herein, particularly example 1, wherein the frame includes a plurality of marker settings each configured to receive one of the radiopaque markers.

Example 3. The docking station of any example herein, particularly example 1-2, wherein the plurality of radiopaque markers is affixed to the impermeable material.

Example 4. The docking station of any example herein, particularly example 1-3, wherein the radiopaque markers are each disposed within a pocket in the impermeable material.

Example 5. The docking station of any example herein, particularly example 1-4, wherein each of the radiopaque markers include an aperture extending through a central portion of the radiopaque marker.

Example 6. The docking station of any example herein, particularly example 5, wherein the radiopaque markers are affixed to the impermeable member through the aperture.

Example 7. The docking station of any example herein, particularly examples 1-6, wherein the radiopaque markers indicate a deployment location for a transcatheter heart valve.

Example 8. The docking station of any example herein, particularly examples 1-7, wherein the frame includes a plurality of marker settings each configured to receive one of the radiopaque markers.

Example 9. The docking station of any example herein, particularly examples 1-8, wherein the frame further comprises a plurality of outflow cells.

Example 10. The docking station of any example herein, particularly examples 1-9, wherein the struts in the valve seat have a larger cross-sectional width than the remaining struts.

Example 11. The docking station of any example herein, particularly examples 1-10, wherein the impermeable member is attached to the frame by a coating material.

Example 12. The docking station of any example herein, particularly examples 1-11, wherein the radiopaque markers are affixed to a plurality of junctions of the frame.

Example 13. A docking station for a medical device, the docking station comprising: a frame comprising: a proximal end and a distal end; a valve seat; a plurality of rungs of struts extending from the proximal end to the distal end, wherein the struts define a plurality of cells, a plurality of junctions, and a plurality of apices at the proximal and distal ends; and a plurality of eyelets on the apices of at least one of the proximal end and the distal end; and an impermeable material attached to the frame.

Example 14. The docking station of any example herein, particularly example 13, wherein the impermeable material is attached to the frame by a plurality of vertical stitches.

Example 15. The docking station of any example herein, particularly examples 13-14, wherein the frame includes four rungs of struts.

Example 16. The docking station of any example herein, particularly examples 13-14, wherein the frame includes six rungs of struts.

Example 17. The docking station of any example herein, particularly examples 13-16, wherein the frame includes twelve apices at the proximal end.

Example 18. The docking station of any example herein, particularly examples 13-16, wherein the frame includes fourteen apices at the distal end.

Example 19. The docking station of any example herein, particularly examples 13-18, wherein the frame further comprises a plurality of uncovered outflow cells.

Example 20. The docking station A docking station for a medical device, the docking station comprising: a frame comprising: a proximal end and a distal end; a valve seat; a plurality of rungs of struts extending from the proximal end to the distal end; and a plurality of apices at the proximal and distal ends; and an impermeable material comprising: a proximal portion having a first edge; a distal portion having a second edge; and a stitch connecting the proximal portion to the distal portion near the first edge and second edge; wherein the stitch increases the radial strength of the station of the valve seat.

Example 21. The docking station of any example herein, particularly example 20, further comprising a plurality of radiopaque markers attached to the impermeable material.

Example 22. The docking station of any example herein, particularly examples 20-21, further comprising a plurality of radiopaque markers; wherein each radiopaque marker is disposed in a pocket in the impermeable member.

Example 23. The docking station of any example herein, particularly examples 20-22, wherein the impermeable material is attached to the frame by a coating material.

Example 24. A docking station for a medical device, the docking station comprising: a frame comprising: a proximal end and a distal end; a valve seat; a plurality of rungs of struts extending from the proximal end to the distal end; a plurality of outflow cells near one of the proximal end and the distal end; and an impermeable material attached to the frame; wherein at least a portion of the outflow cells are not covered by the impermeable material such that blood can flow through the outflow cells.

Example 25. The docking station of any example herein, particularly example 24, wherein the outflow cells form a portion of a permeable portion of the docking station.

Example 26. The docking station of any example herein, particularly examples 25, further comprising a plurality of cells defined by the plurality of struts; wherein the outflow cells are larger than the cells defined by the plurality of struts.

Example 27. The docking station of any example herein, particularly examples 24-26, wherein the cells closest to the distal end include eyelets.

Example 28. The docking station of any example herein, particularly examples 24-27, wherein each outflow cell is defined in part by an outflow strut.

Example 29. The docking station of any example herein, particularly examples 24-28, wherein each outflow cell includes a narrow end.

Example 30. A docking station for a medical device, the docking station comprising: a frame comprising: a proximal end and a distal end; a valve seat; a plurality of rungs of struts extending from the proximal end to the distal end and defining a plurality of cells; and an impermeable material attached to the frame; wherein struts in the valve seat are thicker than the other struts in the frame.

Example 31. The docking station of any example herein, particularly example 30, wherein the impermeable material includes an inelastic waistband.

Example 32. The docking station of any example herein, particularly examples 30-31, further comprising a plurality of radiopaque markers disposed in the valve seat.

Example 33. The docking station of any example herein, particularly examples 30-32, further comprising a plurality of apices at the proximal and distal ends.

Example 34. The docking station of any example herein, particularly example 33, further comprising a plurality of eyelets near the apices at the proximal end.

Example 35. A docking station for a medical device, the docking station comprising: a frame comprising: a proximal end and a distal end; a valve seat; a plurality of rungs of struts extending from the proximal end to the distal end and defining a plurality of cells; and a plurality of apices at the proximal and distal ends; and an impermeable material; wherein a portion of the cells near the distal end are not covered by the impermeable material.

Example 36. The docking station of any example herein, particularly example 35, wherein the frame further comprises a plurality of openings near the proximal and distal ends; wherein the openings near the distal ends are not covered by the impermeable material.

Example 37. The docking station of any example herein, particularly examples 35-36, wherein the openings near the proximal end are not covered by the impermeable member.

Example 38. The docking station of any example herein, particularly examples 35-37, wherein the impermeable material comprises a proximal portion and a distal portion.

Example 39. The docking station of any example herein, particularly examples 35-38, wherein blood can flow between the impermeable material and the struts near the distal end when the docking station is deployed.

Example 40. A docking station for a medical device, the docking station comprising: a frame comprising: a proximal end and a distal end; a valve seat; a plurality of rungs of struts extending from the proximal end to the distal end and defining a plurality of cells; a plurality of apices at the proximal and distal ends; and an impermeable material configured to attach to the frame; wherein the impermeable material is attached to the frame by a deposited coating.

Example 41. The docking station of any example herein, particularly example 40, wherein the impermeable material comprises a proximal portion and a distal portion; wherein the proximal portion is attached to the distal portion to form an inelastic waistband.

Example 42. The docking station of any example herein, particularly examples 40-41, further comprising a plurality of radiopaque markers disposed in the valve seat.

Example 43. The docking station of any example herein, particularly examples 42, wherein the radiopaque markers are disposed in a plurality of pockets in the impermeable material.

Example 44. A medical device comprising: a frame comprising: a proximal end and a distal end; a valve seat; and a plurality of rungs of struts extending from the proximal end to the distal end and defining a plurality of cells; and an impermeable member comprising: a plurality of pockets disposed circumferentially around the impermeable member; and a radiopaque marker disposed in each of the pockets; wherein the pockets are disposed in the valve seat when the impermeable member is attached to the frame.

Example 45. The medical device of any example herein, particularly example 44, wherein the pockets are rectangular.

Example 46. The medical device of any example herein, particularly example 45, wherein the pockets extend radially outward from the remainder of the impermeable member.

Example 47. The medical device of any example herein, particularly example 45, further comprising a plurality of pocket coverings; wherein one of the pocket coverings covers each of the pockets.

Example 48. The medical device of any example herein, particularly example 47, wherein each of the radiopaque markers comprise an aperture extending through a central portion of the radiopaque marker.

Example 49. The medical device of any example herein, particularly example 48, wherein each of the pocket coverings are secured to the remainder of the impermeable member by a stitch extending through the aperture of one of the radiopaque markers.

Example 50. A system comprising: a tube having one or more radiopaque markers; a docking station frame disposed in the tube; wherein the docking station includes one or more radiopaque markers; wherein a position of one or more radiopaque markers of the docking station relative to the radiopaque markers of the tube indicate an amount of deployment of the docking station from the tube.

Example 51. The system of any example herein, particularly example 50, wherein the radiopaque markers of the tube are disposed at or near a distal end of the tube.

Example 52. The system of any example herein, particularly example 50, wherein the docking station frame is deployed by retracting the tube proximally relative to the docking station.

Example 53. The system of any example herein, particularly examples 50-52, wherein the one or more radiopaque markers of the tube is a radiopaque band embedded in the tube.

Example 54. The system of any example herein, particularly examples 50-53, wherein the docking station frame includes a plurality of radiopaque markers disposed around a valve seat of the docking station frame.

Example 55. The system of any example herein, particularly examples 50-54, wherein alignment of one of the radiopaque markers of the tube and the radiopaque markers of the docking station frame indicates an amount of deployment of the docking station frame.

Example 56. A method of deploying a docking station frame comprising: positioning a radiopaque marker of a docking station frame at a target location for deployment of a valve seat of a docking station frame; deploying a portion of the docking station frame from a tube such that a radiopaque marker of the tube becomes substantially aligned with the radiopaque marker of the docking station frame; visually confirming that the radiopaque marker of the tube and the radiopaque marker of the docking station frame are at the target location; further deploying and releasing the docking station frame from the tube.

Example 57. The method of any example herein, particularly example 56, wherein the radiopaque markers of the tube are disposed at or near a distal end of the tube.

Example 58. The method of any example herein, particularly examples 56-57, wherein a position of the radiopaque marker of the docking station relative to the radiopaque marker of the tube indicates an amount of deployment of the docking station from the tube.

Example 59. The method of any example herein, particularly examples 56-58, wherein the docking station frame is deployed by retracting the tube proximally relative to the docking station.

Example 60. The method of any example herein, particularly examples 56-59, wherein the docking station frame includes a plurality of radiopaque markers disposed around a valve seat of the docking station frame.

Example 61. A system comprising: a delivery catheter assembly comprising: an outer tube having a distal end and one or more radiopaque markers disposed at or near the distal end; and a connecting tube having one or more radiopaque markers disposed in the outer tube; a docking station frame disposed in the outer tube and coupled to the connecting tube; wherein the docking station frame is deployed by retracting the outer tube proximally relative to the connecting tube; wherein a position of one or more radiopaque markers of the connecting tube relative to the one or more radiopaque markers of the outer tube indicate an amount of deployment of the docking station from the outer tube.

Example 62. The system of any example herein, particularly example 61, wherein the one or more radiopaque markers of the outer tube is a radiopaque band embedded in the outer tube.

Example 63. The system of any example herein, particularly examples 61-62, wherein the frame includes a plurality of radiopaque markers disposed around a valve seat.

Example 64. The system of any example herein, particularly example 63, wherein alignment of one of the radiopaque markers of the outer tube and the radiopaque markers of the frame indicates an amount of deployment of the frame.

Example 65. The system of any example herein, particularly examples 61-64, wherein the connecting tube includes a plurality of radiopaque markers disposed along a length of the connecting tube.

Example 66. The system of any example herein, particularly examples 61-65, wherein the alignment of one or more of the radiopaque markers of the outer tube and one or more of the radiopaque markers of the connecting tube indicates an amount of deployment of the frame.

Example 67. The system of any example herein, particularly examples 61-66, wherein the alignment of one or more of the radiopaque markers of the outer tube and one or more of the radiopaque markers of the connecting tube indicates a point of release for the frame.

Example 68. The system of any example herein, particularly examples 61-67, wherein the frame is configured to be recaptured by the outer tube at any point before one of the radiopaque markers of the outer tube moves proximally past one of the radiopaque markers of the connecting tube.

Example 69. A method of deploying a docking station frame comprising: deploying a portion of a docking station frame from an outer tube with a connecting tube such that a radiopaque marker of the outer tube moves closer to a radiopaque marker of the connecting tube; wherein substantial alignment of the radiopaque marker of the outer tube with the radiopaque marker of the connecting tube indicates a final point at which the docking station frame is recapturable by the outer tube.

Example 70. The method of any example herein, particularly example 69, further comprising releasing the docking station frame from the tubes.

Example 71. The method of any example herein, particularly examples 69-70, wherein the radiopaque markers of the outer tube are disposed at or near a distal end of the outer tube.

Example 72. The method of any example herein, particularly examples 69-71, wherein a position of a radiopaque marker of the docking station relative to the radiopaque marker of the outer tube indicates an amount of deployment of the docking station from the outer tube.

Example 73. The method of any example herein, particularly examples 69-72, wherein the docking station frame is deployed by retracting the outer tube proximally relative to the docking station.

Example 74. The method of any example herein, particularly examples 69-73, wherein the docking station frame includes a plurality of radiopaque markers disposed around a valve seat of the docking station frame.

Example 75. A system comprising: a delivery catheter assembly comprising: an elongated nosecone; an outer tube having a distal end and one or more radiopaque markers disposed at or near the distal end; a docking station connector moveable within the outer tube; and a connecting tube disposed in the outer tube, wherein the connecting tube includes one or more radiopaque markers disposed between the elongated nosecone and the docking station connector; and a docking station frame disposed in the outer tube and coupled to the docking station connector, wherein the docking station frame includes one or more radiopaque markers, wherein the docking station frame is deployed by retracting the outer tube proximally from the elongated nosecone, and wherein the radiopaque markers of the outer tube, the radiopaque markers of the connecting tube, and the radiopaque markers of the docking station frame are configured to visually determine correct placement of the docking station frame and a final point at which the docking station frame is recapturable by the outer tube.

Example 76. The system of any example herein, particularly example 75, wherein the one or more radiopaque markers of the outer tube is a radiopaque band embedded in the outer tube.

Example 77. The system of any example herein, particularly examples 75-76, wherein the frame includes a plurality of radiopaque markers disposed around the valve seat.

Example 78. The system of any example herein, particularly examples 75-77 wherein alignment of one of the radiopaque markers of the outer tube and the radiopaque markers of the frame indicates an amount of deployment of the frame.

Example 79. The system of any example herein, particularly examples 75-78, wherein alignment of one or more radiopaque markers of the outer tube and one or more of the radiopaque markers of the connecting tubes indicates an amount of deployment of the frame.

Example 80. The system of any example herein, particularly examples 75-79, wherein the alignment of one or more radiopaque markers of the outer tube and one or more of the radiopaque markers of the connecting tube indicates a point of release for the frame.

Example 81. The system of any example herein, particularly examples 75-80, wherein the frame is configured to be recaptured by the outer tube at any point before one of the radiopaque markers of the outer tube moves proximally past one of the radiopaque markers of the connecting tube.

Example 82. An assembly comprising: a frame having a valve seat and a plurality of radiopaque markers disposed around the valve seat; an elongated nosecone at a distal portion of the assembly; an outer tube having a distal end and one or more radiopaque markers disposed at or near the distal end; a docking station connector moveable within the outer tube; and a connecting tube disposed between the elongated nosecone and the docking station connector; wherein the frame is deployed by retracting the outer tube proximally from the elongated nosecone.

Example 83. The assembly of any example herein, particularly example 82, wherein the connecting tube further includes one or more radiopaque markers disposed along a length of the connecting tube.

Example 84. The assembly of any example herein, particularly examples 82-83, wherein the alignment of the one or more radiopaque markers of the outer tube with the radiopaque markers of the frame or one of the radiopaque markers of the connecting tube indicates an amount of deployment of the frame.

Example 85. The assembly of any example herein, particularly examples 82-84, wherein the indicated amount of deployment is the maximum amount the frame is deployed before being recaptured by the outer tube.

Example 86. The assembly of any example herein, particularly examples 82-85, wherein the radiopaque markers of the frame indicate a deployment location for a transcatheter valve.

Example 87. The assembly of any example herein, particularly examples 82-86, wherein the elongated nosecone is radiopaque.

Example 88. A docking station for a medical device, the docking station comprising: a frame having a plurality of struts extending from a proximal end to a distal end and defining a plurality of cells and a valve seat; an impermeable material attached to the frame; and a radiopaque suture disposed around the impermeable material.

Example 89. The docking station of any example herein, particularly example 88, wherein the radiopaque suture is disposed around the valve seat.

Example 90. The docking station of any example herein, particularly examples 88-89, wherein the radiopaque suture is at least partially disposed around one of the plurality of struts of the frame.

Example 91. The docking station of any example herein, particularly examples 88-90, wherein the radiopaque suture indicates a deployment location for a transcatheter heart valve.

Example 92. The docking station of any example herein, particularly examples 88-91, further comprising a plurality of radiopaque markers.

Example 93. The docking station of any example herein, particularly example 92, wherein the radiopaque markers are affixed to the frame.

In view of the many possible embodiments to which the principles of the disclosed invention may be applied, it should be recognized that the illustrated embodiments are only preferred examples of the invention and should not be taken as limiting the scope of the invention. All combinations or sub-combinations of features of the foregoing exemplary embodiments are contemplated by this application. The scope of the invention is defined by the following claims. We therefore claim as our invention all that comes within the scope and spirit of these claims.

What is claimed is:

1. A system comprising:

a delivery catheter assembly comprising:

an outer tube having a distal end and one or more radiopaque markers disposed at or near the distal end, wherein the one or more radiopaque markers of the outer tube comprise a radiopaque band embedded in the outer tube; and a connecting tube having one or more radiopaque markers, wherein the connecting tube is disposed in the outer tube;

a docking station frame disposed in the outer tube and coupled to the connecting tube;

wherein the docking station frame is deployed by retracting the outer tube proximally relative to the connecting tube;

wherein a position of one or more radiopaque markers of the connecting tube relative to the one or more radiopaque markers of the outer tube indicate an amount of deployment of the docking station from the outer tube.

2. The system of claim 1, wherein the frame includes a plurality of radiopaque markers disposed around a valve seat.

3. The system of claim 2, wherein alignment of one of the radiopaque markers of the outer tube and the radiopaque markers of the frame indicates an amount of deployment of the frame.

4. The system of claim 1, wherein the connecting tube includes a plurality of radiopaque markers disposed along a length of the connecting tube.

5. The system of claim 1, wherein the alignment of one or more of the radiopaque markers of the outer tube and one or more of the radiopaque markers of the connecting tube indicates an amount of deployment of the frame.

6. The system of claim 1, wherein the alignment of one or more of the radiopaque markers of the outer tube and one or more of the radiopaque markers of the connecting tube indicates a point of release for the frame.

7. The system of claim 1, wherein the frame is configured to be recaptured by the outer tube at any point before one of the radiopaque markers of the outer tube moves proximally past one of the radiopaque markers of the connecting tube.

8. A system comprising:

a delivery catheter assembly comprising:

an elongated nosecone;

an outer tube having a distal end and one or more radiopaque markers disposed at or near the distal end; and a docking station connector moveable within the outer tube; and a connecting tube disposed in the outer tube;

wherein the connecting tube includes one or more radiopaque markers disposed between the elongated nosecone and the docking station connector; and a docking station frame disposed in the outer tube and coupled to the docking station connector;

wherein the docking station frame includes one or more radiopaque markers disposed around a valve seat;

wherein the docking station frame is deployed by retracting the outer tube proximally from the elongated nosecone; and wherein the radiopaque markers of the outer tube, the radiopaque markers of the connecting tube, and the radiopaque markers of the docking station frame are configured to visually determine correct placement of the docking station frame and a final point at which the docking station frame is recapturable by the outer tube.

9. The system of claim 8, wherein the one or more radiopaque markers of the outer tube is a radiopaque band embedded in outer tube.

10. The system of claim 8, wherein alignment of one of the radiopaque markers of the outer tube and the radiopaque markers of the frame indicates an amount of deployment of the frame.

11. The system of claim 8, wherein alignment of one or more radiopaque markers of the outer tube and one or more of the radiopaque markers of the connecting tube indicates an amount of deployment of the frame.

12. The system of claim 8, wherein the alignment of one or more radiopaque markers of the outer tube and one or more of the radiopaque markers of the connecting tube indicates a point of release for the frame.

13. The system of claim 8, wherein the frame is configured to be recaptured by the outer tube at any point before one of the radiopaque markers of the outer tube moves proximally past one of the radiopaque markers of the connecting tube.

* * * * *